US007709007B2

(12) United States Patent
Murphy et al.

(10) Patent No.: US 7,709,007 B2
(45) Date of Patent: *May 4, 2010

(54) PRODUCTION OF ATTENUATED RESPIRATORY SYNCYTIAL VIRUS VACCINES FROM CLONED NUCLEOTIDE SEQUENCES

(75) Inventors: Brian R. Murphy, Bethesda, MD (US); Peter L. Collins, Rockville, MD (US); Stephen S. Whitehead, Gaithersburg, MD (US); Alexander A. Bukreyev, Rockville, MD (US); Katalin Juhasz, Rockville, MD (US); Michael N. Teng, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1249 days.

This patent is subject to a terminal disclaimer.

(21) Appl. No.: 10/934,003

(22) Filed: Sep. 2, 2004

(65) Prior Publication Data

US 2006/0159703 A1 Jul. 20, 2006

Related U.S. Application Data

(60) Continuation of application No. 09/444,221, filed on Nov. 19, 1999, now abandoned, which is a division of application No. 08/892,403, filed on Jul. 15, 1997, now Pat. No. 5,993,824.

(60) Provisional application No. 60/047,634, filed on May 23, 1997, provisional application No. 60/046,141, filed on May 9, 1997, provisional application No. 60/021,773, filed on Jul. 15, 1996.

(51) Int. Cl.
*A61K 39/155* (2006.01)

(52) U.S. Cl. ................ 424/211.1; 424/199.1; 435/5; 435/69.1

(58) Field of Classification Search ............ None
See application file for complete search history.

(56) References Cited

U.S. PATENT DOCUMENTS

| 5,716,821 | A | 2/1998 | Wertz |
| 5,789,229 | A | 8/1998 | Wertz |
| 5,869,036 | A | 2/1999 | Belshe |
| 5,882,651 | A | 3/1999 | Murphy |
| 5,922,326 | A | 7/1999 | Murphy |
| 5,993,824 | A | 11/1999 | Murphy |
| 6,033,886 | A | 3/2000 | Conzelmann |
| 6,264,957 | B1 | 7/2001 | Collins |
| 6,364,957 | B1 | 4/2002 | Schneider |
| 6,699,476 | B1 | 3/2004 | Collins |

FOREIGN PATENT DOCUMENTS

| EP | 0 440 219 A1 | 8/1991 |
| EP | 0 702 085 A1 | 3/1996 |
| WO | WO-93 14207 | 7/1993 |
| WO | WO93/21310 | * 10/1993 |
| WO | WO-93 21310 | 10/1993 |
| WO | WO-97 11093 | 3/1997 |
| WO | WO-97 12032 | 4/1997 |
| WO | WO-97 20468 | 6/1997 |
| WO | WO-98 02530 | 1/1998 |
| WO | WO-98 43668 | 10/1998 |
| WO | WO-98 53078 | 11/1998 |
| WO | WO-99 02657 | 1/1999 |
| WO | WO-99 15631 | 4/1999 |
| WO | WO-99 24564 | 5/1999 |
| WO | WO-00 61611 | 10/2000 |
| WO | WO-00 61737 | 10/2000 |
| WO | WO-01 04271 | 1/2001 |
| WO | WO-01 04321 | 1/2001 |

OTHER PUBLICATIONS

Collins et al. PNAS USA, Dec. 1995, 92:11563-67.*
Crowe et al. Vaccine, 1994, 12(9):783-790.*
Chen et al. J Virol 1993, 67(3):1218-26.*
Doyle et al. J Cell Biol 1986, 103(4):1193-1204.*
Anderson et al., Antigenic Characterization of Respiratory Syncytial Virus Strains With Monoclonal Antibodies, Journal Infectious Diseases, vol. 151, No. 4, 626-633 (1985).
Anderson et al., Analysis of the Local and Systemic Immune Responses Induced In BALBc Mice By Experimental Respiratory Syncytial Virus Infection, J Gen Virology vol. 71 1561-1570 (1990).
Anderson et al., Pollactosaminoglycan Modification of the Respiratory Syncytial Virus, Virology 191, 417-430 (1992).
Ausubel et al., Current Protocols in Molecular Biology, John Wiley and Sons, Inc., NY (1987) Book.
Bailly et al., A Recombinant Human Parainfluenza Virus Type 3 (PIV3) In Which the Nucleocapsid N Protein Has Been Replaced, Journal Virology, vol. 74, No. 7, 3188-3195 (2000).

(Continued)

*Primary Examiner*—Stacy B Chen
(74) *Attorney, Agent, or Firm*—Woodcock Washburn LLP

(57) ABSTRACT

Attenuated respiratory syncytial virus (RSV) and vaccine compositions thereof are produced by introducing specific mutations associated with attenuating phenotypes into wild-type or RSV which is incompletely attenuated by cold-passage or introduction of mutations which produce virus having a temperature sensitive (ts) or cold adapted (ca) phenotype. Alternatively, recombinant RSV and vaccine compositions thereof incorporate attenuating and other mutations specifying desired structural and or phenotypic characteristics in an infectious RSV. Recombinant RSV incorporate desired mutations specified by insertion, deletion, substitution or rearrangement of a selected nucleotide sequence, gene, or gene segment in an infectious RSV clone. The immune system of an individual is stimulated to induce protection against natural RSV infection, or multivalently against infection by RSV and another pathogen, such as PIV, by administration of attenuated, biologically derived or recombinant RSV.

46 Claims, 24 Drawing Sheets

OTHER PUBLICATIONS

Belshe et al., Experimental Respiratory Syncytial Virus Infection of Four Species of Primates, Journal Medical Virology, vol. 1, 157-162 (1977).

Belshe et al., Evaluation of Five Temperature-Sensitive Mutants of Respiratory Syncytial Virus In Primates, Journal Medical Virology, vol. 3, 101-110 (1978).

Buchholz et al., Generation of Bovine Respiratory Syncytial Virus (BRSV) from cDNA, Journal Virology, vol. 73, No. 1, 251-259 (1999).

Buchholz et al., Chimeric Bovine Respiratory Syncytial Virus With Glycoprotein Gene Substitutions, Journal Virology, vol. 74, No. 3, 1187-1199 (2000).

Bukreyev et al., Complete Nucleotide Sequences, Biochem. Mol. Biol. Int. vol. 35, No. 3 605-613 (1995).

Bukreyev et al., Recovery of Infectious Respiratory Syncytial Virus Expressing an Additional, Foreign Gene, Journal Virology, vol. 70, No. 10, 6634-6641 (1996).

Bukreyev et al., Recombinant Respiratory Syncytial Virus From Which Entire SH Gene Deleted Grows In Cell Culture, Journal Virology, vol. 71, No. 12, 8973-8982 (1997).

Bukreyev et al., Interferon Gamma Expressed By A Recombinant Respiratory Syncytial Virus, Proc. Natl. Acad. Sci., vol. 96 2367-2372 (1999).

Byrappa et al., A Highly Efficient Procedure for Site-Specific Mutagenesis Of Full-Length Plasmids Using Vent DNA Polymerase, Genome Research, vol. 5 404-407 (1995).

Chanock et al., Viral Infections of Humans 3rd Ed. A.S. Evans ed., Plenum Press N.Y. (1989).

Cheng et al., Effective Amplification of Long Targets From Cloned Inserts, Proc. Natl. Acad. Sci. USA, vol. 91 5695-5699 (1994).

Chin et al., Field Evaluation of A Respiratory Syncytial Virus Vaccine and A Trivalent Parainfluenza Virus Vaccine In A Pediatric Population, Am. J. Epidemiol. vol. 89 No. 4 449-463 (1968).

Clements et al., Evaluation of Bovine Cold-Adapted Human, and Wild-Type Human Parainfluenza Type 3 Viruses in Adult Volunteers, J. Clinical Microbiology, vol. 29, 1175-1182 (1991).

Collins et al., cDNA Cloning and Transcriptional Mapping of Nine Polyadenylylated RNAs, Proc. Natl. Acad. Sci. USA, vol. 80 3208-3212 (1983).

Collins et al., Envelope-Associated 22K Protein of Human Respiratory Syncytial Virus, Journal Virology, vol. 54, No. 1, 65-71 (1985).

Collins et al., Nucleotide Sequence of the 1B and 1C Nonstructural Protein mRNAs of Human Respiratory Syncytial Virus, Virol. 143 442-451 (1985).

Collins et al., Nucleotide Sequences For The Gene Junction of Human Respiratory Syncytial Virus Reveal, Proc. Natl. Acad. Sci. vol. 83 4594-4598 (1986).

Collins et al., Gene Overlap and Site Specific Attenuation of Transcription, Proc. Natl. Acad. Sci. vol. 84 5134-5138 (1987).

Collins et al., Evaluation In Chimpanzees of Vaccinia Virus Recombinants That express The Surface, Vaccine vol. 8 164-168 (1990).

Collins et al., Two Open Reading Frames of 22K mRNA of Human Respiratory Syncytial Virus, Journal General Virology, vol. 71, 3015-3020 (1990).

Collins et al., Rescue of Synthetic Analogs of Respiratory Syncytial Virus Genomic RNA, Proc. Natl. Acad. Sci., vol. 88 9663-9667 (1991).

Collins et al., Production of Infectious Human Respiratory Syncytial Virus From Cloned cDNA, Pro. Natl. Acad. Sci., vol. 92, 11563-11567 (1995).

Collins et al., Transcription Elongation of Respiratory Syncytial Virus A Nonsegmented Negative-Strand RNA Virus, Proc. Natl, Acad, Sci., vol. 93 81-85 (1996).

Collins et al., Respiratory Syncytial Virus, Fields Virology, Third Ed., 1313-1351, (1996).

Connors et al., Resistance To Respiratory Syncytial Virus (RSV), Journal Virology, vol. 66, No. 2, 1277-1281 (1992).

Connors et al., A Cold Passaged Attenuated Strain of Human Respiratory Syncytial Virus Contains Mutations in the F and L Genes, Virology, vol. 208, 478-484 (1995).

Conzelmann et al., Rescue of Synthetic Genomic RNA Analogs of Rabies Virus By Plasmid-Encoded Proteins, Journal Virology, vol. 68, No. 2, 713-719 (1994).

Conzelmann et al., Genetic Manipulation of Non-Segmented Negative-Strand RNA Viruses, Journal General Virology, vol. 77, 381-389 (1996).

Corsoro et al., Enhancing the Efficiency of DNA Mediated Gene Transfer in Mammalian Cells, Somatic Cell Genetics vol. 7, No. 5 603-616 (1981).

Crowe et al., A Comparison In Chimpanzees of Immunogenic Efficacy of Live Attenuated Respiratory Syncytial Virus (RSV), Vaccine, vol. 11, Issue 14, 1395-1404 (1993).

Crowe et al., Satisfactorily Attenuated Protective Mutants Derived From Partially Attenuated Cold Passaged Respiratory Syncytial Virus, Vaccine, vol. 12, No. 8, 691-699 (1994).

Crowe et al., A Further Attenuated Derivative of Cold-Passaged Temperature-Sensitive Mutant of Human Respiratory Syncytial Virus, Vaccine, vol. 12, No. 9, 783-790 (1994).

Crowe et al., Acquisition of the ts Phenotype by Chemically Mutagenized Cold Passaged Human Respiratory Syncytial Virus Vaccine, Virus Genes, vol. 13-3, 269-273 (1996).

Delenda et al., Normal Cellular Replication of Sendai Virus Without Trans-Frame, Nonstructural V Protein, Virology, vol. 228, 55-62 (1997).

Elango et al., mRNA Sequence and Deduced Amino Acid Sequence of the Mumps Virus Small Hydrophobic Protein Gene, J. Virology, vol. 63, No. 3 1413-1415 (1989).

Emerson et al., A Simian Strain of Hepatitis A Virus, AGM-27, Functions As An Attenuated Vaccine for Chimpanzees, Journal Infectious Diseases, vol. 173, 592-597 (1996).

Firestone et al., Nucleotide Sequence Analysis Of Respiratory Syncytial Virus Subgroup A, Virology, vol. 225 419-422 (1996).

Flexner et al., Prevention of Vaccinia Virus Infection in Immunodeficient Mice by Vector-Directed IL-2 Expression, Nature, vol. 330, 259-262 (1987).

Fridewald et al., Low-Temperature-Grown RS Virus In Adult Volunteers, JAMA, vol. 204, No. 8, 690-694 (1968).

Fuerst et al., Eukaryotic Transient-Expression System Based On Recombinant Vaccinia Virus That Synthesizes Bacteriophage T7 RNA Polymerase, Proc. Natl. Acad. Sci., vol. 83, 8122-8126 (1986).

Garcin et al., A Highly Recombinogenic System For Recovery of Infectious Sendai Paramyxovirus for cDNA, EMBO Journal, vol. 14, No. 24 6087-6094 (1995).

Gharpure et al., Temperature-Sensitive Mutants of Respiratory Syncytial Virus, J. Virol. vol. 3 No. 4 414-421 (1969).

Graham et al., A New Technique for The Assay of Infectivity of Human Adenovirus 5 DNA, Virology 52 456-467 (1973).

Grosfeld et al., RNA Replication By Respiratory Syncytial Virus (RSV) Is Directed By N, P, and L Proteins, Journal Virology, vol. 69, No. 9, 5677-5686 (1995).

Haas et al. Codon Usage Limitation In The Expression Of HIV-1 Envelope Glycoprotein, Current Biology, vol. 6, No. 3315-324 (1996).

Hawley-Nelson et al., A New Higher Efficiency Polyatomic Liposome Transfection Reagent, Focus vol. 15, No. 3 73-79 (1993).

He et al., The Paramyxovirus SV5 Small Hydrophobic (SH) Protein Is Not Essential For Virus Growth In Tissue Culture Cells, Virology, vol. 250, 30-40 (1998).

Heminway et al., Analysis of Respirator Syncytial Virus F, G and SH Proteins In Cell Fusion, Virology 200, 801-805 (1994).

Hemming et al., Studies of Passive Immunotherapy for Infections of Respiratory Syncytial Virus In the Respiratory Tract of a Primate Model, J Infect. Dis. vol. 152, No. 5 1083-1087 (1985).

Hemming et al., Intravenous Immunoglobulin Treatment of Respiratory Syncytial Virus Infections in Infants and Young Children, Antimicrobial Agents and Chemotherapy, vol. 31, No. 12, 1882-1886 (1987).

Hendricks et al., Further Characterization of the Soluble Form of the G Glycoprotein of Respiratory Syncytial Virus, Journal Virology, vol. 62, No. 7, 2228-2233 (1988).

Hiebert et al., Identification and Predicted Sequence of A Previously Unrecognized Small Hydrophobic Protein, J. Virol. vol. 55 No. 3 744-751 (1985).

Hodes et al., Genetic Alteration In A Temperature Sensitive Mutant of Respiratory Syncytial Virus After Replication In Vivo (37972), Proc. Soc. Exp. Biol. Med. vol. 145 1158-1164 (1974).

Hoffman et al., An Infectious Clone of Human Parainfluenza Virus Type 3, Journal Virology, vol. 71, No. 6, 4272-4277 (1997).

Holland et al., RNA Virus Population As Quasispecies, Curr. Top Microbiol. Immunol. vol. 176 1-20 (1992).

Hurwitz et al., Intranasal Sendai Virus Vaccine Protects African Green Monkeys From Infection With Human Parainfluenza Virus Type One, Vaccine, vol. 15, No. 5, 533-540 (1997).

Johnson et al., The G Glycoprotein of Human Respiratory Syncytial Viruses of Subgroups A and B, Proc. Natl. Acad. Sci., vol. 84, 5625-5629 (1987).

Johnson et al., Antigenic Relatedness Between Glycoproteins of Human Respiratory Syncytial Virus Subgroups A and B, Journal Virology, vol. 61, No. 10, 3161-3166 (1987).

Johnson et al., The Fusion Glycoproteins of Human Respiratory Syncytial Virus of Subgroups A and B, Journal General Virology, vol. 69, 2623-2628 (1988).

Johnson et al., The A and B Subgroups of Human Respiratory Syncytial Virus, J Gen Virology vol. 69 2901-2906 (1988).

Johnson et al., Priming with Secreted Glycoprotein G of Respiratory Syncytial Virus (RSV) Augments Interleukin 5 Production, Journal Virology, vol. 72, No. 4, 2871-2880 (1998).

Kapikian et al., An Epidemiologic Study of Altered Clinical Reactivity to Respiratory Syncytial (RS) Virus, Am J Epidemiology vol. 89 No. 4 405-421 (1968).

Karron et al., A Live Human Parainfluenza Type 3 Virus Vaccine Is attenuated and Immunogenic In Healthy Infants and Children, Journal Infectious Diseases, vol. 172, 1445-1450 (1995).

Kato et al., The Paramyxovirus Sendai Virus V Protein Encodes A Luxury Function Required For Viral Pathogenesis, EMBO Journal, vol. 16, No. 3, 578-587 (1997).

Kim et al., Respiratory Syncytial Virus Disease In Infants Despite Prior Administration of Antigenic Inactivated Vaccine, Am J Epidemiol. vol. 89, No. 4 422-434 (1968).

Kim et al., Clinical and Immunological Response of Infants and Children to Administration of Low Temperature Adapted Respiratory Syncytial Virus, Pediatrics, vol. 48, No. 5, 745-755 (1971).

Kim et al., Safety and Antigenicity of Temperature Sensitive (TS) Mutant Respiratory Syncytial Virus (RSV) In Infants and Children, Pediatrics, vol. 52, No. 1, 56-62 (1973).

Kretzschmar et al., Normal Replication of Vesicular Stomatitis Virus Without C Proteins, Virology, vol. 216, 309-316 (1996).

Kunkel et al., Rapid and Efficient Site-Specific Mutagenesis Without Phenotypic Selection, Methods Enzymol. vol. 154 367-383 (1987).

Kuo et al., Effect of Mutations in Gene Start and Gene End Sequence Motifs On Transcription, Journal Virology, vol. 70, No. 10, 6892-6901 (1996).

Kuo et al., Analysis of the Gene Start and Gene End Signals of Human Respiratory Syncytial Virus, J Virology, vol. 71, No. 7 4944-4953 (1997).

Kurotani et al., Sendai Virus C Proteins Are Categorically Nonessential Gene Products, Genes to Cells, vol. 3, 111-124 (1998).

Lamb et al. Do Vpu and Vpr of Human Immunodeficiency Virus Type 1 and NB of Influenza B Virus Have Ion Channel Activities in the Viral Life Cycles, Virology vol. 229 1-11 (1997).

Latorre et al., The Various Sendai Virus C Proteins Are Not Functionally Equivalent, Journal Virology, vol. 72, No. 7, 5984-5993 (1998).

Lawson et al., Recombinant Vesicular Stomatitis Viruses From DNA, Proc. Natl. Acad. Sci., vol. 91, 4477-4481 (1995).

Ling et al., Sequence Analysis of the 22K, SH and G Genes of Turkey Rhinotracheitis Virus and Their Intergenic Regions Reveals A Gene, Journal General Virology, vol. 73, 1709-1715 (1992).

Mallipeddi et al., Sequence Comparison Between the Phosphoprotein mRNAs of Human and Bovine Respiratory Syncytial Viruses, Journal General Virology, vol. 73, 2441-2444 (1992).

Mallipeddi et al., Sequence Variability of the Glycoprotein Gene of Bovine Respiratory Syncytial Virus, Journal General Virology, vol. 74, 2001-2004 (1993).

Maramorosh et al., Modification of Membrane Permeability By Animals Viruses, Advances in Virus Research vol. 45 61-112 (1995).

McIntosh et al., Attenuated Respiratory Syncytial Virus Vaccines in Asthmatic Children, J Pediatrics Res. 689-696 (1974).

Mills et al., Experimental Respiratory Syncytial Virus Infection of Adults, J Immunol. vol. 107, No. 1 123-130 (1971).

Mink et al., Nucleotide Sequences of the 3 Leader and 5 Trailer Regions of Human Respiratory Syncytial Virus Genomic RNA, Virology, vol. 185, 615-624 (1991).

Mufson et al., Two Distant Subtypes of Human Respiratory Syncytial Virus, Journal General Virology, vol. 66, 2111-2124 (1985).

Murphy et al., Production and Level of Genetic Stability of an Influenza A Virus Temperature Sensitive Mutant Containing Two Genes, vol. 37, No. 1, 235-242 (1982).

Murphy et al., Current Approaches to the Development of Vaccines Effective Against Parainfluenza, Virus Research, vol. 11, 1-15 (1988).

Murphy et al., Enhanced Pulmonary Histopathology Is Observed In Cotton Rats Immunized, Vaccine, vol. 8, 497-502 (1990).

Needleman et al., A General Method Applicable to the Search For Similarities In The Amino Acid Sequence Of Two Proteins, J. Mol. Biol. vol. 48, 443-453 (1970).

Neumann et al., Gene Transfer Into Mouse Lymoa Cells By Electroporation In High Electric Fields, EMBO J. vol. 1, 841-845 (1982).

Olmsted et al., Expression of the F Glycoprotein of Respiratory Syncytial Virus By A Recombinant Vaccinia Virus, Proc. Natl. Acad. Sci. vol. 83, 7462-7466 (1986).

Olmsted et al., The 1A Protein of Respiratory Syncytial Virus Is An Integral Membrane Protein, J. Virol. vol. 63 No. 5 2019-2029 (1989).

Palese et al., Negative Strand RNA Viruses Genetic Engineering and Applications, Proc. Natl, Acad. Sci., vol. 93, 11354-11358 (1996).

Pastey et al., Structure and Sequence Comparison of Bovine Respiratory Syncytial Virus Fusion Protein, Virus Research, vol. 29, 195-202 (1993).

Pastey et al., Nucleotide Sequence Analysis of the Non-Structural NS1 (1C) and NS2 (1B) Protein Genes of Bovine Respiratory Syncytial Virus, Journal General Virology, vol. 76, 193-197 (1995).

Pearson et al., Improved Tools For Biological Sequence Comparison, Proc. Natl. Acad. Sci. USA, vol. 85, 2444-2448 (1988).

Perez-Schael et al., Journal Medicine, Efficacy of Rhesus Rotavirus Based Quadrivalent Vaccine In Infants and Young Children In Venezuela, vol. 337, No. 17, 1181-1187 (1997).

Perrotta et al. A Pseudoknot-Like Structure Required For Efficient Self-Cleavage Of Hepatitis Delta Virus RNA, Nature vol. 350 434-436 (1991).

Poch et al., Identification of Four conserved Motifs Among the RNA Dependent Polymerase Encoding Elements, EMBO J. vol. 8 No. 12 3867-3874 (1989).

Prince et al., Immunoprophylaxis And Immunotherapy Of Respiratory Syncytial Virus Infection In The Cotton Rat, Virus Res. vol. 3 193-206 (1985).

Prince et al., Failure of A Huma Imunodeficiency Virus (HIV) Immune Golbulin To Protect Chimpanzees Againat Experimental Challenge With HIV, PNAS vol. 85 6944-6948 (1987).

Radecke et al., Rescue of Measles Viruses from Cloned DNA, EMBO Journal, vol. 14, No. 23, 5773-5784 (1995).

Radecke et al., The Nonstructural C. Protein Is Not Essential for Multiplication of Edmonstron B Strain Measles Virus In Cultured Cells, Virology, vol. 217, 418-421 (1996).

Randhawa et al., Nucleotide Sequences of Genes Encoding the Putative Attachment Glycoprotein (G) of Mouse and Tissue Culture Passaged Strains of Pneumonia. Virology, vol. 207 240-245 (1995).

Smith & Waterman, Comparison of Biosequences, Adv. Appl. Math. 2, 482-489 (1981).

Snyder et al., Restricted Replication of a Cold Adapted Reassortant Influenza A Virus, J Infect. Dis. vol. 154, No. 2 370-371 (1986).

Srikiatkhachorn et al., Virus Specific CD8 T Lymphocytes Downregulate T Helper Cell Type 2 Cytokine Secretion, Journal Exp. Med., vol. 186, No. 3, 421-432 (1997).

Stec et al., Sequence Analysis of Polymerase L Gene of Human Respiratory Syncytial Virus, Virology, vol. 183, 273-287 (1991).

Steinhoff et al., A Mallard 6750 78 Avian Human By Not A Ann Arbor 6 60 Cold Adapted Influenza, Journal Infectious Diseases, vol. 163, 1023-1028 (1991).

Tang et al., Requirement of Cysteines and Length of Human Respiratory Syncytial Virus M2-1 Protein, Journal Virology, vol. 75, No. 23, 11328-11335 (2001).

Teng et al., Identification of Respiratory Syncytial Virus Proteins Required for Formation and Passage, Journal Virology, vol. 72, No. 7, 5707-5716 (1998).

Teng et al., Altered Growth Characteristic of Recombinant Respiratory Syncytial Viruses, Journal Virology, vol. 73, No. 1, 466-473 (1999).

Van Wyke et al., Attenuation of Bovine Parainfluenza Virus Type 3 in Nonhuman Primates Journal Infectious Diseases, vol. 157, No. 4, 655-662 (1988).

Walsh et al., Immunization with Glycoprotein Subunits of Respiratory Syncytial Virus To Protect Cotton Rats Against Viral Infection, J Infec. Dis. vol. 155, No. 6 1198-1204 (1987).
Wathen et al., Characterization of A Novel Human Respiratory syncytial virus Chimeric FG Glycoprotein Expressed Using a Baculovirus Vector, Journal General Virology, vol. 70, 2625-2635 (1989).
Whelan et al., Efficient Recovery of Infectious Vesicular Stomatitis Virus Entirely from cDNA Clones, Proc. Natl. Acad. Sci., vol. 92, 8388-8392 (1995).
Whitehead et al., A Single Nucleotide Substitution In Transcription Start Signal of M2 Gene, Virology, vol. 247, 232-239 (1998).
Whitehead et al., Recombinant Respiratory Syncytial Virus (RSV) Bearing a Set of Mutations, Journal Virology, vol. 72, No. 5, 4467-4471 (1998).
Whitehead et al., Recombinant Respiratory Syncytial Virus Bearing A Deletion of Either the NS2 or SH Gene, Journal Virology, vol. 73, No. 4, 3438-3442 (1999).
Wigler et al., Biochemical Transfer of Single Copy Eukaryotic Genes Using Total Cellular DNA As Donor, Cell vol. 14 725-731 (1978).
Wright et al., Temperature Sensitive Mutants Of Respiratory Syncytial Virus In Vivo Studies In Hamsters, J. Infect. Dis. vol. 122, No. 6 501-512 (1970).
Wright et al., Genetic Studies Of Respiratory Syncytial Virus Temperature Sensitive Mutants, Arch. Ges. Virusforsch. vol. 41, 238-247 (1973).
Wright et al., Evaluation of a Live Attenuated Respiratory Syncytial Virus Vaccine In Infants, Journal Pediatrics, vol. 88, No. 6, 931-936 (1976).
Wright et al., Administration of A Highly Attenuated Live Respiratory Syncytial Virus Vaccine to Adults and Children, Infection and Immunity, vol. 37, No. 1, 397-400 (1982).
Wyatt et al., Replication Deficient Vaccinia Virus Encoding Bacteriophage T7 RNA, Virology 210 202-205 (1995).
Zamora et al., Sequence Analysis of M2 mRNA of Bovine Respiratory Syncytial Virus, Journal General Virology, vol. 73, 737-741 (1992).
Zamora et al., Gene Junction Sequences of Bovine Respiratory Syncytial Virus, Virus Research, vol. 24, 115-151 (1992).
Zoller and Smith, Oligonucleotide Directed Mutagenesis: A Simple Method Using Two Oligonucleotide Primers and A Single Stranded DNA Template, DNA vol. 3, No. 6 479-488 (1984).

* cited by examiner

FIG. 7

The SH-minus mutant has a steeper gradient of polar transcription

| Relative mRNA abundance: SH-minus / wild type |||||
|---|---|---|---|---|
| M | G | F | M2 | L |
| 1.1 | 1.3 | 0.61 | 0.32 | 0.17 |

| Positions of genes in 3´- 5´ map |
|---|
|                 5     6   7        10<br>WT:    3´- M - SH - G - F - M2 - L<br><br>                5        6         9<br>SH-minus:  3´- M - - - - G - F - M2 - L |

```
              ter ter XhoI
                   A   A
                       C
ATG AGA CCG TTG TCA CTT GAG ACC ATA
 M   R   P   L   S   L   E   T   I
18                              26
```

T7 promoter — AatII — NS1 — NS2 — 1099 AflII — (PacI) — 4623

NS1 — NS2 — N — P — M — SH

D13

Insertion of two tandem translational stop codons into the NS2 translational open reading frame to ablate expression of the encoded protein Modification of the Gene End (GE) signals of the NS1 and NS2 genes.

Deletion of the NS1 gene. The deletion (arrow) begins immediately upstream of the NS1 ATG and extends to immediately upstream of the NS2 ATG. Note: only the first three genes of the c Deletion of the NS2 gene. The deletion (arrow) begins after the NS1 gene and extends to immediately after the NS2 gene. Note that only the first three genes of the cDNA insert of plas Ablation of the secreted form of the G protein by mutation of its translational start site. The open rectangle illustrates the G ORF, with the hydrophobic signal-anchor portion filled in. An *MfeI* site created by the mutation is indicated by underlining.

Growth Curve of Membrane G Mutants

Fig. 24

PRODUCTION OF ATTENUATED RESPIRATORY SYNCYTIAL VIRUS VACCINES FROM CLONED NUCLEOTIDE SEQUENCES

RELATED APPLICATIONS

This application is a continuation of, and claims the respective priority benefits of, U.S. patent application Ser. No. 09/444,221, filed on Nov. 19, 1999 and now abandoned, which is a divisional of U.S. patent application Ser. No. 08/892,403, filed Jul. 15, 1997 (now U.S. Pat. No. 5,993,824), which claims priority to United States Provisional Applications No. 60/047,634, filed May 23, 1997, No. 60/046,141, filed May 9, 1997 and No. 60/021,773, filed Jul. 15, 1996.

BACKGROUND OF THE INVENTION

Human respiratory syncytial virus (RSV) outranks all other microbial pathogens as a cause of pneumonia and bronchiolitis in infants under one year of age. Virtually all children are infected by two years of age, and reinfection occurs with appreciable frequency in older children and young adults (Chanock et al., in *Viral Infections of Humans*, 3rd ed., A. S. Evans, ed., Plenum Press, N.Y. (1989)). RSV is responsible for more than one in five pediatric hospital admissions due to respiratory tract disease, and causes an estimated 91,000 hospitalizations and 4,500 deaths yearly in the United States alone. Although most healthy adults do not have serious disease due to RSV infection, elderly patients and immunocompromised individuals often suffer severe and possibly life-threatening infections from this pathogen.

Despite decades of investigation to develop effective vaccine agents against RSV, no safe and effective vaccine has yet been achieved to prevent the severe morbidity and significant mortality associated with RSV infection. Failure to develop successful vaccines relates in part to the fact that small infants have diminished serum and secretory antibody responses to RSV antigens. Thus, these individuals suffer more severe infections from RSV, whereas cumulative immunity appears to protect older children and adults against more serious impacts of the virus. One antiviral compound, ribavarin, has shown promise in the treatment of severely infected infants, although there is no indication that it shortens the duration of hospitalization or diminishes the infant's need for supportive therapy.

The mechanisms of immunity in RSV infection have recently come into focus. Secretory antibodies appear to be most important in protecting the upper respiratory tract, whereas high levels of serum antibodies are thought to have a major role in resistance to RSV infection in the lower respiratory tract. Purified human immunoglobulin containing a high titer of neutralizing antibodies to RSV may prove useful in some instances of immunotherapeutic approaches for serious lower respiratory tract disease in infants and young children. Immune globulin preparations, however, suffer from several disadvantages, such as the possibility of transmitting blood-borne viruses and difficulty and expense in preparation and storage.

Formalin-inactivated virus vaccine was tested against RSV in the mid-1960s, but failed to protect against RSV infection or disease, and in fact exacerbated symptoms during subsequent infection by the virus. (Kim et al., *Am. J. Epidemiol.*, 89:422-434 (1969), Chin et al., *Am J. Epidemiol.*, 89:449-463 (1969); Kapikian et al., *Am. J. Epidemiol.*, 89:405-421 (1969)).

More recently, vaccine development for RSV has focused on attenuated RSV mutants. Friedewald et al., *J. Amer. Med. Assoc.* 204:690-694 (1968) reported a cold passaged mutant of RSV (cpRSV) which appeared to be sufficiently attenuated to be a candidate vaccine. This mutant exhibited a slight increased efficiency of growth at 26° C. compared to its wild-type parental virus, but its replication was neither temperature sensitive nor significantly cold-adapted. The cold-passaged mutant, however, was attenuated for adults. Although satisfactorily attenuated and immunogenic for infants and children who had been previously infected with RSV (i.e., seropositive individuals), the cpRSV mutant retained a low level virulence for the upper respiratory tract of seronegative infants.

Similarly, Gharpure et al., *J. Virol.* 3:414-421 (1969) reported the isolation of temperature sensitive RSV (tsRSV) mutants which also were promising vaccine candidates. One mutant, ts-1, was evaluated extensively in the laboratory and in volunteers. The mutant produced asymptomatic infection in adult volunteers and conferred resistance to challenge with wild-type virus 45 days after immunization. Again, while seropositive infants and children underwent asymptomatic infection, seronegative infants developed signs of rhinitis and other mild symptoms. Furthermore, instability of the ts phenotype was detected, although virus exhibiting a partial or complete loss of temperature sensitivity represented a small proportion of virus recoverable from vaccinees, and was not associated with signs of disease other than mild rhinitis.

These and other studies revealed that certain cold-passaged and temperature sensitive RSV strains were underattenuated and caused mild symptoms of disease in some vaccinees, particularly seronegative infants, while others were overattenuated and failed to replicate sufficiently to elicit a protective immune response, (Wright et al., *Infect. Immun.*, 37:397-400 (1982)). Moreover, genetic instability of candidate vaccine mutants has resulted in loss of their temperature-sensitive phenotype, further hindering development of effective RSV vaccines. See generally, Hodes et al., *Proc. Soc. Exp. Biol. Med.* 145:1158-1164 (1974), McIntosh et al., *Pediatr. Res.* 8:689-696 (1974), and Belshe et al., *J. Med. Virol.*, 3:101-110 (1978).

Abandoning the attenuated RS virus vaccine approach, investigators tested potential subunit vaccine candidates using purified RS virus envelope glycoproteins from lysates of infected cells. The glycoproteins induced resistance to RS virus infection in the lungs of cotton rats, Walsh et al., *J. Infect. Dis.* 155:1198-1204 (1987), but the antibodies had very weak neutralizing activity and immunization of rodents with purified subunit vaccine led to disease potentiation (Murphy et al., *Vaccine* 8:497-502 (1990)).

Vaccinia virus recombinant-based vaccines which express the F or G envelope glycoprotein have also been explored. These recombinants express RSV glycoproteins which are indistinguishable from the authentic viral counterpart, and small rodents infected intradermally with the vaccinia-RSV F and G recombinant viruses developed high levels of specific antibodies that neutralized viral infectivity. Indeed, infection of cotton rats with vaccinia-F recombinants stimulated almost complete resistance to replication of RSV in the lower respiratory tract and significant resistance in the upper tract. Olmsted et al., *Proc. Natl. Acad. Sci. USA* 83:7462-7466 (1986). However, immunization of chimpanzees with vaccinia F and vaccinia G recombinant provided almost no protection against RSV challenge in the upper respiratory tract (Collins et al., *Vaccine* 8:164-168 (1990)) and inconsistent protection in the lower respiratory tract (Crowe et al., *Vaccine* 11:1395-1404 (1993)).

The unfulfilled promises of attenuated RSV strains, subunit vaccines, and other strategies for RSV vaccine development underscores a need for new methods to identify genetic targets for recombinant engineering of novel RSV vaccines, and to develop methods for manipulating recombinant RSV to incorporate genetic changes to yield new phenotypic properties in viable, attenuated RSV recombinants. However, manipulation of the genomic RNA of RSV and other negative-sense RNA viruses has heretofore proven difficult. Major obstacles in this regard include non-infectivity of naked genomic RNA of these viruses, poor viral growth in tissue culture, lengthy replication cycles, virion instability, a complex genome, and a refractory organization of gene products.

Methods for direct genetic manipulation of nonsegmented, negative stranded RNA viruses have only recently begun to be developed (for reviews, see Conzelmann, *J. Gen. Virol.* 77:381-89 (1996); Palese et al., *Proc. Natl. Acad. Sci. U.S.A.* 93:11354-58, (1996)). Successful rescue has been achieved for infectious rabies virus, vesicular stomatitis virus (VSV), measles virus, and Sendai virus from cDNA-encoded antigenomic RNA in the presence of the nucleocapsid N, phosphoprotein P, and large polymerase subunit L (Garcin et al., *EMBO J.* 14:6087-6094 (1995); Lawson et al., *Proc. Natl. Acad. Sci. U.S.A.* 92:4477-81 (1995); Radecke et al., *EMBO J.* 14:5773-5784 (1995); Schnell et al., *EMBO J.* 13:4195-203 (1994); Whelan et al., *Proc. Natl. Acad. Sci. U.S.A.* 92:8388-92 (1995)). Successful rescue of RSV also requires an additional protein, the M2 ORF1 transcriptional elongation factor (Collins et al., *Proc. Natl. Acad. Sci. USA* 92:11563-7 (1995)).

Rescue of infectious RSV has been complicated by a number of factors. Specifically, RSV possesses several properties which distinguish it and other members of the genus Pneumovirus from better characterized paramyxoviruses of the genera Paramyxovirus, Rubulavirus and Morbillivirus. These differences include a greater number of mRNAs, an unusual gene order at the 3' end of the genome, species-to-species variability in the order of the glycoprotein and M2 genes, a greater diversity in intergenic regions, an attachment protein that exhibits mucin-like characteristics, extensive strain-to-strain sequence diversity, and several proteins not found in other nonsegmented negative stranded RNA viruses.

In view of the foregoing, an urgent need exists in the art for tools and methods to engineer safe and effective vaccines to alleviate the serious health problems attributable to RSV, particularly illnesses among infants and children. Quite surprisingly, the present invention satisfies these and other related needs.

SUMMARY OF THE INVENTION

The present invention provides novel methods and compositions for designing and producing isolated attenuated respiratory syncytial virus (RSV). RSV of the invention are either biologically derived from wild-type or selected RSV mutant parental stocks or are recombinantly engineered to incorporate phenotype-specific genetic changes. RSV designed and selected for vaccine use have at least two and sometimes at least three attenuating mutations. In one embodiment, at least one attenuating mutation occurs in the RSV polymerase gene and involves a nucleotide substitution specifying an amino acid change in the polymerase protein resulting in a temperature-sensitive (ts) phenotype. Exemplary biologically derived and recombinant RSV incorporate one or more nucleotide substitutions in the large polymerase gene L resulting in an amino acid change at amino acid $Phe_{521}$, $Gln_{831}$, $Met_{1169}$ or $Tyr_{1321}$, as exemplified by the changes, Leu for $Phe_{521}$, Leu for $Gln_{831}$, Val for $Met_{1169}$, and Asn for $Tyr_{1321}$. Alternately or additionally, RSV of the invention may comprise a nucleotide substitution in a different RSV gene, e.g., in the M2 gene.

Attenuating mutations may be selected in coding portions of a RSV gene, or in a non-coding portion such as a cis-regulatory sequence. Exemplary non-coding mutations include single or multiple base changes in a gene start sequence, as exemplified by a single or multiple base substitution in the M2 gene start sequence at nucleotide 7605. Preferably, two or three mutations are incorporated in a codon specifying an attenuating mutation, e.g., in a codon specifying a ts mutation at amino acid $Phe_{521}$, $Gln_{831}$, $Met_{1169}$, or $Tyr_{1321}$, thereby decreasing any likelihood of reversion from the ts phenotype.

In other embodiments of the invention, biologically derived or recombinant RSV are selected or engineered to incorporate at least two attenuating ts mutations, e.g., in the polymerase gene at amino acid $Phe_{521}$ and $Met_{1169}$ as exemplified by the novel, biologically derived vaccine strain cpts-530/1009, ATCC No. VR 2451, at $Phe_{521}$ and $Tyr_{1321}$, as exemplified by the biologically derived strain cpts-530/1030, ATCC No. VR 2455, at $Gln_{831}$, and the M2 gene start mutation at nt 7605, as exemplified by the biologically derived RSV strain cpts-248/404, ATCC No. VR 2454, or at the M2 gene start mutation at nt 7605, and $Phe_{521}$ as exemplified by the recombinant RSV rA2cp/248/404/530.

Biologically derived RSV into which selected attenuating mutations can be introduced include wild-type RSV, a host range-restricted cold-passaged RSV, a cold adapted mutant of host range-restricted cold-passaged RSV, or a temperature sensitive strain. For example, the cold-passaged respiratory syncytial virus can be the cpRSV strain, including cpRSV into which at least two temperature-sensitive mutations have been introduced. The attenuated RSV virus can be subgroup A, as exemplified by cpts RSV 248 (ATCC VR 2450), cpts 248/404 (ATCC VR 2454), cpts 248/955 (ATCC VR 2453), cpts RSV 530 (ATCC VR 2452), cpts 530/1009 (ATCC VR 2451), or cpts 530/1030 (ATCC VR 2455) (all deposited on Mar. 22, 1994), or subgroup B, as exemplified by B-1 cp52/2B5 (ATCC VR 2542) (deposited on Sep. 26, 1996) or B-1 cp-23 (ATCC VR 2579) (deposited on Jul. 15, 1997). Each of the deposits was made under the terms of the Budapest Treaty with the American Type Culture Collection (ATCC) of 10801 University Blvd., Manassas, Va. 20110-2209, USA.

In another aspect of the invention, an isolated infectious recombinant RSV is provided which is generated from a RSV genome or antigenome, a nucleocapsid (N) protein, a nucleocapsid phosphoprotein (P), a large (L) polymerase protein, and an RNA polymerase elongation factor. The RNA polymerase elongation factor can be M2(ORF1) of RSV. The isolated infectious RSV can be a viral or subviral particle. The genome or antigenome can comprise a wild-type RSV sequence, a biologically derived mutant sequence specifying an attenuated phenotype, or a recombinant RSV sequence encoding a wild-type RSV genome or antigenome or a recombinantly modified RSV sequence comprising an engineered mutation or combination of mutations not found in any biologically derived RSV strain.

The infectious RSV clone can incorporate coding or non-coding nucleotide sequences from any RSV or RSV-like virus, e.g., human, bovine or, murine RSV (pneumonia virus of mice, or avian RSV (turkey rhinotracheitis virus, or from another virus, e.g., parainfluenza virus (PIV). In exemplary aspects, the recombinant RSV comprises a chimera of a human RSV genomic or antigenomic sequence recombinantly joined with a heterologous RSV sequence. Exemplary heterologous sequences include RSV sequences from one human RSV strain combined with sequences from a different human RSV strain (e.g., a chimera of sequences from two or more strains selected from cpts RSV 248, cpts 248/404, cpts 248/955, cpts RSV 530, cpts 530/1009, or cpts 530/1030), or subgroup (e.g. a combination of RSV subgroup A and subgroup B sequences), from a nonhuman RSV, or from another virus such as PIV.

In one embodiment of the invention, recombinant RSV are provided wherein the genome or antigenome is recombinantly altered, e.g., compared to a wild-type or biologically derived mutant sequence. Mutations incorporated within recombinantly altered RSV clones may be selected based on their ability to alter expression and/or function of a selected RSV protein, yielding a desired phenotypic change, or for a variety of other purposes. Desired phenotypic changes include, e.g., changes in viral growth in culture, temperature sensitivity, plaque size, attenuation, and immunogenicity. For example, a polynucleotide sequence encoding the genome or antigenome can be modified by a nucleotide insertion, rearrangement, deletion or substitution to specify attenuation, temperature-sensitivity, cold-adaptation, small plaque size, host range restriction, alteration in gene expression, or a change in an immunogenic epitope.

In one aspect, recombinant RSV are provided wherein at least one attenuating mutation occurs in the RSV polymerase gene L and involves a nucleotide substitution specifying a (ts) phenotype. Exemplary RSV clones incorporate a nucleotide substitution resulting in an amino acid change in the polymerase gene at $Phe_{521}$, $Gln_{831}$, $Met_{1169}$ or $Tyr_{1321}$. Preferably, two or three mutations are incorporated in a codon specifying an attenuating mutation. Other exemplary RSV clones incorporate at least two attenuating ts mutations.

Mutations occurring in biologically derived, attenuated RSV can be introduced individually or in combination into a full-length RSV clone, and the phenotypes of rescued recombinant viruses containing the introduced mutations can be readily determined. In exemplary embodiments, amino acid changes displayed by attenuated, biologically-derived viruses over a wild-type RSV, for example changes exhibited by cold-passaged RSV (cpRSV) or a further attenuated RSV strain such as a temperature-sensitive derivative of cpRSV (cptsRSV), are incorporated within recombinant RSV clones. These changes from a wild-type or biologically derived mutant RSV sequence specify desired characteristics in the resultant clones, e.g., an attenuated or further attenuated phenotype. These changes are preferably introduced into recombinant virus using two or three nucleotide changes compared to a corresponding wild type or biologically derived mutant sequence, which has the effect of stabilizing the mutation against genetic reversion.

The present invention also provides recombinant RSV having multiple, phenotype-specific mutations introduced in selected combinations into the genome or antigenome of an infectious clone. This process, coupled with evaluation of phenotype, provides mutant recombinant RSV having such desired characteristics as attenuation, temperature sensitivity, cold-adaptation, small plaque size, host range restriction, etc. Mutations thus identified are compiled into a "menu" and introduced in various combinations to calibrate a vaccine virus to a selected level of attenuation, immunogenicity and stability. In preferred embodiments, the invention provides for supplementation of one or more mutations adopted from biologically derived RSV, e.g., cp and ts mutations, with additional types of mutations involving the same or different genes. Target genes for mutation in this context include the attachment (G) protein, fusion (F) protein, small hydrophobic (SH), RNA binding protein (N), phosphoprotein (P), the large polymerase protein (L), the transcription elongation factor (M2), M2 ORF2, the matrix (M) protein, and two nonstructural proteins, NS1 and NS2. Each of these proteins can be selectively deleted, substituted or rearranged, in whole or in part, alone or in combination with other desired modifications, to achieve novel RSV recombinants. In one aspect, the SH gene, is deleted to yield a recombinant RSV having novel phenotypic characteristics, including enhanced growth in vitro and/or attenuation in vivo. In a related aspect, this gene deletion, or another selected, non-essential gene or gene segment deletion, such as a NS1 or NS2 gene deletion is combined in a recombinant RSV with one or more mutations specifying an attenuated phenotype, e.g., a mutation adopted directly (or in modified form, e.g., by introducing multiple nucleotide changes in a codon specifying the mutation) from a biologically derived attenuated RSV mutant. For example, the SH gene or NS2 gene may be deleted in combination with one or more cp and/or ts mutations adopted from cpts248/404, cpts530/1009, cpts530/1030, or another selected mutant RSV strain, to yield a recombinant RSV having increased yield of virus, enhanced attenuation, and genetic resistance to reversion from an attenuated phenotype, due to the combined effects of the different mutations.

In addition, a variety of other genetic alterations can be produced in a recombinant RSV genome or antigenome for incorporation into infectious recombinant RSV, alone or together with one or more attenuating point mutations adopted from a biologically derived mutant RSV. Heterologous genes (e.g. from different RSV strains or subgroups or non-RSV sources) may be inserted in whole or in part, the order of genes changed, gene overlap removed, the RSV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

In exemplary embodiments, individual genes, gene segments, or single or multiple nucleotides of one RSV may be substituted by counterpart sequence(s) from a heterologous RSV or other source. For example, a selected, heterologous gene segment, such as one encoding a cytoplasmic tail, transmembrane domain or ectodomain, an epitopic site or region, a binding site or region, an active site or region containing an active site, etc., of a selected protein from one RSV, can be substituted for a counterpart gene segment in another RSV to yield novel recombinants, for example recombinants expressing a chimeric protein having a cytoplasmic tail and/or transmembrane domain of one RSV fused to an ectodomain of another RSV. In one embodiment, F and/or G protective antigens of one RSV strain or subgroup are substituted into an RSV clone of a different strain or subgroup to produce a recombinant virus capable of stimulating a cross-protective immune response against both strains or subgroups in an immunized host. In additional aspects, a chimeric RSV clone having a mutation involving alteration of a gene or gene segment, e.g., a substituted, heterologous F and/or G gene or gene segment, is further modified by introducing one or more attenuating ts or cp point mutations adopted from a biologically derived mutant RSV strain, e.g., cpts248/404, cpts530/1009, or cpts530/1030. In yet additional aspects, one or more human RSV coding or non-coding polynucleotides are substituted with a counterpart sequence from bovine or murine RSV, alone or in combination with one or more selected cp or ts mutations, to yield novel attenuated vaccine strains. In one embodiment, a chimeric bovine-human RSV incorporates a substitution of the human RSV NP gene or gene segment with a counterpart bovine NP gene or gene segment, which chimera can optionally be constructed to incorporate a SH gene deletion, one or more cp or ts point mutations, or various combinations of these and other mutations disclosed herein.

Alternatively, the polynucleotide molecule encoding the RSV genome or antigenome can be modified to encode non-RSV sequences, e.g., a cytokine, a T-helper epitope, a restriction site marker, or a protein of a microbial pathogen (e.g., virus, bacterium or fungus) capable of eliciting a protective immune response in the intended host.

In another aspect of the invention, novel methods are provided for introducing the aforementioned structural and phenotypic changes into a recombinant RSV to yield infectious, attenuated vaccine viruses. In one embodiment, an expression vector is provided which comprises an isolated polynucleotide molecule encoding a RSV genome or antigenome. Also provided is the same or different expression vector comprising one or more isolated polynucleotide molecules encoding N, P, L and RNA polymerase elongation factor proteins. The vector(s) is/are coexpressed in a cell or cell-free lysate, thereby producing an infectious RSV particle. The RSV genome or antigenome and the N, P, L and RNA polymerase elongation factor proteins can be coexpressed by the same or different expression vectors. In some instances the N, P, L and RNA polymerase elongation factor proteins are each encoded on different expression vectors. The polynucleotide molecule encoding the RSV genome or antigenome is from a human, bovine or murine RSV sequence, or can be a chimera of different RSV or non-RSV sequences, for example a polynucleotide containing sequences from a subgroup A RSV operably joined with sequences from a subgroupe B RSV, or containing RSV sequences operably joined with PIV sequences. The RSV genome or antigenome can be modified from a wild-type or biologically derived mutant RSV strain by insertion, rearrangement, deletion or substitution of one or more nucleotides, including point mutations, site-specific nucleotide changes, and changes involving entire genes or gene segments. These alterations typically specify a selected phenotypic change in the resulting recombinant RSV, such as a phenotypic change that results in attenuation, temperature-sensitivity, cold-adaptation, small plaque size, host range restriction, alteration in gene expression, or a change in an immunogenic epitope.

In other embodiments the invention provides a cell or cell-free lysate containing an expression vector which comprises an isolated polynucleotide molecule encoding a RSV genome or antigenome and an expression vector which comprises one or more isolated polynucleotide molecules that encodes N, P, L and RNA polymerase elongation factor proteins of RSV. Upon expression the genome or antigenome and N, P, L, and RNA polymerase elongation factor proteins combine to produce an infectious RSV particle, such as viral or subviral particle.

The attenuated RSV of the invention is capable of eliciting a protective immune response in an infected human host, yet is sufficiently attenuated so as to not cause unacceptable symptoms of severe respiratory disease in the immunized host. The attenuated virus may be present in a cell culture supernatant, isolated from the culture, or partially or completely purified. The virus may also be lyophilized, and can be combined with a variety of other components for storage or delivery to a host, as desired.

The invention further provides novel vaccines comprising a physiologically acceptable carrier and/or adjuvant and an isolated attenuated RSV strain. In one embodiment, the vaccine is comprised of infectious RSV having at least two and sometimes three or more attenuating mutations, at least one of which results in a temperature-sensitive substitution at amino acid $Phe_{521}$, $Gln_{831}$, $Met_{1169}$, or $Tyr_{1321}$ in the respiratory syncytial virus polymerase gene. In other embodiments, the vaccine comprises a recombinant, attenuated RSV. The vaccine can be formulated in a dose of $10^3$ to $10^6$ PFU of attenuated virus. The vaccine may comprise attenuated virus of either antigenic subgroup A or B, or virus of both subgroups A and B can be combined in vaccine formulations for more comprehensive coverage against prevalent RSV infections.

In other aspects the invention provides a method for stimulating the immune system of an individual for more comprehensive coverage against prevalent RSV or to induce protection against RSV. The method comprises administering a vaccine formulated in an immunologically sufficient amount of an attenuated respiratory syncytial virus of the invention. In one embodiment, the vaccine comprises infectious RSV having multiple attenuating mutations, at least one of which specifies a ts substitution at amino acid $Phe_{521}$, $Gln_{831}$, $Met_{1169}$, or $Tyr_{1321}$ in the L gene. In alternate embodiments, the vaccine comprises a recombinant, attenuated RSV. The virus will typically be administered with an acceptable carrier and/or adjuvant. The method may include administering attenuated virus of subgroup A and/or subgroup B to the individual, in an amount of $10^3$ to $10^6$ PFU to the upper respiratory tract by spray, droplet, aerosol, or the like. Generally the attenuated virus is administered intranasally to an individual seronegative for antibodies to said virus, or to an individual who possesses transplacentally acquired maternal anti-RSV antibodies.

BRIEF DESCRIPTION OF THE DRAWINGS

FIG. 2 shows the structures of the cDNA and the encoded antigenome RNA (not to scale). For the purposes of the present Figures, and in all subsequent Examples hereinbelow, the specific cDNAs and viruses used were of strain A2 of subgroup A RSV. The diagram of the antigenome includes the following features: the 5'-terminal nonviral G triplet contributed by the T7 promoter, the four sequence markers at positions 1099 (which adds one nt to the length), 1139, 5611, and 7559 (numbering referring to the first base of the new restriction site), the ribozyme and tandem T7 terminators, and the single nonviral 3'-phosphorylated U residue contributed to the 3' end by ribozyme cleavage (the site of cleavage is indicated with an arrow). Note that the nonviral 5'-GGG and 3'-U residues are not included in length values given here and thereafter for the antigenome. However, the nucleotide insertion at position 1099 is included, and thus the numbering for cDNA-derived antigenome is one nucleotide greater downstream of this position than for biologically derived antigenome. The 5' to 3' positive-sense sequence of D46 (the genome itself being negative-sense) is depicted in SEQ ID NO: 1, where the nucleotide at position four can be either C or G. Also note that the sequence positions assigned to restriction sites in this Figure and throughout are intended as a descriptive guide and do not alone define all of the nucleotides involved. The length values assigned to restriction fragments here and throughout also are descriptive, since length assignments may vary based on such factors as sticky ends left following digestion. Cloned cDNA segments representing in aggregate the complete antigenome are also shown. The box illustrates the removal of the BamHI site from the plasmid vector, a modification that facilitated assembly: the naturally occurring BamHI-SalI fragment (the BamHI site is shown in the top line in positive sense, underlined) was replaced with a PCR-generated BglII-SalI fragment (the BglII site is shown in the bottom line, underlined; its 4-nt sticky end, shown in italics, is compatible with that of BamHI). This resulted in a single nt change (middle line, underlined) which was silent at the amino acid level. FIG. 3 shows the sequence markers contained in the cDNA-encoded antigenome RNA, where sequences are positive sense and numbered relative to the first nt of the leader region complement as 1; identities between strains A2 and 18537, representing RSV subgroups A and B, respectively, are indicated with dots; sequences representing restriction sites in the cDNA are underlined; gene-start (GS) and gene-end (GE) transcription signals are boxed; the initiation codon of the N translational open reading frame at position 1141 is italicized, and the restriction sites are shown underneath each sequence. In the top sequence (SEQ ID NO: 22), a single C residue was inserted at position 1099 to create an AflII site in the NS2-N intergenic region, and the AG at positions 1139 and 1140 immediately upstream of the N translational open reading frame were replaced with CC to create a new NcoI site. In the middle sequence (SEQ ID NO: 23), substitution of G and U at positions 5612 and 5616, respectively, created a new StuI site in the G-F intergenic region. In the bottom sequence (SEQ ID NO: 24), a C replacement at position 7560 created a new SphI site in the F-M2 intergenic region.

FIG. 7 is a diagram (not to scale) of the parental wild type D46 plasmid encoding an RSV antigenome (top), and the D46/6368 derivative in which the SH gene has been deleted (bottom). The RSV genes are shown as open rectangles with the GS and GE transcription signals shown as filled boxes on the upstream and downstream ends, respectively. The T7 phage promoter (left) and hammerhead ribozyme and T7 terminators used to generate the 3' end of the RNA transcript (right) are shown as small open boxes. The ScaI and PacI fragment of D46 was replaced with a short synthetic fragment, resulting in D46/6368. The sequence (SEQ ID NOS: 27 and 28) flanking the SH gene in D46, and the sequence (SEQ ID NO: 29)of the engineered region in D46/6368, are each shown framed in a box over the respective plasmid map. The sequence of the ScaI-PacI fragment in D46, and its replacement in D46/6368, are shown in bold and demarcated with arrows facing upward. The M GE, SH GS, SH GE and G GS sites are indicated with overlining. The new M-G intergenic region in D46/6368 is labeled 65 in the diagram at the bottom to indicate its nucleotide length. The positive-sense T7 transcript of the SH-minus D46/6368 construct is illustrated at the bottom; the three 5'-terminal nonviral G residues contributed by the T7 promoter and the 3'-terminal U residue are shown (Collins, et al. 1995, *Proc. Natl. Acad. Sci. USA* 92:11563-11567, incorporated herein by reference). These nonviral nucleotides are not included in length measurements.

FIG. 16 shows a comparison of the transcription products and gene order of SH-minus virus compared to its wild type counterpart. The upper panel summarizes an analysis of the amounts of certain mRNAs produced by the SH-minus virus compared with the wild type parent recombinant virus. Intracellular mRNAs were isolated from cells infected with the SH-minus or wild type virus and analyzed by Northern blot hybridization with gene-specific probes. The amount of hybridized radioactivity was quantitated, and the relative abundance of each individual mRNA produced by the SH-minus virus versus its wild type parent is shown. The lower panel shows the gene order of the wild type virus from the M gene (position 5 in the gene order) to the L gene (position 10). This is compared to that of the SH-minus virus, in which the positions in the gene order of the G, F, M2 and L genes are altered due to deletion of the SH gene.

FIG. 18 depicts the introduction of tandem translation stop codons into the translational open reading frame (ORF) encoding the NS2 protein. Plasmid D13 contains the left end of the antigenome cDNA, including the T7 promoter (shaded box), the leader region, and the NS1, NS2, N, P, M and SH genes. Only the cDNA insert of D13 is shown. The AatII-AflII fragment containing the T7 promoter and NS1 and NS2 genes was subcloned into a pGem vector, and site-directed mutagenesis was used to modify the NS2 ORF in the region illustrated by the sequence. The wild type sequence (SEQ ID NO: 32) of codons 18 to 26 is shown (the encoded amino acids (SEQ ID NO: 33) are indicated below), and the three nucleotides above are the three substitutions which were made to introduce two termination codons (ter) and an XhoI site (underlined) as a marker. The resulting cDNA and subsequent recovered virus are referred to as NS2-knockout (KO).

FIG. 24 shows the results of a comparison of production of infectious virus by wild type RSV (D53) versus that of two isolates of recovered D53/M48I membrane G mutant virus.

DESCRIPTION OF THE SPECIFIC EMBODIMENTS

Figure 1:
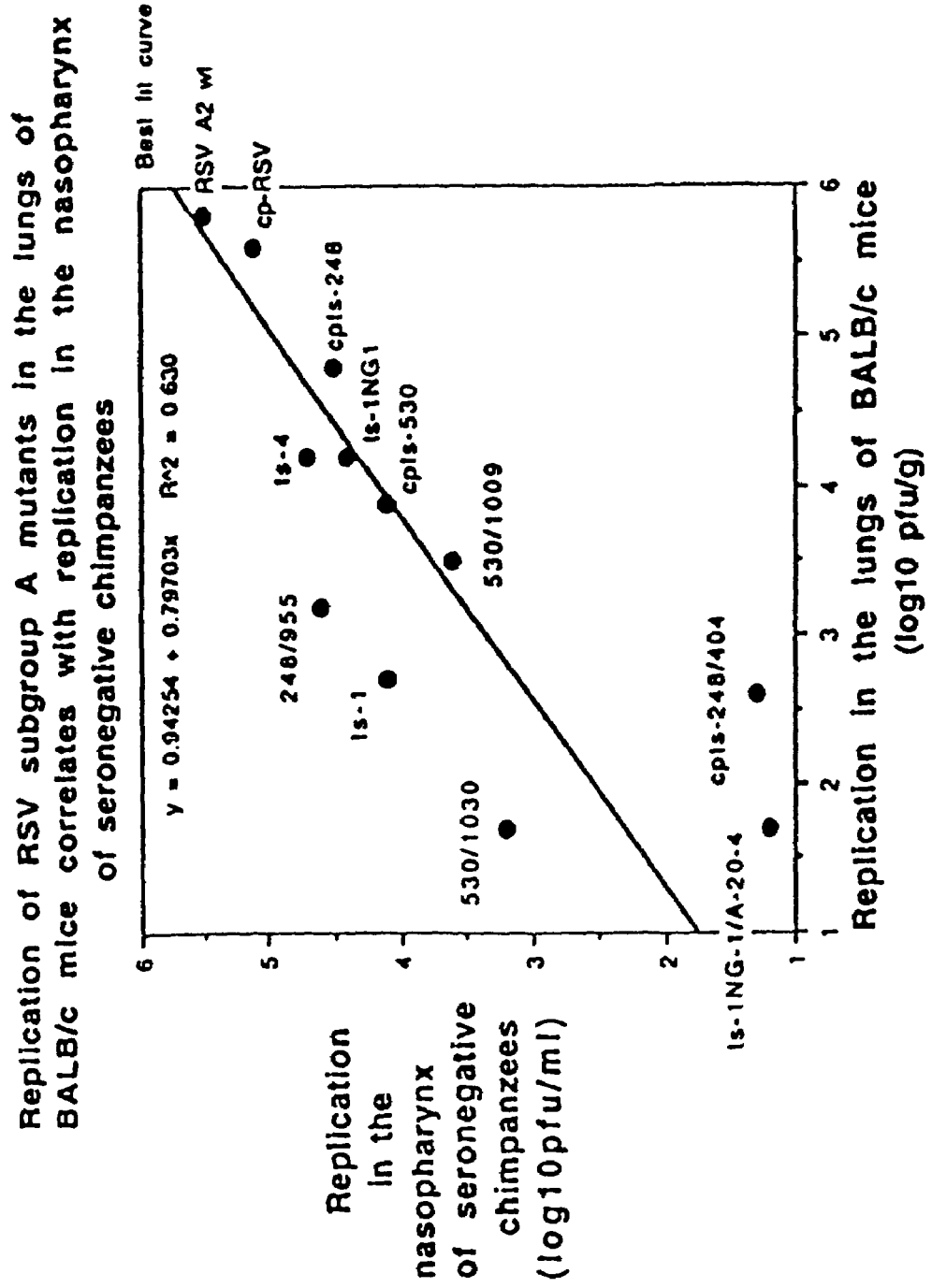
FIG. 1 is a graph demonstrating the substantially complete correlation between the replication of a series of subgroup A respiratory syncytial viruses in the lungs of mice with their replication in the chimpanzee.

The present invention provides biologically derived and recombinant RSV suitable for vaccine use in humans. Attenuated RSV described herein are produced by introducing and/or combining specific attenuating mutations into incompletely attenuated strains of RSV, such as a temperature sensitive (ts) or cold-passaged (cp) RS virus, or into wild-type virus, e.g. RSV strain A2. The mutations in biologically derived RSV may occur naturally or may be introduced into selected RSV strains by well known mutagenesis or similar procedures. For example, incompletely attenuated parental RSV strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) in cell culture, as generally described herein and in U.S. Ser. No. 08/327,263, incorporated herein by reference.

By "biologically derived RSV" is meant any RSV not produced by recombinant means. Thus, biologically derived RSV include naturally occurring RSV of all subgroups and strains, including, e.g., naturally occurring RSV having a wild-type genomic sequence and RSV having genomic variations from a reference wild-type RSV sequence, e.g., RSV having a mutation specifying an attenuated phenotype. Likewise, biologically derived RSV include RSV mutants derived from a parental RSV strain by, inter alia, artificial mutagenesis and selection procedures.

To produce a satisfactorily attenuated RS virus of the invention, mutations are preferably introduced into a parental viral strain which has been incompletely or partially attenuated, such as the ts-1 or ts-4 mutant, or cpRSV. For virus of subgroup A, the incompletely attenuated parental virus is preferably ts-1 or ts-1NG or cpRSV, which are widely known mutants of the A2 strain of subgroup A, or derivatives or subclones thereof. In other embodiments the specific mutations which are associated with attenuated phenotypes are identified and introduced into strains suitable for vaccine use. The strains into which the specific attenuating mutations are introduced can be wild-type virus or can be already partially attenuated, in which case the additional mutation(s) further attenuate the strain, e.g., to a desired level of restricted replication in a mammalian host while retaining sufficient immunogenicity to confer protection in vaccinees.

Partially attenuated mutants of the subgroup A or B virus can be produced by biologically cloning wild-type virus in an acceptable cell substrate and developing cold-passaged mutants thereof, subjecting the virus to chemical mutagenesis to produce ts mutants, or selecting small plaque or similar phenotypic mutants thereof (see, e.g., Murphy et al., International Publication WO 93/21310, incorporated herein by reference). For virus of subgroup B, an exemplary, partially attenuated parental virus is cp 52/2B5, which is a mutant of the B1 strain of subgroup B. The various selection techniques may be combined to produce partially attenuated mutants from non-attenuated subgroup A or B strains which are useful for further derivatization as described herein. Further, mutations specifying attenuated phenotypes may be introduced individually or in combination in incompletely attenuated subgroup A or B virus to produce vaccine virus having multiple, defined attenuating mutations that confer a desired level of attenuation and immunogenicity in vaccinees.

Once a desired, partially attenuated parental strain is selected, further attenuation sufficient to produce a vaccine acceptable for use in humans according to the present invention may be accomplished in several ways as described herein. For example, a cpRSV mutant can be further mutagenized in several ways. In one embodiment the procedure involves subjecting the partially attenuated virus to passage in cell culture at progressively lower, attenuating temperatures. For example, whereas wild-type virus is typically cultivated at about 34-37° C., the partially attenuated mutants are produced by passage in cell cultures (e.g., primary bovine kidney cells) at suboptimal temperatures, e.g., 20-26° C. Thus, in one method of the present invention the cp mutant or other partially attenuated strain, e.g., ts-1 or sp, is adapted to efficient growth at a lower temperature by passage in MRC-5 or Vero cells, down to a temperature of about 20-24° C., preferably 20-22° C. This selection of mutant RS virus during cold-passage substantially eliminates any residual virulence in the derivative strains as compared to the partially attenuated parent. Alternatively, specific mutations can be introduced into a recombinant version via mutagenesis or other methods to further mutagenize a cp mutant, e.g., mutations responsible for ts, sp or ca.

In one embodiment of the invention the incompletely attenuated RSV strains are subjected to chemical mutagenesis to introduce ts mutations or, in the case of viruses which are already ts, additional ts mutations sufficient to confer increased stability of the ts phenotype on the attenuated derivative. Means for the introduction of ts mutations into RS virus include replication of the virus in the presence of a mutagen such as 5-fluorouridine or 5-fluorouracil in a concentration of about $10^{-3}$ to $10^{-5}$ M, preferably about $10^{-4}$ M, exposure of virus to nitrosoguanidine at a concentration of about 100 μg/ml, according to the general procedure described in, e.g., Gharpure et al., J. Virol. 3:414-421 (1969) and Richardson et al., J. Med. Virol. 3:91-100 (1978), or genetic introduction of specific ts mutations. Other chemical mutagens can also be used. Attenuation can result from a ts mutation in almost any RS virus gene, and as identified herein ts mutations are typically associated with the polymerase (L) gene.

The level of temperature sensitivity of replication in exemplary attenuated RSV of the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of RSV correlate with the mutant's shutoff temperature. Replication of mutants with a shutoff temperature of 39° C. is moderately restricted, whereas mutants with a shutoff of 38° C. replicate less well and symptoms of illness are mainly restricted to the upper respiratory tract. A virus with a shutoff temperature of 35 to 37° C. will typically be fully attenuated in humans. Thus, the attenuated RSV of the invention which is ts will have a shutoff temperature in the range of about 35 to 39° C., and preferably from 35 to 38° C. The addition of a ts mutation to a partially attenuated strain produces multiply attenuated virus useful in the vaccine compositions of the present invention.

A number of attenuated RSV strains as candidate vaccines for intranasal administration have been developed using multiple rounds of chemical mutagenesis to introduce multiple mutations into a virus which had already been attenuated during cold-passage (e.g., Connors et al., *Virology* 208: 478-484 (1995); Crowe et al., *Vaccine* 12: 691-699 (1994); and Crowe et al., *Vaccine* 12: 783-790 (1994), incorporated herein by reference). Evaluation in rodents, chimpanzees, adults and infants indicate that certain of these candidate vaccine strains are relatively stable genetically, are highly immunogenic, and may be satisfactorily attenuated. Nucleotide sequence analysis of some of these attenuated viruses, as exemplified hereinbelow, indicates that each level of increased attenuation is associated with specific nucleotide and amino acid substitutions. The present invention provides the ability to distinguish between silent incidental mutations versus those responsible for phenotype differences by introducing the mutations, separately and in various combinations, into the genome or antigenome of infectious RSV clones. This process coupled with evaluation of phenotype characteristics of parental and derivative virus identifies mutations responsible for such desired characteristics as attenuation, temperature sensitivity, cold-adaptation, small plaque size, host range restriction, etc. Mutations thus identified are compiled into a "menu" and are then be introduced as desired, singly or in combination, to calibrate a vaccine virus to an appropriate level of attenuation, immunogenicity, genetic resistance to reversion from an attenuated phenotype, etc., as desired.

The specific mutations which have been introduced into RSV by serial random chemical mutagenesis to create further attenuated RSV having a ts phenotype are identified by sequence analysis and comparison to the parental background, e.g., a cpRSV background. In an exemplary embodiment, substitution within the polymerase (L) gene of nucleotide 10,989 (A changed to T, resulting in gln to leu amino acid substitution at amino acid residue 831) to create cptsRSV 248, or at nucleotide 10,060 (C changed to A, resulting in a phe to leu amino acid substitution at amino acid residue 521) yielded cptsRSV 530. These combined attenuating mutations specify a greater attenuation phenotype than determined for the parental cpRSV. cptsRSV 248 has a shutoff temperature of 38° C., it is attenuated, immunogenic, and fully protective against wild-type RSV challenge in seronegative chimpanzees, and it is more stable genetically during replication in vivo than previously evaluated RSV mutants. The attributes of genetic resistance to phenotypic reversion, and restriction of replication in vivo, also indicate that this exemplary strain is a desirable parental strain into which additional mutations are introduced.

In another exemplary embodiment, the cptsRSV 248 mutant was subjected to chemical mutagenesis, and a series of further attenuated mutants, e.g., having increased temperature sensitivity or small plaque phenotype characteristics over the parental strain, were produced. One such mutant, designated cptsRSV 248/404, is characterized by a reduced shutoff temperature of 36° C. which is the consequence of an additional mutation at nucleotide 7605 (T changed to C), with this being in a noncoding highly conserved gene start cis-acting regulatory sequence and not resulting in an amino acid change.

In another embodiment of the invention, RSV mutants are produced having two or more attenuating mutations. For example, the multiply attenuated virus cptsRSV 530, which has a shutoff temperature of 39° C., was subjected to chemical mutagenesis to introduce one or more additional mutations specifying an attenuating phenotype in a non-attenuated background. In one example, the clone cptsRSV 530/1009 was isolated and determined to have a shutoff temperature of 36° C. due to a single nucleotide substitution at 12,002 (A changed to G, resulting in a met to val amino acid substitution at amino acid residue 1169), also in the polymerase (L) gene.

The present invention also provides infectious RSV produced by recombinant methods, e.g., from cDNA. In one embodiment, infectious RSV is produced by the intracellular coexpression of a cDNA that encodes the RSV genome or antigenome RNA, together with those viral proteins necessary to generate a transcribing, replicating nucleocapsid, preferably one or more sequences that encode major nucleocapsid (N) protein, nucleocapsid phosphoprotein (P), large (L) polymerase protein, and a transcriptional elongation factor M2 ORF1 protein.

The ability to produce infectious RSV from cDNA permits the introduction of specific engineered changes, including site specific attenuating mutations and a broad spectrum of other recombinant changes, into the genome of a recombinant virus to produce safe, effective RSV vaccines.

The infectious, recombinant RSV of the invention are employed herein for identification of specific mutation(s) in biologically derived, attenuated RSV strains, for example mutations which specify ts, ca, att and other phenotypes. Accordingly, the invention permits incorporation of biologically derived mutations, along with a broad range of other desired changes, into recombinant RSV vaccine strains. For example, the capability of producing virus from cDNA allows for incorporation of mutations occurring in attenuated RSV vaccine candidates to be introduced, individually or in various selected combinations, into a full-length cDNA clone, and the phenotypes of rescued recombinant viruses containing the introduced mutations to be readily determined. In exemplary embodiments, amino acid changes identified in attenuated, biologically-derived viruses, for example in a cold-passaged RSV (cpRSV), or in a further attenuated strain derived therefrom, such as a temperature-sensitive derivative of cpRSV (cptsRSV), are incorporated within recombinant RSV clones. These changes from a wild-type or biologically derived mutant RSV sequence specify desired characteristics in the resultant clones, e.g., an attenuated or further attenuated phenotype compared to a wild-type or incompletely attenuated parental RSV phenotype.

By identifying and incorporating specific, biologically derived mutations associated with desired phenotypes, e.g., a cp or ts phenotype, into infectious RSV clones, the invention provides for other, site-specific modifications at, or within the region of, the identified mutation. Whereas most attenuating mutations produced in biologically derived RSV are single nucleotide changes, other site specific mutations can also be incorporated by recombinant techniques into biologically derived or recombinant RSV. As used herein, site-specific mutations include insertions, substitutions, deletions or rearrangements of from 1 to 3, up to about 5-15 or more altered nucleotides (e.g., altered from a wild-type RSV sequence, from a sequence of a selected mutant RSV strain, or from a parent recombinant RSV clone subjected to mutagenesis). Such site-specific mutations may be incorporated at, or within the region of, a selected, biologically derived point mutation. Alternatively, the mutations can be introduced in various other contexts within an RSV clone, for example at or near a cis-acting regulatory sequence or nucleotide sequence encoding a protein active site, binding site, immunogenic epitope, etc. Site-specific RSV mutants typically retain a desired attenuating phenotype, but may exhibit substantially altered phenotypic characteristics unrelated to attenuation, e.g., enhanced or broadened immunogenicity, or improved growth. Further examples of desired, site-specific mutants include recombinant RSV designed to incorporate additional, stabilizing nucleotide mutations in a codon specifying an attenuating point mutation. Where possible, two or more nucleotide substitutions are introduced at codons that specify attenuating amino acid changes in a parent mutant or recombinant RSV clone, yielding a biologically derived or recombinant RSV having genetic resistance to reversion from an attenuated phenotype. In other embodiments, site-specific nucleotide substitutions, additions, deletions or rearrangements are introduced upstream (N-terminal direction) or downstream (C-terminal direction), e.g, from 1 to 3, 5-10 and up to 15 nucleotides or more 5' or 3', relative to a targeted nucleotide position, e.g., to construct or ablate an existing cis-acting regulatory element.

In addition to single and multiple point mutations and site-specific mutations, changes to recombinant RSV disclosed herein include deletions, insertions, substitutions or rearrangements of whole genes or gene segments. These mutations affect small numbers of bases (e.g., from 15-30 bases, up to 35-50 bases or more), or large blocks of nucleotides (e.g., 50-100, 100-300, 300-500, 500-1,000 bases) depending upon the nature of the change (i.e., a small number of bases may be changed to insert or ablate an immunogenic epitope or change a small gene segment, whereas large block(s) of bases are involved when genes or large gene segments are added, substituted, deleted or rearranged.

In additional aspects, the invention provides for supplementation of mutations adopted from biologically derived RSV, e.g., cp and ts mutations which occur mainly in the L gene, with additional types of mutations involving the same or different genes in a recombinant RSV clone. RSV encodes ten mRNAs and ten or eleven proteins. Three of these are transmembrane surface proteins, namely the attachment G protein, fusion F protein involved in penetration, and small hydrophobic SH protein. G and F are the major viral neutralization and protective antigens. Four additional proteins are associated with the viral nucleocapsid, namely the RNA binding protein N, the phosphoprotein P, the large polymerase protein L, and the transcription elongation factor M2 ORF1. The matrix M protein is part of the inner virion and probably mediates association between the nucleocapsid and the envelope. Finally, there are two nonstructural proteins, NS1 and NS2, of unknown function. These proteins can be selectively altered in terms of its expression level, or can be added deleted, substituted or rearranged, in whole or in part, alone or in combination with other desired modifications, in a recombinant RSV to obtain novel infectious RSV clones.

Thus, in addition to, or in combination with, attenuating mutations adopted from biologically derived RSV mutants, the present invention also provides entirely new methods of attenuation based on recombinant engineering of infectious RSV clones. In accordance with this aspect of the invention, a variety of alterations can now be produced in an isolated polynucleotide sequence encoding the RSV genome or antigenome for incorporation into infectious recombinant RSV. More specifically, to achieve desired structural and phenotypic changes in recombinant RSV, the invention allows for introduction of modifications which delete, substitute, introduce, or rearrange a selected nucleotide or plurality of nucleotides from a parent RSV sequence, as well as mutations which delete, substitute, introduce or rearrange whole gene(s) or gene segment(s), within an infectious RSV clone.

Desired modifications of infectious recombinant RSV are typically selected to specify a desired phenotypic change, e.g., a change in viral growth, temperature sensitivity, ability to elicit a host immune response, attenuation, etc. These changes can be brought about by, e.g., mutagenesis of a parent RSV clone to ablate, introduce or rearrange a specific gene(s) or gene region(s) (e.g., a gene segment that encodes a protein structural domain, such as a cytoplasmic, transmembrane or extracellular domain, an immunogenic epitope, binding region, active site, etc.). Genes of interest in this regard include all of the genes of the RSV genome: 3'-NS1-NS2-N-P-M-SH-G-F-M2-L-5', as well as heterologous genes from other RSV, other viruses and a variety of other non-RSV sources as indicated herein. Also provided are modifications which simply alter or ablate expression of a selected gene, e.g., by introducing a termination codon within a selected RSV coding sequence; changing the position of an RSV gene relative to an operably linked promoter; introducing an upstream start codon to alter rates of expression; modifying (e.g., by changing position, altering an existing sequence, or substituting an existing sequence with a heterologous sequence) GS and/or GE transcription signals to alter phenotype (e.g., growth, temperature restrictions on transcription, etc.); and various other deletions, substitutions, additions and rearrangements that specify quantitative or qualitative changes in viral replication, transcription of selected gene(s), or translation of selected protein(s).

As described herein, cDNA-based methods are used to construct a series of recombinant viruses offering improved characteristics of attenuation and immunogenicity for use as vaccine agents. Among desired phenotypic changes in this context are resistance to reversion from an attenuated phenotype, improvements in attenuation in culture or in a selected host environment, immunogenic characteristics (e.g., as determined by enhancement, or diminution, of an elicited immune response), upregulation or downregulation of transcription and/or translation of selected viral products, etc. Foreign genes may be inserted in whole or in part, the order of genes changed, gene overlap removed, the RSV genome promoter replaced with its antigenome counterpart, portions of genes (e.g., the cytoplasmic tails of glycoprotein genes) added (e.g., to duplicate an existing sequence or incorporate a heterologous sequence), removed or substituted, and even entire genes deleted.

In one aspect of the invention, a selected gene segment, such as one encoding a selected protein or protein region (e.g., a cytoplasmic tail, transmembrane domain or ectodomain, an epitopic site or region, a binding site or region, an active site or region containing an active site, etc.) from one RSV, can be substituted for a counterpart gene segment from the same or different RSV or other source, to yield novel recombinants having desired phenotypic changes compared to wild-type or parent RSV strains. For example, recombinants of this type may express a chimeric protein having a cytoplasmic tail and/or transmembrane domain of one RSV fused to an ectodomain of another RSV. Other exemplary recombinants of this type express duplicate protein regions, such as duplicate immunogenic regions. As used herein, "counterpart" genes, gene segments, proteins or protein regions, are typically from heterologous sources (e.g., from different RSV genes, or representing the same (i.e., homologous or allelic) gene or gene segment in different RSV strains). Typical counterparts selected in this context share gross structural features, e.g., each counterpart may encode a comparable structural "domain," such as a cytoplasmic domain, transmembrane domain, ectodomain, binding site or region, epitopic site or region, etc. Counterpart domains and their encoding gene segments embrace an assemblage of species having a range of size and amino acid (or nucleotide) sequence variations, which range is defined by a common biological activity among the domain or gene segment variants. For example, two selected protein domains encoded by counterpart gene segments within the invention may share substantially the same qualitative activity, such as providing a membrane spanning function, a specific binding activity, an immunological recognition site, etc. More typically, a specific biological activity shared between counterparts, e.g., between selected protein segments or proteins, will be substantially similar in quantitative terms, i.e., they will not vary in respective quantitative activity profiles by more than 30%, preferably by no more than 20%, more preferably by no more than 5-10%.

Counterpart genes and gene segments, as well as other polynucleotides involved in producing recombinant RSV within the invention, preferably share substantial sequence identity with a selected polynucleotide reference sequence, e.g., with another selected counterpart sequence. As used herein, a "reference sequence" is a defined sequence used as a basis for a sequence comparison, for example, a segment of a full-length cDNA or gene, or a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988) (each of which is incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

In addition to these polynucleotide sequence relationships, proteins and protein regions encoded by recombinant RSV of the invention are also typically selected to have conservative relationships, i.e., to have substantial sequence identity or sequence similarity, with selected reference polypeptides. As applied to polypeptides, the term "sequence identity" means peptides share identical amino acids at corresponding positions. The term "sequence similarity" means peptides have identical or similar amino acids (i.e., conservative substitutions) at corresponding positions. The term "substantial sequence identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). The term "substantial similarity" means that two peptide sequences share corresponding percentages of sequence similarity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Stereoisomers (e.g., D-amino acids) of the twenty conventional amino acids, unnatural amino acids such as $\alpha,\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\omega$-N-methylarginine, and other similar amino acids and imino acids (e.g., 4-hydroxyproline). Moreover, amino acids may be modified by glycosylation, phosphorylation and the like.

In alternative aspects of the invention, the infectious RSV produced from a cDNA-expressed genome or antigenome can be any of the RSV or RSV-like strains, e.g., human, bovine, murine, etc., or of any pneumovirus, e.g., pneumonia virus of mice or turkey rhinotracheitis virus. To engender a protective immune response, the RSV strain may be one which is endogenous to the subject being immunized, such as human RSV being used to immunize humans. The genome or antigenome of endogenous RSV can be modified, however, to express RSV genes or gene segments from a combination of different sources, e.g., a combination of genes or gene segments from different RSV species, subgroups, or strains, or from an RSV and another respiratory pathogen such as PIV (see, e.g., Hoffman et al., *J. Virol.* 71:4272-4277 (1997); Durbin et al., Virology (1997) (In Press); Murphy et al., U.S. Patent Application Ser. No. 60/047,575 entitled PRODUCTION OF INFECTIOUS PARAINFLUENZA VIRUS FROM CLONED NUCLEOTIDE SEQUENCES, filed May 23, 1997, incorporated herein by reference, and the following plasmids for producing infectious PIV clones: p3/7(131) (ATCC 97990); p3/7(131)2G (ATCC 97889); and p218(131) (ATCC 97991); each deposited Apr. 18, 1997 under the terms of the Budapest Treaty with the American Type Culture Collection (ATCC) of 10801 University Blvd., Manassas, Va. 20110-2209, USA., and granted the above identified accession numbers.

In certain embodiments of the invention, recombinant RSV are provided wherein individual internal genes of a human RSV are replaced with, e.g., a bovine murine or other RSV counterpart, or with a counterpart or foreign gene from another respiratory pathogen such as PIV. Substitutions, deletions, etc. of RSV genes or gene segments in this context can include part or all of one or more of the NS1, NS2, N, P, M, SH, M2(ORF1), M2(ORF2) and L genes, or non-immunogenic parts of the G and F genes. Also, human RSV cis-acting sequences, such as promoter or transcription signals, can be replaced with, e.g., their bovine RSV counterpart. Reciprocally, means are provided to generate live attenuated bovine RSV by inserting human attenuating genes or cis-acting sequences into a bovine RSV genome or antigenome background.

Recombinant RSV bearing heterologous genes or cis-acting elements are selected for host range restriction and other desired phenotypes favorable for vaccine use. In exemplary embodiments, bovine RSV sequences are selected for introduction into human RSV based on available descriptions of bovine RSV structure and function, as provided in, e.g., Pastey et al., *J. Gen. Viol.* 76:193-197 (1993); Pastey et al., *Virus Res.* 29:195-202 (1993); Zamora et al., *J. Gen. Virol.* 73:737-741 (1992); Mallipeddi et al., *J. Gen. Virol.* 74:2001-2004 (1993); Mallipeddi et al., *J. Gen. Virol.* 73:2441-2444 (1992); and Zamora et al., *Virus Res.* 24:115-121 (1992), each of which is incorporated herein by reference, and in accordance with the methods and compositions disclosed herein. In other embodiments, mutations of interest for introduction within recombinant RSV are modeled after a tissue culture-adapted nonpathogenic strain of pneumonia virus of mice (the murine counterpart of human RSV) which lacks a cytoplasmic tail of the G protein (Randhawa et al., *Virology* 207: 240-245 (1995)). Accordingly, in one aspect of the invention the cytoplasmic and/or transmembrane domains of one or more of the human RSV glycoproteins, F, G and SH, are added, deleted, modified, or substituted with a heterologous, counterpart sequence (e.g., a sequence from a cytoplasmic, or transmembrane domain of a F, G, or SH protein of bovine RSV or murine pneumonia virus) to achieve a desired attenuation. As another example, a nucleotide sequence at or near the cleavage site of the F protein, or the putative attachment domain of the G protein, can be modified by point mutations, site-specific changes, or by alterations involving entire genes or gene segments to achieve novel effects on viral growth in tissue culture and/or infection and pathogenesis in experimental animals.

Thus, infectious recombinant RSV intended for administration to humans can be a human RSV that has been modified to contain genes from, e.g., a bovine or murine RSV or a PIV, such as for the purpose of attenuation. For example, by inserting a gene or gene segment from PIV, a bivalent vaccine to both PIV and RSV is provided. Alternatively, a heterologous RSV species, subgroup or strain, or a distinct respiratory pathogen such as PIV, may be modified, e.g., to contain genes that encode epitopes or proteins which elicit protection against human RSV infection. For example, the human RSV glycoprotein genes can be substituted for the bovine glycoprotein genes such that the resulting bovine RSV, which now bears the human RSV surface glycoproteins and would retain a restricted ability to replicate in a human host due to the remaining bovine genetic background, elicits a protective immune response in humans against human RSV strains.

The ability to analyze and incorporate other types of attenuating mutations into infectious RSV for vaccine development extends to a broad assemblage of targeted changes in RSV clones. For example, deletion of the SH gene yields a recombinant RSV having novel phenotypic characteristics, including enhanced growth. In the present invention, an SH gene deletion (or any other selected, non-essential gene or gene segment deletion), is combined in a recombinant RSV with one or more additional mutations specifying an attenuated phenotype, e.g., a point mutation adopted from a biologically derived attenuated RSV mutant. In exemplary embodiments, the SH gene or NS2 gene is deleted in combination with one or more cp and/or ts mutations adopted from cpts248/404, cpts530/1009, cpts530/1030, or another selected mutant RSV strain, to yield a recombinant RSV having increased yield of virus, enhanced attenuation, and genetic to phenotypic reversion, due to the combined effects of the different mutations. In this regard, any RSV gene which is not essential for growth, for example the SH, NP, NS1 and NS2 genes, can be ablated or otherwise modified to yield desired effects on virulence, pathogenesis, immunogenicity and other phenotypic characters. For example, ablation by deletion of a non-essential gene such as SH results in enhanced viral growth in culture. Without wishing to be bound by theory, this effect is likely due in part to a reduced nucleotide length of the viral genome. In the case of one exemplary SH-minus clone, the modified viral genome is 14,825 nt long, 398 nucleotides less than wild type. By engineering similar mutations that decrease genome size, e.g., in other coding or noncoding regions elsewhere in the RSV genome, such as in the P, M, F and M2 genes, the invention provides several readily obtainable methods and materials for improving RSV growth.

In addition, a variety of other genetic alterations can be produced in a recombinant RSV genome or antigenome for incorporation into infectious recombinant RSV, alone or together with one or more attenuating point mutations adopted from a biologically derived mutant RSV. Heterologous genes (e.g. from different RSV strains or types or non-RSV sources) may be inserted in whole or in part, the order of genes changed, gene overlap removed, the RSV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

In exemplary embodiments, individual genes, gene segments, or single or multiple nucleotides of one RSV may be substituted by counterpart sequence(s) from a heterologous RSV or other source. For example, a selected, heterologous gene segment, such as one encoding a cytoplasmic tail, transmembrane domain or ectodomain, an epitopic site or region, a binding site or region, an active site or region containing an active site, etc., of a selected protein from one RSV, can be substituted for a counterpart gene segment in another RSV to yield novel recombinants, for example recombinants expressing a chimeric protein having a cytoplasmic tail and/or transmembrane domain of one RSV fused to an ectodomain of another RSV. Useful genome segments in this regard range from about 15-35 nucleotides in the case of gene segments encoding small functional domains of proteins, e.g., epitopic sites, to about 50, 75, 100, 200-500, and 500-1,500 or more nucleotides for gene segments encoding larger domains or protein regions. In one embodiment, F and/or G protective antigens of one RSV strain or subgroup are substituted into an RSV clone of a different strain or subgroup to produce a recombinant virus capable of stimulating a cross-protective immune response against both strains or subgroups in an immunized host. In additional aspects, a chimeric RSV clone having a mutation involving alteration of a gene or gene segment, e.g., a substituted, heterologous F and/or G gene or gene segment, is further modified by introducing one or more attenuating ts or cp point mutations adopted from a biologically derived mutant RSV strain, e.g., cpts248/404, cpts530/1009, or cpts530/1030.

In yet additional aspects, one or more human RSV coding or non-coding polynucleotides are substituted with a counterpart sequence from bovine or murine RSV, alone or in combination with one or more selected cp or ts mutations, to yield novel attenuated vaccine strains. In one embodiment, a chimeric bovine-human RSV incorporates a substitution of the human RSV NP gene or gene segment with a counterpart bovine NP gene or gene segment, which chimera can optionally be constructed to incorporate a SH, NP, NS1, NS2 or other gene deletion, one or more cp or ts point mutations, or various combinations of these and other mutations disclosed herein. The replacement of a human RSV coding sequence (e.g., of NS1, NS2, NP, etc.) or non-coding sequence (e.g., a promoter, gene-end, gene-start, intergenic or other cis-acting element) with a counterpart bovine or murine RSV sequence yields attenuated recombinants having a variety of possible attenuating effects. For example, a host range effect may arise from a heterologous RSV gene not functioning efficiently in a human cell, from incompatibility of the heterologous sequence or protein with a biologically interactive human RSV sequence or protein (e.g., a sequence or protein that ordinarily cooperates with the substituted sequence or protein for viral transcription, translation, assembly, etc.), among other useful attenuating effects.

In yet another aspect of the invention, insertion of foreign genes or gene segments, and in some cases of noncoding nucleotide sequences, into the RSV genome results in a desired increase in genome length causing yet additional, desired phenotypic effects. Increased genome length results in attenuation of the resultant RSV, dependent in part upon the length of the insert. In addition, the expression of certain proteins from a gene inserted into recombinant RSV will result in attenuation of the virus due to the action of the protein. This has been described for IL-2 expressed in vaccinia virus (e.g. Flexner et al., *Nature* 33:-259-62 (1987)) and also would be expected for gamma interferon.

Deletions, insertions, substitutions and other mutations involving changes of whole viral genes or gene segments in recombinant RSV of the invention yield highly stable vaccine candidates, which are particularly important in the case of immunosuppressed individuals. Many of these mutations will result in attenuation of resultant vaccine strains, whereas others will specify different types of desired phenotypic changes. For example, certain viral genes are known which encode proteins that specifically interfere with host immunity (see, e.g., Kato et al., *EMBO. J.* 16:578-87 (1997), incorporated herein by reference). Ablation of such genes in vaccine viruses is expected to reduce virulence and pathogenesis and/or improve immunogenicity.

Also provided within the invention are genetic modifications in a recombinant RSV which alter or ablate the expression of a selected gene or gene segment without removing the gene or gene segment from the RSV clone, e.g., by introducing a termination codon within a selected coding sequence; changing the position of a gene or introducing an upstream start codon to alter its rate of expression; changing GS and/or GE transcription signals to alter phenotype (e.g., growth, temperature restrictions on transcription, etc.) Preferred mutations in this context include mutations directed toward cis-acting signals, which can be identified, e.g., by mutational analysis of RSV minigenomes. For example, insertional and deletional analysis of the leader and trailer and flanking sequences identified viral promoters and transcription signals and provided a series of mutations associated with varying degrees of reduction of RNA replication or transcription. Saturation mutagenesis (whereby each position in turn is modified to each of the nucleotide alternatives) of these cis-acting signals also has identified many mutations which reduced (or in one case increased) RNA replication or transcription. Any of these mutations can be inserted into the complete antigenome or genome as described herein. Evaluation and manipulation of trans-acting proteins and cis-acting RNA sequences using the complete antigenome cDNA is assisted by the use of RSV minigenomes (see, e.g., Grosfeld et al., *J. Virol.* 69: 5677-5686 (1995), incorporated herein by reference), whose helper-dependent status is useful in the characterization of those mutants which are too inhibitory to be recovered in replication-independent infectious virus.

Other mutations within RSV of the present invention involve replacement of the 3' end of genome with its counterpart from antigenome, which is associated with changes in RNA replication and transcription. In addition, the intergenic regions (Collins et al., *Proc. Natl. Acad. Sci. USA* 83:4594-4598 (1986), incorporated herein by reference) can be shortened or lengthened or changed in sequence content, and the naturally-occurring gene overlap (Collins et al., *Proc. Natl. Acad. Sci. USA* 84:5134-5138 (1987), incorporated herein by reference) can be removed or changed to a different intergenic region by the methods described herein.

In one exemplary embodiment, the level of expression of specific RSV proteins, such as the protective F and G antigens, can be increased by substituting the natural sequences with ones which have been made synthetically and designed to be consistent with efficient translation. In this context, it has been shown that codon usage can be a major factor in the level of translation of mammalian viral proteins (Haas et al., *Current Biol.* 6:315-324 (1996)). Examination of the codon usage of the mRNAs encoding the F and G proteins of RSV, which are the major protective antigens, shows that the usage is consistent with poor expression. Thus, codon usage can be improved by the recombinant methods of the invention to achieve improved expression for selected genes.

In another exemplary embodiment, a sequence surrounding a translational start site (preferably including a nucleotide in the −3 position) of a selected RSV gene is modified, alone or in combination with introduction of an upstream start codon, to modulate RSV gene expression by specifying up- or down-regulation of translation.

Alternatively, or in combination with other RSV modifications disclosed herein, RSV gene expression can be modulated by altering a transcriptional GS signal of a selected gene(s) of the virus. In one exemplary embodiment, the GS signal of NS2 is modified to include a defined mutation (e.g., the 404(M2) mutation described hereinbelow) to superimpose a ts restriction on viral replication.

Yet additional RSV clones within the invention incorporate modifications to a transcriptional GE signal. For example, RSV clones are provided which substitute or mutate the GE signal of the NS1 and NS2 genes for that of the N gene, resulting in decreased levels of readthrough mRNAs and increased expression of proteins from downstream genes. The resulting recombinant virus exhibits increased growth kinetics and increased plaque size, providing but one example of alteration of RSV growth properties by modification of a cis-acting regulatory element in the RSV genome.

In another exemplary embodiment, expression of the G protein is increased by modification of the G mRNA. The G protein is expressed as both a membrane bound and a secreted form, the latter form being expressed by translational initiation at a start site within the G translational open reading frame. The secreted form can account for as much as one-half of the expressed G protein. Ablation of the internal start site (e.g., by sequence alteration, deletion, etc.), alone or together with altering the sequence context of the upstream start site yields desired changes in G protein expression. Ablation of the secreted form of G also will improve the quality of the host immune response to exemplary, recombinant RSV, because the soluble form of G is thought to act as a "decoy" to trap neutralizing antibodies. Also, soluble G protein has been implicated in enhanced immunopathology due to its preferential stimulation of a Th2-biased response.

In alternative embodiments, levels of RSV gene expression are modified at the level of transcription. In one aspect, the position of a selected gene in the RSV gene map can be changed to a more promoter-proximal or promotor-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild-type levels. In one example, the NS2 gene (second in order in the RSV gene map) is substituted in position for the SH gene (sixth in order), yielding a predicted decrease in expression of NS2. Increased expression of selected RSV genes due to positional changes can be achieved up to 10-fold, 30-fold, 50-fold, 100-fold or more, often attended by a commensurate decrease in expression levels for reciprocally, positionally substituted genes.

In other exemplary embodiments, the F and G genes are transpositioned singly or together to a more promoter-proximal or promoter-distal site within the (recombinant) RSV gene map to achieve higher or lower levels of gene expression, respectively. These and other transpositioning changes yield novel RSV clones having attenuated phenotypes, for example due to decreased expression of selected viral proteins involved in RNA replication.

In more detailed aspects of the invention, a recombinant RSV is provided in which expression of a viral gene, for example the NS2 gene, is ablated at the translational level without deletion of the gene or of a segment thereof, by, e.g., introducing two tandem translational termination codons into a translational open reading frame (ORF). This yields viable virus in which a selected gene has been silenced at the level of translation, without deleting its gene. These forms of "knockout" virus exhibit reduced growth rates and small plaque sizes in tissue culture. Thus, the methods and compositions of the invention provide yet additional, novel types of RSV attenuating mutations which ablate expression of a viral gene that is not one of the major viral protective antigens. In this context "knockout" virus phenotypes produced without deletion of a gene or gene segment can be alternatively produced by deletion mutagenesis, as described herein, to effectively preclude correcting mutations that may restore synthesis of a target protein. Several other gene "knock-outs" for RSV can be made using alternate designs. For example, insertion of translation termination codons into ORFs, or disruption of the RNA editing sites, offer alternatives to silencing or attenuating the expression of selected genes. Methods for producing these and other knock-outs are well known in the art (as described, for example, in Kretzschmar et al., *Virology* 216: 309-316 (1996); Radecke et al., *Virology* 217:418-412 (1996); and Kato et al., *EMBO J.* 16:178-587 (1987); and Schneider et al., *Virology* 277:314-322 (1996), each incorporated herein by reference).

In yet other embodiments, RSV useful in a vaccine formulation can be conveniently modified to accommodate antigenic drift in circulating virus. Typically the modification will be in the G and/or F proteins. The entire G or F gene, or the segments encoding particular immunogenic regions thereof, is incorporated into the RSV genome or antigenome cDNA by replacement of the corresponding region in the infectious clone or by adding one or more copies of the gene such that several antigenic forms are represented. Progeny virus produced from the modified RSV cDNA are then used in vaccination protocols against the emerging strains. Further, inclusion of the G protein gene of RSV subgroup B as a gene addition will broaden the response to cover a wider spectrum of the relatively diverse subgroup A and B strains present in the human population.

An infectious RSV clone of the invention can also be engineered according to the methods and compositions disclosed herein to enhance its immunogenicity and induce a level of protection greater than that provided by infection with a wild-type RSV or an incompletely attenuated parental virus or clone. For example, an immunogenic epitope from a heterologous RSV strain or type, or from a non-RSV source such as PIV, can be added by appropriate nucleotide changes in the polynucleotide sequence encoding the RSV genome or antigenome. Alternatively, recombinant RSV can be engineered to identify and ablate (e.g., by amino acid insertion, substitution or deletion) epitopes associated with undesirable immunopathologic reactions. In other embodiments, an additional gene is inserted into or proximate to the RSV genome or antigenome which is under the control of an independent set of transcription signals. Genes of interest include those encoding cytokines (e.g., IL-2 through IL-15, especially IL-2, IL-6 and IL-12, etc.), gamma-interferon, and include those encoding cytokines (e.g., IL-2 through IL-15, especially IL-2, IL-6 and IL-12, etc.), gamma-interferon, and proteins rich in T helper cell epitopes. The additional protein can be expressed either as a separate protein or as a chimera engineered from a second copy of one of the RSV proteins, such as SH. This provides the ability to modify and improve the immune response against RSV both quantitatively and qualitatively.

In another aspect of the invention the recombinant RSV can be employed as a vector for protective antigens of other respiratory tract pathogens, such as parainfluenza virus (PIV), e.g., by incorporating sequences encoding those protective antigens from PIV into the RSV genome or antigenome used to produce infectious vaccine virus, as described herein. The cloning of PIV cDNA and other disclosure is described in United States Provisional Patent Application entitled PRODUCTION OF PARAINFLUENZA VIRUS FROM CLONED NUCLEOTIDE SEQUENCES, filed May 23, 1997, Ser. No. 60/047,575 and incorporated herein by reference. In alternate embodiments, a modified RSV is provided which comprises a chimera of a RSV genomic or antigenomic sequence and at least one PIV sequence, for example a polynucleotide containing sequences from both RSV and PIV1, PIV2, PIV3 or bovine PIV. For example, individual genes of RSV may be replaced with counterpart genes from human PIV, such as the HN and/or F glycoprotein genes of PIV1, PIV2, or PIV3. Alternatively, a selected, heterologous gene segment, such as a cytoplasmic tail, transmembrane domain or ectodomain of HN or F of HPIV1, HPIV2, or HPIV3 can be substituted for a counterpart gene segment in, e.g., the same gene in an RSV clone, within a different gene in the RSV clone, or into a non-coding sequence of the RSV genome or antigenome. In one embodiment, a gene segment from HN or F of HPIV3 is substituted for a counterpart gene segment in RSV type A, to yield constructs encoding chimeric proteins, e.g. fusion proteins having a cytoplasmic tail and/or transmembrane domain of RSV fused to an ectodomain of RSV to yield a novel attenuated virus, and/or a multivalent vaccine immunogenic against both PIV and RSV.

In addition to the above described modifications to recombinant RSV, different or additional modifications in RSV clones can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

Introduction of the foregoing, defined mutations into an infectious RSV clone can be achieved by a variety of well known methods. By "infectious clone" is meant cDNA or its product, synthetic or otherwise, which can be transcribed into genomic or antigenomic RNA capable of serving as template to produce the genome of an infectious virus or subviral particle. Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA as described herein has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. This can be through the intermediate of a single-stranded phagemid form, such as using the Muta-gene® kit of Bio-Rad Laboratories (Richmond, Calif.) or a method using the double-stranded plasmid directly as template such as the Chameleon mutagenesis kit of Stratagene (La Jolla, Calif.) or by the polymerase chain reaction employing either an oligonucleotide primer or template which contains the mutation(s) of interest. A mutated subfragment can then be assembled into the complete antigenome or genome cDNA. A variety of other mutagenesis techniques are known and available for use in producing the mutations of interest in the RSV antigenome or genome cDNA. Mutations can vary from single nucleotide changes to replacement of large cDNA pieces containing one or more genes or genome regions.

Thus, in one illustrative embodiment mutations are introduced by using the Muta-gene phagemid in vitro mutagenesis kit available from Bio-Rad. In brief, cDNA encoding a portion of an RSV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome fragment is then amplified and the mutated piece is then reintroduced into the full-length genome or antigenome clone.

The ability to introduce defined mutations into infectious RSV has many applications, including the analyses of RSV molecular biology and pathogenesis. For example, the functions of the RSV proteins, including the NS1, NS2, SH, M2(ORF1) and M2(ORF2) proteins, can be investigated and manipulated by introducing mutations which ablate or reduce their level of expression, or which yield mutant protein. In one exemplary embodiment hereinbelow, RSV virus was constructed in which expression of a viral gene, namely the SH gene, was ablated by deletion of the mRNA coding sequence and flanking transcription signals. Surprisingly, not only could this virus be recovered, but it grew efficiently in tissue culture. In fact, its growth was substantially increased over that of the wild type, based on both yield of infectious virus and on plaque size. This improved growth in tissue culture from the SH deletion and other RSV derivatives of the invention provides useful tools for developing RSV vaccines, which overcome the problem of RSV's poor yield in tissue culture that had complicated production of vaccine virus in other systems. These deletions are highly stable against genetic reversion, rendering the RSV clones derived therefrom particularly useful as vaccine agents.

The invention also provides methods for producing an infectious RSV from one or more isolated polynucleotides, e.g., one or more cDNAs. According to the present invention cDNA encoding a RSV genome or antigenome is constructed for intracellular or in vitro coexpression with the necessary viral proteins to form infectious RSV. By "RSV antigenome" is meant an isolated positive-sense polynucleotide molecule which serves as the template for the synthesis of progeny RSV genome. Preferably a cDNA is constructed which is a positive-sense version of the RSV genome, corresponding to the replicative intermediate RNA, or antigenome, so as to minimize the possibility of hybridizing with positive-sense transcripts of the complementing sequences that encode proteins necessary to generate a transcribing, replicating nucleocapsid, i.e., sequences that encode N, P, L and M2(ORF1) protein. In an RSV minigenome system, genome and antigenome were equally active in rescue, whether complemented by RSV or by plasmids, indicating that either genome or antigenome can be used and thus the choice can be made on methodologic or other grounds.

A native RSV genome typically comprises a negative-sense polynucleotide molecule which, through complementary viral mRNAs, encodes eleven species of viral proteins, i.e., the nonstructural species NS1 and NS2, N, P, matrix (M), small hydrophobic (SH), glycoprotein (G), fusion (F), M2(ORF1), M2(ORF2), and L, substantially as described in Mink et al., Virology 185: 615-624 (1991), Stec et al., Virology 183: 273-287 (1991), and Connors et al., Virol. 208:478-484 (1995), incorporated herein by reference. For purposes of the present invention the genome or antigenome of the recombinant RSV of the invention need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule.

By recombinant RSV is meant a RSV or RSV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in RSV gene expression, for example, a promoter, a structural or coding sequence which is transcribed into RSV RNA, and appropriate transcription initiation and termination sequences.

To produce infectious RSV from cDNA-expressed genome or antigenome, the genome or antigenome is coexpressed with those RSV proteins necessary to (i) produce a nucleocapsid capable of RNA replication, and (ii) render progeny nucleocapsids competent for both RNA replication and transcription. Transcription by the genome nucleocapsid provides the other RSV proteins and initiates a productive infection. Alternatively, additional RSV proteins needed for a productive infection can be supplied by coexpression.

An RSV antigenome may be constructed for use in the present invention by, e.g., assembling cloned cDNA segments, representing in aggregate the complete antigenome, by polymerase chain reaction (PCR; described in, e.g., U.S. Pat. Nos. 4,683,195 and 4,683,202, and PCR Protocols: A Guide to Methods and Applications, Innis et al., eds., Academic Press, San Diego (1990), incorporated herein by reference) of reverse-transcribed copies of RSV mRNA or genome RNA. For example, cDNAs containing the lefthand end of the antigenome, spanning from an appropriate promoter (e.g., T7 RNA polymerase promoter) and the leader region complement to the SH gene, are assembled in an appropriate expression vector, such as a plasmid (e.g., pBR322) or various available cosmid, phage, or DNA virus vectors. The vector may be modified by mutagenesis and/or insertion of synthetic polylinker containing unique restriction sites designed to facilitate assembly. For example, a plasmid vector described herein was derived from pBR322 by replacement of the PstI-EcoR1 fragment with a synthetic DNA containing convenient restriction enzyme sites. Use of pBR322 as a vector stabilized nucleotides 3716-3732 of the RSV sequence, which otherwise sustained nucleotide deletions or insertions, and propagation of the plasmid was in bacterial strain DH10B to avoid an artifactual duplication and insertion which otherwise occurred in the vicinity of nt 4499. For ease of preparation the G, F and M2 genes can be assembled in a separate vector, as can be the L and trailer sequences. The righthand end (e.g., L and trailer sequences) of the antigenome plasmid may contain additional sequences as desired, such as a flanking ribozyme and tandem T7 transcriptional terminators. The ribozyme can be hammerhead type (e.g., Grosfeld et al., J. Virol. 69:5677-5686 (1995)), which would yield a 3' end containing a single nonviral nucleotide, or can any of the other suitable ribozymes such as that of hepatitis delta virus (Perrotta et al., Nature 350:434-436 (1991)) which would yield a 3' end free of non-RSV nucleotides. A middle segment (e.g., G-to-M2 piece) is inserted into an appropriate restriction site of the leader-to-SH plasmid, which in turn is the recipient for the L-trailer-ribozyme-terminator piece, yielding a complete antigenome. In an illustrative example described herein, the leader end was constructed to abut the promoter for T7 RNA polymerase which included three transcribed G residues for optimal activity; transcription donates these three nonviral G's to the 5' end of the antigenome. These three nonviral G residues can be omitted to yield a 5' end free of nonviral nucleotides. To generate a nearly-correct 3' end, the trailer end was constructed to be adjacent to a hammerhead ribozyme, which upon cleavage would donate a single 3'-phosphorylated U residue to the 3' end of the encoded RNA.

In certain embodiments of the invention, complementing sequences encoding proteins necessary to generate a transcribing, replicating RSV nucleocapsid are provided by one or more helper viruses. Such helper viruses can be wild type or mutant. Preferably, the helper virus can be distinguished phenotypically from the virus encoded by the RSV cDNA. For example, it is desirable to provide monoclonal antibodies which react immunologically with the helper virus but not the virus encoded by the RSV cDNA. Such antibodies can be neutralizing antibodies. In some embodiments, the antibodies can be used in affinity chromatography to separate the helper virus from the recombinant virus. To aid the procurement of such antibodies, mutations can be introduced into the RSV cDNA to provide antigenic diversity from the helper virus, such as in the HN or F glycoprotein genes.

A variety of nucleotide insertions and deletions can be made in the RSV genome or antigenome. The nucleotide length of the genome of wild type human RSV (15,222 nucleotides) is a multiple of six, and members of the Paramyxovirus and Morbillivirus genera typically abide by a "rule of six," i.e., genomes (or minigenomes) replicate efficiently only when their nucleotide length is a multiple of six (thought to be a requirement for precise spacing of nucleotide residues relative to encapsidating NP protein). Alteration of RSV genome length by single residue increments had no effect on the efficiency of replication, and sequence analysis of several different minigenome mutants following passage showed that the length differences were maintained without compensatory changes. Thus, RSV lacks the strict requirement of genome length being a multiple of six, and nucleotide insertions and deletions can be made in the RSV genome or antigenome without defeating replication of the recombinant RSV of the present invention.

Alternative means to construct cDNA encoding the genome or antigenome include by reverse transcription-PCR using improved PCR conditions (e.g., as described in Cheng et al., Proc. Natl. Acad. Sci. USA 91:5695-5699 (1994); Samal et al., J. Virol 70:5075-5082 (1996), each incorporated herein by reference) to reduce the number of subunit cDNA components to as few as one or two pieces. In other embodiments different promoters can be used (e.g., T3, SP6) or different ribozymes (e.g., that of hepatitis delta virus. Different DNA vectors (e.g., cosmids) can be used for propagation to better accommodate the large size genome or antigenome.

The N, P and L proteins, necessary for RNA replication, require an RNA polymerase elongation factor such as the M2(ORF1) protein for processive transcription. Thus M2(ORF1) or a substantially equivalent transcription elongation factor for negative strand RNA viruses is required for the production of infectious RSV and is a necessary component of functional nucleocapsids during productive infection. The need for the M2(ORF1) protein is consistent with its role as a transcription elongation factor. The need for expression of the RNA polymerase elongation factor protein for negative strand RNA viruses is a feature of the present invention. M2(ORF1) can be supplied by expression of the complete M2-gene, although in this form the second ORF2 may also be expressed and have an inhibitory effect on RNA replication. Therefore, for production of infectious virus using the complete M2 gene the activities of the two ORFs should be balanced to permit sufficient expression of M(ORF1) to provide transcription elongation activity yet not so much of M(ORF2) to inhibit RNA replication. Alternatively, the ORF1 protein is provided from a cDNA engineered to lack ORF2 or which encodes a defective ORF2. Efficiency of virus production may also be improved by co-expression of additional viral protein genes, such as those encoding envelope constituents (i.e., SH, M, G, F proteins).

Isolated polynucleotides (e.g., cDNA) encoding the genome or antigenome and, separately, the N, P, L and M2(ORF1) proteins, are inserted by transfection, electroporation, mechanical insertion, transduction or the like, into cells which are capable of supporting a productive RSV infection, e.g., HEp-2, FRhL-DBS2, MRC, and Vero cells. Transfection of isolated polynucleotide sequences may be introduced into cultured cells by, for example, calcium phosphate-mediated transfection (Wigler et al., *Cell* 14: 725 (1978); Corsaro and Pearson, *Somatic Cell Genetics* 7: 603 (1981); Graham and Van der Eb, *Virology* 52: 456 (1973)), electroporation (Neumann et al., *EMBO J.* 1: 841-845 (1982)), DEAE-dextran mediated transfection (Ausubel et al., (ed.) *Current Protocols in Molecular Biology*, John Wiley and Sons, Inc., NY (1987), cationic lipid-mediated transfection (Hawley-Nelson et al., *Focus* 15:73-79 (1993)) or a commercially available transfection regent, e.g., LipofectACE® (Life Technologies) (each of the foregoing references are incorporated herein by reference).

The N, P, L and M2(ORF1) proteins are encoded by one or more expression vectors which can be the same or separate from that which encodes the genome or antigenome, and various combinations thereof. Additional proteins may be included as desired, encoded by its own vector or by a vector encoding a N, P, L, or M2(ORF1) protein or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., *Virology*, 210:202-205 (1995), incorporated herein by reference). The viral proteins, and/or T7 RNA polymerase, can also be provided from transformed mammalian cells, or by transfection of preformed mRNA or protein.

Alternatively, synthesis of antigenome or genome can be done in vitro (cell-free) in a combined transcription-translation reaction, followed by transfection into cells. Or, antigenome or genome RNA can be synthesized in vitro and transfected into cells expressing RSV proteins.

To select candidate vaccine viruses from the host of biologically derived and recombinant RSV strains provided herein, the criteria of viability, attenuation and immunogenicity are determined according to well known methods. Viruses which will be most desired in vaccines of the invention must maintain viability, have a stable attenuation phenotype, exhibit replication in an immunized host (albeit at lower levels), and effectively elicit production of an immune response in a vaccinee sufficient to confer protection against serious disease caused by subsequent infection from wild-type virus. Clearly, the heretofore known and reported RS virus mutants do not meet all of these criteria. Indeed, contrary to expectations based on the results reported for known attenuated RSV, viruses of the invention are not only viable and more attenuated then previous mutants, but are more stable genetically in vivo than those previously studied mutants, retaining the ability to stimulate a protective immune response and in some instances to expand the protection afforded by multiple modifications, e.g., induce protection against different viral strains or subgroups, or protection by a different immunologic basis, e.g., secretory versus serum immunoglobulins, cellular immunity, and the like. Prior to the invention, genetic instability of the ts phenotype following replication in vivo has been the rule for ts viruses (Murphy et al., *Infect. Immun.* 37:235-242 (1982)).

To propagate a RSV virus for vaccine use and other purposes, a number of cell lines which allow for RSV growth may be used. RSV grows in a variety of human and animal cells. Preferred cell lines for propagating attenuated RS virus for vaccine use include DBS-FRhL-2, MRC-5, and Vero cells. Highest virus yields are usually achieved with epithelial cell lines such as Vero cells. Cells are typically inoculated with virus at a multiplicity of infection ranging from about 0.001 to 1.0, or more, and are cultivated under conditions permissive for replication of the virus, e.g., at about 30-37° C. and for about 3-5 days, or as long as necessary for virus to reach an adequate titer. Virus is removed from cell culture and separated from cellular components, typically by well known clarification procedures, e.g., centrifugation, and may be further purified as desired using procedures well known to those skilled in the art.

RSV which has been attenuated as described herein can be tested in various well known and generally accepted in vitro and in vivo models to confirm adequate attenuation, resistance to phenotypic reversion, and immunogenicity for vaccine use. In in vitro assays, the modified virus (e.g., a multiply attenuated, biologically derived or recombinant RSV) is tested for temperature sensitivity of virus replication, i.e. ts phenotype, and for the small plaque phenotype. Modified viruses are further tested in animal models of RSV infection. A variety of animal models have been described and are summarized in Meignier et al., eds., *Animal Models of Respiratory Syncytial Virus Infection*, Merieux Foundation Publication, (1991), which is incorporated herein by reference. A cotton rat model of RS infection is described in U.S. Pat. No. 4,800,078 and Prince et al., *Virus Res.* 3:193-206 (1985), which are incorporated herein by reference, and is believed to be predictive of attenuation and efficacy in humans. A primate model of RSV infection using the chimpanzee is predictive of attenuation and efficacy in humans, and is described in detail in Richardson et al., *J. Med. Virol.* 3:91-100 (1978); Wright et al., *Infect. Immun.*, 37:397-400 (1982); Crowe et al., *Vaccine* 11:1395-1404 (1993), which are incorporated herein by reference.

The interrelatedness of data derived from rodents and chimpanzees relating to the level of attenuation of RSV candidates can be demonstrated by reference to FIG. 1, which is a graph correlating the replication of a spectrum of respiratory syncytial subgroup A viruses in the lungs of mice with their replication in chimpanzees. The relative level of replication compared to that of wt RSV is substantially identical, allowing the mouse to serve as a model in which to initially characterize the level of attenuation of the vaccine RSV candidate. The mouse and cotton rat models are especially useful in those instances in which candidate RS viruses display inadequate growth in chimpanzees. The RSV subgroup B viruses are an example of the RS viruses which grow poorly in chimpanzees.

Moreover, the therapeutic effect of RSV neutralizing antibodies in infected cotton rats has been shown to be highly relevant to subsequent experience with immunotherapy of monkeys and humans infected with RSV. Indeed, the cotton rat appears to be a reliable experimental surrogate for the response of infected monkeys, chimpanzees and humans to immunotherapy with RSV neutralizing antibodies. For example, the amount of RSV neutralizing antibodies associated with a therapeutic effect in cotton rats as measured by the level of such antibodies in the serum of treated animals (i.e., serum RSV neutralization titer of 1:302 to 1:518) is in the same range as that demonstrated for monkeys (i.e., titer of 1:539) or human infants or small children (i.e., 1:877). A therapeutic effect in cotton rats was manifest by a one hundred fold or greater reduction in virus titer in the lung (Prince et al., *J. Virol.* 61:1851-1854) while in monkeys a therapeutic effect was observed to be a 50-fold reduction in pulmonary virus titer. (Hemming et al., *J. Infect. Dis.* 152:1083-1087 (1985)). Finally, a therapeutic effect in infants and young children who were hospitalized for serious RSV bronchiolitis or pneumonia was manifest by a significant increase in oxygenation in the treated group and a significant decrease in amount of RSV recoverable from the upper respiratory tract of treated patients. (Hemming et al., *Antimicrob. Agents Chemother.* 31:1882-1886 (1987)). Therefore, based on these studies, the cotton rat constitutes a relevant model for predicting success of RSV vaccines in infants and small children. Other rodents, including mice, will also be similarly useful because these animals are permissive for RSV replication and have a core temperature more like that of humans (Wright et al., *J. Infect. Dis.* 122:501-512 (1970) and Anderson et al., *J. Gen. Virol.* 71:(1990)).

In accordance with the foregoing description and based on the Examples below, the invention also provides isolated, infectious RSV compositions for vaccine use. The attenuated virus which is a component of a vaccine is in an isolated and typically purified form. By isolated is meant to refer to RSV which is in other than a native environment of a wild-type virus, such as the nasopharynx of an infected individual. More generally, isolated is meant to include the attenuated virus as a component of a cell culture or other artificial medium. For example, attenuated RSV of the invention may be produced by an infected cell culture, separated from the cell culture and added to a stabilizer which contains other non-naturally occurring RS viruses, such as those which are selected to be attenuated by means of resistance to neutralizing monoclonal antibodies to the F-protein.

RSV vaccines of the invention contain as an active ingredient an immunogenically effective amount of RSV produced as described herein. Biologically derived or recombinant RSV can be used directly in vaccine formulations, or lyophilized. Lyophilized virus will typically be maintained at about 4° C. When ready for use the lyophilized virus is reconstituted in a stabilizing solution, e.g., saline or comprising SPG, Mg$^{++}$ and HEPES, with or without adjuvant, as further described below. The biologically derived or recombinantly modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum, which are materials well known in the art. Preferred adjuvants also include Stimulon™ QS-21 (Aquila Biopharmaceuticals, Inc., Worchester, Mass.), MPL™ (3-0-deacylated monophosphoryl lipid A; RIBI ImmunoChem Research, Inc., Hamilton, Mont.), and interleukin-12 (Genetics Institute, Cambridge, Mass.).

Upon immunization with a RSV vaccine composition as described herein, via aerosol, droplet, oral, topical or other route, the immune system of the host responds to the vaccine by producing antibodies specific for RSV virus proteins, e.g., F and G glycoproteins. As a result of the vaccination the host becomes at least partially or completely immune to RSV infection, or resistant to developing moderate or severe RSV disease, particularly of the lower respiratory tract.

The host to which the vaccine is administered can be any mammal susceptible to infection by RSV or a closely related virus and capable of generating a protective immune response to antigens of the vaccinizing strain. Thus, suitable hosts include humans, non-human primates, bovine, equine, swine, ovine, caprine, lagamorph, rodents, etc. Accordingly, the invention provides methods for creating vaccines for a variety of human and veterinary uses.

The vaccine compositions containing the attenuated RSV of the invention are administered to a patient susceptible to or otherwise at risk of RS virus infection in an "immunogenically effective dose" which is sufficient to induce or enhance the individual's immune response capabilities against RSV. In the case of human subjects, the attenuated virus of the invention is administered according to well established human RSV vaccine protocols, as described in, e.g., Wright et al., *Infect Immun.* 37:397-400 (1982), Kim et al., *Pediatrics* 52:56-63 (1973), and Wright et al., *J. Pediatr.* 88:931-936 (1976), which are each incorporated herein by reference. Briefly, adults or children are inoculated intranasally via droplet with an immunogenically effective dose of RSV vaccine, typically in a volume of 0.5 ml of a physiologically acceptable diluent or carrier. This has the advantage of simplicity and safety compared to parenteral immunization with a non-replicating vaccine. It also provides direct stimulation of local respiratory tract immunity, which plays a major role in resistance to RSV. Further, this mode of vaccination effectively bypasses the immunosuppressive effects of RSV-specific maternally-derived serum antibodies, which typically are found in the very young. Also, while the parenteral administration of RSV antigens can sometimes be associated with immunopathologic complications, this has never been observed with a live virus.

In all subjects, the precise amount of RSV vaccine administered and the timing and repetition of administration will be determined based on the patient's state of health and weight, the mode of administration, the nature of the formulation, etc. Dosages will generally range from about $10^3$ to about $10^6$ plaque forming units (PFU) or more of virus per patient, more commonly from about $10^4$ to $10^5$ PFU virus per patient. In any event, the vaccine formulations should provide a quantity of attenuated RSV of the invention sufficient to effectively stimulate or induce an anti-RSV immune response, e.g., as can be determined by complement fixation, plaque neutralization, and/or enzyme-linked immunosorbent assay, among other methods. In this regard, individuals are also monitored for signs and symptoms of upper respiratory illness. As with administration to chimpanzees, the attenuated virus of the vaccine grows in the nasopharynx of vaccinees at levels approximately 10-fold or more lower than wild-type virus, or approximately 10-fold or more lower when compared to levels of incompletely attenuated RSV.

In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) RSV infection. Similarly, adults who are particularly susceptible to repeated or serious RSV infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered RSV strain expressing a cytokine or an additional protein rich in T cell epitopes may be particularly advantageous for adults rather than for infants. RSV vaccines produced in accordance with the present invention can be combined with viruses of the other subgroup or strains of RSV to achieve protection against multiple RSV subgroups or strains, or selected gene segments encoding, e.g., protective epitopes of these strains can be engineered into one RSV clone as described herein. Typically the different viruses will be in admixture and administered simultaneously, but may also be administered separately. For example, as the F glycoproteins of the two RSV subgroups differ by only about 11% in amino acid sequence, this similarity is the basis for a cross-protective immune response as observed in animals immunized with RSV or F antigen and challenged with a heterologous strain. Thus, immunization with one strain may protect against different strains of the same or different subgroup.

The vaccines of the invention elicit production of an immune response that is protective against serious lower respiratory tract disease, such as pneumonia and bronchiolitis when the individual is subsequently infected with wild-type RSV. While the naturally circulating virus is still capable of causing infection, particularly in the upper respiratory tract, there is a very greatly reduced possibility of rhinitis as a result of the vaccination and possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup.

The attenuated RS virus of the present invention exhibits a very substantial diminution of virulence when compared to wild-type virus that is circulating naturally in humans. The attenuated virus is sufficiently attenuated so that symptoms of infection will not occur in most immunized individuals. In some instances the attenuated virus may still be capable of dissemination to unvaccinated individuals. However, its virulence is sufficiently abrogated such that severe lower respiratory tract infections in the vaccinated or incidental host do not occur.

The level of attenuation of vaccine virus may be determined by, for example, quantifying the amount of virus present in the respiratory tract of an immunized host and comparing the amount to that produced by wild-type RSV or other attenuated RS viruses which have been evaluated as candidate vaccine strains. For example, the attenuated virus of the invention will have a greater degree of restriction of replication in the upper respiratory tract of a highly susceptible host, such as a chimpanzee, compared to the levels of replication of wild-type virus, e.g., 10- to 1000-fold less. Also, the level of replication of the attenuated RSV vaccine strain in the upper respiratory tract of the chimpanzee should be less than that of the RSV A2 ts-1 mutant, which was demonstrated previously to be incompletely attenuated in seronegative human infants. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of RS virus in the nasopharynx of an infected host are well known in the literature. Specimens are obtained by aspiration or washing out of nasopharyngeal secretions and virus quantified in tissue culture or other by laboratory procedure. See, for example, Belshe et al., *J. Med. Virology* 1:157-162 (1977), Friedewald et al., *J. Amer. Med. Assoc.* 204:690-694 (1968); Gharpure et al., *J. Virol.* 3:414-421 (1969); and Wright et al., *Arch. Ges. Virusforsch.* 41:238-247 (1973). The virus can conveniently be measured in the nasopharynx of host animals, such as chimpanzees.

In some instances it may be desirable to combine the RSV vaccines of the invention with vaccines which induce protective responses to other agents, particularly other childhood viruses. For example, the RSV vaccine of the present invention can be administered simultaneously with parainfluenza virus vaccine, such as described in Clements et al., *J. Clin. Microbiol.* 29:1175-1182 (1991), which is incorporated herein by reference. In another aspect of the invention the RSV can be employed as a vector for protective antigens of other respiratory tract pathogens, such as parainfluenza, by incorporating the sequences encoding those protective antigens into the RSV genome or antigenome which is used to produce infectious RSV, as described herein.

In yet another aspect of the invention recombinant RSV is employed as a vector for transient gene therapy of the respiratory tract. According to this embodiment the recombinant RSV genome or antigenome incorporates a sequence which is capable of encoding a gene product of interest. The gene product of interest is under control of the same or a different promoter from that which controls RSV expression. The infectious RSV produced by coexpressing the recombinant RSV genome or antigenome with the N, P, L and M2(ORF1) proteins and containing a sequence encoding the gene product of interest is administered to a patient. Administration is typically by aerosol, nebulizer, or other topical application to the respiratory tract of the patient being treated. Recombinant RSV is administered in an amount sufficient to result in the expression of therapeutic or prophylactic levels of the desired gene product. Examples of representative gene products which are administered in this method include those which encode, for example, those particularly suitable for transient expression, e.g., interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

The following examples are provided by way of illustration, not limitation.

EXAMPLE I

Isolation and Characterization of Mutagenized Derivatives of Cold-passaged RSV

This Example describes the chemical mutagenesis of incompletely attenuated host range-restricted cpRSV to produce derivative ts and sp mutations which are more highly attenuated and thus are preferred for use in RSV vaccine preparations.

A parent stock of cold-passaged RSV (cpRSV) was prepared. Flow Laboratories Lot 3131 virus, the cpRSV parent virus that is incompletely attenuated in humans, was passaged twice in MRC-5 cells at 25° C., terminally diluted twice in MRC-5 cells at 25° C., then passaged three times in MRC-5 to create cpRSV suspension for mutagenesis.

The cpRSV was mutagenized by growing the parent stock in MRC-5 cells at 32° C. in the presence of 5-fluorouracil in the medium at a concentration of $4 \times 10^{-4}$M. This concentration was demonstrated to be optimal in preliminary studies, as evidenced by a 100-fold decrease in virus titer on day 5 of growth in cell culture, compared to medium without 5-fluorouracil. The mutagenized stock was then analyzed by plaque assay on Vero cells that were maintained under an agar overlay, and after an appropriate interval of incubation, plaques were stained with neutral red dye. 854 plaques were picked and the progeny of each plaque were separately amplified by growth on fresh monolayers of Vero cells. The contents of each of the tissue cultures inoculated with the progeny of a single plaque of cpRSV-mutagenized virus were separately harvested when cytopathic effects on the Vero cells appeared maximal. Progeny virus that exhibited the temperature-sensitive (ts) or small-plaque (sp) phenotype was sought by titering these plaque pools on HEp-2 cells at 32° C. and 38° F. Any virus exhibiting a sp phenotype (plaque size that was reduced by 50% or more compared to parental virus at 32° C.) or a ts phenotype (100-fold or greater reduction in titer at restrictive temperature [37° to 40° C.] compared to 32° C.) was evaluated further. These strains were biologically cloned by serial plaque-purification on Vero cells three times, then amplified on Vero cells. The cloned strains were titered at 32°, 37°, 38°, 39° and 40° C. (in an efficiency of plaque formation (EOP) assay) to confirm their sp and ts phenotypes. Because titers of some cloned strains were relatively low even at the permissive temperature (32°), these viruses were passaged once in HEp-2 cells to create virus suspensions for in vitro analysis. The phenotypes of the progeny of the mutagenized cpRSV are presented on Table 1.

TABLE 1

The efficiency of plaque formation of nine derivatives of cold-passaged RSV (cpts or cpsp mutants) in HEp-2 cells at permissive and restrictive temperatures

| Virus | The titer of virus ($log_{10}$pfu/ml) at the indicated temperature (° C.) 32 | 37 | 38 | 39 | 40 | Shut-off temperature (° C.)[1] | Small-plaques at 32 C. |
|---|---|---|---|---|---|---|---|
| A2 wild-type | 4.5 | 4.4 | 4.5 | 3.8 | 3.8 | >40 | no |
| cp-RSV | 6.0 | 5.8 | 5.8 | 6.2 | 5.4 | >40 | no |
| ts-1 | 5.7 | 4.5 | 2.7 | 2.4 | 1.7* | 38 | no |
| cpsp143 | 4.2* | 4.1* | 3.8* | 3.9* | 3.8* | >40 | yes |
| cpts368 | 6.7 | 6.3 | 6.1* | 5.8** | 2.0** | 40 | no |
| cpts274 | 7.3 | 7.1 | 6.6 | 5.8* | 1.0** | 40 | no |
| cpts347 | 6.2 | 6.1 | 5.7* | 5.5** | <0.7 | 40 | no |
| cpts142 | 5.7 | 5.1 | 4.5* | 3.7** | <0.7 | 39 | no |
| cpts299 | 6.2 | 5.5 | 5.1* | 2.0** | <0.7 | 39 | no |
| cpts475 | 5.4 | 4.8* | 4.2** | <0.7 | <0.7 | 39 | no |
| cpts530 | 5.5 | 4.8* | 4.5* | <0.7 | <0.7 | 39 | no |
| cpts248 | 6.3 | 5.3** | <0.7 | <0.7 | <0.7 | 38 | no |

[1]Shut-off temperature is defined as the lowest restrictive temperature at which a 100-fold or greater reduction of plaque titer is observed (bold figures in table).
*Small-plaque phenotype (<50% wild-type plaque size)
**Pinpoint-plaque phenotype (<10% wild-type plaque size)

One of the mutant progeny had the small plaque phenotype, RSV cpsp143 (sp refers to the small plaque (sp) phenotype), and the remaining mutant progeny had the ts phenotype. The RSV cpts mutants exhibit a variation in ability to produce plaques in monolayer cultures in vitro over the temperature range 37° C. to 40° C., with cpts368 retaining the ability to produce plaques at 40° C., whereas the most temperature-sensitive (ts) virus, cpts248, failed to produce plaques at 38° C. Thus, several of the mutagenized cpRSV progeny exhibit a marked difference from their cpRSV parent virus with respect to temperature-sensitivity of plaque formation.

Replication and Genetic Stability Studies in Mice

The level of replication of the cpRSV derived mutants in the upper and lower respiratory tracts of BALB/c mice was studied next (Table 2). It was found that cpts530 and cpts248, two of the mutants exhibiting the greatest temperature sensitivity (see Table 1), were about 7- to 12-fold restricted in replication in the nasal turbinates of the mice (Table 2). However, none of the viruses was restricted in replication in the lungs compared to the cpRSV parent virus. This greater restriction of replication in the nasal turbinates than in the lungs is not characteristic of ts mutants, which generally are more restricted in replication in the warmer lower respiratory tract (Richman and Murphy, *Rev. Infect. Dis.* 1:413-433 (1979). The virus produced in the lungs and nasal turbinates retained the ts character of the input virus (data not presented). The present findings suggested that the combination of the ts mutations on the background of the mutations of the cp parent virus has resulted in cpRSV ts progeny with a higher level of stability of the ts phenotype after replication in vivo than had been seen with previously studied ts mutants.

To further explore the level of genetic stability of the ts phenotype of the cpRSV derived mutants, the efficiency of plaque formation of virus present in the lungs and nasal turbinates of nude mice was studied for two mutagenized cpRSV progeny that were among the most ts, namely cpts248 and cpts530. Nude mice were selected because they are immunocompromised due to congenital absence of functional T-cells, and a virus can replicate for a much longer period of time in these hosts. This longer period of replication favors the emergence of virus mutants with altered phenotype. The virus present on day 12 (NOTE: in normal mice, virus is no longer detectable at this time) was characterized and found to retain an unaltered ts phenotype (Table 3). As expected, the ts-1 mutant included in the test as a positive control exhibited an unstable ts phenotype in vivo. Thus, contrary to previous evaluation of ts mutant viruses in rodents, the results show that a high level of stability of the ts phenotype of the cpRSV derived mutants following prolonged replication in rodents was achieved, which represents a significant and heretofore unattained very desirable property in the viruses of the invention.

TABLE 2

Replication of cpts and cpsp- RSV mutants in BALB/c mice[1]
Virus titer at 32° C.
(mean $log_{10}$pfu/g tissue from the tissues of 8 animals ± standard error)

| Animals infected with | Shutoff Temp. of virus (° C.) | Day 4 Nasal Turbinates | Day 4 Lungs | Day 5 Nasal Turbinates | Day 5 Lungs |
|---|---|---|---|---|---|
| A2 wild-type | >40 | 5.0 ± 0.16 | 5.8 ± 0.20 | 5.0 ± 0.11 | 5.8 ± 0.19 |
| cpRSV | >40 | 4.7 ± 0.07 | 5.3 ± 0.18 | 4.8 ± 0.16 | 5.3 ± 0.21 |
| ts-1 | 38 | 4.0 ± 0.19 | 4.7 ± 0.27 | 3.8 ± 0.33 | 4.9 ± 0.13 |
| cpsp143 | >40 | 4.5 ± 0.14 | 4.1 ± 0.37 | 4.4 ± 0.39 | 4.6 ± 0.39 |
| cpts368 | 40 | 4.8 ± 0.15 | 5.1 ± 0.35 | 4.7 ± 0.08 | 5.4 ± 0.23 |
| cpts274 | 40 | 4.2 ± 0.19 | 5.0 ± 0.15 | 4.2 ± 0.11 | 5.1 ± 0.55 |
| cpts347 | 40 | 4.4 ± 0.32 | 4.9 ± 0.40 | 4.5 ± 0.33 | 5.2 ± 0.35 |
| cpts142 | 39 | 4.1 ± 0.34 | 5.0 ± 0.19 | 4.3 ± 0.24 | 5.8 ± 0.40 |
| cpts299 | 39 | 3.9 ± 0.11 | 5.2 ± 0.15 | 3.9 ± 0.32 | 5.0 ± 0.29 |
| cpts475 | 39 | 4.0 ± 0.18 | 5.3 ± 0.25 | 4.1 ± 0.23 | 4.9 ± 0.42 |
| cpts530 | 39 | 3.9 ± 0.18 | 5.3 ± 0.15 | 3.9 ± 0.14 | 5.3 ± 0.19 |
| cpts248 | 38 | 3.9 ± 0.33 | 5.1 ± 0.29 | 4.2 ± 0.13 | 5.5 ± 0.35 |

[1]Mice were administered $10^{6.3}$ p.f.u. intranasally in a 0.1 ml inoculum on day 0, then sacrificed on day 4 or 5.

TABLE 3

The genetic stability of RSV cpts-248 and cpts-530 following prolonged replication in nude mice Efficiency of plaque formation at indicated temperature of virus present in nasal turbinates (n.t.) or lungs of nude mice sacrificed 12 days after virus administration[1]

| Animals infected with | Tissue harvest or input virus tested | Number of animals | 32° C. | | 37° C. | | | 38° C. | | | 40° C. | | |
|---|---|---|---|---|---|---|---|---|---|---|---|---|---|
| | | | % animals with virus detectable | Mean titer ($log_{10}$pfu per gram tissue or ml inoculum)[2] | % animals with virus detectable | % animals with virus with altered ts phenotype | Mean titer ($log_{10}$pfu per gram tissue or ml inoculum)[2] | % animals with virus detectable | % animals with virus with altered ts phenotype | Mean titer ($log_{10}$pfu per gram tissue or ml inoculum)[2] | % animals with virus detectable | % animals with virus with altered ts phenotype | Mean titer ($log_{10}$pfu per gram tissue or ml inoculum)[2] |
| cpts-248 | n.t. | 19 | 100 | 3.8 ± 0.34 | 0 | 0 | <2.0 | 0 | 0 | <2.0 | 0 | 0 | <2.0 |
| " | lungs | " | 90 | 2.0 ± 0.29 | 0 | 0 | <1.7 | 0 | 0 | <1.7 | 0 | 0 | <1.7 |
| cpts-530 | n.t. | 20 | 100 | 3.0 ± 0.26 | 0 | 0 | <2.0 | 0 | 0 | <2.0 | 0 | 0 | <2.0 |
| " | lungs | " | 100 | 2.4 ± 0.29 | 0 | 0 | <1.7 | 0 | 0 | <1.7 | 0 | 0 | <1.7 |
| ts-1 | n.t. | 19 | 100 | 3.7 ± 0.23 | 74 | 74 | 2.7 ± 0.57 | 63 | 63 | 2.4 ± 0.36 | 10 | 10 | 2.0 ± 0.13 |
| " | lungs | " | 100 | 2.5 ± 0.30 | 74 | 74 | 1.8 ± 0.21 | 35 | 32 | 1.8 ± 0.15 | 0 | 0 | <1.7 |
| Efficiency of plaque formation of input viruses | cpts-248 | — | — | 4.9 | — | | <0.7 | — | | <0.7 | — | | <0.7 |
| | cpts-530 | — | — | 5.5 | — | | 3.7* | — | | <0.7 | — | | <0.7 |
| | ts-1 | — | — | 6.1 | — | | 3.3 | — | | 2.7 | — | | <0.7 |

[1]Plaque titers shown represent the mean $log_{10}$pfu/gram tissue of 19 or 20 samples ± standard error.
[2]Each animal received $10^{6.3}$ p.f.u. intranasally in a 0.1 ml inoculum of the indicated virus on day 0.
*Small-plaque phenotype only.

In Chimpanzees

The level of attenuation of the cpRSV ts derivative was next evaluated in the seronegative chimpanzee, a host most closely related to humans. Trials in chimpanzees or owl monkeys are conducted according to the general protocol of Richardson et al., J. Med. Virol. 3:91-100 (1979); Crowe et al., Vaccine 11:1395-1404 (1993), which are incorporated herein by reference. One ml of suspension containing approximately $10^4$ plaque-forming units (PFU) of mutagenized, attenuated virus is given intranasally to each animal. An alternate procedure is to inoculate the RSV into both the upper and lower respiratory tract at a dose of $10^4$ PFU delivered to each site. Chimpanzees are sampled daily for 10 days, then every 3-4 days through day 20. The lower respiratory tract of chimpanzees can be sampled by tracheal lavage according to the protocol of Snyder et al., J. Infec. Dis. 154:370-371 (1986) and Crowe et al., Vaccine 11:1395-1404 (1993). Some animals are challenged 4 to 6 weeks later with the wild-type virus. Animals are evaluated for signs of respiratory disease each day that nasopharyngeal specimens are taken. Rhinorrhea is scored from 0 to 4+, with 2+ or greater being considered as evidence of significant upper respiratory disease.

Virus is isolated from nasal and throat swab specimens and tracheal lavage fluids by inoculation into RSV-sensitive HEp-2 cells as described above. Quantities of virus can also be determined directly by the plaque technique using HEp-2 cells as described in Schnitzer et al., J. Virol. 17:431-438 (1976), which is incorporated herein by reference. Specimens of serum are collected before administration of virus and at 3 to 4 weeks post-inoculation for determination of RSV neutralizing antibodies as described in Mills et al., J. Immununol. 107:123-130 (1970), which is incorporated herein by reference.

The most ts and attenuated of the cpRSV derivative (cpts248) was studied and compared to wild-type RSV and the cpRSV parent virus (Table 4). Replication of the cpRSV parent virus was slightly reduced in the nasopharynx compared to wild-type, there was a reduction in the amount of rhinorrhea compared to wild-type virus, and there was an approximate 600-fold reduction in virus replication in the lower respiratory tract compared to wild-type. Clearly, the cp virus was significantly restricted in replication in the lower respiratory tract of chimpanzees, a very desirable property not previously identified from prior evaluations of cpRSV in animals or humans. More significantly, the cpts 248 virus was 10-fold restricted in replication in the nasopharynx compared to wild-type, and this restriction was associated with a marked reduction of rhinorrhea. These findings indicated that the cpRSV derived mutant possesses two highly desirable properties for a live RSV vaccine, namely, evidence of attenuation in both the upper and the lower respiratory tracts of highly susceptible seronegative chimpanzees. The level of genetic stability of the virus present in the respiratory tract of chimpanzees immunized with cpts248 was evaluated next (Table 5). The virus present in the respiratory tract secretions retained the ts phenotype, and this was seen even with the virus from chimpanzee No. 3 on day 8 that was reduced 100-fold in titer at 40° C. and exhibited the small plaque phenotype at 40° C., indicating that its replication was still temperature-sensitive. This represents the most genetically stable ts mutant identified prior to the time of this test. The increased stability of the ts phenotype of the cpts248 and cpts530 viruses reflects an effect of the cp mutations on the genetic stability of the mutations that contribute to the ts phenotype in vivo. Thus, the ts mutations in the context of the mutations already present in the cp3131 parent virus appear to be more stable than would be expected in their absence. This important property has not been previously observed or reported. Infection of chimpanzees with the cpts 248 induced a high titer of serum neutralizing antibodies, as well as antibodies to the F and G glycoproteins (Table 6). Significantly, immunization with cpts248 protected the animals from wild-type RSV challenge (Table 7), indicating that this mutant functions as an effective vaccine virus in a host that is closely related to humans.

These above-presented findings indicate that the cpts248 virus has many properties desirable for a live RSV vaccine, including: 1) attenuation for the upper and lower respiratory tract; 2) increased genetic stability after replication in vivo, even after prolonged replication in immunosuppressed animals; 3) satisfactory immunogenicity; and 4) significant protective efficacy against challenge with wild-type RSV. The cpts530 virus shares with cpts248 similar temperature sensitivity of plaque formation, a similar degree of restriction of replication in the nasal turbinates of mice, and a high level of genetic stability in immunodeficient nude mice, whereby it also represents an RS virus vaccine strain.

TABLE 4

Replication of cpts-RSV 248, cp-RSV, or wild-type RSV A2 in the upper and lower respiratory tract of seronegative chimpanzees

| Animal infected with indicated virus | Route of Inoculation | Chimpanzee number | Virus recovery | | | | Rhinorrhea score | |
|---|---|---|---|---|---|---|---|---|
| | | | Nasopharynx | | Trachea | | | |
| | | | Duration[b] (days) | Peak titer ($\log_{10}$pfu/ml) | Duration[b] (days) | Peak titer ($\log_{10}$pfu/ml) | Mean[c] | Peak |
| cpts-248 | IN + IT | 1 | 10 | 4.6 | 8[d] | 5.4 | 0.2 | 1 |
| | IN + IT | 2 | 10 | 4.5 | 6 | 2.2 | 0.1 | 1 |
| | IN + IT | 3 | 9 | 4.7 | 10 | 2.1 | 0.1 | 1 |
| | IN + IT | 4 | 9 | 4.2 | 8[d] | 2.2 | 0.1 | 1 |
| | | | mean 9.5 | mean 4.5 | mean 8.0 | mean 3.0 | mean 0.1 | |
| cp-RSV | IN | 5 | 20 | 5.3 | 8[d] | 2.9 | 1.0 | 3 |
| | IN | 6 | 16 | 5.8 | 6[d] | 3.0 | 1.8 | 3 |
| | IN + IT | 7 | 13 | 4.3 | 6[d] | 3.0 | 0.6 | 1 |
| | IN + IT | 8 | 16 | 5.0 | 10[d] | 2.8 | 0.5 | 1 |
| | | | mean 16 | mean 5.1 | mean 7.5 | mean 2.9 | mean 1.0 | |
| A2 wild-type | IN | 9 | 9 | 5.1 | 13 | 5.4 | 1.0 | 1 |
| | IN | 10 | 9 | 6.0 | 8 | 6.0 | 1.7 | 4 |
| | IN + IT | 11 | 13 | 5.3 | 8 | 5.9 | 2.1 | 3 |
| | IN + IT | 12 | 9 | 5.4 | 8 | 5.6 | 1.0 | 3 |
| | | | mean 10 | mean 5.5 | mean 9.3 | mean 5.7 | mean 1.4 | |

[a]IN = Intranasal administration only, at a dose of $10^4$ p.f.u. in a 1.0 ml inoculum; IN + IT = Both intranasal and intratracheal administration, $10^4$ p.f.u. in a 1.0 ml inoculum at each site.
[b]Indicates last day post-infection on which virus was recovered.
[c]Mean rhinorrhea score represents the sum of daily scores for a period of eight days surrounding the peak day of virus shedding, divided by eight. Four is the highest score; zero is the lowest score.
[d]Virus isolated only on day indicated.

TABLE 5

Genetic stability of virus present in original nasopharyngeal (NP) swabs or tracheal lavage (TL) specimens obtained from animals experimentally infected with cptsRSV 248.

| Chimpanzee number | NP swab or TL specimen | Virus obtained on post-infection day | Titer of RSV at indicated temperature ($\log_{10}$pfu/ml) | | |
|---|---|---|---|---|---|
| | | | Titer at 32° C. | Titer at 39° C. | Titer at 40° C. |
| 1[a] | NP | 3 | 3.2 | <0.7 | NT |
| | " | 4 | 2.7 | <0.7 | NT |
| | " | 5 | 4.2 | <0.7 | NT |
| | " | 6 | 3.8 | <0.7 | NT |
| | " | 7 | 4.6 | <0.7 | NT |
| | " | 8 | 4.5 | <0.7 | NT |
| | " | 9 | 2.6 | <0.7 | NT |
| | " | 10 | 2.0 | <0.7 | NT |
| | TL | 6 | 5.4 | <0.7 | NT |
| | " | 8 | 2.7 | <0.7 | NT |
| 2[a] | NP | 3 | 3.2 | <0.7 | NT |
| | " | 4 | 3.7 | <0.7 | NT |
| | " | 5 | 4.5 | <0.7 | NT |
| | " | 6 | 4.1 | <0.7 | NT |
| | " | 7 | 3.3 | <0.7 | NT |
| | " | 8 | 4.2 | <0.7 | NT |
| | " | 9 | 2.8 | <0.7 | NT |
| | " | 10 | 1.6 | <0.7 | NT |
| | TL | 6 | 2.2 | <0.7 | NT |
| 3 | NP | 3 | 2.7 | <0.7 | <0.7 |
| | " | 4 | 3.4 | <0.7 | <0.7 |
| | " | 5 | 2.9 | <0.7 | <0.7 |
| | " | 6 | 3.3 | <0.7 | <0.7 |
| | " | 7 | 3.4 | 0.7[b] | <0.7 |
| | " | 8 | 4.7 | 3.5[b] | 2.0[c] |
| | " | 9 | 1.9 | <0.7 | <0.7 |
| | TL | 6 | 1.8 | <0.7 | <0.7 |
| | " | 8 | 1.9 | 1.2[b] | <0.7 |
| | " | 10 | 2.1 | 1.3[b] | <0.7 |
| 4 | NP | 3 | 3.2 | <0.7 | NT |
| | " | 4 | 2.7 | <0.7 | NT |
| | " | 5 | 3.4 | <0.7 | NT |
| | " | 6 | 3.3 | <0.7 | NT |
| | " | 7 | 4.2 | <0.7 | NT |
| | " | 8 | 3.5 | <0.7 | NT |

TABLE 5-continued

Genetic stability of virus present in original nasopharyngeal (NP) swabs or tracheal lavage (TL) specimens obtained from animals experimentally infected with cptsRSV 248.

| Chimpanzee number | NP swab or TL specimen | Virus obtained on post-infection day | Titer of RSV at indicated temperature ($\log_{10}$pfu/ml) | | |
|---|---|---|---|---|---|
| | | | Titer at 32° C. | Titer at 39° C. | Titer at 40° C. |
| | " | 9 | 2.1 | <0.7 | NT |
| | TL | 8 | 2.2 | <0.7 | NT |

NT = Not tested

[a] Isolates (once-passaged virus suspensions with average titer $\log_{10}$pfu/ml of 4.0) were generated from these chimpanzees from each original virus-containing nasopharyngeal swab specimen or tracheal lavage specimen and tested for efficiency of plaque formation at 32°, 39° and 40° C. No isolate was able to form plaques at 39° C. Isolates from chimpanzees 3 and 4 were not tested in this manner.

[b] The percent titer at 39° C. versus that at 32° C.: NP swab day 7 = 0.2%, NP swab day 8 = 6T, TL day 8–20%, TL day 10 = 16%. All plaques were of small-plaque phenotype only; no wild-type size plaques seen.

[c] The percent titer at 40° C. versus that at 32° C. was 0.2%. All plaques were of pinpoint-plaque phenotype; wild-type size plaques were not detected.

TABLE 6

Serum antibody responses of chimpanzees infected with RSV cpts-248, cp-RSV, or RSV A2 wild-type

| | | Serum antibody titers (reciprocal mean $\log_2$) | | | | | |
|---|---|---|---|---|---|---|---|
| | | Neutralizing | | ELISA-F | | ELISA-G | |
| Animals immunized with | No. of Chimpanzees | Day 0 | Day 28 | Day 0 | Day 28 | Day 0 | Day 28 |
| cpts-248 | 4 | <3.3 | 10.7 | 7.3 | 15.3 | 6.3 | 9.8 |
| cp-RSV | 4 | <3.3 | 11.2 | 11.3 | 15.3 | 9.3 | 12.3 |
| RSVA2 wild-type | 4 | <3.3 | 11.2 | 8.3 | 15.3 | 7.3 | 10.3 |

Further Attenuations

Since RS virus produces more symptoms of lower respiratory tract disease in human infants than in the 1-2 year old chimpanzees used in these experimental studies, and recognizing that mutants which are satisfactorily attenuated for the chimpanzee may not be so for seronegative infants and children, the cpts248 and 530 derivatives, which possess the very uncharacteristic ts mutant properties of restricted replication and attenuation in the upper respiratory tract and a higher level of genetic stability, were further mutagenized.

Progeny viruses that exhibited a greater degree of temperature-sensitivity in vitro than cpts248 or that had the small plaque phenotype were selected for further study. Mutant derivatives of the cpts248 that possessed one or more additional ts mutations were produced by 5-fluorouracil mutagenesis (Table 8). Ts mutants that were more temperature-sensitive (ts) than the cpts248 parental strain were identified, and some of these had the small plaque (sp) phenotype. These cpts248 derivatives were administered to mice. cpts248/804, 248/955, 248/404, 248/26, 248/18, and 248/240 mutants were more restricted in replication in the upper and lower respiratory tract of the mouse than their cpts248 parental virus (Table 9). Thus, viable mutants of cpts248 which were more attenuated than their cpts248 parental virus were identified, and these derivatives of cpts248 exhibited a wide range of replicative efficiency in mice, with cpts248/26 being the most restricted. The ts phenotype of the virus present in nasal turbinates and lungs of the mice was almost identical to that of the input virus, indicating genetic stability. A highly attenuated derivative of cpts248, the cpts248/404 virus, was 1000-fold more restricted in replication in the nasopharynx compared to wild-type. The cpts248/404 mutant, possessing at least three attenuating mutations, was also highly restricted in replication in the upper and lower respiratory tracts of four seronegative chimpanzees and infection did not induce rhinorrhea (Table 10). Again, this virus exhibited a high degree of reduction in replication compared to wild-type, being 60,000-fold reduced in the nasopharynx and 100,000-fold in the

TABLE 7

Immunization of chimpanzees with cpts-248 induces resistance to RSV A2 wild-type virus challenge on day 28

Response to challenge with $10^4$ p.f.u. wild-type virus administered on day 28

| | | Virus Recovery | | | | Rhinorrhea | | Serum neutralizing antibody titer (reciprocal $\log_2$) on day indicated | |
|---|---|---|---|---|---|---|---|---|---|
| | | Nasopharynx | | Trachea | | score | | | |
| Virus used to immunize animal | Chimpanzee number | Duration (days) | Peak titer ($\log_{10}$pfu/ml) | Duration (days) | Peak titer ($\log_{10}$pfu/ml) | Mean* | Peak | Day 28 | Day 42 or 56 |
| cpts-248 | 1 | 5 | 2.7 | 0 | <0.7 | 0 | 0 | 10.1 | 11.0 |
| | 2 | 9 | 1.8 | 0 | <0.7 | 0 | 0 | 10.3 | 14.5 |
| cp-RSV | 5 | 5 | 1.0 | 0 | <0.7 | 0 | 0 | 11.1 | 13.3 |
| | 6 | 8 | 0.7 | 0 | <0.7 | 0 | 0 | 11.4 | 12.9 |
| none | 9 | 9 | 5.1 | 13 | 5.4 | 1.0 | 1 | <3.3 | 12.4 |
| | 10 | 9 | 6.0 | 8 | 6.0 | 1.7 | 4 | <3.3 | 13.2 |
| | 11 | 13 | 5.3 | 8 | 5.9 | 2.1 | 3 | <3.3 | 11.6 |
| | 12 | 9 | 5.4 | 8 | 5.6 | 1.0 | 3 | <3.3 | 11.2 |

*Mean rhinorrhea score represents the sum of scores during the eight days of peak virus shedding divided by eight. Four is the highest score. A score of zero indicates no rhinorrhea detected on any day of the ten-day observation period.

lungs. Nonetheless, two chimpanzees which were subsequently challenged with RSV wild-type virus were highly resistant (Table 11).

Five small-plaque mutants of cpts248/404 were derived by chemical mutagenesis in a similar fashion to that described above. Suspensions of once-amplified plaque progeny were screened for the small-plaque (sp) phenotype by plaque titration at 32° C. on HEp-2 cells, and working suspensions of virus were prepared as described above.

Five of the plaque progeny of the mutagenized cpts248/404 virus exhibited a stable sp phenotype. The shut-off temperature of each mutant was 35° C. or less (Table 12), suggesting that each of these sp derivatives of the cpts248/404 virus also had acquired an additional ts mutation. Following intranasal inoculation of Balb/c mice with $10^{6.3}$ p.f.u. of a sp derivative of the cpts248/404, virus could not be detected in the nasal turbinates of mice inoculated with any of these sp derivatives. However, virus was detected in low titer in the lungs in one instance. These results indicate >300-fold restriction of replication in the nasal turbinates and >10,000-fold restriction in lungs compared with wild-type RSV.

Further ts derivatives of the cpts530 virus were also generated (Table 13). As with the cpts248 derivatives, the cpts-530 derivatives were more restricted in replication in mice than the cpts530 parental strain. One mutant, cpts-530/1009, was 30 times more restricted in replication in the nasal turbinates of mice. This cpts530 derivative, is also highly restricted in replication in the upper and lower respiratory tract of seronegative chimpanzees (Table 14). In the nasopharynx, cpts530 was 30-fold restricted in replication, while cpts530/1009 was 100-fold restricted compared to wild-type virus. Both of the cpts mutants were highly restricted (20,000 to 32,000-fold) in the lower respiratory tract compared with wild-type virus, even when the mutants were inoculated directly into the trachea. Also, chimpanzees previously infected with cpts530/1009, cpts530 or cpRSV exhibited significant restriction of virus replication in the nasopharynx and did not develop significant rhinorrhea following subsequent combined intranasal and intratracheal challenge with wild-type RSV (Table 15). In addition, chimpanzees previously infected with any of the mutants exhibited complete resistance in the lower respiratory tract to replication of wild-type challenge virus.

These results were completely unexpected based on experience gained during prior studies. For example, the results of an earlier study indicated that the in vivo properties of RSV ts mutants derived from a single cycle of 5-fluorouracil mutagenesis could not be predicted a priori.

Moreover, although one of the first four ts mutants generated in this manner exhibited the same shut off temperature for is plaque formation as the other mutants, it was overattenuated when tested in susceptible chimpanzees and susceptible infants and young children (Wright et al., *Infect Immun.* 37 (1):397-400 (1982). This indicated that the acquisition of the ts phenotype resulting in a 37-38° C. shut off temperature for plaque formation did not reliably yield a mutant with the desired level of attenuation for susceptible chimpanzees, infants and children. Indeed, the results of studies with heretofore known ts mutants completely fail to provide any basis for concluding that introduction of three independent mutations (or sets of mutations) into RSV by cold-passage followed by two successive cycles of chemical mutagenesis could yield viable mutants which retain infectivity for chimpanzees (and by extrapolation, young infants) and exhibit the desired level of attenuation, immunogenicity and protective efficacy required of a live virus vaccine to be used for prevention of RSV disease.

The above-presented results clearly demonstrate that certain ts derivatives of the cpRSV of the invention have a satisfactory level of infectivity and exhibit a significant degree of attenuation for mice and chimpanzees. These mutant derivatives are attenuated and appear highly stable genetically after replication in vivo. These mutants also induce significant resistance to RSV infection in chimpanzees. Thus, these derivatives of cpRSV represent virus strains suitable for use in a live RSV vaccine designed to prevent serious human RSV disease.

TABLE 8

The efficiency of plaque formation of ten mutants derived from RSV cpts248 by additional 5FU mutagenesis.

| Virus | The titer of virus ($\log_{10}$pfu/ml) at the indicated temperature (° C.) | | | | | | | Shutoff temperature (° C.)[1] | Small-plaques at 32 C. |
|---|---|---|---|---|---|---|---|---|---|
| | 32 | 35 | 36 | 37 | 38 | 39 | 40 | | |
| A2 wild-type | 4.5 | 4.6 | 4.4 | 4.5 | 4.5 | 3.8 | 3.8 | >40 | no |
| cpRSV | 4.7 | 4.4 | 4.3 | 4.3 | 4.2 | 3.7 | 3.5 | >40 | no |
| ts-1 | 5.6 | 5.4 | 4.9 | 4.4 | 2.7 | 2.0 | <0.7 | 38 | no |
| cpts-248 | 3.4 | 3.0 | 2.6* | 1.7** | <0.7 | <0.7 | <0.7 | 38 | no |
| 248/1228 | 5.5* | 5.3* | 5.3 | <0.7** | <0.7 | <0.7 | <0.7 | 37 | yes |
| 248/1075 | 5.3* | 5.3* | 5.1 | <0.7** | <0.7 | <0.7 | <0.7 | 37 | yes |
| 248/965 | 4.5 | 4.2 | 4.2* | <0.7 | <0.7 | <0.7 | <0.7 | 37 | no |
| 248/967 | 4.4 | 3.7 | 3.6* | <0.7 | <0.7 | <0.7 | <0.7 | 37 | no |
| 248/804 | 4.9 | 4.5 | 4.0* | <0.7 | <0.7 | <0.7 | <0.7 | 37 | no |
| 248/955 | 4.8 | 3.7 | 2.8* | <0.7 | <0.7 | <0.7 | <0.7 | 36 | no |
| 248/404 | 3.6 | 2.9* | <0.7 | <0.7 | <0.7 | <0.7 | <0.7 | 36 | no |
| 248/26 | 3.1 | 2.9* | <0.7 | <0.7 | <0.7 | <0.7 | <0.7 | 36 | no |
| 248/18 | 4.0* | 4.0 | <0.7** | <0.7 | <0.7 | <0.7 | <0.7 | 36 | yes |
| 248/240 | 5.8* | 5.7 | <0.7** | <0.7 | <0.7 | <0.7 | <0.7 | 36 | yes |

[1]Shut-off temperature is defined as the lowest restrictive temperature at which a 100-fold or greater reduction of plaque titer in Hep-2 cells is observed (bold figures in table).
*Small-plaque phenotype (<50% wild-type plaque size).
**Pinpoint-plaque phenotype (<10% wild-type plaque size).

TABLE 9

Replication and genetic stability of ten mutants derived from RSV cpts-248 in Balb/c mice[1]

| Virus used to infect animal | Shutoff temperature of virus (° C.) | Virus titer (mean $\log_{10}$pfu/g tissue of six animals ± standard error) | | | | | | | |
|---|---|---|---|---|---|---|---|---|---|
| | | Nasal turbinates | | | | Lungs | | | |
| | | 32° C. | 36° C. | 37° C. | 38° C. | 32° C. | 36° C. | 37° C. | 38° C. |
| A2 wild-type | >40 | 5.1 ± 0.15 | 5.2 ± 0.23 | 5.2 ± 0.14 | 5.2 ± 0.27 | 6.1 ± 0.14 | 5.8 ± 0.23 | 6.0 ± 0.12 | 5.9 ± 0.17 |
| cp-RSV | >40 | 4.9 ± 0.20 | 5.1 ± 0.16 | 4.9 ± 0.24 | 4.9 ± 0.22 | 6.0 ± 0.16 | 5.9 ± 0.23 | 5.6 ± 0.15 | 5.6 ± 0.13 |
| ts-1 | 38 | 3.9 ± 0.25 | 2.7 ± 0.27 | 2.4 ± 0.42 | 2.5 ± 0.29 | 4.1 ± 0.21 | 3.5 ± 0.23 | 2.6 ± 0.18 | 2.0 ± 0.23 |
| cpts-248 | 38 | 4.0 ± 0.16 | 2.5 ± 0.34 | <2.0 | <2.0 | 4.4 ± 0.37 | 1.8 ± 0.15 | <1.7 | <1.7 |
| 248/1228 | 37 | 4.1 ± 0.15 | 2.4 ± 0.48 | <2.0 | <2.0 | 2.0 ± 0.37 | <1.7 | <1.7 | <1.7 |
| 248/1075 | 37 | 4.2 ± 0.18 | 2.4 ± 0.40 | <2.0 | <2.0 | 5.5 ± 0.16 | 3.5 ± 0.18 | <1.7 | <1.7 |
| 248/965 | 37 | 3.8 ± 0.23 | <2.0 | <2.0 | <2.0 | 4.5 ± 0.21 | 3.4 ± 0.16 | <1.7 | <1.7 |
| 248/967 | 37 | 4.4 ± 0.20 | <2.0 | <2.0 | <2.0 | 5.4 ± 0.20 | 3.6 ± 0.19 | <1.7 | <1.7 |
| 248/804 | 37 | 2.9 ± 0.19 | <2.0 | <2.0 | <2.0 | 3.6 ± 0.19 | <1.7 | <1.7 | <1.7 |
| 248/955 | 36 | 3.2 ± 0.10 | <2.0 | <2.0 | <2.0 | 3.2 ± 0.22 | <1.7 | <1.7 | <1.7 |
| 248/404 | 36 | 2.1 ± 0.31[2] | <2.0 | <2.0 | <2.0 | 4.4 ± 0.12[2] | 1.8 ± 0.20 | <1.7 | <1.7 |
| 248/26 | 36 | <2.0 | <2.0 | <2.0 | <2.0 | 2.3 ± 0.20 | <1.7 | <1.7 | <1.7 |
| 248/18 | 36 | 2.9 ± 0.99 | <2.0 | <2.0 | <2.0 | 4.3 ± 0.23 | 1.8 ± 0.15 | <1.7 | <1.7 |
| 248/240 | 36 | 2.9 ± 0.82 | <2.0 | <2.0 | <2.0 | 3.9 ± 0.12 | <1.7 | <1.7 | <1.7 |

[1]Mice were administered $10^{6.3}$ p.f.u. intranasally under light anesthesia on day 0, then sacrificed by $CO_2$ asphyxiation on day 4.
[2]In a subsequent study, the level of replication of the cpts-248/404 virus was found to be 2.4 ± 0.24 and 2.6 ± 0.31 in the nasal turbinates and lungs, respectively.

TABLE 10

Replication of cpts-RSV 248/404, cpts-RSV 248/18, cpts-RSV 248, cp-RSV, or wild-type RSV A2 in the upper and lower respiratory tract of seronegative chimpanzees

| Animal infected with indicated virus | Route of Inoculation | Chimpanzee number | Virus recovery | | | | Rhinorrhea scores | |
|---|---|---|---|---|---|---|---|---|
| | | | Nasopharynx | | Trachea | | | |
| | | | Duration[b] (days) | Peak titer ($\log_{10}$pfu/ml) | Duration[b] (days) | Peak titer ($\log_{10}$pfu/ml) | Mean[c] | Peak |
| cpts-248/404 | IN + IT | 13 | 0 | <0.7 | 0 | <0.7 | 0 | 0 |
| | IN + IT | 14 | 0 | <0.7 | 0 | <0.7 | 0 | 0 |
| | IN + IT | 15 | 8 | 1.9 | 0 | <0.7 | 0.3 | 2 |
| | IN + IT | 16 | 9 | 2.0 | 0 | <0.7 | 0.2 | 1 |
| | | | mean 4.3 | mean 1.3 | mean 0 | mean <0.7 | mean 0.1 | mean 0.8 |
| cpts-248# | IN + IT | 1 | 10 | 4.6 | 8[d] | 5.4 | 0.2 | 1 |
| | IN + IT | 2 | 10 | 4.5 | 6 | 2.2 | 0.1 | 1 |
| | IN + IT | 3 | 9 | 4.7 | 10 | 2.1 | 0.1 | 1 |
| | IN + IT | 4 | 9 | 4.2 | 8[d] | 2.2 | 0.1 | 1 |
| | | | mean 9.5 | mean 4.5 | mean 8.0 | mean 3.0 | mean 0.1 | mean 1.0 |
| cp-RSV# | IN | 5 | 20 | 5.3 | 8[d] | 2.9 | 1.0 | 3 |
| | IN | 6 | 16 | 5.8 | 6[d] | 3.0 | 1.8 | 3 |
| | IN + IT | 7 | 13 | 4.3 | 6[d] | 3.0 | 0.6 | 1 |
| | IN + IT | 8 | 16 | 5.0 | 10[d] | 2.8 | 0.5 | 1 |
| | | | mean 16 | mean 5.1 | mean 7.5 | mean 2.9 | mean 1.0 | mean 2.0 |
| A2 wild-type# | IN | 9 | 9 | 5.1 | 13 | 5.4 | 1.0 | 1 |
| | IN | 10 | 9 | 6.0 | 8 | 6.0 | 1.7 | 4 |
| | IN + IT | 11 | 13 | 5.3 | 8 | 5.9 | 2.1 | 3 |
| | IN + IT | 12 | 9 | 5.4 | 8 | 5.6 | 1.0 | 3 |
| | | | mean 10 | mean 5.5 | mean 9.3 | mean 5.7 | mean 1.4 | mean 2.8 |

[a]IN Intranasal administration only; IN + IT = Both intranasal and intratracheal administration.
[b]Indicates last day post-infection on which virus was recovered.
[c]Mean rhinorrhea score represents the sum of daily scores for a period of eight days surrounding the peak day of virus shedding, divided by eight. Four is the highest score; zero is the lowest score.
[d]Virus isolated only on day indicated.
These are the same animals included in Tables 4 and 7.

TABLE 11

Immunization of chimpanzees with cpts-248/404 induces resistance to RSV A2 wild-type virus challenge on day 28

| Virus used to immunize animal | Chimpanzee number | Virus Recovery | | | | Rhinorrhea scores | | Serum neutralizing antibody titer (reciprocal $\log_2$) on day indicated[b] | |
|---|---|---|---|---|---|---|---|---|---|
| | | Nasopharynx | | Tracheal lavage | | | | | |
| | | Duration (days) | Peak titer ($\log_{10}$pfu/ml) | Duration (days) | Peak titer ($\log_{10}$pfu/ml) | Mean[a] | Peak | Day 28 | Day 49 or 56 |
| cpts-248/404 | 13 | 0 | <0.7 | 0 | <0.7 | 0 | 0 | 7.9 | 9.0 |
| | 14 | 8 | 3.4 | 0 | <0.7 | 0 | 0 | 7.0 | 12.5 |
| | | mean 4.0 | mean 2.0 | mean 0 | mean <0.7 | mean 0 | mean 0 | mean 7.5 | mean 10.8 |
| cpts-248# | 1 | 5 | 2.7 | 0 | <0.7 | 0 | 0 | 11.5 | 13.0 |
| | 2 | 9 | 1.8 | 0 | <0.7 | 0 | 0 | 12.7 | 14.5 |
| | | mean 7.0 | mean 2.3 | mean 0 | mean <0.7 | mean 0 | mean 0 | mean 12.1 | mean 13.8 |
| cp-RSV# | 5 | 5 | 1.0 | 0 | <0.7 | 0 | 0 | 12.2 | 11.1 |
| | 6 | 8 | 0.7 | 0 | <0.7 | 0 | 0 | 11.9 | 9.9 |
| | | mean 6.5 | mean 0.9 | mean 0 | mean 0.7 | mean 0 | mean 0 | mean 12.1 | mean 10.5 |
| None | 9 | 9 | 5.1 | 13 | 5.4 | 1.0 | 1 | <3.3 | 11.0 |
| | 10 | 9 | 6.0 | 8 | 6.0 | 1.7 | 4 | <3.3 | 9.8 |
| | 11 | 13 | 5.3 | 8 | 5.9 | 2.1 | 3 | <3.3 | 9.4 |
| | 12 | 9 | 5.4 | 8 | 5.6 | 1.0 | 3 | <3.3 | 14.5 |
| | | mean 10 | mean 5.5 | mean 9.2 | mean 5.7 | mean 1.4 | mean 2.8 | mean <3.3 | mean 11.2 |

[a]Mean rhinorrhea score represents the sum of scores during the eight days of peak virus shedding divided by eight. Four is the highest score. A score of zero indicates no rhinorrhea detected on any day of the ten-day observation period.
These are the same animals included in Tables 4, 7 and 10.
[b]Serum neutralizing titers in this table, including those from animals previously described, were determined simultaneously in one assay.

TABLE 12

The efficiency of plaque formation and replication of Balb/c mice of five small-plaque derivatives of RSV cpts-248/404.

| Virus | The titer of virus ($\log_{10}$pfu/ml) at the indicated temperature (° C.) | | | | | | | Shut-off temp (° C.)[1] | Small-plaques at 32° C. | Replication in Balb/c mice[2] | |
|---|---|---|---|---|---|---|---|---|---|---|---|
| | 32 | 35 | 36 | 37 | 38 | 39 | 40 | | | Nasal turbinates[3] | Lungs[3] |
| A2 wild-type | 6.0 | 6.1 | 6.0 | 5.8 | 5.9 | 5.4 | 5.4 | >40 | no | 4.5 ± 0.34 | 5.6 ± 0.13 |
| cp-RSV | 6.2 | 6.2 | 6.0 | 6.0 | 5.9 | 5.6 | 5.4 | >40 | no | 4.5 ± 0.10 | 5.3 ± 0.20 |
| cpts-248 | 7.5 | 7.3 | 6.2 | 5.3** | <0.7 | <0.7 | <0.7 | 37 | no | 3.3 ± 0.35 | 4.8 ± 0.14 |
| 248/404 | 5.5 | 3.6 | <0.7** | <0.7 | <0.7 | <0.7 | <0.7 | 36 | no | 2.4 ± 0.24 | 2.6 ± 0.31 |
| 248/404/774 | 2.9* | <0.7 | <0.7 | <0.7 | <0.7 | <0.7 | <0.7 | ≦35 | yes | <2.0 | 1.8 ± 0.24 |
| 248/404/832 | 5.5 | <0.7** | <0.7 | <0.7 | <0.7 | <0.7 | <0.7 | ≦35 | yes | <2.0 | <1.7 |
| 248/404/886 | 5.0 | <0.7** | <0.7 | <0.7 | <0.7 | <0.7 | <0.7 | ≦35 | yes | <2.0 | <1.7 |
| 248/404/893 | 5.4 | <0.7** | <0.7 | <0.7 | <0.7 | <0.7 | <0.7 | ≦35 | yes | <2.0 | <1.7 |
| 248/404/1030 | 4.4* | 2.2 | <0.7 | <0.7 | <0.7 | <0.7 | <0.7 | 35 | yes | <2.0 | <1.7 |

[1]Shut-off temperature is defined as the lowest restrictive temperature at which at 100-fold or greater reduction of plaque titer is observed (bold figures in table).
[2]Mice were administered $10^{6.3}$ p.f.u. intranasally under light anesthesia on day 0, then sacrificed by $CO_2$ asphyxiation on day 4 when tissues were harvested for virus titer.
[3]Mean $\log_{10}$pfu/g tissue of six animals ± standard error.
*Small-plaque phenotype (<50% wild-type plaque size).
**Pinpoint-plaque phenotype (<10% wild-type plaque size).

TABLE 13

The efficiency of plaque formation and level of replication in mice of 14 mutants derived from RSV cpts530, compared with controls

| | In vitro efficiency of plaque formation The titer of virus ($\log_{10}$pfu/ml) at the indicated temperature (° C.) | | | | | | | | Shut-off Temp. (° C.)[1] | Replication in mice[2] (mean $\log_{10}$ pfu/g tissue of six animals ± SE) | |
|---|---|---|---|---|---|---|---|---|---|---|---|
| RSV | 32 | 34 | 35 | 36 | 37 | 38 | 39 | 40 | | Nasal turbinates | Lungs |
| A2 | 6.3 | 6.3 | 6.1 | 6.2 | 6.3 | 6.3 | 6.1 | 5.6 | >40 | 5.0 ± 0.14 | 5.8 ± 0.05 |
| cpRSV | 6.5 | 6.2 | 6.2 | 6.2 | 6.1 | 6.0 | 6.1 | 5.6 | >40 | n.d. | n.d |
| cpts248 | 6.3 | 6.3 | 6.3 | 6.3 | **3.7\*\*** | <0.7 | <0.7 | <0.7 | 37/38 | 4.1 ± 0.08 | 5.1 ± 0.13 |
| 248/404 | 6.3 | 5.7* | **4.3\*\*** | <0.7 | <0.7 | <0.7 | <0.7 | <0.7 | 35/36 | 2.1 ± 0.19 | 3.6 ± 0.10 |
| cpts530 | 6.2 | 6.3 | 6.2 | 6.1 | 6.2\* | **5.5\*\*** | <0.7 | <0.7 | 39 | 3.4 ± 0.09 | 4.3 ± 0.14 |
| 530/346 | 5.9 | 5.9 | 5.7 | 4.7 | 3.5 | <0.7 | <0.7 | <0.7 | 37 | 3.3 ± 0.11 | 4.7 ± 0.09 |
| 530/977 | 5.0 | 4.4 | 3.6 | 3.4 | 2.8\* | <0.7 | <0.7 | <0.7 | 37 | 3.4 ± 0.11 | 2.7 ± 0.05 |
| 530/9 | 6.0 | 5.6 | 5.0 | 3.5\* | 3.5* | <0.7 | <0.7 | <0.7 | 36 | 2.1 ± 0.06 | 3.5 ± 0.08 |
| 530/1009 | 4.8 | 4.0 | 3.7* | **2.0\*\*** | 1.5** | <0.7 | <0.7 | <0.7 | 36 | 2.2 ± 0.15 | 3.5 ± 0.13 |
| 530/667 | 5.5 | 4.9 | 4.5* | **2.0\*\*** | 0.7 | <0.7 | <0.7 | <0.7 | 36 | 2.4 ± 0.12 | 2.9 ± 0.15 |
| 530/1178 | 5.7 | 4.0 | 5.5 | **3.7\*\*** | 2.0** | <0.7 | <0.7 | <0.7 | 36 | 3.3 ± 0.06 | 42 ± 0.11 |
| 530/464 | 6.0 | 5.0* | 4.7* | **1.8\*\*** | <0.7 | <0.7 | <0.7 | <0.7 | 36 | <2.0 | 2.6 ± 0.10 |
| 530/403 | 5.7 | 5.1 | 4.3 | 2.9 | <0.7 | <0.7 | <0.7 | <0.7 | 36 | <2.0 | <1.7 |
| 530/1074 | 5.1 | 4.6 | 4.1* | <0.7 | <0.7 | <0.7 | <0.7 | <0.7 | 36 | 3.0 ± 0.13 | 3.8 ± 0.13 |
| 530/963 | 5.3 | 5.0 | 4.2* | 0.7 | <0.7 | <0.7 | <0.7 | <0.7 | 36 | 2.0 ± 0.05 | <1.7 |
| 530/653 | 5.4 | 5.1 | 4.5 | <0.7 | <0.7 | <0.7 | <0.7 | <0.7 | 36 | 2.2 ± 0.10 | 3.1 ± 0.16 |
| 530/1003 | 5.6 | 4.1 | 2.5 | **2.1\*\*** | <0.7 | <0.7 | <0.7 | <0.7 | 35 | <2.0 | <1.7 |
| 530/1030 | 4.3 | 3.7* | **1.7\*\*** | <0.7 | <0.7 | <0.7 | <0.7 | <0.7 | 35 | <2.0 | 1.8 ± 0.13 |
| 530/188 | 5.0* | 1.0\* | 1.0 | <0.7 | <0.7 | <0.7 | <0.7 | <0.7 | ≦34 | <2.0 | <1.7 | n.d. = not done
*Small-plaque phenotype (<50% wild-type plaque size)
**Pinpoint-plaque phenotype (<10% wild-type plaque size)
[1]Shut-off temperature is defined as the lowest restrictive temperature at which a 100-fold or greater reduction of plaque titer is observed (bold figures in table).
[2]Mice were administered $10^{6.3}$ p.f.u. intranasally under light anesthesia on day 0, then sacrificed by $CO_2$ asphyxiation on day 4.

TABLE 14

Replication of cpts-530/1009, cp-RSV, or wild-type RSV A2 in the upper and lower respiratory tract of seronegative chimpanzees induces serum neutralizing antibodies.

| Animals Infected with $10^4$ pfu of indicated virus | Route of Inoculation | Chimpanzee Number | Virus Replication | | | | Rhinorrhea Scores | | Day 28 reciprocal serum neutralizing antibody titer[g] |
|---|---|---|---|---|---|---|---|---|---|
| | | | Nasopharynx | | Trachea | | | | |
| | | | Duration[b] (days) | Peak Titer ($\log_{10}$pfu/ml) | Duration[b] (days) | Peak Titer ($\log_{10}$pfu/ml) | Mean[c] | Peak | |
| cpts-530/1009 | IN + IT | 1 | 9 | 3.1 | 0 | <1.0 | 0.5 | 2 | 1,097 |
| | IN + IT | 2 | 10 | 4.0 | 10[a] | 1.8 | 0.5 | 2 | 416 |
| | IN + IT | 3 | 9 | 4.0 | 0 | <1.0 | 0.8 | 2 | 1,552 |
| | IN + IT | 4 | 9 | 3.3 | 0 | <1.0 | 0.4 | 1 | 1,176 |
| | | | mean 9.3 | mean 3.6 | mean 2.5 | mean 1.2 | mean 0.5 | mean 1.3 | mean 1,060 |
| cpts-530 | IN + IT | 5 | 9 | 3.5 | 4[e] | 2.6 | 0.3 | 1 | 10,085 |
| | IN + IT | 6 | 9 | 5.2 | 0 | <1.0 | 1.1 | 3 | 3,566 |
| | IN + IT | 7 | 8 | 3.3 | 0 | <1.0 | 0.6 | 2 | 588 |
| | IN + IT | 8 | 8 | 4.4 | 0 | <1.0 | 0.5 | 2 | 1,911 |
| | | | mean 8.5 | mean 4.1 | mean 1.0 | mean 1.4 | mean 0.6 | mean 2.0 | mean 4,038 |
| cp-RSV | IN | 9[d] | 20 | 5.3 | 8[e] | 2.9 | 1.0 | 3 | 416 |
| | IN | 10[d] | 16 | 5.8 | 6[e] | 3.0 | 1.8 | 3 | 2,048 |
| | IN + IT | 11[d] | 13 | 4.3 | 6[e] | 3.0 | 0.6 | 1 | 776 |
| | IN + IT | 12[d] | 16 | 5.0 | 10[e] | 2.8 | 0.5 | 1 | 891 |
| | | | mean 16 | mean 5.1 | mean 7.5 | mean 2.9 | mean 1.0 | mean 2.0 | mean 1,033 |

TABLE 14-continued

Replication of cpts-530/1009, cp-RSV, or wild-type RSV A2 in the upper and lower respiratory tract of seronegative chimpanzees induces serum neutralizing antibodies.

| Animals Infected with $10^4$ pfu of indicated virus | Route of Inoculation | Chimpanzee Number | Virus Replication | | | | Rhinorrhea Scores | | Day 28 reciprocal serum neutralizing antibody titer[g] |
|---|---|---|---|---|---|---|---|---|---|
| | | | Nasopharynx | | Trachea | | | | |
| | | | Duration[b] (days) | Peak Titer ($\log_{10}$pfu/ml) | Duration[b] (days) | Peak Titer ($\log_{10}$pfu/ml) | Mean[c] | Peak | |
| A2 wild-type | IN | 13[f] | 9 | 5.1 | 13 | 5.4 | 1.0 | 1 | 1,351 |
| | IN | 14[f] | 9 | 6.0 | 8 | 6.0 | 1.7 | 4 | 676 |
| | IN + IT | 15[d] | 13 | 5.3 | 8 | 5.9 | 2.1 | 3 | 1,261 |
| | IN + IT | 16[d] | 9 | 5.4 | 8 | 5.6 | 1.0 | 3 | 20,171 |
| | | | mean 10 | mean 5.5 | mean 9.3 | mean 5.7 | mean 1.4 | mean 2.8 | mean 5,865 |

[a]IN = Intranasal only; IN + IT = Both intranasal and intratracheal administration.
[b]Indicates last day post-infection on which virus was recovered.
[c]Mean rhinorrhea score represents the sum of daily scores for a period of eight days surrounding the peak day of virus shedding, divided by eight. Four is the highest score; zero is the lowest score.
[d]Animals from Crowe, et al., Vaccine 12: 691-699 (1994).
[e]Virus isolated only on day indicated.
[f]Animals from Collins, et al., Vaccine 8: 164-168 (1990).
[g]Determined by complement-enhanced 60% plaque reduction of RSV A2 in HEp-2 cell monolayer cultures. All titers were determined simultaneously in a single assay. The reciprocal titer of each animal on day 0 was <10.

TABLE 15

Immunization of chimpanzees with cpts-530/1009 or cpts-530 induces resistance to wild-type RSV A2 virus challenge on day 28

| Virus used for immunization | Chimpanzee number | Virus replication | | | | Rhinorrhea scores | | Serum neutralizing antibody (reciprocal $\log_2$) on day indicated[d] | |
|---|---|---|---|---|---|---|---|---|---|
| | | Nasopharynx | | Tracheal lavage | | | | | |
| | | Duration (days) | Peak titer ($\log_{10}$pfu/ml) | Duration (days) | Peak titer ($\log_{10}$pfu/ml) | Mean[a] | Peak | Day 28 | Day 49 or 56 |
| cpts-530/1009 | 3 | 7 | 2.1 | 0 | <0.7 | 0 | 0 | 1,552 | 3,823 |
| | 4 | 0 | <0.7 | 0 | <0.7 | 0 | 0 | 1,176 | 1,911 |
| cpts-530 | 5 | 0 | <0.7 | 0 | <0.7 | 0 | 0 | 10,085 | 6,654 |
| | 6 | 0 | <0.7 | 0 | <0.7 | 0.3 | 2 | 3,566 | 1,911 |
| cp-RSV | 11[b] | 5 | 1.0 | 0 | <0.7 | 0 | 0 | 776 | 2,048 |
| | 12[b] | 8 | 0.7 | 0 | <0.7 | 0 | 0 | 891 | 1,783 |
| None | 13[b] | 9 | 5.1 | 13 | 5.4 | 1.0 | 1 | <10 | 1,351 |
| | 14[b] | 9 | 6.0 | 8 | 6.0 | 1.7 | 4 | <10 | 676 |
| | 15[c] | 13 | 5.3 | 8 | 5.9 | 2.1 | 3 | <10 | 1,261 |
| | 16[c] | 9 | 5.4 | 8 | 5.6 | 1.0 | 3 | <10 | 20,171 |

[a]Mean rhinorrhea scores represent the sum of scores during the eight days of peak virus shedding divided by eight. Four is the highest score.
[b]Animals from Crowe et al. Vaccine 12: 691-699 (1994).
[c]Animals from Collins et al. Vaccine 8: 164-168 (1990).
[d]Serum neutralizing titers in this table, including those from animals previously described, were determined simultaneously in one assay.

Effect of Passively-Acquired Serum RSV Antibodies on cpts Mutants in Chimpanzees In order to examine the effect of passively-acquired serum RSV antibodies on attenuation, immunogenicity and protective efficacy of various cpts mutants of the invention in chimpanzees, the in vivo replication of cpts248, cpts248/404, and cpts530/1009, was evaluated in seronegative chimpanzees which were infused with RSV immune globulin two days prior to immunization (Table 16). Antibody was passively transferred in order to simulate the conditions which obtain in young infants who possess maternally-derived RSV antibodies. In this way, it was possible to assess the immunogenicity of each indicated mutant in the presence of passive RSV antibodies to determine whether the replication of highly attenuated viruses might be so reduced in infants with a moderate to high titer of passive antibodies as to preclude the induction of a protective immune response. It would also be possible to define the nature of the antibody response to immunization in the presence of passively acquired antibodies, and to define the extent and functional activity of the antibody response to virus challenge. The level of virus replication in the nasopharynx and the associated clinical score for the attenuated mutants was either not altered or only moderately altered by the presence of serum RSV antibodies when the infection of those animals was compared to that of non-infused seronegative chimpanzees. In contrast, the presence of passively-acquired antibodies effectively prevented virus replication of cpts248 in the lower respiratory tract. Because the other two mutants were already highly restricted in the lungs, the similar effect of passive antibodies could not be evaluated against those mutants.

Infusion of human RSV immune globulin yielded moderately high serum levels of RSV F antibodies (titer 1:640 to 1:1600), and neutralizing antibodies (titer 1:199 to 1:252), but not appreciable amounts of serum RSV G antibody detectable above background (Table 17). Chimpanzees who were infused with human RSV antibodies prior to immunization with cpts248/404, cpts530/1009, or cpts248 developed only one-tenth the quantity of RSV F antibodies and about one-half the titer of neutralizing antibodies by day 42 postimmunization, compared to non-infused immunized animals tested 28 days post-immunization. Because the infused human IgG contained substantial amounts of RSV F and RSV neutralizing antibodies, the residual antibodies from the infusion present in the 42-day serum samples could not be distinguished from antibodies produced de novo in response to immunization. Given the half-life of human serum IgG antibodies in chimpanzees (Prince et al., *Proc. Natl. Acad. Sci. USA* 85:6944-6948), the observed levels of F and neutralizing antibodies on day 42 following immunization with cpts are higher than would be predicted for a residuum of the infusion. In addition, the RSV G antibody response following immunization of the infused animals confirms that these chimpanzees mounted an immune response to immunization.

Four to six weeks following immunization the chimpanzees were challenged with wild-type RSV. Each of the animals exhibited complete resistance in their lower respiratory tract, whether or not human IgG was infused two days before immunization (Table 18). Non-infused animals developed a modest neutralizing antibody response to challenge or none at all (Table 17). In contrast, the infused chimpanzees uniformly developed an unusually high titer of RSV neutralizing antibodies in response to wild-type virus challenge despite the fact that virus replication had been severely restricted (Tables 17 and 18). Moreover, following immunization in the presence of antibodies the most attenuated virus, cpts248/404, which exhibited the lowest level of virus replication and immunization, had the highest post-challenge neutralizing antibody titers (Table 17). In contrast, the least attenuated virus, cpts248, had the lowest post-challenge neutralizing antibody titer of the three groups of infused animals. In addition to an increase in the quantity of the antibodies induced by immunization in the presence of antibodies, the quality of the antibodies, as measured by the neutralizing to ELISA F antibody titer ratio, was significantly greater than that induced by immunization in seronegative animals (Table 17). The neutralizing/ELISA F ratio of the antibodies produced in the infused immunized animals post-challenge was about 10- to 20-fold higher than in the non-infused animals and was consistent in all groups, regardless of mutant used to immunize (Table 17).

The presence of passively-acquired antibodies at the time of immunization with a live virus vaccine might alter the immune response to vaccine in three distinct ways. First, a significant decrease in the level of replication of vaccine virus might occur that results in decreased immunogenicity. It is possible that the passively-transferred RSV antibodies could restrict the replication of the vaccine viruses, especially the most defective mutants, and greatly decrease their immunogenicity. The results presented herein indicate that replication of the least attenuated mutant (cpts248) in the lower respiratory tract was indeed abrogated by the presence of passively-acquired serum IgG RSV antibodies, whereas replication in the upper respiratory tract did not appear to be significantly affected. The replication of the least attenuated mutant tested, cpts248, was $\geq$200-fold more (i.e. completely) restricted in the lower respiratory tract in the presence of antibodies. The level of replication of the more attenuated mutants, cpts530/1009 and cpts248/404, in the lower respiratory tract was highly restricted even in the seronegative animals. Therefore, a significant effect of passive antibodies on virus replication could not be detected. Immunization with each of the three attenuated mutants induced a high degree of protection against wild-type challenge in both the upper and lower respiratory tracts, whether or not passively-acquired RSV antibodies were present at the time of immunization. Thus, the level of replication of the vaccine viruses in the upper respiratory tract of passively-immunized chimpanzees was sufficient to induce a high level of resistance to wild-virus challenge which was comparable to that induced in non-infused animals.

Second, passive antibodies can alter the immune response to infection by causing a decrease in the amount and functional activity of antibodies that are induced. For this reason the magnitude and the character of the antibody response to live virus immunization in the presence of passive antibodies was analyzed. Postimmunization serum ELISA IgG F antibody titers of immunized, infused animals were 10-fold lower than the postimmunization F titers of non-infused seronegative animals. The serum RSV neutralizing antibody response was also slightly decreased in those animals, on average being 2-fold lower than in non-infused animals. Because some of the ELISA F and neutralizing antibodies detected postimmunization represent residual antibodies from the infusion, the actual decrease of the neutralizing and F antibody response caused by preexisting antibodies is probably even more significant than is apparent. Moreover, the human immune globulin preparation used contained a low level of antibodies to the G glycoprotein of RSV (Table 17). This petted an examination of the IgG RSV G glycoprotein antibody response of the chimpanzees to infection with the candidate vaccine viruses. The G antibody responses demonstrated at least a 4-fold or greater increase, indicating that each of the passively-immunized animals was infected by vaccine virus, including chimpanzees immunized with cpts248/404 which did not shed virus. The magnitude of the G antibody response to immunization did not appear to be adversely influenced by the passively transferred antibodies.

Thirdly, the antibody response to RSV wild-type virus challenge of animals immunized in the presence of passively-acquired antibodies could be altered. Chimpanzees immunized in the absence of infused antibodies exhibited significant resistance to subsequent RSV challenge. In addition, these animals failed to develop an appreciable antibody response to challenge virus. Although each of the 6 infused, immunized animals also exhibited significant resistance to RSV, a greatly enhanced antibody response to challenge was observed. Post-challenge F or G antibody levels in the treated animals immunized with cpts530/1009 or cpts248/404 were increased at least 10-fold, while the neutralizing antibody response represented as much as an 800-fold increase. These results suggest that repeated immunization of infants possessing maternal antibodies with live attenuated mutants beginning very early in life might stimulate effective resistance and an associated enhanced secondary antibody response of high quality. The mechanism responsible for an enhanced immune response to second infection in the absence of appreciable replication of the challenge virus is not understood. The presence of serum antibodies at the time of immunization, while allowing a modest antibody response to immunization in infused animals, favors the development of a B cell repertoire that elaborates antibodies of highly functional activity following subsequent RSV challenge.

The results reported herein are highly significant in that for the first time live attenuated RSV virus vaccine has been shown to be efficacious in an animal model which mimics the target population for an RSV vaccine, i.e. the four to six week old infant having passively acquired RSV neutralizing antibodies as a result of transplacental transfer from the mother. The importance of this finding is clear from the fact that, as discussed, supra, the high expectation that the passively transferred RSV antibodies would have inhibited the replication of the cpts vaccine, rendering it non-immunogenic and non-protective has, surprisingly, not been borne out.

TABLE 16

Replication of RSV cpts-248/404, cpts-248, or cpts-530/1009 in the upper and lower respiratory tract of seronegative chimpanzees, some of which were infused with RSV neutralizing antibodies two days prior to immunization.

| Animal Infected with $10^4$ pfu of indicated virus | Reciprocal serum RSV neutralizing antibody titer at time of immunization | Chimpanzee Number | Virus Replication ||||  Rhinorrhea Scores ||
|---|---|---|---|---|---|---|---|---|
| | | | Nasopharynx || | Trachea || | |
| | | | Duration (days) | Peak Titer ($\log_{10}$pfu/ml) | Duration (days) | Peak Titer ($\log_{10}$pfu/ml) | Peak | Mean |
| cpts-248/404 | <10 | 17 | 0 | <0.7 | 0 | <0.7 | 0 | 0 |
| | <10 | 20 | 9 | <0.7 | 0 | <0.7 | 0 | 0 |
| | <10 | 19 | 8 | 1.9 | 0 | <0.7 | 2 | 0.3 |
| | <10 | 20 | 9 | 2.0 | 0 | <0.7 | 1 | 0.2 |
| | | | (mean 4.3) | (mean 1.3) | (mean 0) | (mean <0.7) | (mean 0.8) | (mean 0.1) |
| | 142 | 21 | 0 | <0.7 | 0 | <0.7 | 2 | 0.6 |
| | 156 | 22 | 0 | <0.7 | 0 | <0.7 | 1 | 0.1 |
| | | | (mean 0) | (mean <0.7) | (mean 0) | (mean <0.7) | (mean 1.5) | (mean 0.4) |
| cpts-530/1009 | <10 | 1 | 9 | 3.1 | 0 | <1.0 | 1 | 0.3 |
| | <10 | 2 | 10 | 4.0 | 10 | 1.8 | 1 | 1.1 |
| | <10 | 3 | 9 | 4.0 | 0 | <1.0 | 1 | 0.6 |
| | <10 | 4 | 9 | 3.3 | 0 | <1.0 | 1 | 0.5 |
| | | | (mean 9.3) | (mean 3.6) | (mean 2.5) | (mean 1.2) | (mean 1.0) | (mean 0.6) |
| | 259 | 23 | 8 | 3.0 | 0 | <0.7 | 1 | 0.1 |
| | 190 | 24 | 7 | 1.2 | 0 | <0.7 | 1 | 0.2 |
| | | | (mean 7.5) | (mean 2.1) | (mean 0) | (mean <0.7) | (mean 1.0) | (mean 0.2) |
| cpts-248 | <10 | 25 | 10 | 4.6 | 8 | 5.4 | 1 | 0.2 |
| | <10 | 26 | 10 | 4.5 | 6 | 2.2 | 1 | 0.1 |
| | <10 | 27 | 9 | 4.7 | 10 | 2.1 | 1 | 0.1 |
| | <10 | 28 | 9 | 4.2 | 8 | 2.2 | 1 | 0.1 |
| | | | (mean 9.5) | (mean 4.5) | (mean 8.0) | (mean 3.0) | (mean 1.0) | (mean 0.1) |
| | 290 | 29 | 13 | 4.2 | 0 | <0.7 | 2 | 0.4 |
| | 213 | 30 | 16 | 4.7 | 0 | <0.7 | 3 | 0.9 |
| | | | (mean 14.5) | (mean 4.5) | (mean 0) | (mean <0.7) | (mean 2.5) | (mean 0.7) |

TABLE 17

Serum antibody response of chimpanzees immunized on day 0 with RSV cpts-248/404, cpts-248, or cpts-530/1009, in the presence or absence of passively-transferred antibodies, and challenged 4 to 6 weeks later with wild-type RSV A2.

| Animals infected with indicated virus | No. of animals | Infused with antibodies | RSV F |||| RSV G ||||
|---|---|---|---|---|---|---|---|---|---|---|
| | | | Prior to study | Day 0 (48 hrs. after infusion of antibodies) | Postimmunization[1] | 28 days post-challenge[2] | Prior to study | Day 0 (48 hrs. after infusion of antibodies) | Postimmunization[1] | 28 days post-challenge[2] |
| cpts-248/404 | 4 | no | <40 | <40 | 6,400 | 2,560 | 60 | 60 | 1,000 | 1,600 |
| | 2 | yes | <40 | 1,600 | 640 | 25,600 | 100 | 100 | 1,600 | 21,760 |
| cpts-530/1009 | 4 | no | <40 | <40 | 6,400 | 10,240 | <40 | <40 | 10,240 | 2,560 |
| | 2 | yes | <40 | 1,600 | 640 | 10,240 | 40 | 100 | 400 | 10,240 |
| cpts-248 | 4 | no | <40 | <40 | 7,840 | 6,400 | <40 | <40 | 250 | 2,560 |
| | 2 | yes | <40 | 640 | 1,600 | 5,400 | 40 | 40 | 1,600 | 5,440 |

TABLE 17-continued

Serum antibody response of chimpanzees immunized on day 0 with RSV cpts-248/404, cpts-248, or cpts-530/1009, in the presence or absence of passively-transferred antibodies, and challenged 4 to 6 weeks later with wild-type RSV A2.

|  | Animals infected with indicated virus | Neutralizing[3] | | | | |
|---|---|---|---|---|---|---|
|  |  | Prior to study | Day 0 (48 hrs. after infusion of antibodies) | Postimmunization[1] | 28 days post challenge[2] | F  G |
|  | cpts-248/404 | <10 | <10 | 208 | 382 | 0.2  0.1 |
|  |  | <10 | 199 | 111 | 92,681 | 4.3  3.6 |
|  | cpts-530/1009 | <10 | <10 | 256 | 2,521 | 1.0  0.3 |
|  |  | <10 | 225 | 52 | 37,641 | 3.7  3.7 |
|  | cpts-248 | <10 | <10 | 147 | 338 | 0.1  0.1 |
|  |  | <10 | 252 | 119 | 26,616 | 4.9  4.9 |

[1]The day on which postimmunization titer was determined was also the day on which challenge was performed, i.e., day 28 for animals not infused with antibody, day 42 for animals infused.
[2]Values determined from samples taken 28 days after challenge. Challenge performed on day 28 postimmunization for animals not infused with antibody, day 42 for animals infused.
[3]Determined by complement-enhanced 60% plaque reduction of RSV A2 in HEp-2 cell monolayer cultures. Neutralizing antibody titer represents the mean value from two tests.

TABLE 18

Immunization of chimpanzees with RSV cpts-248, cpts-248/404, or cpts-530/1009 cpts-530/1009 induces resistance to wild-type RSV A2 challenge 4-6 weeks later.

| Virus used for immunization | Passively-transferred RSV antibodies present | Chimpanzee Number | Replication of RSV A2 challenge virus[a] | | | | Rhinorrhea Scores | |
|---|---|---|---|---|---|---|---|---|
|  |  |  | Nasopharynx | | Trachea | | | |
|  |  |  | Duration (days) | Peak Titer ($\log_{10}$pfu/ml) | Duration (days) | Peak Titer ($\log_{10}$pfu/ml) | Mean[b] | Peak |
| cpts-248/404 | no | 17[c] | 0 | <0.7 | 0 | <0.7 | 0 | 0 |
|  | no | 18[c] | 8 | 3.4 | 0 | <0.7 | 0 | 0 |
|  | yes | 21 | 6 | 2.7 | 0 | <0.7 | 0.5 | 2 |
|  | yes | 22 | 0 | <0.7 | 0 | <0.7 | 0 | 0 |
| cpts-530/1009 | no | 1 | 7 | 2.1 | 0 | <0.7 | 0 | 0 |
|  | no | 2 | 0 | <0.7 | 0 | <0.7 | 0 | 0 |
|  | yes | 23 | 6 | 2.5 | 0 | <0.7 | 0.5 | 1 |
|  | yes | 24 | 7 | 2.0 | 0 | <0.7 | 0.2 | 1 |
| cpts-248 | no | 25[c] | 5 | 2.7 | 0 | <0.7 | 0 | 0 |
|  | no | 26[c] | 9 | 1.8 | 0 | <0.7 | 0 | 0 |
|  | yes | 29 | 0 | <0.7 | 0 | <0.7 | 0 | 0 |
|  | yes | 30 | 6 | 2.4 | 0 | <0.7 | 1.2 | 3 |
| none | no | 13[d] | 9 | 5.1 | 13 | 5.4 | 1.0 | 1 |
|  | no | 14[d] | 9 | 6.0 | 8 | 6.0 | 1.7 | 4 |
|  | no | 15[c] | 13 | 5.3 | 8 | 5.9 | 2.1 | 3 |
|  | no | 16[c] | 9 | 5.4 | 8 | 5.6 | 1.0 | 3 |

[a]Animals which were immunized with indicated virus 4 to 6 weeks prior were challenged with 10 pfu of RSV A2 wild-type virus.
[b]Mean rhinorrhea scores represent the sum of scores during the eight days of peak virus shedding divided by eight.
[c]Animals from Crowe, et al., Vaccine 12: 691-699 (1994).
[d]Animals from Collins, et al., Vaccine 8: 164-168 (1990).

EXAMPLE II

Use of Cold Adaptation to Attenuate cpRSV Mutants

This Example describes the introduction of growth restriction mutations into incompletely attenuated host range-restricted cpRSV strains by further passage of the strains at increasingly reduced temperatures to produce derivative strains which are more satisfactorily attenuated for use in human vaccines.

These cold-adaptation (ca) approaches were used to introduce further attenuation into the cpRSV 3131 virus, which is incompletely attenuated in seronegative children.

Under the first strategy, a parent stock of cold-passaged RSV A2 (cpRSV 3131) obtained from Flow Laboratories was prepared by passage in MRC-5 cells at 25° C. as described in Example 1. Briefly, cold-passaged virus was inoculated into MRC-5 or Vero cell monolayer culture at a multiplicity of infection of ≧0.01 and the infected cells were incubated for 3 to 14 days before subsequent passage. Virus was passaged over 20 times at 20-22° C. to derive more attenuated virus.

The technique of rapid passage, as soon as the first evidence of virus replication is evident (i.e., 3 to 5 days), was preferable for selection of mutants able to replicate efficiently at low temperatures. Additionally, an RSV subgroup B strain, St. Louis/14617/85 clone 1A1, was isolated in primary African Green monkey kidney cells, passaged and cloned in MRC cells (1A1-MRC14), and cold-passaged 52 times in MRC-5 or Vero cells at 32 to 22° C.

A second strategy employed a biologically cloned derivative of the uncloned parental cpRSV 3131 virus. This virus was biologically cloned in bovine embryonic kidney (BEK) cells [the tissue used to originally derive the cpRSV 3131 virus—see Friedewald et al., *J. Amer. Med. Assoc.* 204:690-694 (1968)]. This cloned virus was then passaged at 10 day intervals in Vero cells at low temperature. Alternatively, the cpRSV 3131 virus was cloned by two serial terminal dilutions (TD2P4) in MRC-5 cells and passaged at 10-day intervals in MRC-5 or Vero cells.

The third strategy involved selection of mutants that produce large plaques at low temperature. An RSV 3131 derivative virus designated plaque D1 that produces large plaques at 25° C. has been identified. This virus was derived from the third passage (P3) level of the cp3131-1 (BEK) lineage cp3131-17 (BEK) lineage. The largest plaque produced by P3 virus was amplified at 32° C., then re-plaqued at 25° C. Once again the largest plaque was selected, amplified, and re-plaqued. After five such cycles, large placque mutant virus D1 was obtained. D1 was biologically cloned by two additional cycles of plaque-to-plaque purification at 25° C.

Biologically cloned virus D1 produces distinctly and uniformly larger plaques at 25° C. than cp3131 or wild type virus A2. Thus D1 is cold adapted by the criterion of large plaque size at 25° C. Efficiency of plaque formation studies demonstrated that D1 is not temperature sensitive. At 37° C., D1 plaques are indistinguishable from those of wild-type RSV or cp3131, suggesting that D1 is not restricted in growth at this temperature. Consistent with this, D1 produces extensive cytopathic effects in Vero cell monolayers at 37° C. and 40° C. (i.e. the highest temperatures tested).

EXAMPLE III

Introduction of Further Attenuating Mutations into ts-RSV

This Example describes the use of ts mutants as parental viruses to produce more completely attenuated strains. Two RSV A2 ts mutants were selected for this process, namely ts-4 and ts-1 NG1. Two distinct methods were chosen to introduce additional mutations into the RSV ts mutants. First, the incompletely attenuated RSV ts mutant was subjected to chemical mutagenesis, and mutagenized progeny that are more temperature-sensitive with regard to plaque formation were selected for further analysis. Second, the RSV ts mutants were passaged at low temperature to select RSV nts mutants with the ca phenotype, i.e., increased capacity to replicate at suboptimal temperature compared to wild-type parental virus.

A parent stock of ts-1 NG1 virus was prepared from Flow Laboratories Lot M4 of live Respiratory Syncytial Virus (A-2) ts-1 NG-1 mutant, MRC-5 grown virus. This mutant, derived from the ts-1 mutant by a second round of mutagenesis using nitrosoguanidine, possesses two or more independent ts mutations, but still induces substantial rhinorrhea in susceptible chimpanzees. This virus was passaged twice in Vero cells at 32° C. to create a ts-1 NG-1 suspension for mutagenesis. The virus was then grown in the presence of $4 \times 10^{-4}$M 5-fluorouracil to induce additional mutations during replication or was exposed to 5-azacytidine at 36° C. after 5-fluorouracil treatment. The mutagenized stock was then analyzed by plaque assay on Vero cells that were maintained under an agar overlay, and, after an appropriate interval of incubation, plaques were identified microscopically. 586 plaques were picked, and the progeny of each plaque were separately amplified by growth on fresh monolayers of Vero cells. The contents of each of the tissue cultures inoculated with the progeny of a single plaque of mutagenized ts-1 NG-1 virus were separately harvested when cytopathic effects on the Vero cells appeared maximal. Progeny virus that was more temperature-sensitive than ts-1 NG1 was sought by titering these plaque pools on HEp2 cells at 32° C. and 36° C. Any virus exhibiting greater temperature sensitivity than ts-1 NG1 (i.e., 100-fold or greater reduction in titer at restrictive temperature [36° C.] compared to 32° C.) was evaluated further. Six plaque progeny more ts than the tsRSV ts-1 NG-1 parent virus were identified and these strains were biologically cloned by serial plaque-purification on Vero cells three times, then amplified on Vero cells. The cloned strains were titered at 32° C., 35° C., 36° C., 37° C., and 38° C. (efficiency of plaque formation assay) to confirm their ts phenotype. Efficiency of plaque formation data generated by assay on HEp-2 cells further confirmed the phenotype of the six mutants (Table 19).

The two most ts viruses, A-20-4 and A-37-8, were highly attenuated in mice compared to their ts-1 NG1 parent virus, indicating that acquisition of increased level of temperature sensitivity was accompanied by augmented attenuation (Table 20). These viruses were infectious for mice because they induced an antibody response. The ts-1 NG1/A-20-4 virus is attenuated for chimpanzees (Table 21) and infection of chimpanzees with ts-1 NG1/A-20-4 induced resistance to wild-type virus challenge (Table 22). Significantly, rhinorrhea does not occur.

Mutagenesis of the ts-4 virus was also performed, using the same method as for mutagenesis of ts-1 NG1, virus. Mutations were also introduced into the ts-4 viruses by cold-passage. The ts-4 virus replicates to high titer at 22° C. after 43 cold-passages. Six plaque progeny that were more ts than the RSV ts-4 parent virus were identified (Table 23). The ts-4 cp-43 is even further restricted in replication in Balb/c mice (Table 24).

TABLE 19

Efficacy of plaque formation of ts-1NG1 derivatives

| Virus | Titer ($log_{10}$pfu/ml) at indicated temperature | | | | |
|---|---|---|---|---|---|
| | 32° | 35° | 36° | 37° | 38° |
| A-204 (4-1)[a] | 5.9* | <1 | <1 | <1 | <1 |
| A-37-8 (1-2)[a] | 6.3 | 6.3 | <1 | <1 | <1 |
| A-15-7 | 3.5 | ND | 2.1 | 1.5 | <1 |
| A-25-8 | 5.3 | ND | 5.0* | 4.8* | <1 |
| A-21 | 5.1** | ND | 4.8** | 4.5** | <1 |
| Ts1NG1 | 6.6 | 6.6 | 6.5 | 6.6 | <1 |

[a]3x plaque purified
*Small-plaque phenotype (<50% wild-type plaque size)
**Pinpoint-plaque phenotype (<10% wild-type plaque size)
ND = Not Done

TABLE 20

Replication of ts-1 NG1 parent and progency viruses in Balb/c mice

| Virus | Dose ($\log_{10}$pfu) | Day Post-Infection | Titer in Lung 32° | Titer in Lung 38° | Titer in Lung 32° | Titer in Lung 38° |
|---|---|---|---|---|---|---|
| A2 wt | 6.1 | 4 | 4.66 ± 0.32[a] | 4.80 ± 0.16 | 3.18 ± 4.0 | 3.29 ± 0.33 |
|  |  | 5 | 5.18 ± 0.33 | 5.25 ± 0.23 | 3.40 ± 2.0 | 3.47 ± 0.17 |
| Ts1NG1 | 5.8 | 4 | 4.31 ± 0.17 | <2.0 | 2.82 ± 0.25 | <2.0 |
|  |  | 5 | 3.98 ± 0.12 | <2.0 | 2.74 ± 0.31 | <2.0 |
| Ts1NG1/A-20-4 | 6.1 | 4 | <2.0 | <2.0 | <2.0 | <2.0 |
|  |  | 5 | <2.0 | <2.0 | <2.0 | <2.0 |
| Ts1NG1/A-37-8 | 6.3 | 4 | <2.0 | <2.0 | <2.0 | <2.0 |
|  |  | 5 | <2.0 | <2.0 | <2.0 | <2.0 |

[a]Mean $\log_{10}$ pfu/g of indicated tissue ± standard error. 6 animals/group.

TABLE 21

Replication of of ts-1 NG1/A-20-4, ts-1 NG1, ts-1 or wild-type RSV A2 in the upper and lower respiratory tract of seronegative chimpanzees

| Animal infected with indicated virus | Route of Inoculation[a] | Chimpanzee number | Nasopharynx Duration[b] (Days) | Nasopharynx Peak titer ($\log_{10}$pfu/ml) | Trachea Duration[b] (Days) | Trachea Peak titer ($\log_{10}$pfu/ml) | Rhinorrhea Scores Mean[c] | Rhinorrhea Scores Peak |
|---|---|---|---|---|---|---|---|---|
| ts-1NG1/A-20-4 | IN + IT | 15 | 0 | <0.7 | 0 | <0.7 | 0 | 0 |
|  | IN + IT | 16 | 0 | <0.7 | 0 | <0.7 | 0 | 0 |
|  | IN + IT | 17 | 0 | <0.7 | 0 | <0.7 | 0 | 0 |
|  | IN + IT | 18 | 16[d] | 2.7 | 0 | <0.7 | 0 | 0 |
|  |  |  | mean 4.0 | mean 1.2 | mean 0 | mean <0.7 | mean 0 | mean 0 |
| ts-1 NG1 | IN | 19[e] | 8 | 4.2 | 0 | <1.1 | 0.6 | 1 |
|  | IN | 20[e] | 7 | 3.9 | 0 | <1.1 | 0.7 | 1 |
|  | IN | 21[e] | 13 | 5.4 | 0 | <1.1 | 0.4 | 1 |
|  | IN | 22[e] | 10 | 5.2 | 10d | 3.7[d] | 0.6 | 2 |
|  |  |  | mean 9.5 | mean 4.7 | mean 2.5 | mean 1.8 | mean 0.6 | mean 1.3 |
| ts-1 | IN | 23[e] | 16 | 3.4 | 0 | <1.1 | 0.4 | 1 |
|  | IN | 24[e] | 13 | 4.4 | 0 | <1.1 | 1.0 | 3 |
|  | IN | 25[e] | 13 | 5.0 | 13d | 2.2 | 2.0 | 4 |
|  | IN | 26[e] | 10 | 3.4 | 0 | <1.1 | 1.0 | 2 |
|  |  |  | mean 13 | mean 4.1 | mean 3.3 | mean 1.4 | mean 1.1 | mean 2.5 |
| A2 wild-type | IN | 9[b] | 9 | 5.1 | 13 | 5.4 | 1.0 | 1 |
|  | IN | 10[b] | 9 | 6.0 | 8 | 6.0 | 1.7 | 4 |
|  | IN + IT | 11[e] | 13 | 5.3 | 8 | 5.9 | 2.1 | 3 |
|  | IN + IT | 12[e] | 9 | 5.4 | 8 | 5.6 | 1.0 | 3 |
|  |  |  | mean 10 | mean 5.5 | mean 9.3 | mean 5.7 | mean 1.4 | mean 2.8 |

[a]IN = Intranasal only; IN + IT = Both intranasal and intratracheal administration.
[b]Indicates last day post-infection on which virus was recovered.
[c]Mean rhinorrhea score represents the sum of daily scores for a period of eight days surrounding the peak day of virus shedding, divided by eight. Four is the highest score; zero is the lowest score.
[d]Virus isolated only on day indicated.
[e]Animals from Crowe, et al., Vaccine 11: 1395-1404 (1993).

TABLE 22

Immunization of chimpanzees with $10^4$ pfu of RSV ts-1 NG1/A-20-4, ts-1 NG1, or ts-1 induces resistance to $10^4$ pfu RSV A2 wild-type virus challenge on day 28.

| Virus used to immunize animal | Chipanzee number | Nasopharynx Duration (Days) | Nasopharynx Peak titer ($\log_{10}$pfu/ml) | Trachea Duration (Days) | Trachea Peak titer ($\log_{10}$pfu/ml) | Rhinorrhea scores Mean[a] | Rhinorrhea scores Peak | Serum neutralizing antibody titer (reciprocal $\log_2$) on day indicated[b]) Day 28 | Day 49 or 56 |
|---|---|---|---|---|---|---|---|---|---|
| ts-1 NG1/A-20-4 | 15 | 0 | <0.7 | 0 | <0.7 | 0 | 0 | <3.3 | 10.7 |
|  | 16 | 0 | <0.7 | 0 | <0.7 | 0 | 0 | <3.3 | 11.9 |
|  | 17 | 0 | <0.7 | 0 | <0.7 | 0 | 0 | 5.3 | 10.3 |
|  | 18 | 3 | 2.0 | 0 | <0.7 | 0 | 0 | 8.2 | 11.8 |
|  |  | mean 0.8 | mean 1.0 | mean 0 | mean <0.7 | mean 0 | mean 0 | mean 5.0 | mean 11.2 |

TABLE 22-continued

Immunization of chimpanzees with $10^4$ pfu of RSV ts-1 NG1/A-20-4, ts-1 NG1, or ts-1 induces resistance to $10^4$ pfu RSV A2 wild-type virus challenge on day 28.

| Virus used to immunize animal | Chipanzee number | Virus Recovery | | | | Rhinorrhea scores | | Serum neutralizing antibody titer (reciprocal $log_2$) on day indicated[b]) | |
|---|---|---|---|---|---|---|---|---|---|
| | | Nasopharynx | | Trachea | | | | | |
| | | Duration (Days) | Peak titer ($log_{10}$pfu/ml) | Duration (Days) | Peak titer ($log_{10}$pfu/ml) | Mean[a] | Peak | Day 28 | Day 49 or 56 |
| ts-1 NG1 | 19[b] | 0 | <0.7 | 0 | <1.1 | 0 | 0 | 11.1 | 9.8 |
| | 20[b] | 0 | <0.7 | 0 | <1.1 | 0 | 0 | 12.7 | 9.1 |
| | 21[b] | 0 | <0.7 | 0 | <1.1 | 0 | 0 | 10.8 | 11.0 |
| | 22[b] | 0 | <0.7 | 0 | <1.1 | 0 | 0 | 10.0 | 8.6 |
| | | mean 0 | mean <0.7 | mean 0 | mean <1.1 | mean 0 | mean 0 | mean 11.1 | mean 9.6 |
| ts-1 | 23[b] | 0 | <0.7 | 0 | <1.1 | 0 | 0 | 9.4 | 10.5 |
| | 29[b] | 0 | <0.7 | 0 | <1.1 | 0 | 0 | 12.4 | 12.8 |
| | 25[b] | 5 | 0.7 | 0 | <1.1 | 0 | 0 | 9.0 | 9.6 |
| | 26[b] | 5 | 0.7 | 0 | <1.1 | 0 | 0 | 13.4 | 12.0 |
| | | mean 2.5 | mean 0.7 | mean 0 | mean <1.1 | mean 0 | mean 0 | mean 11.0 | mean 11.2 |
| none | 9[c] | 9 | 5.1 | 13 | 5.4 | 1.0 | 1 | <3.3 | 11.0 |
| | 10[c] | 9 | 6.0 | 8 | 6.0 | 1.7 | 4 | <3.3 | 9.8 |
| | 11[b] | 13 | 5.3 | 8 | 5.9 | 2.1 | 3 | <3.3 | 9.4 |
| | 12[b] | 9 | 5.4 | 8 | 5.6 | 1.0 | 3 | <3.3 | 14.5 |
| | | mean 10 | mean 5.5 | mean 9.3 | mean 5.7 | mean 1.5 | mean 2.8 | mean <3.3 | mean 11.1 |

[a]Mean rhinorrhea score represents the sum of scores during the eight days of peak virus shedding divided by eight. Four is the highest score; zero is the lowest score.
[b]Animals from Crowe, et al., Vaccine 11: 1395-1404 (1993).
[c]Animals from Collins, et al., Vaccine 8: 164-168 (1990).
[d]Serum neutralizing titers in this table were determined in a new assay simultaneously with other specimens represented in the table.

TABLE 23

The efficiency of plaque formation of six mutants derived from RSV ts-4 and tested in HEp-2 cells at permissive and restrictive temperatures, compared with controls.

| Virus | The titer of virus ($log_{10}$pfu/ml) at the indicated temperature (° C.) | | | | | | | | | Small-plaques at 32° C. | Shut-off temperature (° C.)[1] |
|---|---|---|---|---|---|---|---|---|---|---|---|
| | 32 | 33 | 34 | 35 | 36 | 37 | 38 | 39 | 40 | | |
| A2 wild-type | 5.7 | 5.8 | 5.5 | 5.5 | 5.3 | 5.5 | 5.5 | 5.4 | 5.5 | no | >40 |
| ts-4 | 4.5 | 4.7 | 4.4 | 4.7 | 4.7 | 4.1 | 3.7 | 3.0 | 2.5 | no | 40 |
| ts-4 cp-43 | 6.2 | 6.1 | 6.1 | 6.0 | 4.4* | 4.2 | 1.7** | <0.7**** | <0.7 | no | 37 |
| ts-4/20.7.1 | 6.0 | 5.9 | 5.7 | 5.7* | 4.5** | 1.8 | <0.7 | <0.7 | <0.7 | no | 37 |
| ts-4/19.1.2 | 5.8 | 5.7 | 5.5 | 5.6* | 4.4** | <0.7 | <0.7 | <0.7 | <0.7 | no | 37 |
| ts-4/15.8.2 | 5.3* | 5.4* | 4.8* | 4.9* | 2.8** | <0.7 | <0.7 | <0.7 | <0.7 | yes | 36 |
| ts-4/29.7.4 | 5.7 | 5.6 | 5.6 | 5.7* | <0.7 | <0.7 | <0.7 | <0.7 | <0.7 | no | 36 |
| ts-4/31.2.4 | 4.7 | 4.2 | 4.1 | 4.0* | <0.7 | <0.7 | <0.7 | <0.7 | <0.7 | no | 36 |

[1]Shut-off temperature is defined as the lowest restrictive temperature at which a 100-fold or greater reduction of plaque titer is observed (bold figures in table).
*Small-plaque phenotype (<50% wild-type plaque size)
**Pinpoint-plaque phenotype (<10% wild-type plaque size)

TABLE 24

Replication of RSV ts-4 and RSV ts-4 cp-43 in Balb/c mice[1]

| Virus used to infect animals: | Shutoff temperature of virus (° C.) | Virus titer (mean $log_{10}$pfu/g tissue of six animals ± standard error) | |
|---|---|---|---|
| | | Nasal turbinates | Lungs |
| A2 wild-type | >40 | 5.0 ± 0.14 | 5.2 ± 0.05 |
| ts-4 | 39 | 4.3 ± 0.09 | 4.7 ± 0.11 |
| ts-4 cp-43 | 37 | 2.1 ± 0.09 | 2.7 ± 0.27 |

[1]Mice were administered $10^{6.3}$ p.f.u. intranasally under light anesthesia on day 0, then sacrificed by $CO_2$ asphyxiation on day 4.

EXAMPLE IV

RSV Subgroup B Vaccine Candidates

This Example describes the development of RSV subgroup B virus vaccine candidates. The same approach used for the development of the subgroup A mutants of the invention was utilized for the subgroup B viruses. A parent stock of wild-type B-1 RS virus was cold-passaged 52 times in Vero cells at low temperature (20-25° C.) and the virus was subjected to plaque purification at passages 19 and 52. Three of the clones derived from the passage 52 suspension were evaluated independently, and one clone, designated RSV B-1cp52/2B5, was selected for further evaluation because it was highly attenuated in the upper and lower respiratory tract of the cotton rat (Table 25). An evaluation of several clones at different passage levels of the cp RSV B-1 virus indicate that the RSV B-1cp52/2B5 mutant sustained multiple mutations that independently contribute to its attenuation phenotype. The RSV B-1cp52/2B5 mutant retained its attenuation phenotype following prolonged replication in immunosuppressed cotton rats (Table 26). This finding of a high level of genetic stability is consistent with the fact that it possesses three mutations contributing to the attenuation phenotype.

Further evaluation of the subgroup B mutants in order to characterize them in a similar manner as the subgroup A mutants, was carried out in Caribbean Green monkeys (Tables 27 and 28) and chimpanzees (Table 29). Monkeys immunized with either RSV B-1 cp-23 or cp52/2B5 were resistant to replication of RSV B-1 wild-type virus, indicating that infection with the highly attenuated derivatives of the RSV B-1 wild-type virus was sufficient to induce resistance to wild-type challenge (Table 27).

The results in the seronegative chimpanzee, like that in the Green monkeys, clearly evidence the attenuation of the RSV B-1cp52/2B5 in the upper and lower respiratory tracts.

The RSV B-152/2B5 mutant has been further mutagenized with 5-fluorouracil and the resulting plaques picked and screened at 32° vs. 38° C. for the ts phenotype. The selected cpts mutants were plaque-purified three times in Vero cells and then amplified twice in Vero cells. As a result, seven cpts mutants of RSV B-1cp52/2B5 have been identified (Table 30) and their level of replication in cotton rats has been studied (Table 31). One of these mutants, namely cpts176, was further mutagenized and a series of mutant derivatives were obtained that were more ts in vitro than the RSV B-1cpts 176 parent virus (Table 32).

As with the subgroup A mutants of the invention, the subgroup B mutants are infectious and exhibit a significant degree of attenuation for cotton rats, monkeys, and chimpanzees. Despite attenuation in vivo, the RSV B-1 cp mutant viruses induced resistance in monkeys against wild-type challenge. The ts mutants of the RSV B-1 cpts52/2B5 virus are attenuated and demonstrate a more restricted level of replication in the nasopharynx and lungs of the cotton rat than the RSV B-1 52/2B5 parent virus.

TABLE 25

Replication in cotton rats of RSV B-1 wild-type compared with five plaque-purified cold-passaged mutants derived from RSV B-1, in two separate experiments.

| Virus used to infect | Virus recovery ($\log_{10}$pfu/g tissue) on day 4* | | | |
|---|---|---|---|---|
| | Nasal turbinates | | Lungs | |
| animals on day 0** | Exp. 1 | Exp. 2 | Exp. 1 | Exp. 2 |
| RSV B-1 wild-type | 4.7 ± 0.14 | 5.1 ± 0.10 | 5.4 ± 0.15 | 5.8 ± 0.08 |
| RSV B-1 cp-12/B1A | nd | 3.3 ± 0.15 | nd | 4.4 ± 0.10 |
| RSV B-1 cp-23 | nd | 2.4 ± 0.36 | nd | 3.2 ± 0.31 |
| RSV B-1 cpsp-52/1A1 | 1.7 ± 0.11 | 2.1 ± 0.27 | 3.0 ± 0.13 | 2.3 ± 0.07 |
| RSV B-1 cp-52/2B5 | 1.8 ± 0.25 | 2.2 ± 0.3 | 1.8 ± 0.11 | 1.5 |
| RSV B-1 cp-52/3C1 | 1.8 ± 0.14 | nd | 1.8 ± 0.14 | nd |
| RSV A2 | 5.9 ± 0.09 | 5.4 ± 0.07 | 6.6 ± 0.06 | 6.1 ± 0.06 |
| RSV A2 cpts530/1009 | 3.2 ± 0.11 | 2.1 ± 0.22 | 2.1 ± 0.19 | 1.7 ± 0.12 |

*Virus recovery determined by titration of tissue homogenates on Vero cell monolayer cultures at 32° C. with a 10-day incubation in Experiment 1, 7-day incubation in Experiment 2.
**Cotton rats infected intranasally with $10^{5.5}$ pfu of indicated virus.
nd = not done

TABLE 26

Growth in cotton rats of day 14 isolates* from RSV B-1 cp52/2B5 infected immunosuppressed cotton rats compared with controls

| Virus infected animals[a] | Virus Recovery Virus titer on day 4 in indicated tissue (mean $\log_{10}$pfu/g tissue ± standard error of the mean) | | RSV B-1 wild-type ($\log_{10}$pfu/g) | |
|---|---|---|---|---|
| | Nasal turbinates[b] | Lungs[c] | Nasal turbinates | Lungs |
| RSV B-1 wild-type | 3.9 ± 0.03 (6/6) | 4.8 ± 0.12 (6/6) | — | — |
| RSV B-1 cp 52/2B5 | 2.0 ± 0.07 (8/8) | <1.5 (0/8) | 1.9 | >3.3 |
| isolate 1 | 1.5 ± 0.13 (5/8) | 1.5 ± 0.04 (1/8) | 2.5 | 3.3 |
| isolate 2 | 1.5 ± 0.13 (6/8) | <1.5 (0/8) | 2.4 | >3.3 |
| isolate 3 | 1.5 ± 0.16 (3/8) | <1.5 (0/8) | 2.5 | >3.3 |
| isolate 4 | 1.3 ± 0.09 (4/8) | <1.5 (0/8) | 2.6 | >3.3 |
| isolate 5 | 1.2 ± 0.00 (2/8) | <1.5 (0/8) | 2.7 | >3.3 |
| isolate 6 | 1.2 ± 0.00 (3/8) | <1.5 (0/8) | 2.7 | >3.3 |
| isolate 7 | 1.3 ± 0.06 (3/8) | <1.5 (0/8) | 2.7 | >3.3 |

*Isolates were virus suspensions obtained following amplification by one Vero cell tissue culture passage of virus present in the original nasal turbinate homogenate on day 14 of an immunosuppressed cotton rat.
[a]Groups of 8 cotton rats infected with $10^{5.5}$ pfu of indicated virus in a 0.1 ml inoculum on day 0.
[b]( )indicates the numbers of animals from which virus was detected at 1.2 $\log_{10}$pfu/g or greater.
[c]( )indicates the numbers of animals from which virus was detected at 1.5 $\log_{10}$pfu/g or greater.

TABLE 27

Table 27. Replication in Caribbean Green monkeys of RSV A2 and RSV B-1 wild-types compared with that of two cold-passaged mutants derived from RSV B-1, followed by homologous or heterologous RSV A2 or B-1 wild-type challenge

| Virus used to infect animals on day 0[a] | Immunization | | | | Challenge | | |
|---|---|---|---|---|---|---|---|
| | NP swab | | Tracheal Lavage | | Chal- lenge virus | NP swab | Tracheal Lavage |
| | Peak titer[b] | Days shed[b] | Peak titer | Days shed | | Peak titer[b] | Peak titer[b] |
| A2 | 3.4 | 9 | <0.7 | 0 | A2 | <0.7 | <0.7 |
| | 3.5 | 7 | <0.7 | 0 | A2 | <0.7 | <0.7 |
| | 3.5 | 9 | 4.8 | 10 | A2 | <0.7 | <0.7 |
| | 3.2 | 8 | 0.7 | 7 | A2 | <0.7 | <0.7 |
| | 1.7 | 6 | <0.7 | 0 | B-1 | <0.7 | <0.7 |
| | 3.5 | 10 | <0.7 | 0 | B-1 | <0.7 | <0.7 |
| | 2.4 | 8 | 0.7 | 0 | B-1 | <0.7 | <0.7 |
| | 4.2 | 9 | <0.7 | 0 | B-1 | <0.7 | <0.7 |
| | mean 3.2 | mean 8.3 | mean 1.2 | | | | |
| B-1 | 2.8 | 9 | 1.5 | 10* | B-1 | <0.7 | <0.7 |
| | 2.3 | 9 | 1.9 | 7 | B-1 | <0.7 | <0.7 |
| | 2.2 | 7 | 1.7 | 10* | B-1 | <0.7 | <0.7 |
| | 2.2 | 9 | 1.3 | 10* | B-1 | <0.7 | <0.7 |
| | 1.6 | 8* | 1.2 | 5* | A2 | <0.7 | <0.7 |
| | 2.1 | 10 | 1.7 | 7* | A2 | <0.7 | <0.7 |
| | mean 2.2 | mean 8.7 | mean 1.6 | | | mean <0.7 | mean <0.7 |
| B-1 cp-23 | 1.8 | 14 | <0.7 | 0 | B-1 | <0.7 | <0.7 |
| | 1.3 | 5 | <0.7 | 0 | B-1 | <0.7 | <0.7 |
| | 2.0 | 8 | 0.7 | 10 | B-1 | <0.7 | <0.7 |
| | 1.7 | 4 | <0.7 | 0 | B-1 | <0.7 | <0.7 |
| | mean 1.7 | mean 7.8 | mean <0.7 | | | mean <0.7 | mean <0.7 |
| B-1 cp-52 | 1.3 | 8 | <0.7 | 0 | B-1 | <0.7 | <0.7 |
| | 1.3 | 4 | <0.7 | 0 | B-1 | <0.7 | <0.7 |
| | 1.3 | 7 | <0.7 | 0 | B-1 | <0.7 | <0.7 |
| | 0.7 | 3* | <0.7 | 0 | B-1 | <0.7 | <0.7 |

TABLE 27-continued

Table 27. Replication in Caribbean Green monkeys of RSV A2 and RSV B-1 wild-types compared with that of two cold-passaged mutants derived from RSV B-1, followed by homologous or heterologous RSV A2 or B-1 wild-type challenge

| Virus used to infect animals on day 0[a] | Immunization | | | | Challenge virus | Challenge | |
|---|---|---|---|---|---|---|---|
| | NP swab | | Tracheal Lavage | | | NP swab | Tracheal Lavage |
| | Peak titer[b] | Days shed[b] | Peak titer | Days shed | | Peak titer[b] | Peak titer[b] |
| | mean 1.2 | mean 5.5 | mean <0.7 | | | mean <0.7 | mean <0.7 |

[a]Animals infected intratracheally and intranasally with $10^{5.5}$ p.f.u. virus at each site in a 1.0 ml inoculum on day 0.
[b]Log$_{10}$pfu/ml titers determined by plaque assay on HEp-2 cell monolayer cultures for RSV A2, and Vero cell monolayer cultures for RSV B-1 and its derivatives.
*Virus detected only on day indicated.

TABLE 28

Neutralizing antibody response of Caribbean Green Monkeys infected with RSV A2, RSV B-1, or B-1 cp derivatives, then challenged with homologous or heterologous wild-type virus one month later.

| Animals infected on day 0 with indicated virus (number of animals) | Day 28 challenge virus (number of animals) | 60% Plaque reduction serum neutralizing titer against indicated virus (reciprocal mean) | | | | | |
|---|---|---|---|---|---|---|---|
| | | RSV A2 | | | RSV B-1 | | |
| | | Day 0 | Post-infection (day 28) | Post-challenge (day 56) | Day 0 | Post-infection (day 28) | Post-challenge (day 56) |
| A2 (8) | A2 (4) | <10 | 53,232 | 40,342 | <10 | 1,552 | 1,911 |
| | B-1 (4) | | | 23,170 | | | 1,911 |
| B-1 (6) | B-1 (4) | <10 | 3,327 | 3,822 | <10 | 2,048 | 2,521 |
| | A2 (2) | | | 30,574 | | | 35,120 |
| B-1 cp23 (4) | B-1 (4) | <10 | 6,208 | 10,086 | <10 | 4,705 | 7,132 |
| B-1 cp-52/2B5 (4) | B-1 (4) | <10 | 194 | 16,384 | <10 | 239 | 3,822 |

TABLE 29

The replication of RSV B-1 or RSV B-1 cp-52 in seronegative chimpanzees following simultaneous intratracheal and intranasal administration.[a]

| Animal infected with indicated virus on day 0 | Infection dose (pfu) | Exp. | Virus replication | | | | Rhinorrhea score | |
|---|---|---|---|---|---|---|---|---|
| | | | Nasopharynx | | Trachea | | | |
| | | | Duration[b] (days) | Peak titer (log$_{10}$pfu/ml) | Duration[b] (days) | Peak titer (log$_{10}$pfu/ml) | Peak | Mean[c] |
| RSV B-1 wild-type | $10^4$ | 1 | 9 | 3.7 | 8 | 3.2 | 1 | 0.5 |
| | | 1 | 10 | 3.5 | 0 | <0.7 | 2 | 0.9 |
| | | 1 | 10 | 2.8 | 0 | <0.7 | 3 | 1.1 |
| | | 1 | 10 | 2.7 | 8 | 3.4 | 3 | 0.9 |
| | | | avg. 9.8 | mean 3.2 | avg. 4.0 | mean 2.0 | mean 2.3 | mean 0.9 |
| | $10^5$ | 2 | 7 | 2.8 | 8 | 1.0 | 1 | 1.0 |
| | | 2 | 7 | 3.3 | 4 | 3.9 | 3 | 1.3 |
| | | | avg. 7.5 | mean 3.1 | avg. 6.0 | mean 2.5 | mean 2.0 | mean 1.1 |
| B-1 cp-52/2B5 | $10^4$ | 1 | 5 | 1.5 | 0 | <0.7 | 0 | 0 |
| | | 1 | 0 | <0.7 | 0 | <0.7 | 0 | 0 |
| | $10^5$ | 3 | 0 | <0.7 | 0 | <0.7 | 0 | 0 |
| | | 3 | 0 | <0.7 | 0 | <0.7 | 0 | 0 |
| | | | avg. 1.2 | mean 0.9 | mean 0 | mean <0.7 | mean 0 | mean 0 |

[a]These data were combined from three separate experiments, the infection dose of indicated virus in the first experiment was $10^4$, the second and third experiments were $10^5$.
[b]Indicates the last day post-infection on which virus was recovered.
[c]Mean rhinorrhea score represents the sum of daily scores for a period of eight days surrounding the peak day of virus shedding, divided by eight. Four is the highest score; zero is the lowest score.

TABLE 30

The efficiency of plaque formation of eight mutants derived from RSV B-1 cp52/2B5 Plaque titer ($\log_{10}$pfu/ml in Vero of HEp-2 Cells at indicated temperatures (° C.)

| RVS | Vero 32 | HEp-2 32 | 35 | 36 | 37 | 38 | 39 | HEp-2 Shutoff temp (° C.) |
|---|---|---|---|---|---|---|---|---|
| B-1 wild-type | 6.1 | 5.8 | 5.7 | 5.6 | 5.6 | 5.7 | 5.5 | >39 |
| B-1 cp52/2B5 | 5.9 | 5.4 | 5.2 | 5.1 | 5.0 | 5.0 | 4.7** | >39 |
| cpts452 | 6.1 | 5.6 | 5.2 | 5.2 | 3.3** | 3.1** | <0.7 | 37 |
| cpts1229 | 5.7 | 5.1 | 4.9 | 5.1 | 4.4** | <0.7 | <0.7 | 38 |
| cpts1091 | 5.7 | 5.1* | 4.7** | 5.2** | <0.7 | <0.7 | <0.7 | 37 |
| cpts784 | 5.1 | 4.3* | 4.0** | 4.1** | <0.7 | <0.7 | <0.7 | 37 |
| cpts176 | 6.1 | 5.4* | 4.8* | 5.0** | <0.7 | <0.7 | <0.7 | 37 |
| cptssp1415[a] | 5.8 | <0.7 | <0.7 | <0.7 | <0.7 | <0.7 | <0.7 | 38 |
| cpts1324 | 5.9 | 5.1 | 5.0* | 5.0 | <0.7 | <0.7 | <0.7 | 37 |
| cpts1313 | 5.7 | 3.9** | 3.0** | <0.7 | <0.7 | <0.7 | <0.7 | 36 |
| AS | 6.4 | 6.3 | 6.3 | 6.3 | 6.3 | 6.3 | 6.3 | >39 |
| A2/248 | 6.3 | 6.3 | 6.2 | 6.3 | 5.8 | <0.7 | <0.7 | 38 |
| A2/248/404 | 4.4 | 4.3 | 3.3 | 4.0 | <0.7 | <0.7 | <0.7 | 37 |
| A2/248/955 | 4.8 | 4.8 | 4.8 | 4.4 | <0.7 | <0.7 | <0.7 | 37 |

*Small-plaque phenotype (<50% wild-type plaque size).
**Pinpoint-plaque phenotype (<10% wild-type plaque size).
[a]At 32° C., no plaques were observed. Therefore, no shut-off temperature was determined by efficiency of plaque formation. The mutant was assigned a shutoff temperature of 38° C. in HEp-2 cell culture as determined by a 100-fold decrease in virus yield ($TCID_{50}$) in liquid medium overlay.
Bold figures denote shutoff temperatures (defined as the lowest restrictive temperature at which a 100-fold or greater reduction of plaque titer was observed).

TABLE 31

Level of replication in cotton rats of seven ts mutants derived from RSV B-1 cp-52/2B5

| RSV | Replication in cotton rats[1] (mean $\log_{10}$pfu/g tissue of six animals ± s.e.) | | | |
|---|---|---|---|---|
| | Nasal turbinates | | Lungs | |
| B-1 wild-type | 4.3 ± 0.05 | (6/6)[2] | 4.4 ± 0.25 | (6/6) |
| B-1 cp52/2B5 | 1.7 ± 0.11 | (6/6) | <1.5 | (0/6) |
| cpts452 | 1.4 ± 0.1 | (3/6) | <1.5 | (0/6) |
| cpts1091 | 1.7 ± 0.07 | (4/6) | <1.5 | (0/6) |
| cpts784 | 1.5 | (1/6) | <1.5 | (0/6) |
| cpts1229 | 1.4 ± 0.15 | (3/6) | <1.5 | (0/6) |
| cpts176 | 1.5 ± 0.17 | (3/6) | <1.5 | (0/6) |
| cptssp1415 | <1.2 | (0/6) | <1.5 | (0/6) |
| cpts1324 | <1.2 | (0/6) | <1.5 | (0/6) |

[1]Cotton rats were inoculated intranasally with 4.5-5.8 $\log_{10}$pfu under light anesthesia on day 0, then sacrificed by $CO_2$ asphyxiation on day 4.
[2]Titer from samples containing virus only. Parentheses indicate fraction of samples containing virus.

TABLE 32

The efficiency of plaque formation of 14 mutants derived from RSV B-1 cpts176, compared with controls
In vitro efficiency of plaque formation in HEp-2 cell monolayer culture

| RSV | The titer of virus ($\log_{10}$pfu/ml) at the indicated temperature (° C.) | | | | Shut-off temperature (° C.)[1] |
|---|---|---|---|---|---|
| | 32 | 35 | 36 | 37 | |
| B-1 wild-type | 5.6 | 5.5 | 5.4 | 5.3 | >39 |
| B-1 cp52/2B5 | 5.7 | 5.7 | 5.6 | 5.3 | >39 |
| B-1 cpts176 | 5.5 | 3.5 | 3.0 | 1.9 | 36/37 |
| 176/645 | 3.8 | 3.0 | 2.6 | <0.7** | 37 |
| 176/860 | 3.1 | 2.5 | 2.4 | <0.7 | 37 |
| 176/196 | 3.3 | 2.5 | 2.0** | <0.7 | 37 |
| 176/219 | 2.6 | 2.3 | 2.0** | <0.7 | 37 |
| 176/18 | 4.0 | 3.2 | <0.7 | <0.7 | 36 |
| 176/73 | 2.6 | 2.0 | <0.7 | <0.7 | 36 |
| 176/1072 | 3.2 | 2.3 | <0.7 | <0.7 | 36 |
| 176/1038 | 2.8 | 2.2 | <0.7 | <0.7 | 36 |
| 176/81 | 2.2 | 2.0 | <0.7 | <0.7 | 36 |
| 176/1040 | 3.2 | 2.0 | <0.7 | <0.7 | 36 |
| 176/1045 | 2.5 | 1.9 | <0.7 | <0.7 | 36 |
| 176/517 | 3.1 | 2.0 | <0.7** | <0.7 | 36 |
| 176/273 | 2.3 | <0.7 | <0.7 | <0.7 | 35 |
| 176/427 | 3.5 | <0.7 | <0.7 | <0.7 | 35 |

**Pinpoint-plaque phenotype (<10% wild-type plaque size)
[1]Shut-off temperature is defined as the lowest restrictive temperature at which a 100-fold or greater reduction of plaque titer is observed (bold figures in table).

To aid in the evaluation and manipulation of RSV B subgroup vaccine candidates, the complete nucleotide sequence of the wild-type B-1 virus has been determined [SEQ ID NO:2]. This sequence was compared with the sequence of the attenuated B-1 derivative, cp-52/2B5 (cp-52), described above. This sequence analysis revealed a large deletion in cp-52 spanning most of the SH and G genes, with no predicted ORF for either gene. More specifically, most of the region spanning the SH and G genes of the cp-52 virus was deleted, retaining only the SH gene-start signal and a portion of the 3' (downstream) end of the G gene and its gene-end signal. The remaining SH:G region could encode a chimeric transcript of ~91 nucleotides with no ORF. Northern blot analysis of cp-52 confirmed that multiple unique polytranscripts contained SH:G read-through mRNAs, consistent with a deletion mutation spanning the SH:G gene junction. Western blot and immunostain assays confirmed that intact G glycoprotein was not produced by the cp-52 virus. In addition to the long deletion, cp-52 virus contains seven nucleotide differences (Table 33), five of which are coding changes (one in the F gene and four in the L gene), one is silent (F gene), and one is in the noncoding G:F intergenic region. Importantly, this RSV mutant remains highly infectious in tissue culture despite the absence of SH and G proteins. These data identify a novel class of replication competent deletion mutants which provide for alternative or combinatorial approaches to developing recombinant RSV vaccine candidates.

TABLE 33

Sequence comparison of RSV B1 and cp-52

| Gene | Genomic position | Nucleotide* B1 | cp-52† | Amino acid change (#) B1→cp-52 |
|---|---|---|---|---|
| G/F | 5626 | C | A** | non-coding intergenic |
| F | 6318 | A | G | Glu→Gly (218) |

TABLE 33-continued

Sequence comparison of RSV B1 and cp-52

| Gene | Genomic position | Nucleotide* B1 | Nucleotide* cp-52† | Amino acid change (#) B1→cp-52 |
|---|---|---|---|---|
| L | 6460 | U | C** | silent (265) |
|   | 10973 | G | A | Arg→Lys (822) |
|   | 13492 | A | C | Asn→His (1662) |
|   | 14164 | U | A** | Leu→Ile (1886) |
|   | 14596 | U | C** | Phe→Leu (2030) |

*Positive (+) sense.
† Nucleotide position 4249-5540 spanning the SH and G genes is deleted in cp-52.
**Mutations present in cp-23

Other subgroup B mutants isolated at different passage levels in the cp-52 passage history incorporate various of the cp-52 mutations, depending on passage level (Table 34). Exemplary subgroup B mutants in this context include RSV B-1 cp-12, RSV B-1 cp-23, RSV B-1 cp-32, RSV B-1 cp-42. Table 34 depicts (as negative sense) the distribution of these specific mutations among exemplary B subgroup mutants. This varied distribution of mutations allows for more refined characterization of the attenuating effects of these mutations in the designated strains. For example, cp-23 incorporates the mutations at nucleotide positions 5626, 6460, 14164 and 14596 found in cp-52 (Table 34), but has no differences from the parental B-1 wild-type strain in the SH and G gene region that is deleted in cp-52. cp-42 incorporates the same SH and G deletion as cp-52, while cp32 presents a distinct deletion of sequences within the SH and G genes.

TABLE 34

Sequence comparison between RSVB1, RSVB1cp12, cp 23, cp32, cp 42, and cp 52

Nucleotide Changes genome (−) sense

| Gene | Nucl. Pos. | RSVB1 | RSVB1 CP12 | RSVB1 ••CP23 | RSVB1 CP32 | RSVB1 CP42 | RSVB1 •CP52 | Amino Acid Changes |
|---|---|---|---|---|---|---|---|---|
| G/F | 5626 | G | G | T | T | *ND | T | non-coding IGr |
| F | 6318 | T | ND | T | T | ND | C | Glu→Gly (218) |
|   | 6460 | A | A | G | G | *ND | G | silent (265) |
| L | 10973 | C | ND | C | C | T | T | Arg→Lys (822) |
|   | 13492 | T | ND | T | T | T | G | Asn→His (1662) |
|   | 14164 | A | A | T | T | T | T | Leu→Ile (1886) |
|   | 14596 | A | G | G | G | G | G | Phe→**Leu (2030) |

•Nucleotide region (position 4249-5540) spanning the SH and G genes is deleted in cp52.
••No nucleotide differences from B1 parent found in the SH and G gene region which is deleted in cp52.
*These nucleotides are most likely the same as in cp23 and cp 52.
**A Leucine at amino acid position 2030 in the L polymerase is also found in RSV2B.

EXAMPLE V

Bivalent RSV Subgroup A and B Vaccine

Studies with subgroup A and B viruses demonstrate that in vitro, no interference occurs between wild-type A2 and B-1 viruses, nor between cpts530/1009 and RSV B-1 cp52/2B5 derivatives in Vero cell monolayer cultures. The in vivo results of bivalent infection in cotton rats are presented in Table 34. These results confirm the in vitro results, which show no interference between A-2 and B-1 wild-type RSV, and cpts530/1009 and RSV B-1 cp52/2B5. It is expected, therefore, that each vaccine virus will induce homotypic immunity against wild-type virus, since each component of the bivalent vaccine replicates to a level in the dual infection comparable to that seen during single infection. Each virus alone is capable of inducing homotypic resistance against RSV wild-type challenge.

TABLE 35

Bivalent infection of cotton rats with RSV A2 and RSV B-1 viruses or mutant derivatives indicates no in vivo interference Virus recovery from indicated tissue ($\log_{10}$pfu/g)

| Viruses used to infect animals* | Nasal turbinates RSV A titer | Nasal turbinates RSV B titer | Lungs RSV A titer | Lungs RSV B titer |
|---|---|---|---|---|
| A2 | 5.4 ± 0.08 | — | 5.8 ± 0.07 | — |
| B-1 | — | 4.6 ± 0.03 | — | 5.4 ± 0.12 |
| A2 + B-1 | 5.2 ± 0.11 | 3.6 ± 0.07 | 5.7 ± 0.08 | 5.0 ± 0.05 |
| A2 cpts530/1009 | 3.2 ± 0.09 | — | 1.9 ± 0.15 | — |
| B-1 cp52 | — | 2.4 ± 0.08 | — | <1.5 |
| A2 cpts530/1009+ B1 cp-52 | 2.8 ± 0.13 | 2.0 ± 0.14 | 1.8 ± 0.08 | <1.5 |

*Groups of six animals infected with $10^5$ pfu intranasally on day 0 in a 0.1 ml inoculum.

EXAMPLE VI

A Single Mutation in Polymerase (L) Gene Elicits ts Phenotype

This Example describes the specific mutations in the polymerase gene (L) that were produced by chemical mutagenesis of incompletely attenuated host range-restricted cpRSV to produce ts strains, cpts248 and cpts530, which are more highly attenuated and suitable for use in RSV vaccine preparations. As described in the Examples above, cpts248 has been found to be attenuated, immunogenic, and fully protective against wild-type challenge in seronegative chimpanzees and is more stable genetically during in vivo replication than previously evaluated tsRSV mutants. As described above, the cpts248 strain was subjected to chemical mutagenesis to further reduce residual reactogenicity, yielding a series of mutants with increased temperature sensitivity or small plaque phenotype, including cpts248/404. In a like manner, cpts530/1009 was derived from cpts530.

The genetic bases for increased attenuation and ts phenotype of cpts248 and cpts530 were determined by comparing the complete genomic sequence of these viruses with that of the previously determined sequence of the cpRSV parental virus. The complete nucleotide sequence of cpRSV was determined and compared with that of RSV A2 wild-type virus (a laboratory strain which was not part of the direct passage lineage), as well as with the sequence of its low passaged wild-type parent virus (RSV A2/HEK7). The cpRSV differs from its RSV A2/HEK7 parent virus by five nucleotide changes, one in the nucleoprotein (N), two in the fusion protein (F) gene and two in the polymerase (L) gene. The complete 15,222 nucleotide sequence and amino acid sequence of cpts248, cpts248/404, cpts530, cpts530/1009, and cpts530/1030 were determined.

The derivation of the RSV mutants cpts248 and cpts530 from their cpRSV parent by random chemical mutagenesis was described in Example 1. The virus suspension used for infecting cells for production of virus to be used as a source of purified viral RNA was a clarified tissue culture supernatant containing virus that had been passaged four times in liquid medium in Vero cell monolayer culture following biological cloning (i.e., three plaque-to-plaque passages in Vero cell monolayers under agar).

Cell monolayers were infected at a multiplicity of infection (moi) of 0.1 with cpts248, cpts248/404, cpts530, cpts530/1009, or cpts530/1030 viruses. Total RNA was prepared from infected cell monolayers when moderate CPE was observed (average of 4-5 days postinfection). The supernatant fluid was removed by aspiration, and infected cell monolayers were harvested by lysis with guanidinium isothiocynanate, followed by phenol-chloroform extraction. RNA was reverse transcribed using Superscript II™ reverse transcriptase (Life Technologies) random hexamer primers, and reaction conditions as described in protocols supplied by the manufacturer.

The resulting cDNA was separated from primers using TE-100 spin columns (Clontech, Palo Alto, Calif.) and used as template in polymerase chain reactions (PCR) to generate a series of ten overlapping cDNA clones spanning the entire RSV genome. The oligonucleotide primers for PCR were designed from the nucleotide sequence of the prototype A2 virus (Mink et al., *Virology* 185:615-624 (1991); Stec et al., *Virology* 183:273-287 (1991); Collins et al., *Proc. Natl. Acad. Sci. U.S.A.* 88:9663-9667 (1991); Connors et al., *Virology* 208:478-484 (1995)), and had been demonstrated previously to amplify both the RSV A2 wild-type virus and its derivative, the cpRSV parental virus. Uracil-containing oligonucleotide primers were used for cloning RSV sequences into the pAMP1 vector using the CloneAmp uracil DNA glycosylase system (Life Technologies). PCR reactions were performed according to the manufacturer's protocols (Perkin-Elmer, Norwalk, Conn.) and carried out for 34 cycles of each 1 min. at 92.5° C., 1 min. at 55° C., and 3 min. at 72° C. Each fragment was electrophoresed in a 1% agarose/TAE gel, recovered by the Geneclean II System (Bio101, Vista, Calif.), and cloned into the pAMP1 vector. Two or more separate clones of each fragment were generated from separate PCR reactions. For analysis of the 3' leader region, viral RNA (vRNA) was polyadenylated as described in Mink et al., *Virology* 185:615-624 (1991) in a 50 µl reaction. Following incubation at 37° C. for 10 minutes, the reaction was stopped with 2 µl of 0.5 M EDTA. The polyadenylated RNA product was purified by extraction with phenol chloroform and ethanol precipitation, and then reverse transcribed into cDNA, amplified by PCR, and cloned using a rapid amplification by the 3' RACE system (Life Technologies). Similarly, for analysis of the 5' trailer region, vRNA was reverse transcribed into cDNA, tailed using terminal deoxynucleotidyl transferase and dCTP, column purified, made double-stranded and amplified by PCR, and cloned using a 5' RACE system (Life Technologies).

Cloned cDNAs for cpts248 were sequenced from double stranded plasmids by the dideoxynucleotide method using synthetic oligonucleotide primers (either plasmid primers or RSV specific primers), [$\alpha^{35}$S]dATP and Sequenase 2.0 (United States Biochemicals, Cleveland, Ohio). Differences between the observed sequences and those of the previously published parental virus cpRSV were confirmed by sequencing two or more clones in both forward and reverse directions, and by sequencing uncloned PCR products.

Nucleotide sequences of the cpts248/404, cpts530, cpts530/1009, and cpts530/1030 were determined using a different technique. Three to ten overlapping cDNA clones representing the genome of cptsRSV mutant virus were generated by RT-PCR of total infected-cell RNA or vRNA. The complete nucleotide sequence of each clone was determined by automated DNA sequence at the NCI Frederick Cancer (Frederick, Md.) using Taq kit (ABI, Foster City, Calif.) on a M13 sonicated random library constructed in phage M13 for each plasmid insert. Both strands were sequenced and differences between the cpRSV and the cptsRSV mutant sequences were confirmed by manual sequencing (as above) of a second independently derived RT-PCR product using Sequenase 2.0 (USB, Cleveland, Ohio). The 3'- and 5'-end sequences were determined as described above.

The complete nucleotide sequence of the 15,222-nucleotide RNA genome of the cpts248, cpts248/404, cpts530, cpts530/1009, and cpts530/1030 strains were determined. Changes relative to the published sequences of the cpRSV and RSV A2/HEK7 (wild-type) parental viruses (Conners et al., *Virology* 208:478-484 (1995)) were confirmed on independently derived cDNA clones of these cptsRSV mutants, and were rechecked in the cpRSV virus by sequencing an additional clone of cpRSV. An ambiguity in the sequence of the cpRSV virus (compared with the A2/HEK7 wild-type virus) was identified. The ambiguity occurred at position 1,938 from the 3' end of the negative sense genome and consisted of nucleotide heterogeneity (G or A in positive sense) that would be predicted to encode an amino acid change (Val or Ile) at amino acid position 267 of the 391 amino acid-nucleocapsid (N) protein. Thus, the cpRSV actually consisted of a mixed population of viruses. This accounts for the initial failure to detect the change at position 1938 in Conners et al., supra. A virus with the A mutation at position 1,938 was the immediate parent of the cpts248 derivative as well as of the cpts530 sister clone. Thus, the cpRSV which was the immediate parent virus of the cpts derivative contains five amino acid differences from its A2/HEK parent.

A single nucleotide difference between the cpRSV and cpts248 mutants was found at nucleotide position 10,989 (an A to T change) (Table 36). This mutation occurred within the polymerase (L) translation open reading frame, encoding a predicted amino acid change of gln to leu at amino acid position 831 in the 2,165 amino acid L protein. The cpts248/404 mutant possesses two nucleotide differences from its cpts248 parent, one at nucleotide 12,046 (T to A) in the L gene, and one at nucleotide 7605 (T to C) in the transcription start signal sequence of the M2 gene. The nucleotide substitution in the L gene resulted in an amino acid change from asp to glu at position 1183 in the L protein. Thus after two independent rounds of mutagenesis of cpRSV, the cpts248/404 virus acquired two nucleotide changes in the L gene (corresponding to two amino acid substitutions) and one nucleotide change in the transcription start signal of the M2 gene. Compared to its wild type progenitor, A2/HEK7, the cpts248/404 mutant differs in seven amino acids (four in L, two in F, and one in N) and in one nucleotide in the transcription start signal of the M2 gene.

TABLE 36

Nucleotide Sequence Differences among cp-RSV, cpts-248, cpts-248/404 mutant viruses
Nucleotide and Amino Acid Change

| Nucleotide[1] | Amino Acid | Gene | A2 wt (HEK-7) | cp-RSV | cpts-248 | cpts-248/404 |
|---|---|---|---|---|---|---|
| 1938 | 267 | N | G (val) | A (ile) | A (ile) | A (ile) |
| 3242 | | P | A | A | A | AA[2] |
| 6313 | 218 | F | A (glu) | C (ala) | C (ala) | C (ala) |
| 7228 | 523 | F | C (thr) | T (ile) | T (ile) | T (ile) |
| 7605 | | Gene Start (M2) | T | T | T | C |
| 9453 | 319 | L | G (cys) | A (tyr) | A (tyr) | A (tyr) |
| 10989 | 831 | L | A (gln) | A (gln) | T (leu) | T (leu) |
| 12046 | 1183 | L | T (asp) | T (asp) | T (asp) | A (glu) |
| 13565 | 1690 | L | C (his) | T (tyr) | T (tyr) | T (tyr) |

[1]Positive sense
[2]Increases genome length by 1 nucleotide.

The cpts530 differs from the parental strain cpRSV by the single additional nucleotide substitution of C to A at position 10,060 and results in a phe to leu amino acid change at position 521 of the L protein (Table 37). The cpts530/1009 mutant has a single nucleotide substitution at nucleotide 12,002 (A to G) resulting in a met to val substitution at amino acid 1169 of the L protein. Compared to its wild type progenitor, A2/HEK7, the cpts530/1009 mutant differs in seven amino acids (four in L, two in F, and one in N).

The cpts530/1030 mutant has a single additional nucleotide substitution at nucleotide 12458 (T to A) resulting in a Tyr to Asn substitution at amino acid 1321 of the L protein. Compared to its wt progenitor, A2/HEK, the cpts530/1030 mutant differs in seven amino acids (four in L, two in F, and one in N).

TABLE 37

Nucleotide Sequence Differences among cp-RSV, cpts-530, cpts-530/1009 mutant viruses
Nucleotide and Amino Acid Change

| Nucleotide[1] | Amino Acid | Gene | A2 wt (HEK-7) | cp-RSV | cpts-530 | cpts-530/1009 |
|---|---|---|---|---|---|---|
| 1938 | 267 | N | G (val) | A (ile) | A (ile) | A (ile) |
| 6313 | 218 | F | A (glu) | C (ala) | C (ala) | C (ala) |
| 7228 | 523 | F | C (thr) | T (ile) | T (ile) | T (ile) |
| 9453 | 319 | L | G (cys) | A (tyr) | A (tyr) | A (tyr) |
| 10060 | 521 | L | C (phe) | C (phe) | A (leu) | A (leu) |
| 12002 | 1169 | L | A (met) | A (met) | A (met) | G (val) |
| 13565 | 1690 | L | C (his) | T (tyr) | T (tyr) | T (tyr) |

[1]Positive sense

Thus, the ts and attenuation phenotypes of the cpts248 and cpts530 each are associated with a single nucleotide change in the polymerase gene. The incremental increase in ts and attenuation phenotypes between the cpts530, and cpts530/1009 or cpts530/1030 was also each associated with a one amino change in L. In these four examples (i.e., cpts248, cpts530, cpts530/1009, and cpts530/1030) a single, but different, amino acid substitution in L conferred the ts and attenuation phenotypes on the progenitor strains. These amino acid substitutions are acting in cooperation with the five cpRSV mutations to enhance the stability of the ts phenotype following replication in animals. The incremental increase in attenuation and temperature sensitivity observed between the cpts248 and cpts248/404 was associated with two nucleotide changes, either or both of which could contribute to the ts and attenuation phenotypes. The four specific sites in L (i.e., those specific for the cpts530, cpts530/1009, cpts530/1030 and cpts248 viruses) that are singly associated with the ts and attenuation phenotypes and one or both sites in cpts248/404 are identified by the findings summarized herein as core regions of the RSV genome or L protein at which mutation can lead to attenuation. Although the specific mutations at the four sites in the L protein were specific amino acid substitutions, it is likely that other amino acid substitutions as well as in frame insertions or deletions at these sites and at contiguous amino acids within about five amino acids of a specific site can also result in attenuation.

The encoded amino acid changes in L do not appear to involve the regions of highest sequence conservation among the paramyxovirus polymerase proteins, the proposed ATP binding site (Stec et al., *Virology* 183:273-287 (1991)), nor the regions suggested to be homologous to motifs of RNA-dependent RNA and DNA polymerases (Poch et al., *EMBO J.* 8:3867-3874 (1989)). It is more likely that the effect of these mutations is at amino acid level rather than nucleotide level, given that the mutation does not lie within the 3' and 5' genome termini nor the short gene-start and gene-end sequences. These RNA regions are thought to contain all of the cis-acting RNA sequences required for efficient encapsidation, transcription, replication, and packaging into virions (Collins et al., *Proc. Natl. Acad. Sci. USA* 88:9663-9667 (1991); Collins et al., *Proc. Natl. Acad. Sci. USA* 93:81-85 (1996), each incorporated herein by reference).

These results provide the first full-length sequence of a tsRSV mutant. These results also indicate that pneumoviruses can be attenuated by the substitution of a single nucleotide that causes an amino acid change or change in, e.g, a GS sequence. Since the cpts248 and cpts530 viruses have a high degree of stability of the ts phenotype both in vitro and in vivo, it is remarkable indeed that this phenotype was found to be associated with a single, different amino acid change. Importantly, the cpts248/404, cpts530/1009, and cpts530/1030 contain at least three mutations that contribute to the attenuation phenotype, two ts and one non-ts (e.g., the five cp mutations), and this is a partial non-limiting explanation for the high level of stability of these viruses in vitro and in vivo.

Determination of the complete sequence of RSV vaccine virus strains and of their parental viruses permits analysis at the genetic level of the stability of vaccine viruses during vaccine virus production and during shedding by volunteers in clinical trials. The determination of the genetic basis for the attenuation and ts phenotypes of the cpts248, cpts530, cpts248/404 cpts530/1009 and cpts530/1030 viruses provides important new opportunities. According to the recombinant methods described hereinbelow, it is readily possible to generate novel vaccine candidates by site-directed mutagenesis of full-length RSV cDNA from which infectious viruses can be recovered. For example, it is possible to add to a cDNA clone of, e.g., the cpts248/404 virus, one or both of the ts mutations at amino acid position 521 (in the cpts530 mutant) or 1169 (in the cpts530/1009 mutant) or other attenuating or stabilizing mutations as desired. In this way, the level of attenuation of the cpts248/404 virus can be increased in an incremental fashion and a vaccine strain that has the specific level of attenuation desired for both safety and immunogenicity can be generated in a rational way. Similarly, the level of attenuation of the cpts530/1009 and cpts530/1030 mutants can be increased by the specific introduction of one or more of the attenuating mutations in the cpts248/404 virus. These examples of combinatorial recombinant viruses, incorporating multiple attenuating mutations from biologically derived mutant strains, overcome many of the difficulties which attend isolation and production of genetically stable, satisfactorily attenuated viruses using conventional approaches. Moreover, the phenotypic stability of these recombinant cptsRSV mutants can be enhanced by introducing, where possible, two or more nucleotide substitutions at codons that specify specific amino acids that are known to confer the attenuation phenotype. In this way the stability of the attenuation phenotype can be augmented by site-directed mutagenesis of full-length RSV cDNA.

EXAMPLE VII

Construction of cDNA Encoding RSV Antigenome

Figure 2:
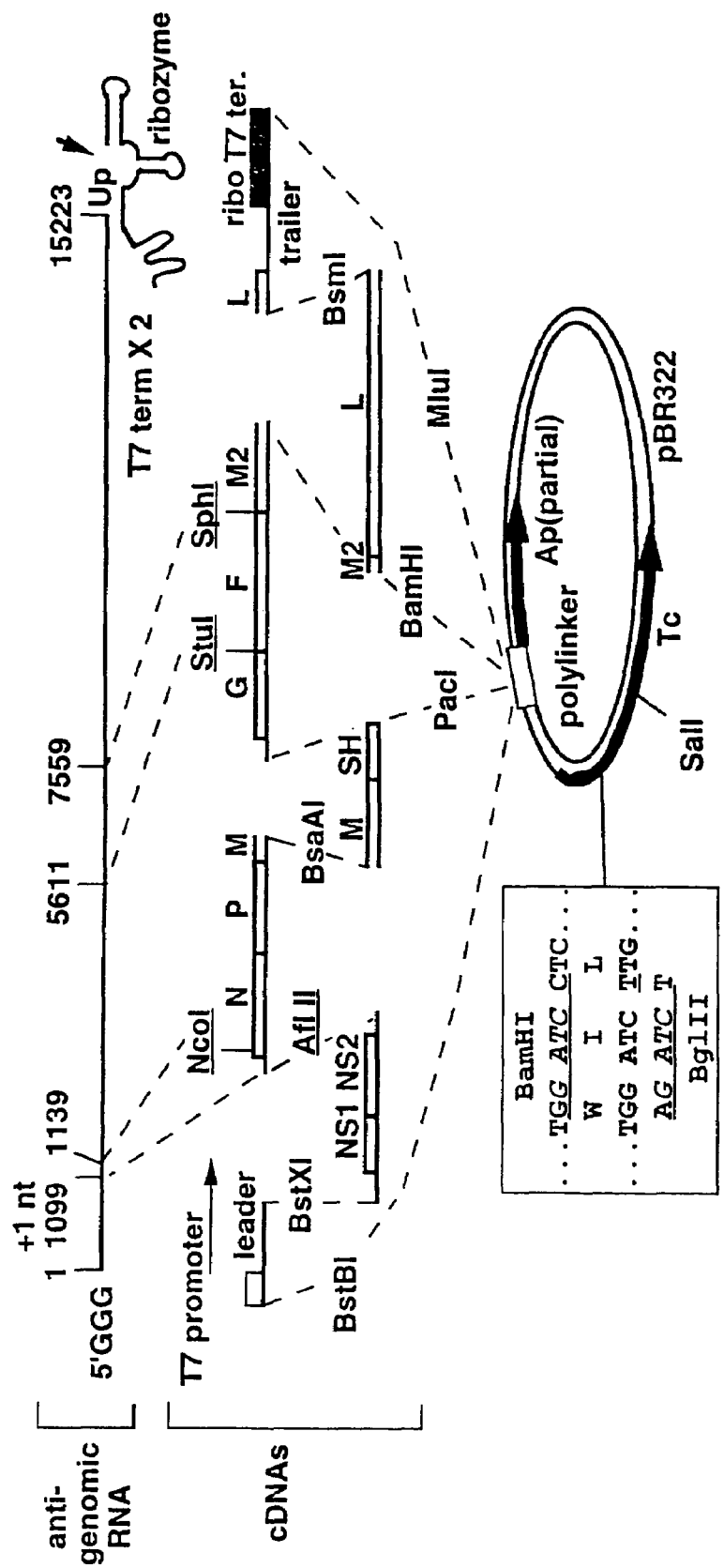
FIGS. 2 and 3 show the construction of cDNA encoding RSV antigenome RNA, where

A cDNA clone encoding the antigenome of RSV strain A2 was constructed, as illustrated in FIG. 2. The cDNA was synthesized in segments by reverse transcription (RT) and polymerase chain reaction (PCR) using synthetic oligonucleotides as primers and intracellular RSV mRNA or genome RNA isolated from purified virions as template. The final cDNA was flanked on the leader end by the promoter for T7 RNA polymerase, which included three transcribed G residues for optimal activity; transcription would result in the donation of these three nonviral G's to the 5' end of the antigenome. To generate a nearly-correct 3' end, the cDNA trailer end was constructed to be adjacent to a previously-described hammerhead ribozyme, which upon cleavage would donate a single 3'-phosphorylated U residue to the 3' end of the encoded RNA (Grosfeld et al., J. Virol. 69:5677-5686 (1995), incorporated herein by reference). The ribozyme sequence was followed by a tandem pair of terminators of T7 RNA polymerase. (The addition of three 5' G residues and one 3' U residue to a cDNA-encoded RSV minigenome containing the chloramphenicol acetyl transferase (CAT) reporter gene had no effect on the expression of CAT when complemented by RSV.)

FIG. 2 shows the structures of the cDNA and the encoded antigenome RNA. The diagram of the antigenome (at top) includes the following features: the 5'-terminal nonviral G triplet contributed by the T7 promoter, the four sequence markers at positions 1099 (which adds one nt to the length), 1139, 5611, and 7559, the ribozyme and tandem T7 terminators, and the single nonviral 3'-phosphorylated U residue contributed to the 3 end by ribozyme cleavage (the site of cleavage is indicated with an arrow).

Cloned cDNA segments (FIG. 2, middle) representing in aggregate the complete antigenome were constructed by RT-PCR of RSV mRNA or genome RNA. The complete antigenome cDNA is called D46 or D53; the different names referring to different preparations of the same plasmid. cDNAs containing the lefthand end of the antigenome, spanning from the T7 promoter and leader region complement to the SH gene and called D13, were assembled in a version of pBR322 (FIG. 2, bottom) in which the naturally-occurring BamHI site had been ablated by mutagenesis and the PstI-EcoRI fragment replaced with a synthetic polylinker containing unique restriction sites (including BstBI, BstXI, PacI, BamHI, MluI) designed to facilitate assembly. The box in FIG. 2 shows the removal of the BamHI site. The naturally occurring BamHI-SalI fragment (the BamHI site is shown in the top line in positive sense, underlined) was replaced with a PCR-generated BglII-SalI fragment (the BglII site is shown in the bottom line, underlined; its 4-nt sticky end [italics] is compatible with that of BamHI). This resulted in a single nt change (middle line, underlined) which was silent at the amino acid level. These modifications to the vector facilitated construction of the cDNA by rendering unique a BamHI site in the antigenome cDNA.

The G, F and M2 genes were assembled in a separate plasmid, as were the L, trailer and flanking ribozyme and tandem T7 transcription terminators. The G-to-M2 piece was then inserted into the PacI-BamHI window of the leader-to-SH plasmid. This in turn was the recipient for the is L-trailer-ribozyme-terminator piece inserted into the BamHI to MluI window, yielding the complete antigenome.

Four restriction site markers (FIG. 3) were introduced into the antigenome cDNA during the original construction by incorporating the changes into oligonucleotide primers used in RT-PCR. This was done to facilitate assembly, provide a means to identify recombinant virus, and illustrate the ability to introduce changes into infectious RSV. Three sites were in intergenic regions and the fourth in a nontranslated gene region, and they involved a total of five nt substitutions and a single nt insertion. This increased the length of the encoded antigenome by one nt from that of wild type to a total of 15,223 nt (SEQ ID NO:1, which depicts the 5' to 3' positive-sense sequence of D46, whereas the genome itself is negative-sense; note that position four can be either G or C).

Figure 3:
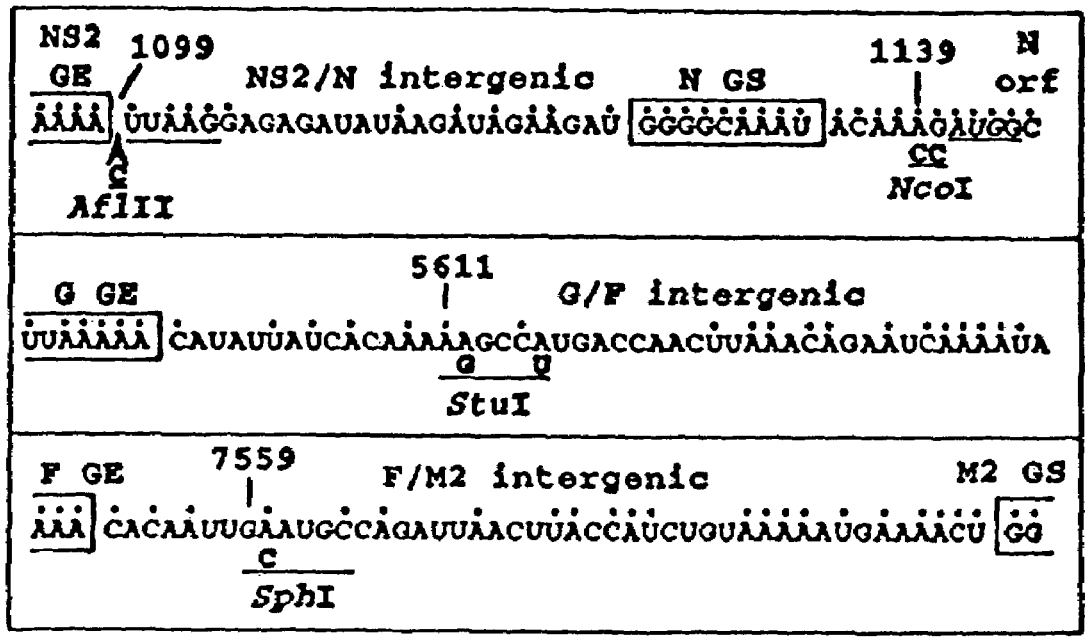

The sequence markers were inserted into the cDNA-encoded antigenome RNA as shown in FIG. 3. Sequences are positive sense and numbered relative to the first nt of the leader region complement as 1; identities between strains A2 and 18537 (Johnson and Collins, J. Gen Virol. 69:2901-2906 (1988), incorporated herein by reference), representing subgroups A and B, respectively, are indicated with dots; sequences representing restriction sites in the cDNA are underlined; GS and GE transcription signals are boxed; the initiation codon of the N translational open reading frame at position 1141 is italicized, and the sequence markers are shown underneath each sequence. In the top sequence, a single C residue was inserted at position 1099 to create an AflII site in the NS2-N intergenic region, and the AG at positions 1139 and 1140 immediately upstream of the N translational open reading frame were replaced with CC to create a new NcoI site. In the middle sequence, substitution of G and U at positions 5612 and 5616, respectively, created a new StuI site in the G-F intergenic region. And, in the bottom sequence of FIG. 3, a C replacement at position 7560 created a new SphI site in the F-M2 intergenic region.

All cDNAs were sequenced in their entirety, in most instances from several independent cDNAs, prior to assembly. The plasmids encoding individual RSV proteins are described in Grosfeld et al., J. Virol. 69:5677-5686 (1995) and Collins et al., supra, (1995), each of which is incorporated herein by reference. The complete cDNA was also sequenced in its entirety following assembly

EXAMPLE VIII

Transfection and Recovery of Recombinant RSV

The method of the invention for producing infectious RSV from cDNA-expressed antigenome involves its coexpression with those RSV proteins which are sufficient to (i) produce an antigenome nucleocapsid capable of RNA replication, and (ii) render the progeny genome nucleocapsid competent for both RNA replication and transcription. Transcription by the genome nucleocapsid provides all of the other RSV proteins and initiates a productive infection.

Plasmid-borne cDNA encoding the antigenome was transfected, together with plasmids encoding proteins N, P, L and M2(ORF1), into HEp-2 cells which had been infected with a recently-described vaccinia virus MVA strain recombinant which expresses the T7 RNA polymerase (Wyatt et al., *Virol.* 210:202-205 (1995), incorporated herein by reference). The MVA strain is a host range mutant which grows permissively in avian cells whereas in mammalian cells there is a block at a late stage in virion maturation that greatly reduces the production of infectious virus. In HEp-2 cells, the MVA recombinant was similar to the more commonly-used WR-based recombinant (Fuerst et al., *Proc. Natl. Acad. Sci. USA* 83: 8122-8126 (1986)) with regard to the level of expression of T7 polymerase and cytopathogenicity, but the level of progeny produced was sufficiently low that supernatants could be passaged to fresh cells with minimal cytopathogenicity. This should facilitate the recovery of any recombinant RSV which might be produced in transfected, vaccinia virus-infected cells.

Transfection and recovery of recombinant RSV was performed as follows. Monolayer cultures of HEp-2 cells received, per single well of a six-well dish, one ml of infection-transfection medium prepared by mixing five plasmids is in a final volume of 0.1 ml opti-MEM (Life Technologies) medium, namely 0.4 µg each of antigenome, N and P plasmids, and 0.1 µg each of L and M2(ORF1) plasmids. This was combined with 0.1 ml of Opti-MEM containing 12 µl LipofectACE (Life Technologies). After 15 min incubation at room temperature, this was combined with 0.8 ml of Opti-MEM containing 2% heat-inactivated fetal bovine serum and $1.5\times10^6$ pfu of strain MVA vaccinia virus recombinant encoding T7 RNA polymerase (Wyatt et al., supra). This was added to the cells and replaced one day later by Opti-MEM containing 2% serum. Cultures were incubated at 32° C. and harvested on day three. Incubation at 32° C. was used because it was found that the MVA virus is slightly temperature sensitive and is much more efficient at this lower temperature.

Three days post-transfection clarified culture supernatants were passaged onto fresh HEp-2 cells and overlaid with methyl cellulose (for subsequent antibody staining) or agarose (for plaque isolation). After incubation for five days under methyl cellulose, the cells were fixed and stained by an indirect horseradish peroxidase method using a mixture of three murine monoclonal antibodies to the RSV F protein followed by an anti-mouse antibody linked to horseradish peroxidase, following the general procedure of Murphy et al., *Vaccine* 8:497-502 (1990).

Numerous RSV-like plaques were detected against a background of cytopathogenicity that presumably was due to a low level of MVA-T7 recombinant virus. The plaques contained an abundant amount of the RSV F protein, as indicated by brown-black coloration, and displayed cytopathic effects characteristic of RSV, notably syncytium formation.

The RSV-like plaques were picked from plates which were incubated under agarose and stained with neutral red. They were propagated and compared to a laboratory strain of RSV strain A2 by plaque assay and antibody staining. The plaques derived from the transfected cultures closely resembled those of the laboratory strain. One difference was that the plaques derived from the transfected cultures appeared to be slightly smaller than those from the laboratory strain, with centers which were less well cleared. The recombinant virus may differ phenotypically from this particular wild type isolate, possibly being slightly more restricted in cell-to-cell spread and exhibiting a reduced rate of cell killing. With regard to the propagation of released virus, the yields of the recombinant versus laboratory virus in HEp-2 cells were essentially identical at 32° or 37° C. In preliminary studies, the recombinant and laboratory viruses were indistinguishable with regard to the accumulation of intracellular RSV mRNAs and proteins.

Plaque-purified, thrice-passaged recombinant RSV was analyzed in parallel with laboratory virus by RT-PCR using three primer pairs flanking the four inserted markers. Three independent plaque-purified recombinant RSV isolates were propagated in parallel with an uninfected control culture. Clarified medium supernatants were treated with polyethylene glycol and high salt (Zoller and Smith, *DNA* 3:479-488 (1984)) to precipitate virus and RNA was extracted from the pellets with Trizol™ (Life Technologies). These RNAs, in parallel with additional controls of no added RNA or 0.1 µg of RNA from a laboratory isolate of strain A2, were treated with DNAse, repurified, annealed each with 50 ng of random hexamers and incubated under standard RT conditions (40 µl reactions) with or without reverse transcriptase (Connors et al., *Virol.* 208: 478-484 (1995), incorporated herein by reference). Aliquots of each reaction were subjected to PCR (35 cycles of 94° C. for 45 s, 37° C. for 30 s, 72° C. for 1 min) using three different pairs of synthetic deoxyoligonucleotide primers. Primer pair (A): positive-sense, positions 925-942 and negative-sense, positions 1421-1440, yielding a predicted product of 516 bp (517 bp in the case of the recombinant viruses) that included the AflII and NcoI sites inserted at, respectively, the junction of the NS2 and N genes and in the N gene. Primer pair (B): positive-sense, positions 5412-5429 and negative-sense, 5930-5949, yielding a predicted product of 538 bp spanning the StuI site inserted at the junction between the G and F genes. Primer pair (C): positive-sense, 7280-7297 and negative-sense, 7690-7707, yielding a 428 bp fragment spanning the SphI site inserted at the junction between the F and M2 genes. PCR products were analyzed by electrophoresis on neutral gels containing 1% agarose and 2% low-melting agarose in parallel with HaeIII-digested X174 DNA molecular length markers and visualized by staining with ethidium bromide. PCR products of the expected sizes were produced. The production of each was dependent on the RT step, indicating that each was derived from RNA rather than contaminating cDNA.

PCR products were analyzed by digestion with restriction enzymes. Digestion of products of primer pair A with AflII or NcoI yielded fragments corresponding to the predicted 177 and 340 bp (AflII) or 217 and 300 bp (NcoI). Digestion of products of primer pair B with StuI yielded fragments comparable to the predicted 201 and 337 bp. Digestion of products from reactions with primer pair C with SphI yielded products corresponding to the predicted 147 and 281 bp. The digests were analyzed by gel electrophoresis as above. The presence of residual undigested PCR product with AflII was due to incomplete digestion, as was confirmed by redigestion. Thus, the restriction enzyme digestion showed that the PCR products representing recombinant virus contained the expected restriction site markers while those representing the laboratory strain did not. Nucleotide sequence analysis of cloned PCR product confirmed the sequences spanning the restriction site markers.

As shown in Table 38, the efficiency of RSV production when complemented by N, P, L and M2(ORF1) was relatively high, ranging in three experiments from an average of 9.9 to 94.8 plaques per 0.4 µg of input antigenome cDNA and 1.5× 10⁶ cells. Since these plaques were derived from liquid overlay, the number of infected cells present in each well of the original transfection was not known. Nearly every transfected well (54 of 56 in Table 38) produced virus. Since the yield of released RSV per infected cell typically is very low (~10 pfu) even under ideal conditions, and since many wells yielded many times this amount (up to 169 plaques), it is likely that several RSV producing cells were present in many of the wells of transfected cells.

RSV was not recovered if any of the plasmids were omitted, as shown in Table 38. The requirement for M2(ORF1) also could be satisfied with the complete gene, M2(ORF1+2), provided the level of its input cDNA was low (0.016 µg per 1.5×10⁶ cells (Table 38). At higher levels, the production of virus was greatly reduced, suggesting that an inhibition of minigenome RNA synthesis associated with M2(ORF2) also operates on the complete genome during productive infection.

These results showed that the production of infectious RSV was highly dependent on expression of the M2(ORF1) protein in addition to N, P and L. Furthermore, it showed that the optimal method of expression of M2(ORF1) was from an engineered cDNA in which ORF2 had been deleted, although the complete cDNA containing both ORFs also supported the production of RSV.

Thus, the present invention demonstrates that transcription by RSV differs from that of from previously-described non-segmented negative strand RNA viruses in requiring a fourth protein designated here as M2(ORF1), and previously called 22K or M2 (Collins et al., *J. Virol.* 54:65-71 (1985)). The M2(ORF1) protein was found to be an RNA polymerase elongation factor essential for processive, sequential transcription. Collins et al., *Proc. Natl. Acad. Sci. USA* 93:81-85 (1996). This requirement provides the capability, as part of this invention, for introducing specific, predetermined changes into infectious RSV.

TABLE 38

Production of infectious RSV was dependent on expression of M2 ORF 1.

| Complementing plasmids (µg cDNA per 1.5 × 10⁶ cells and antigenome | Production of infectious RSV # plaques × # wells* | | |
|---|---|---|---|
| cDNA) 0.4 µg | expt. 1 | expt. 2 | expt. 3 |
| N(0.4) | | | |
| P(0.4) | 0 × 24 | 0 × 12 | 0 × 12 |
| L(0.1) | | | |
| N(0.4) | 0 × 19§ | 0 × 4 | 9 × 1 |
| P(0.4) | 1 × 2 | 3 × 1 | 10 × 1 |
| L(0.1) | 2 × 2 | 5 × 1 | 14 × 2 |
| M2 [ORF1 + 2] (0.016) | 3 × 1 | 6 × 1 | 22 × 1 |
| | | 9 × 1 | 28 × 1 |
| | av. 0.38 | 10 × 1 | 32 × 1 |
| | | 13 × 1 | 49 × 1 |
| | | 34 × 1 | 70 × 2 |
| | | 51 × 1 | 166 × 1 |
| | | | 169 × 1 |
| | | av. 10.9 | |
| | | | av. 48.6 |
| N(0.4) | 0 × 1 | 11 × 1 | 0 × 1 | 55 × 1 |
| P(0.4) | 1 × 1 | 12 × 1 | 2 × 1 | 59 × 1 |

TABLE 38-continued

Production of infectious RSV was dependent on expression of M2 ORF 1.

| Complementing plasmids (µg cDNA per 1.5 × 10⁶ cells and antigenome | Production of infectious RSV # plaques × # wells* | | |
|---|---|---|---|
| cDNA) 0.4 µg | expt. 1 | expt. 2 | expt. 3 |
| L(0.1) | 2 × 2 | 13 × 1 | 4 × 1 | 65 × 1 |
| M2 [ORF1] (0.1) | 3 × 2 | 21 × 1 | 5 × 1 | 71 × 1 |
| | 4 × 1 | 24 × 1 | 8 × 2 | 72 × 1 |
| | 5 × 2 | 26 × 1 | 10 × 3 | 87 × 1 |
| | 6 × 4 | 30 × 2 | 19 × 1 | 97 × 1 |
| | 7 × 2 | 33 × 2 | 20 × 1 | 100 × 1 |
| | 9 × 1 | 42 × 1 | 23 × 1 | 109 × 1 |
| | 10 × 2 | 73 × 1 | | 128 × 1 |
| | | | av. 9.9 | 147 × 1 |
| | | av. 13.7 | | 148 × 1 |
| | | | | av. 94.8 |

*Supernatants from transfected cultures (10⁶ cells per well) were passaged onto fresh HEp-2 cells, overlaid with methyl cellulose, and stained with F-specific monoclonal antibodies.
§Read as follows: 19 wells had 0 plaques, 2 wells had 1 plaque each, 2 wells had 2 plaques each, and 1 well had 3 plaques.

EXAMPLE IX

Construction of an Infectious Recombinant RSV Modified to Incorporate Phenotype-Specific Mutations of RSV Strain cpts530

This Example illustrates the introduction of specific predetermined mutations into infectious RSV using the recombinant methods described herein. As noted above, the complete nucleotide sequence of cpts530 RSV was determined and 5 mutations known to be present in the parent cpRSV were retained in cpts530, the further attenuated derivative. One additional nucleotide change was identified at nucleotide (nt) position 10060, which resulted in a phenylalanine to leucine change at amino acid position 521 in the large polymerase (L) protein (see Tables 37, 39). This single amino acid substitution was introduced alone or in combination with the cp mutations into the full-length cDNA clone of wild-type A2 RSV. Analysis of infectious viruses recovered from mutant cDNAs indicated that this single mutation specified complete restriction of plaque formation of recombinant cp530 in HEp-2 cell monolayer cultures at 40° C., and the level of temperature sensitivity was not influenced by the presence of the 5 cpRSV mutations. These findings identify the phenylalanine to leucine change at amino acid position 521 in the L protein as the mutation that specifies the ts phenotype of cpts530. Similarly, one additional nucleotide change was identified in the cpts530/1009 recombinant in comparison to its cpts530 parent virus (Table 37). This nucleotide substitution at position 12002 resulted in an amino acid change in L at position 1169 at which a methionine in the wild type virus was replaced by a valine in the cpts530/1009 mutant. This mutation has also been introduced into recombinant RSV, and the recovered virus was temperature sensitive. These findings identify the methionine to valine change at position 1169 as the mutation that specifies the greater level of temperature sensitivity of cpts530/1009 over that of cpts530.

The levels of temperature sensitivity among the 530, 530/1009 and 530/1030 recombinant virus have been confirmed with RSV-CAT or RSV-Luciferase minigenome (see above) monitored by enzyme assay or Northern blot analysis. For example, at the elevated temperature of 37° C., the luciferase activity generated by selected mutants relative to wild-type L protein was 18.4%, 1.5% and 0.4% for 1009, 530, and the double mutant pTM1-L support plasmid. These exemplary mutations also decreased L function at 32° C. with 70% activity for 1009, 40% activity for 530, and 12.5% activity for 530/1009 L protein compared to wt L protein. The effects of these mutations on transcription and replication can also be determined using the minigenome system, alone or in combination with the recombinant viral methods disclosed herein.

Figure 4:
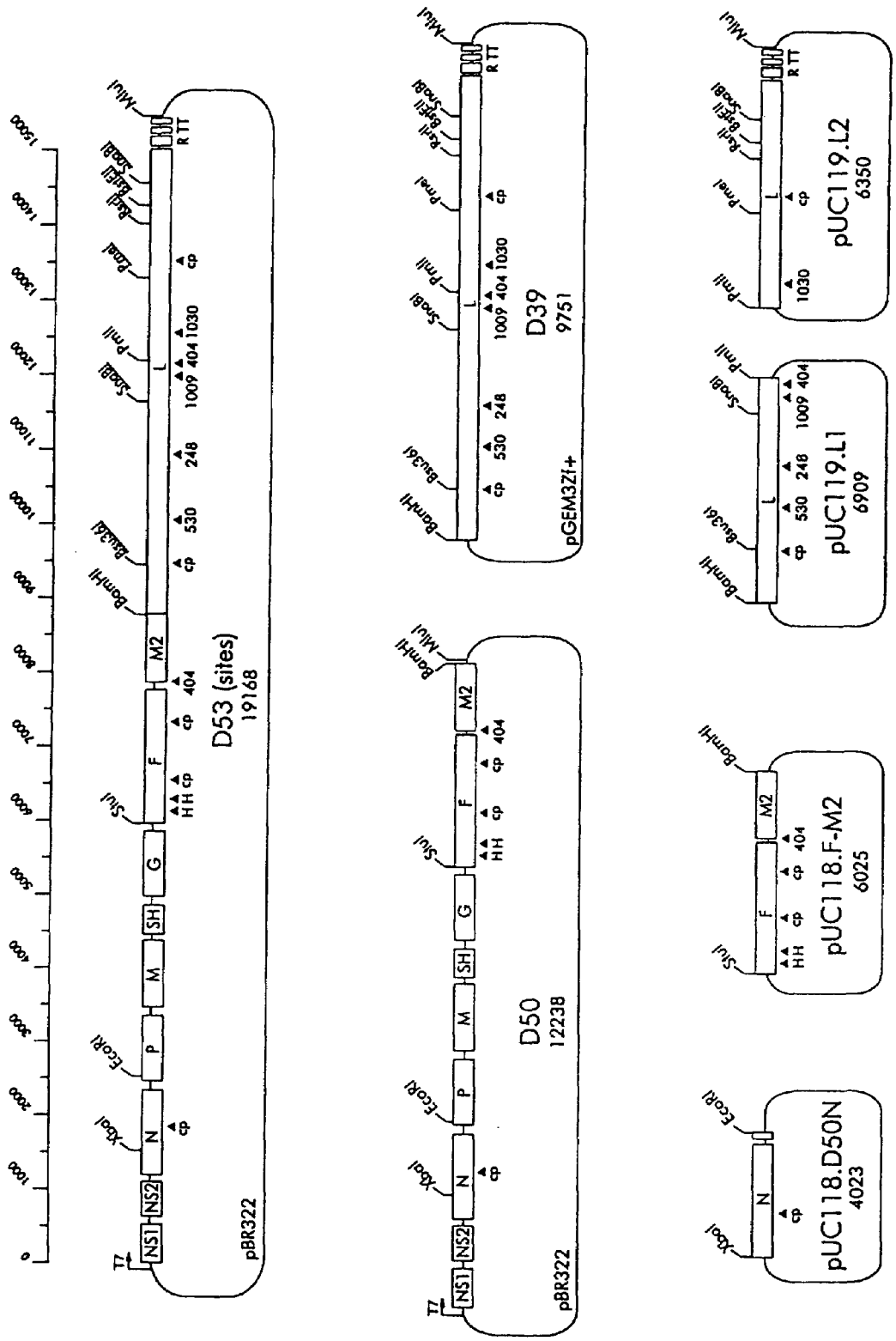
FIG. 4 illustrates structures of cDNAs (approximately to scale) involved in the insertion of mutations, assembly of complete antigenome constructs, and recovery of recombinant virus. Four types of mutations were inserted into the pUC118- or pUC119-borne cDNA subclones shown in the bottom row, namely six silent restriction sites in the L gene (underlined over the D53 diagram on the top), two HEK changes in the F gene (H), five cp changes (cp), and the mutations specific to the various biological mutagenesis steps: 248, 404, 530, 1009, and 1030 (as indicated). The mutagenized subclones were inserted into the D50 (representing the RSV antigenome from the leader to the beginning of the M2-L overlap with the T7 promoter immediately upstream of the leader) or D39 (representing the RSV antigenome from the M2-L overlap to the trailer with the ribozyme and T7 terminators immediately downstream of the trailer) intermediate plasmids shown in the middle row. The appropriate D50 and D39 were assembled into full-length D53 antigenome cDNA as shown on the top row (RTT indicates the location of the hammer-head ribozyme followed by two T7 transcription terminators).

Intermediate clones (D50 and D39) were used to assemble the full-length RSV cDNA clone D53, which encodes positive-sense RSV antigenome (FIG. 4). The D50 plasmid contains the RSV genome from the leader to the M2-L overlap downstream of a T7 promoter, while the D39 plasmid encodes the full-length L gene and the trailer followed by the hammerhead ribozyme and two T7 terminators (approximately 7 kb in length) bordered by BamHI and MluI restriction sites. The full-length RSV cDNA clone (D53) used in transfections to rescue infectious virus was assembled by

TABLE 39

Mutations introduced into the RSV full-length cDNA clone.

| Mutation | Sequence of wt | Sequence of Mutation | Restriction Site | Amino Acid Change |
|---|---|---|---|---|
| site (L)[1] | $_{9398}$CTTAAGA | $_{9398}$CCTAAGG | Bsu36I | — |
| site (L) | $_{11846}$TACATA | $_{11846}$TACGTA | SnaBI | — |
| site (L) | $_{13339}$GTCTTAAT | $_{13339}$GTTTAAAC | PmeI | — |
| site (L) | $_{14082}$CGTACAG | $_{14082}$CGGACCG | RsrII | — |
| site (L) | $_{14318}$TGTAACA | $_{14318}$GGTAACC | BstEI | — |
| site (L) | $_{14475}$TATGTA | $_{14475}$TACGTA | SnaBI | — |
| HEK (F) | $_{5848}$AATATCAAGAAA | $_{5848}$AATATTAAGG*AA | SspI | $_{66}$lys→glu |
| HEK (F) | $_{5956}$AGCACACAA | $_{5956}$AGTACTCC*A | ScaI | $_{101}$gln→pro |
| cp (F) | $_{1935}$ATCAGTT | $_{1935}$ATCGA*TT | ClaI | $_{267}$val→ile |
| cp (F) | $_{6311}$TAGAAA | $_{6311}$TCGC*GA | NruI | $_{218}$glu→ala |
| cp (F) | $_{7228}$ACAAAT | $_{7228}$AT*TAAT | AseI | $_{523}$thr→ile |
| cp (L) | $_{9453}$TGTATAC | $_{9453}$TA*CATAC | lose AccI | $_{319}$cys→tyr |
| cp (L) | $_{13555}$TATTAACTAAACAT | $_{13555}$TGTTAACTAAAT*AC | HpaI | $_{1690}$his→tyr |
| 248 (L) | $_{10982}$TCATGCTCAA | $_{10982}$GCATGCTCT*G | SphI | $_{831}$gln→leu |
| 404 (M2) | $_{7606}$TATGTCACGA | $_{7606}$C*ATGTCGCGA | NruI | — |
| 404 (L) | $_{12042}$TTGGAT | $_{12042}$CTCGAG* | XhoI | $_{1183}$asp→glu |
| 530 (L) | $_{10059}$TTC | $_{10059}$TTA* | — | $_{521}$phe→leu |
| 1009 (L) | $_{11992}$CCACTGAGATGATG | $_{11992}$CCACTGAGATGG*TC | BsfXI | $_{1169}$met→val |
| 1030 (L) | $_{12452}$GTTAACATAT | $_{12452}$GCTAACAA*AT | lose HpaI | $_{1321}$tyr→asn |

Note:
Nucleotide differences between wild-type and mutants (at the corresponding positions of are underlined. Recognition sites of restriction endonucleases are in italics. Codons in which the introduced nucleotide change(s) results in amino acid substitution are in bold. Asterisk identifies the single nucleotide change that was present in the biologically-derived mutant virus. Numbering system reflects the one nucleotide insertion in the full length cDNA.
[1]Indicates the gene into which the mutation was introduced.

To incorporate the cpts530 and the cpts1009 specific mutations into a defined, attenuated recombinant RSV vaccine virus, the cDNA-based recovery system described herein was employed as follows. The previously-described RSV A2 wild-type full-length cDNA clone (Collins et al., supra., (1995)) was designed in the original construction to contain a single nucleotide insertion of C in the cDNA clone at nt position 1099 (which creates an AflII site) and a total of 6 additional nucleotide substitutions at 4 loci. Thus, the nucleotide numbering system for the naturally occurring virus and for the recombinant viruses derived from cDNA are out of register by one nt after position 1099. The nucleotide numbering in Tables 36 and 37, above, represents the positions for the naturally occurring viruses, while those for the cDNA clones (Table 39) and recombinant viruses derived from cDNA clones are one nucleotide more. One of the 6 nucleotide substitutions is a G to C change in genome sense at nt position 4 in the leader sequence. This nucleotide variation has been detected in non-recombinant RSV and was not found to have an effect on the temperature sensitivity of virus replication in tissue culture or in mice (Firestone, et al., Virology, 225:419-522 (1996), incorporated herein by reference). Table 39 lists the various mutations which were inserted into the RSV cDNA in this and subsequent Examples.

inserting the BamHI-MluI fragment of the D39 plasmid into the D50 plasmid (see U.S. patent application Ser. No. 08/720, 132; and published PCT Application No. PCT/US96/15524, each incorporated herein by reference). D50 was further separated into several pieces each placed in a phagemid plasmid for the purposes of facilitating mutagenesis: one piece was an XbaI-EcoRI fragment containing the N gene (cDNA pUC118.D50N), and one was a StuI-BamHI fragment containing the F and M2 genes (pUC118.F-M2). D39 was further separated into two pieces each placed in a separate phagemid plasmid: one piece (left hand half, cDNA pUC119.L1) runs from the BamHI site to the PmlI site at nucleotide 12255 (note that the sequence positions assigned to restriction site locations here and throughout are intended as a descriptive guide and do not alone precisely define all of the nucleotides involved), and the other (right hand half, cDNA pUC119.L2) from the Pm/I site to the end of the T7 terminator.

Mutations were placed into the pUC118- and pUC119-based constructs illustrated in the bottom row of FIG. 4 following standard procedures (see, e.g., Kunkel et al., Methods Enzymol, 54:367-382 (1987), incorporated herein by reference). The plasmids were propagated in a dut ung strain of E. coli., in this case CJ236, and single stranded DNA was prepared by infection with a helper phage, in this case M13KO7. Phosphorylated synthetic oligonucleotides each containing one or more nucleotide changes of interest were prepared, annealed to the single stranded template singly or in combination, and used to direct DNA synthesis by T4 DNA polymerase. The products were ligated and transformed into a non-dut ung strain of *E. coli*, in this case DH5alpha or DH10B. Miniprep DNA of the transformant colonies was screened for the presence of the mutation by restriction enzyme digestion or by nucleotide sequence analysis of the mutagenized region. Fragments containing the appropriate mutations were transferred from the pUC constructs back into the D50 or D39 plasmids, which in turn were assembled into a full-length clone designated D53. Recombinant virus was recovered in HEp-2 cells by complementing the D53 plasmid with a mixture of the four support plasmids encoding the N, P, L and M2 (ORF1) proteins, as described above.

Four types of mutations are involved in this and subsequent examples describing specific recombinant RSV incorporating biologically derived mutations (see Tables 36, 37, 39):

(1) The first group of mutations involves six translationally silent new restriction site markers introduced into the L gene, collectively called the "sites" mutations. The six sites are Bsu36I, SnaBI, PmeI, RsrII, BstEII and a second, downstream SnaBI site, and are underlined in FIG. 4 above the D53 diagram. These six changes, collectively referred to as the "sites" mutations, were inserted for the purpose of facilitating cDNA construction. Also, it is known that recombination can occur during transfection between the D53 plasmid and the support plasmids, i.e., the N, P, M2(ORF1) and L plasmids (Garcin et al., *EMBO J.* 14:6087-6094 (1995), incorporated herein by reference. These restriction sites in L are present in the D53 construct but not in the L support plasmid, and thus provide a marker to confirm that recombination in L did not occur. This is particularly important since many of the attenuating mutations occur in L.

(2) The second group of mutations involves two amino acid changes in the F gene (FIG. 4, Table 39). The cpRSV, and hence all of its derivatives, is derived from a wild type virus called HEK-7. The sequence of the original D53 cDNA differs from that of HEK-7 by single nucleotide substitutions at seven positions. One is at nucleotide 4, which is a C (in negative sense) in the original D53 and G in the HEK virus. However, biologically-derived viruses have been shown to contain either assignment, and can fluctuate between the two, and so this difference is considered incidental and not considered further here. Four other nucleotide substitutions were silent at the amino acid level; these were two changes in F, at positions 6222 and 6387, one in the F-M2 intergenic region at position 7560, and one in L at position 10515). These also are not considered significant and are not considered further. Finally, there were two nucleotide substitutions, each in the F gene, which each resulted in an amino acid substitution (Table 39). These two changes, collectively called the "HEK" assignments, were introduced into D53 such that the encoded recombinant wild type virus would be identical at the amino acid level to the HEK-7 wild type parent of the biologically-derived cpts mutants. Note that each of these changes was designed to also introduce a new restriction enzyme recognition site for the purpose of monitoring the presence of the introduced mutation in cDNA as well as in recovered virus.

(3) The third group of mutations involved the five amino acid substitutions found in the cpRSV virus, collectively called the "cp" mutations. These are present in all of the biologically-derived cpts viruses and contribute to the attenuation phenotype. In biologically-derived cpRSV, each of these amino acid changes is due to a single nucleotide change. As shown in Table 39, when the amino acid coding change was introduced into cDNA to make recombinant virus in four of the five cases each coding change was made to involve two nucleotide substitutions, which renders the recombinant RSV highly resistant to reversion to wild type. Note that four of these changes were designed to introduce a new restriction enzyme site, whereas the fifth was designed to ablate an existing site, thus providing a method for monitoring the presence of the mutation by the presence or absence of the restriction site in cDNA or RT-PCR products generated from recombinant viruses.

(4) The fourth group of mutations involves point mutations specific to individual, biologically derived cpts viruses (Table 39, FIG. 4), which are named after the biological step at which they were acquired. For example, derivation of the cpts248/404 virus from cpRSV in the following Example involved two steps of mutagenesis. The first yielded the cpts248 virus, which sustained a single amino acid change that is therefore called the 248 mutation. The second mutagenesis step, applied to cpts248, yielded the cpts248/404 virus, which contains an amino acid change in L called the 404(L) mutation and a nucleotide change in the gene start (GS) signal of M2, called 404(M2) mutation. The remaining mutations, namely 530, 1009 and 1030, each involve a single (different) amino acid change. The 404(M2) mutation is noteworthy because it involves the GS transcription signal (and does not involve a protein-coding sequence) and because this mutation was shown in a minigenome system to be important for synthesis of the mRNA. Kuo et al., *J. Virol.* 71:4944-4953 (1977) (incorporated herein by reference). As outlined in Tables 36, 37, and 39, the amino acid coding changes of the 248, 404(L), and 1009 mutations were inserted into recombinant virus using two nucleotide substitutions for the purpose of improved genetic stability. Also, the 248, 404(M2), 404(L), and 1009 mutations for recombinant virus were each designed to introduce a new restriction site for monitoring purposes, while the 1030 mutation was designed to ablate an existing site.

Figure 5:
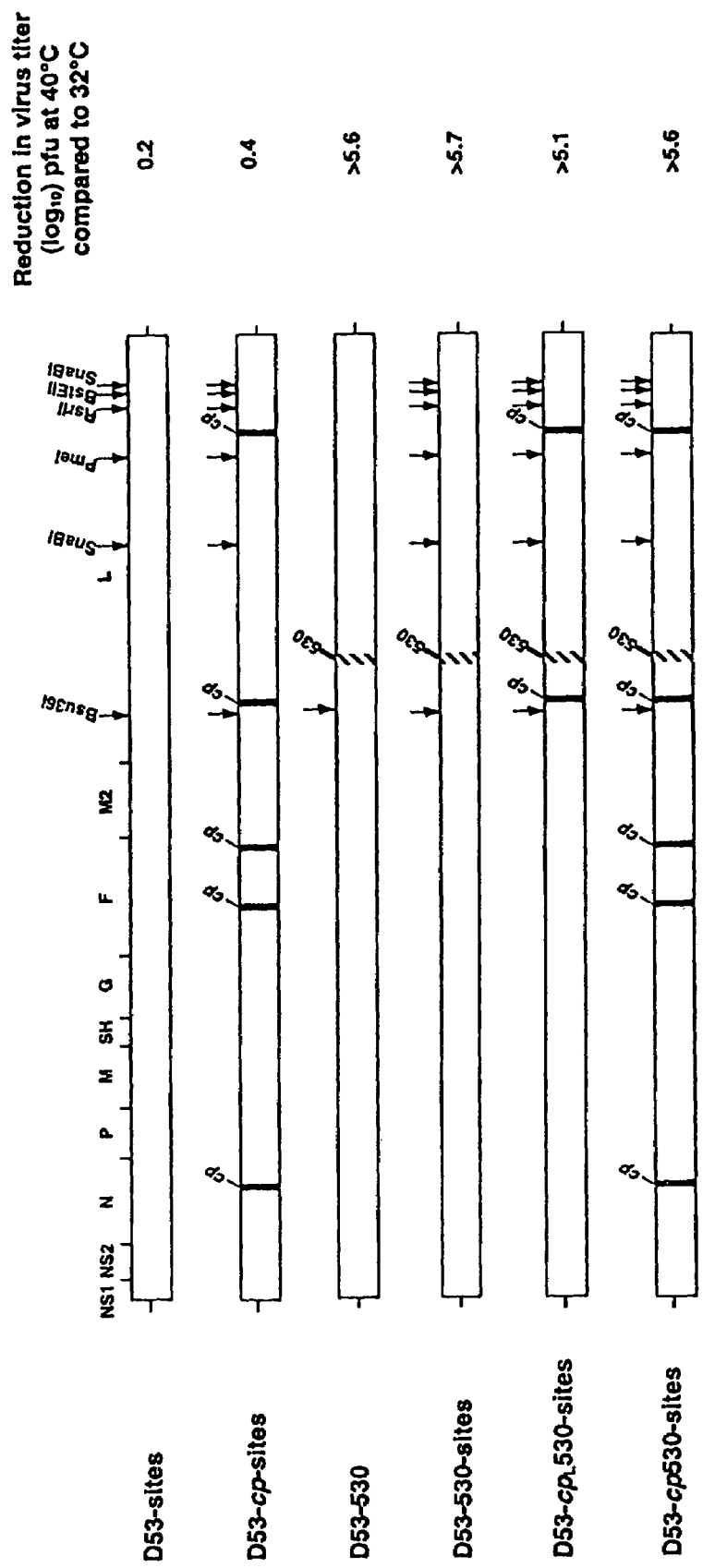
FIG. 5 provides maps of six mutant antigenome cDNAs which were used to recover recombinant RSV. The ts phenotypes of the recombinants are summarized on the right of the figure.

In the present Example, several pUC118- and pUC119-based constructs were derived from the D50 and D39 plasmids and desired mutations were introduced into these constructs (FIGS. 4, 5). Fragments containing the appropriate mutations were transferred from the pUC constructs back into the DS0 or D39 plasmids as indicated, which in turn were assembled into a full-length clone. In this way, six different types of D53 full-length derivative clones were generated (FIGS. 4, 5). In FIG. 5, the D53 constructs lacked the two HEK mutations in F (see FIG. 4).

Mutagenesis was performed using the Muta-Gene® Phagemid in vitro Mutagenesis kit (Bio-Rad, Hercules, Calif.) as recommended by the manufacturer. The mutagenized constructs were transformed into competent *E. coli* DH10B (Life Technologies). Miniprep DNA of the transformant colonies was screened for the presence of the mutation by restriction enzyme digestion (see below) or by nucleotide sequence analysis of the mutagenized region.

The six translationally silent restriction site markers, the 530 mutation ($_{521}$phe→leu), and the 5 cp mutations (Table 39) were introduced into the pUC-based constructs and subcloned into the D50 and D39 plasmids as indicated in FIGS. 4 and 5. The various full-length cDNA constructs were assembled using D50 and D39 constructs containing different combinations of the above mentioned mutations.

In the final cDNA constructs, the presence of the 530 and the cp mutations were confirmed by sequence analysis, while the presence of the silent restriction sites were determined by restriction endonuclease analysis. Each D53-based construct was analyzed using various restriction enzymes (e.g. HpaI, AccI, HindIII, PstI), and the restriction patterns of the newly generated full-length cDNA clones were compared with that of the previously rescued wild-type full-length cDNA clone. This restriction analysis was used to determine if an insertion or deletion of 100 nt or more had occurred during the bacterial amplification of the full-length plasmids.

Transfection was performed as described previously (Collins, et al., *Proc. Natl. Acad. Sci. USA*, 92:11563-11567 (1995), incorporated herein by reference). Briefly, monolayers of HEp-2 cells were infected at an MOI of 1 with recombinant vaccinia virus MVA strain expressing T7 RNA polymerase (MVA-T7) and were transfected using LipofectACE (Life Technologies) with a D53 antigenomic construct plus the N, P, L and M2 (ORF1) pTM1 support plasmids. On day three, supernatants (clarified medium) were passaged onto fresh HEp-2 cells for amplification of rescued virus. Virus suspensions from this first amplification were harvested 5 days after infection and, following inoculation at various dilutions onto monolayers of HEp-2 cells, were overlayed with methylcellulose for plaque enumeration or with agarose for plaque harvest and biological cloning. Plaque enumeration was performed using a monoclonal antibody-horseradish peroxidase staining procedure as previously described (Murphy et al., *Vaccine*, 8:497-502 (1990), incorporated herein by reference). The recovered recombinant viruses were biologically cloned by three successive plaque purifications, and then used to generate virus suspensions following two passages on HEp-2 cells. The biological cloning was important to ensure a homogeneous population of the recovered viruses, as recombination may arise during the first step of the rescue between the plasmid representing the full-length cDNA of RSV and the support plasmids containing RSV genes (Garcin et al., *EMBO J.*, 14:6087-6094 (1995), incorporated herein by reference). These biologically cloned and amplified virus suspensions were used in further molecular genetic or phenotypic characterization of the recombinant viruses. Two biologically cloned recombinant viruses were generated for each of the cDNA constructs (FIG. 5) except for $cp_L530$-sites and cp530-sites, for which only one biological clone was generated. In each case, when there were sister clones, they were indistinguishable on the basis of genetic and biological analyses described below. A representative example of the foregoing constructs corresponding to D53-530-sites (alternatively designated A2 ts530-s cl1cp, or ts530-sites) has been deposited under the terms of the Budapest Treaty with the ATCC and granted the accession number VR-2545.

The recombinant RSVs generated as described above were genetically characterized to determine if they indeed contained each of the introduced mutations. Monolayers of HEp-2 cells were infected with biologically cloned recombinant virus and total RNA was harvested 4 to 5 days post infection as described above. RT was performed using random hexamer primers and the generated cDNA was used as template in PCR using the Advantage™ cDNA PCR Kit (Clontech Lab. Inc., Palo Alto, Calif.) to generate three fragments representing almost the full-length of the recombinant RSV genomes. The PCR fragments corresponded to the RSV genome between nt positions 1-5131, 5949-10751 and 8501-15179. Also, a 544 bp fragment representing a portion of the L gene in the region of the 530 mutation between nt positions 9665 and 10209 was generated. This short PCR fragment was used in cycle sequencing (using 71001 delta TAQ™* Cycle Sequencing Kit, USB, Cleveland, Ohio) to confirm the presence or the absence of the 530 mutation in the recovered recombinant virus, whereas the large PCR products were used in restriction enzyme digestion to confirm the presence of the silent restriction site markers and the cp mutations which were marked with specific restriction sites.

To verify that the recombinant RSVs produced according to the above methods incorporated the desired phenotype, i.e., the phenotype specified by the incorporated sequence change(s), the efficiency of plaque formation (EOP) of the recombinant RSVs and the nonrecombinant control viruses was determined. Specifically, plaque titration at 32, 37, 38, 39 and 40° C. using HEp-2 monolayer cultures in temperature controlled water baths was conducted, as described previously (Crowe et al., *Vaccine*, 11:1395-1404 (1993); Firestone, et al., *Virology* 225:419-522 (1996), each incorporated herein by reference). Plaque identification and enumeration was performed using antibody staining as indicated above.

The level of temperature-sensitivity of the recombinant viruses and the wild-type and biologically derived mutant cpts530 viruses is presented in Table 40. These data show that the introduction of the silent restriction sites or the cp mutations does not confer a ts phenotype. This latter observation is consistent with our previous finding that the cpRSV is a $ts^+$ virus (Crowe, et al., *Vaccine*, 12:691-699 (1994)).

TABLE 40

Comparison of the Efficiency of Plaque Formation[a] of Recombinant and Biologically Derived Viruses in HEp-2 Cells at Various Temperatures.

| Virus | RSV Titer ($log_{10}$pfu/ml at indicated temp.)[b] | | | Reduction in Virus titer ($log_{10}$) at indicated temperature compared to that at 32° C. | | |
|---|---|---|---|---|---|---|
|  | 32 | 38 | 39 | 40 | 39 | 40 |
| Wild-type[c] | 5.7 | 5.5 | 5.4 | 5.3 | 0.3 | 0.4 |
| r-sites | 5.4 | 5.1 | 5.2 | 5.2 | 0.2 | 0.2 |
| rcp-sites | 6.1 | 5.7 | 5.7 | 5.7 | 0.4 | 0.4 |
| r530 | 6.3 | 6.0 | 4.4 | <0.7 | 1.9 | >5.6 |
| r530-sites | 6.4 | 6.1 | 4.4 | <0.7 | 2.0 | >5.7 |
| rcp$_L$530-sites | 5.8 | 5.9 | 3.8 | <0.7 | 2.0 | >5.1 |
| rcp530-sites | 6.3 | 5.0 | 4.1 | <0.7 | 2.2 | >5.6 |
| cpts530[c] | 6.6 | 5.8 | 4.4 | <0.7 | 2.2 | >5.9 |

[a]Efficiency of plaque formation of the various RSV strains was determined by plaque titration on monolayers of HEp-2 cells under semisolid overlay for five days at the indicated temperatures (° C.).
[b]Virus titers are the average of two tests, except for r-sites and r cp-sites where data were derived from a single test.
[c]Biologically derived control viruses.

The above findings confirm that ts phenotype of the biologically derived cpts530 virus is specified by the single mutation identified above as being unique to this attenuated RSV strain. Genetic analysis of the cpts530 strain was confirmed in this context by the introduction of the 530 mutation into a full-length cDNA clone of the A2 wild-type $ts^+$ parent virus, followed by the recovery of a ts recombinant virus bearing the 530 mutation. Analysis of the level of temperature sensitivity of this and additional recombinant viruses containing the 530 and cp mutations revealed that the level of temperature sensitivity specified by the 530 mutation was not influenced by the five cp mutations. Thus, the methods and compositions of the invention identified the 530 mutation as the ts phenotype-specific mutation which is attributed with further attenuation of the cpts530 virus in model hosts over that of its cpRSV parent (Crowe et al., *Vaccine*, 12:783-90 (1994), Crowe et al., *Vaccine*, 13:847-855 (1995), each incorporated herein by reference).

In addition to the above findings, introduction of the 1009 mutation or 1030 mutation into recombinant RSV, in combination with the cpts530 mutation, generated recombinants whose levels of temperature sensitivity were the same as those of the respective, biologically derived cpts530/1009 and cpts530/1030 RSV mutants.

The above findings illustrate several important advantages of the recombinant methods and RSV clones of the invention for developing live attenuated RSV vaccines. The insertion of a selected mutation into recombinant RSV, as well as the recovery of mutations from the RSV A2 cDNA clone were relatively efficient. The antigenome cDNA clone used in this example had been modified in the original construction to contain changes at five different loci, involving 6 nucleotide substitutions and one nucleotide insertion. Mutagenized virus are also described containing mutations at an additional twelve loci involving 24 additional nucleotide substitutions. The fact that only the 530 mutation imparted a phenotype detectable in tissue culture indicates the relative ease of manipulation of this large RNA genome. Although recombination between the support plasmids and the full-length clone that is mediated by the vaccinia virus enzymes can occur (Garcin et al., *EMBO J.*, 14:6087-6094 (1995)), its frequency is sufficiently low that each of the 10 viruses analyzed here possessed the mutations present in the cDNA clone from which it was derived. Thus, it is readily feasible to introduce further attenuating mutations in a sequential manner into RSV, to achieve a desired level of attenuation.

The demonstrated use of the present RSV recovery system for direct identification of attenuating mutations and the established success for manipulating recombinant RSV allow for identification and incorporation of other desired mutations into live infectious RSV clones. Previous findings from clinical studies and sequence analysis of the cpRSV virus suggest that the set of five non-ts mutations present in cpRSV are attenuating mutations for seropositive humans (Connors et al., *Virology*, 208:478-84 (1995), Firestone, et al., *Virology*, 225:419-522 (1996), Friedewald et al., *JAMA*, 203:690-694 (1968), Kim et al., *Pediatrics*, 48:745-755 (1971), each incorporated herein by reference). These and other mutations are selected for their confirmed specificity for attenuated and/or ts phenotypes using the methods described here, and can then be assembled into a menu of attenuating mutations. These and other attenuating mutations, both ts and non-ts, can then be introduced into the RSV A2 wild-type virus to produce a live attenuated virus selected for a proper balance between attenuation and immunogenicity. In this regard, it is advantageous that the 530 and other identified ts mutations are not in the G and F glycoproteins which induce the protective immune responses to RSV in humans. This permits the development of an attenuated RSV cDNA backbone with mutations outside of F and G that can serve as a cDNA substrate into which the F and G glycoproteins of RSV subgroup B or those of an epidemiologically divergent subgroup A strain can be substituted for the A2 F and G glycoproteins. In this way, a live attenuated RSV vaccine can be rapidly updated to accommodate antigenic drift within subgroup A strains, and a subgroup B vaccine component can also be rapidly produced.

EXAMPLE X

Construction of an Infectious Recombinant RSV Modified to Incorporate Phenotype-Specific Mutations of RSV Strain cpts248/404

This Example illustrates additional designs for introducing predetermined attenuating mutations into infectious RSV employing the recombinant procedures and materials described herein.

Previous sequence analysis of the RSV A2 cpts248 mutant also identified a single mutation in the L gene, a glutamine to leucine substitution at amino acid position 831 (Table 39; Crowe et al., *Virus Genes*, 13:269-273 (1996), incorporated herein by reference). This mutation was confirmed by the methods herein to be attenuating and ts. Sequence analysis of the further attenuated RSV mutant cpts248/404 revealed two additional mutations, a nt change in the M2 gene start sequence and an amino acid substitution, aspartic acid to glutamic acid at amino acid position 1183 in the L protein (Table 39; Firestone, et al., *Virology*, 225:419-522 (1996), incorporated herein by reference).

The biologically-derived attenuated RSV strain cpts248/404 was reconstructed as a recombinant virus (rA2cp/248/404) according to the above described methods. cDNA D53 encoding rA2cp/248/404 virus was constructed by insertion of the sites, HEK, cp, 248 and 404 changes (Table 39). Recombinant virus (rA2cp/248/404) was recovered, plaque purified and amplified. The presence of the mutations in recombinant virus was analyzed by RT-PCR of viral RNA followed by restriction enzyme digestion or nucleotide sequencing or both. The rA2cp/248/404 recombinant was recovered using either the pTMLwt or pTML248/404 support plasmid, the latter of which contains all of the mutations in L present in the biologically derived cpts248/404 mutant (Table 39, not including the mutations specific to the 530, 1009, or 1030 viruses). Using the pTML248/404 as a support plasmid precludes loss of 248/404 mutations present in a full length clone by homologous recombination with the support plasmid.

Recombinant viruses were recovered from D53 DNA in which only the sites and HEK mutations were present (rA2 in Table 41), to demonstrate that these changes were indeed phenotypically silent as expected. Recombinant virus containing the sites, HEK and cp mutations was recovered (called rA2cp in Table 41), to evaluate the phenotypes specified by the cp mutations. Also, as shown in Table 41, separate viruses were constructed containing the sites, HEK and cp background together with (i) the 248 mutation (rA2cp/248), (ii) the two 404 mutations (rA2cp/404); and the 404(M2) mutation (rA2cp/404(M2), and the 404(L) mutation (rA2cp/404 (L)).

These viruses were evaluated in parallel for the ability to form plaques in HEp-2 cells at 32° C., 36° C., 37° C., 38° C. and 39° C. This comparison showed that all viruses formed plaques at 32° C., and showed that the titers of the various virus preparations were within approximately three $\log_{10}$ units of each other, which is within the range of experimental variation typically seen among independent preparations of RSV. The introduction of the added "sites" and HEK mutations into wild type recombinant virus (to yield virus rA2) did not alter the virus with regard to its ability to grow at the elevated temperatures, as compared with biologically-derived wild type virus (virus A2 wt). The additional introduction of the cp mutations (to yield virus rA2cp) also did not alter its ability to grow at elevated temperatures. This is the expected result, because the biologically derived cpRSV from which the mutations were derived does not have the ts phenotype; its mutations are of the host range variety. The 404 mutation in L does not appear to be a ts mutation since rA2cp/404(L) was not ts. However, this mutation may otherwise prove to be attenuating, as will be determined by further analysis in accordance with the methods herein. Thus, of the two specific mutations in cpts 248/404 virus only the 404M2 mutation is ts. The further addition of the 248 and 404 mutations (to yield rA2cp/248/404 virus) resulted in a ts phenotype that was essentially equivalent to its biologically-derived equivalent virus as evidenced by being greatly impaired in the ability to form plaques at 36° C.-37° C., with pinpoint plaques being formed at the former temperature. These recombinant viruses incorporated a variety of mutations predicted to have no effect on growth in tissue culture, and additional mutations expected to confer a ts phenotype. Each type of mutation yielded results consistent with these expectations, demonstrating that the RSV genome can be manipulated in a reasonably predictable way.

TABLE 41

Efficiency of Plaque Formation of Selected RSV Mutants

| Virus[1] | Transfectant | Virus titer ($log_{10}$pfu/ml) at indicated temperature (° C.) | | | | | Shut-off temp. |
|---|---|---|---|---|---|---|---|
| | | 32 | 36 | 37 | 38 | 39 | |
| A2 wt[2] | | 5.0 | 4.8 | 5.1 | 4.6 | 4.7 | >39 |
| rA2 | 14-1B-1A2 | 4.9 | 4.2 | 4.4 | 4.5 | 3.9 | >39 |
| rA2cp | 12-2B-1B1 | 5.6 | 5.1 | 4.8 | 3.8 | 3.7 | >39 |
| rA2cp/248 | 12-6A-1A1 | 5.8 | 4.8* | 4.0* | <0.7 | <0.7 | 38 |
| rA2cp/404-L | 16-1A-1A1 | 5.4 | 5.2 | 5.1 | 4.9 | 5.0 | >39 |
| rA2cp/404-M2 | 15-1A-1A1 | 4.9 | <0.7 | <0.7 | <0.7 | <0.7 | 36 |
| rA2cp/404 | 16-4B-1B1 | 3.3 | 1.2* | <0.7 | <0.7 | <0.7 | 36 |
| rA2cp/248/404 | 32-6A-2 | 6.0 | <0.7 | <0.7 | <0.7 | <0.7 | 36 |
| rA2cp/248/404/530 | 13-4B-3 | 5.7 | 4.7* | 2.5* | nd | <0.7 | 37 |
| cpts248/404(WLVP)[2] | | 5.1 | <0.7 | <0.7 | <0.7 | <0.7 | 36 |

[1]Recombinant (r) viruses have been plaque purified and amplified in HEp-2 cells. Note that the stocks of recombinant and biologically-derived viruses had not been adjusted to contain equivalent amounts of pfu/ml: the level of variation seen here is typical for RSV isolates at anearly stage of amplification from plaques. Each recombinant virus contains the L-gene sites and the F-gene HEK mutations. The code in the "Transfectant" column refers to the transfection and plaquing history.
[2]Biologically derived viruses: A2 wt and cpts248/404 (WLVP L16210B-150).
*Pin-point plaque size Table 41 shows further characterization of mutations specific to the 248 and 404 mutagenesis steps. Specifically, viruses were constructed using the sites, HEK and cp background with the addition of: (i) the 248 mutation (to yield virus rA2cp/248), (ii) the two 404 mutations (virus rA2cp/404); or the 404(M2) mutation (virus rA2cp/404(M2)) (Table 39). Each of these three viruses exhibited the ts phenotype, providing direct identification of these mutations as being ts. The 248 mutation provided a lower level of temperature sensitivity, whereas the 404(M2) mutation was highly ts and was not augmented by the addition of the 404(L) mutation. It was remarkable that the 404(M2) mutation is ts, since it is a point mutation in a transcription initiation, or gene start (GS), signal, and this type of mutation has never been shown to be ts.

EXAMPLE XI

Construction of Recombinant RSV Combining Predetermined Attenuating Mutations from Multiple Attenuated Parent Viruses The present Example illustrates a combinatorial design for producing a multiply attenuated recombinant RSV (rA2cp/248/404/530) which incorporates three attenuating mutations from one biologically derived RSV strain (specifically cpts248/404) and an additional attenuating mutation from another RSV strain (cpts530). This recombinant RSV exemplifies the methods of the invention for engineering stepwise attenuating mutations to fine tune the level of attenuation in RSV vaccines, wherein multiple mutations contribute to a further attenuated phenotype of the vaccine strain and provide for enhanced genetic stability.

The cDNAs and methods of Examples IX and X above were used to construct a D53 cDNA containing the sites, HEK, cp, 248, 404 and 530 changes (Table 39). This involved a combination of attenuating mutations from four separate biologically-derived viruses, namely cpRSV, cpts248, cpts248/404 and cpts530. Recombinant virus (rA2cp/248/404/530) was recovered, plaque purified and amplified. The presence of the mutations was analyzed by RT-PCR of viral RNA followed by restriction enzyme digestion or nucleotide sequencing or both. rA2cp/248/404/530 lacked the 248 mutation in L, but possessed the 530 mutation and the other 248/404 mutation.

The rA2cp/248/404 virus was evaluated for its ability to form plaques in HEp-2 cells at 32° C., 36° C., 37° C., 38° C. and 39° C. as described above (Table 41). All of viruses formed plaques at 32° C. and were similar to wild type in the efficiency of growth at this temperature. The rA2cp/248/404/530 virus was essentially equivalent to the biologically-derived cpts248/404 virus with regard to the ts phenotype, evidenced by being greatly impaired in the ability to form plaques at 37° C. Thus, the addition of the 530 mutation to the rA2cp/248/404 background did not increase its ts phenotype, however, the recombinant lacked the 248 mutation in L.

Based on this and the foregoing Examples, the invention allows recovery of a wide variety of recombinant viruses containing two or more ts mutations from the set of mutations which have been identified and confirmed from biologically derived RSV mutants, for example the 248, 404, 530, 1009, or 1030 biological mutants. Examples of such recombinant viruses include RSV having a combination of 248/404/530 mutations, 248/404/1009 mutations, 248/404/1030 mutations, 248/404/530/1009 mutations, 248/404/530/1030 mutations, 248/404/530/1030 mutations, 248/404/1009/1030 mutations, or other combinations of attenuating mutations disclosed herein. In addition, recombinant RSV incorporating one or more ts mutations identified from biologically derived RSV mutants can be combined with other mutations disclosed herein, such as attenuating gene deletions or mutations that modulate RSV gene expression. One such example is to combine 248/404 mutations with an SH gene deletion in a recombinant clone, which yields a viable vaccine candidate. A host of other combinatorial mutants are provided as well, which can incorporate any one or more ts mutations from biologically derived RSV and any one or more other mutations disclosed herein, such as deletions, substitutions, additions and/or rearrangements of genes or gene segments. The cp mutations, which are attenuating host range rather than attenuating ts mutations, also can be included along with one or more other mutations within the invention. This provides a panel of viruses representing a broad spectrum in terms of individual and combined levels of attenuation, immunogenicity and genetic stability. These attenuating mutations from biologically derived RSV mutants can be further combined with the various other structural modifications identified herein, which also specify desired phenotypic changes in recombinant RSV, to yield yet additional RSV having superior vaccine characteristics.

EXAMPLE XII

Recovery of Infectious Respiratory Syncytial Virus Expressing an Additional, Foreign Gene The methods described above were used to construct recombinant RSV containing an additional gene, encoding chloramphenicol acetyl transferase (CAT). The CAT coding sequence was flanked by RSV-specific gene-start and gene-end motifs, the transcription signals for the viral RNA-dependent RNA polymerase. Kuo et al., *J. Virol.* 70:6892-6901 (1996) (incorporated herein by reference). The RSV/CAT chimeric transcription cassette was inserted into the intergenic region between the G and F genes of the complete cDNA-encoded positive-sense RSV antigenome, and infectious CAT-expressing recombinant RSV was recovered. The CAT mRNA was efficiently expressed and the levels of the G and F mRNAs were comparable to those expressed by wild type recombinant RSV. The CAT-containing and wild type viruses were similar with regard to the levels of synthesis of the major viral proteins.

Figure 6:
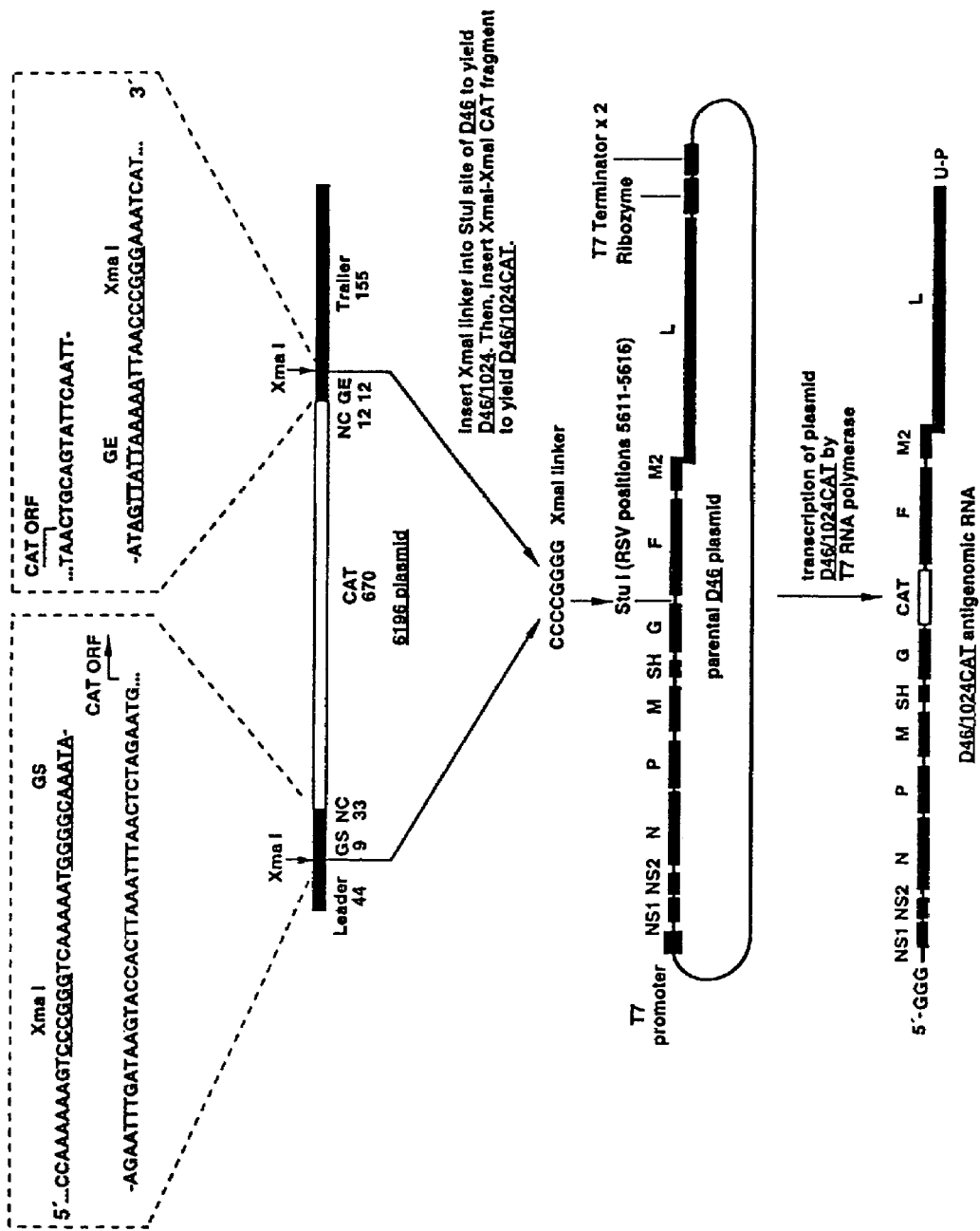
FIG. 6 shows construction of D46/1024CAT cDNA encoding an RSV antigenome containing the CAT ORF flanked by RSV transcription signals (not to scale, RSV-specific segments are shown as filled boxes and CAT sequence as an open box). The source of the CAT gene transcription cassette was RSV-CAT minigenome cDNA 6196 (diagram at top). The RSV-CAT minigenome contains the leader region, GS and GE signals, noncoding (NC) RSV gene sequences, and the CAT ORF, with XmaI restriction endonuclease sites preceding the GS signal and following the GE signal. The nucleotide lengths of these elements are indicated, and the sequences (SEQ ID NOS: 25 and 26)(positive-sense) surrounding the XmaI sites are shown above the diagram. A 8-nucleotide XmaI linker was inserted into StuI site of the parental plasmid D46 to construct the plasmid D46/1024. D46 is the complete antigenome cDNA and is equivalent to D53; the difference in nomenclature is to denote that these represent two different preparations. The Xma-XmaI fragment of the plasmid 6196 was inserted into the plasmid D46/1024 to construct the plasmid D46/1024CAT. The RNA encoded by the D46 cDNA is shown at the bottom, including the three 5'-terminal nonviral G residues contributed by the T7 promoter and the 3'-terminal phosphorylated U residue contributed by cleavage of the hammerhead ribozyme; the nucleotide lengths given for the antigenome do not include these nonviral nucleotides. The L gene is drawn offset to indicate the gene overlap.

Plasmid D46 was used for construction of cDNA encoding RSV antigenomic RNA containing the CAT gene. (Plasmids D46 and D53, the latter being described above, are different preparations of the same antigenome cDNA.) D46 which encodes the complete, 15,223-nucleotide RSV antigenome (one nucleotide longer than that of wild type RSV) and was used to produce recombinant infectious RSV, as described above. During its construction, the antigenome cDNA had been modified to contain four new restriction sites as markers. One of these, a StuI site placed in the intergenic region between the G and F genes (positions 5611-5616 in the 3'-5' sequence of the wild type genome), was chosen as an insertion site for the foreign CAT gene. A copy of the CAT ORF flanked on the upstream end by the RSV GS signal and on the downstream end by the RS GE signal was derived from a previously-described RSV-CAT minigenome (Collins et al., *Proc. Natl. Acad. Sci. USA* 88:9663-9667 (1991) and Kuo et al., *J. Virol.* 70: 6892-6901 (1996), incorporated by reference herein). The insertion of this RSV/CAT transcription cassette into the StuI site yielded the D46/1024CAT cDNA (deposited under the terms of the Budapest Treaty with the ATCC and granted the accession number VR-2544), which increased the length of the encoded antigenome to a total of 15,984 nucleotides. And, whereas wild type RSV encodes ten major subgenomic mRNAs, the recombinant virus predicted from the D46/1024CAT antigenome would encode the CAT gene as an eleventh mRNA. The strategy of construction is shown in FIG. 6.

Producing infectious RSV from cDNA-encoded antigenomic RNA, as described above, involved coexpression in HEp-2 cells of five cDNAs separately encoding the antigenomic RNA or the N, P, L or M2(ORF1) protein, which are necessary and sufficient for viral RNA replication and transcription. cDNA expression was driven by T7 RNA polymerase supplied by a vaccinia-T7 recombinant virus based on the MVA strain. The MVA-T7 recombinant virus produced infectious progeny sufficient to cause extensive cytopathogenicity upon passage, and therefore, cytosine arabinoside, an inhibitor of vaccinia virus replication, was added 24 h following the transfection and maintained during the first six passages. The use of cytosine arabinoside was not required, however, and was not used in later examples herein.

Two antigenome cDNAs were tested for the recovery of RSV: the D46 cDNA, and the D46/1024CAT cDNA. Each one yielded infectious recombinant RSV. Cells infected with the D46/1024CAT recombinant virus expressed abundant levels of CAT enzyme. For each virus, transfection supernatants were passaged to fresh cells, and a total of eight serial passages were performed at intervals of five to six days and a multiplicity of infection of less than 0.1 PFU per cell.

The CAT sequence in the D46/1024CAT genome was flanked by RSV GS and GE signals, and thus should be expressed as an additional, separate, polyadenylated mRNA. The presence of this predicted mRNA was tested by Northern blot hybridization of RNA from cells infected with D46/1024CAT virus or D46 virus at the eighth passage. Hybridization with a negative-sense CAT-specific riboprobe detected a major band which was of the appropriate size to be the predicted CAT mRNA, which would contain 735 nucleotides not including poly(A). This species was efficiently retained by oligo(dT) latex particles, showing that it was polyadenylated. In some cases, a minor larger CAT-specific species was detected which was of the appropriate size to be a G-CAT readthrough mRNA. The D46/1024CAT virus had been subjected to eight passages at low multiplicity of infection prior to the infection used for preparing the intracellular RNA. There was no evidence of shorter forms of the CAT mRNA, as might have arisen if the CAT gene was subject to deletion.

Replicate blots were hybridized with negative-sense riboprobe specific to the CAT, SH, G or F gene, the latter two genes flanking the inserted CAT gene. The blots showed that the expression of the subgenomic SH, G and F mRNAs was similar for the two viruses. Phosphoimagery was used to compare the amount of hybridized radioactivity in each of the three RSV mRNA bands for D46/1024CAT and D46. The ratio of radioactivity between D46/1024CAT and D46 was determined for each mRNA: SH, 0.77; G, 0.87; and F, 0.78. The deviation from unity probably indicates that slightly less RNA was loaded for D46/1024CAT versus D46, although it is also possible that the overall level of mRNA accumulation was slightly less for D46/1024CAT RSV. The demonstration that the three ratios were similar confirms that the level of expression of each of these mRNAs was approximately the same for D46/1024CAT versus D46. Thus, the insertion of the CAT gene between the G and F genes did not drastically affect the level of transcription of either gene.

To characterize viral protein synthesis, infected HEp-2 cells were labeled with [$^{35}$S]methionine, and cell lysates were analyzed by PAGE either directly or following immunoprecipitation under conditions where recovery of labeled antigen was essentially complete. Precipitation with a rabbit antiserum raised against purified RSV showed that the D46/1024CAT and D46 viruses both expressed similar amounts of the major viral proteins $F_1$, N, P, M, and M2. That a similar level of M2 protein was recovered for each virus was noteworthy because its gene is downstream of the inserted CAT gene. Accumulation of the F protein, which is encoded by the gene located immediately downstream of the insertion, also was examined by immunoprecipitation with a mixture of three anti-F monoclonal antibodies. A similar level of the $F_1$ subunit was recovered for each virus. Phosphorimagery analysis of the major viral proteins mentioned above was performed for several independent experiments and showed some sample-to-sample variability, but overall the two viruses could not be distinguished on the basis of the level of recovered proteins. Precipitation with anti-CAT antibodies recovered a single species for the D46/1024CAT but not for the D46 virus. Analysis of the total labeled protein showed that the N, P and M proteins could be detected without immunoprecipitation (although detection of the latter was complicated by its comigration with a cellular species) and confirmed that the two viruses yielded similar patterns. The position corresponding to that of the CAT protein contained more radioactivity in the D46/1024CAT pattern compared to that of D46, as was confirmed by phosphorimagery of independent experiments. This suggested that the CAT protein could be detected among the total labeled proteins without precipitation, although this demonstration was complicated by the presence of a comigrating background band in the uninfected and D46-infected patterns.

RT-PCR was used to confirm the presence of the CAT gene in the predicted location of the genome of recombinant RSV. Total intracellular RNA was isolated from the cell pellet of passage eight of both D46/1024CAT and D46 RSV. Two primers were chosen that flank the site of insertion, the StuI restriction endonuclease site at RSV positions 5611-5616: the upstream positive-sense primer corresponded to positions 5412-5429, and the downstream negative-sense one to positions 5730-5711. The positive-sense primer was used for the RT step, and both primers were included in the PCR.

RT-PCR of the D46 virus yielded a single product that corresponded to the predicted fragment of 318 nucleotides, representing the G/F gene junction without additional foreign sequence. Analysis of D46/1024CAT viral RNA yielded a single product whose electrophoretic mobility corresponded well with the predicted 1079 nucleotide fragment, representing the G/F gene junction containing the inserted CAT transcription cassette. The latter PCR yielded a single major band; the absence of detectable smaller products indicated that the population of recombinant genomes did not contain a large number of molecules with a deletion in this region. When PCR analysis was performed on D46/1024CAT virus RNA without the RT step, no band was seen, confirming that the analysis was specific to RNA. Thus, the RT-PCR analysis confirmed the presence of an insert of the predicted length in the predicted location in the genomic RNA of the D46/1024CAT recombinant virus.

Enzyme expression was used to measure the stability of the CAT gene. Cell pellets from all of the passages beginning with the third were tested for CAT expression. For the virus D46/1024CAT, all these assays displayed conversion of [$^{14}$C] labeled chloramphenicol into acetylated forms. To investigate stability of expression, virus from 20 or 25 individual plaques from passage three or eight, respectively, was analyzed for CAT expression. All samples were positive, and the level of expression of CAT was similar for each of the 25 isolates from passage eight, as judged by assay of equivalent aliquots of cell lysate. This demonstrated that the activity of the CAT protein encoded by each isolate remained unimpaired by mutation.

To determine plaque morphology and size, beginning with the second passage, one-eighth of the medium supernatant (i.e., 0.5 ml) harvested from each passage stage was used to infect fresh HEp-2 cells in six-well plates that were incubated under methylcellulose overlay for five to seven days. The cells were then fixed and stained by incubation with monoclonal antibodies against RSV F protein followed by a second antibody linked to horseradish peroxidase. Earlier, it had been observed that recombinant RSV produced from cDNA D46 was indistinguishable from a naturally-occurring wild type RSV isolate with regard to efficiency of plaque formation over a range of temperatures in vitro, and the ability to replicate and cause disease when inoculated into the respiratory tract of previously uninfected chimpanzees. Thus, the D46 recombinant RSV was considered to be a virulent wild type strain. The plaques produced by the D46 and D46/1024CAT recombinant viruses were compared by antibody staining. Plaque morphology was very similar for the two viruses, although the average diameter of the CAT-containing recombinant plaques was 90 percent of that of the D46 virus, based on measurement of thirty randomly-selected plaques for each virus.

The efficiency of replication in tissue culture of the D46 and D46/1024CAT viruses was compared in a single step growth cycle. Triplicate monolayers of cells were infected with either virus, and samples were taken at 12 h intervals and quantitated by plaque assay. The results showed that the production of D46/1024CAT virus relative to D46 was delayed and achieved a maximum titer which was 20-fold lower.

These results show that it is possible to construct recombinant, helper-independent RSV expressing a foreign gene, in this instance the CAT gene. The recombinant RSV directed expression of the predicted polyadenylated subgenomic mRNA that encoded CAT protein, the protein being detected both by enzyme assay and by radioimmunoprecipitation. Other examples have produced RSV recombinants with the luciferase gene inserted at the same CAT site, or with the CAT or luciferase genes inserted between the SH and G genes. These viruses also exhibit reduced growth, whereas the numerous wild type recombinant viruses recovered exhibit undiminished growth. This indicates that the reduced growth indeed is associated with the inserted gene rather than being due to chance mutation elsewhere in the genome. The level of attenuation appears to increase with increasing length of the inserted gene. The finding that insertion of a foreign gene into recombinant RSV reduced its level of replication and was stable during passage in vitro suggests that this provides yet another means for effecting attenuation for vaccine use. Also, the insertion into recombinant RSV of a gene expressing a protein having antiviral activity, such as gamma interferon and IL-2, among others, will yield attenuation of the virus due to activity of the expressed antiviral protein.

In addition to demonstrating recovery of RSV having modified growth characteristics, the examples herein illustrate other important methods and advantages for gene expression of recombinant RSV and other nonsegmented, negative strand viruses. For example, the data provided herein show that foreign coding sequences can be introduced as a separate transcription cassette which is expressed as a separate mRNA. These results also show that RSV is tolerant of substantial increases in genome length, e.g., of 762 nucleotides in the case of the CAT gene to a total of 15,984 nucleotides (1.05 times that of wild type RSV). The luciferase gene that was successfully recovered is almost three times longer.

The viral RNA-dependent RNA polymerases are known to have an error-prone nature due to the absence of proofreading and repair mechanisms. In RNA virus genomes, the frequency of mutation is estimated to be as high as $10^{-4}$-$10^{-5}$ per site on average (Holland et al., *Curr. Top. Microbiol. Immunol.* 176:1-20 (1992) and references therein). In the case of the recombinant D46/1024CAT RSV produced here, correct expression of the foreign gene would be irrelevant for virus replication and would be free to accumulate mutations. The passages described here involved a multiplicity of infection less than 0.1 PFU per cell, and the duration of each passage level indicated that multiple rounds of infection were involved. While yields of infectious virus from RSV-infected tissue culture cells typically are low, intracellular macromolecular synthesis is robust, and the poor yields of infectious virus seem to represent an inefficient step in packaging rather than low levels of RNA replication. Thus, the maintenance of CAT through eight serial passages involved many rounds of RNA replication. It was surprising that the nonessential CAT gene remained intact and capable of encoding fully functional protein in each of the 25 isolates tested at the eighth passage. Also, RT-PCR analysis of RNA isolated from passage eight did not detect deletions within the CAT gene.

A second infectious RSV-CAT recombinant was constructed in which the CAT transcription cassette was inserted into an XmaI site which had been engineered into the SH-G intergenic region (which is one position closer to the promoter than the F-G intergenic used above). The growth characteristics of this recombinant were similar to those of the D46/1024 CAT recombinant, whereas the level of CAT expression was approximately two to three-fold higher, consistent with its more promoter-proximal location. This illustrates that a foreign gene can be inserted at a second, different site within the genome and its level of expression altered accordingly. In principle, any portion of the genome should be able to accept the insertion of a transcription unit encoding a foreign protein as long as the insertion does not disrupt a mRNA-encoding unit and does not interfere with the cis-acting sequence elements found at both ends of the genome.

An infectious recombinant RSV was also recovered in which the CAT gene was replaced by that of the luciferase (LUC) marker enzyme. The LUC coding sequence is approximately 1,750 bp (three times the size of CAT), and is larger than any of the RSV genes except for F and L. It was inserted at either the SH-G or G-F intergenic regions and infectious recombinant virus was recovered. The LUC viruses were further attenuated relative to the CAT viruses with regard to growth in tissue culture, suggesting that increases in the size of the genome lead to decreases in growth efficiency. Characterization of these CAT and LUC viruses will determine the effect of foreign gene size on virus gene expression and growth, such as how much is due to the introduction of the additional set of transcription signals, and how much is due to increased genome length.

In the minireplicon system, an RSV-CAT minigenome was modified such that the transcriptional unit is in the "sense" orientation in the positive-sense antigenome rather than the minigenome. Thus, subgenomic mRNA can be made only if the polymerase is capable of transcription of the antigenome replicative intermediate. Interestingly, when complemented by plasmid-expressed N, P, L and M2 ORF1 protein, this inverse RSV-CAT minigenome was capable of synthesizing subgenomic, polyadenylated, translatable mRNA. Efficient mRNA synthesis was dependent on the M2 ORF1 protein, as is the case for minigenome transcription. The level of mRNA relative to its antigenome template was approximately the same as the ratio of mRNA to minigenome template made by a standard minireplicon. This indicates that the antigenome, as well as the genome, can be used to accept a foreign transcriptional unit. Thus, expression of a foreign gene can be achieved without placing it into the genome transcriptional order. This had the advantage that the foreign gene is not be part of the transcriptional program of the genome and thus will not perturb the relative levels of expression of these genes.

Because most of the antigenic difference between the two RSV antigenic subgroups resides in the G glycoprotein, recombinant RSV can be constructed to express the G protein of the heterologous subgroup as an additional gene to yield a divalent vaccine. Envelope protein genes of some other respiratory viruses, such as human parainfluenza 3 virus, also can be inserted for expression by recombinant RSV. Other uses include coexpression of immune modulators such as interleukin 6 to enhance the immunogenicity of infectious RSV. Other uses, such as employing modified RSV as described herein as a vector for gene therapy, are also provided.

EXAMPLE XIII

Recombinant RSV Having a Deletion of the SH Gene

This example describes production of a recombinant RSV in which expression of the SH gene has been ablated by removal of a polynucleotide sequence encoding the SH mRNA and protein. The SH protein is a small (64 amino acids in the case of strain A2) protein which contains a putative transmembrane domain at amino acid positions 14-41. It is oriented in the membrane with the C-terminus exposed and there is a potential glycosylation site in both the C-terminal and N-terminal domains (Collins et al., *J. Gen. Virol.* 71:3015-3020 (1990), incorporated herein by reference). In infected cells, the SH protein of strain A2 accumulates in four major forms; (i) SH0 (Mr 7500), the full-length, unglycosylated form that is the most abundant (Olmsted et al., *J. Virol.* 63:2019-2029 (1989), incorporated herein by reference); (ii) SHg (Mr 13,000-15,000), which is the full length form containing a single N-linked carbohydrate chain; (iii) SHp (Mr 21,000-40,000), which is a modified version of SHg in which the single N-linked carbohydrate chain is modified by the addition of polylactosaminoglycan (Anderson et al., *Virology* 191:417-430 (1992), incorporated herein by reference); (iv) SHt (Mr 4800), a truncated unglycosylated form which is initiated from the second methionyl codon (position 23) and which alone among the different forms does not appear to be transported to the cell surface. The SH0 and SHp forms have been detected in purified virions, suggesting that there is a selectivity at the level of virion morphogenesis (Collins et al., supra, (1993)).

Among the paramyxoviruses, ostensibly similar SH proteins have been found in simian virus 5 (Hiebert et al., *J. Virol.* 55:744-751 (1985), incorporated herein by reference), bovine RSV (Samal et al., *J. Gen. Virol.* 72:1715-1720 (1991), incorporated herein by reference), mumps virus (Elango et al., *J. Virol.* 63:1413-1415 (1989), incorporated herein by reference), and turkey rhinotracheitis virus (Ling et al., *J. Gen. Virol.* 73:1709-1715 (1992), incorporated herein by reference). The small hydrophobic VP24 protein of filoviruses is thought to be a surface protein (Bukreyev et al., *Biochem. Mol. Biol. Int.* 35:605-613 (1995), incorporated herein by reference) and is also a putative counterpart of the paramyxovirus SH protein.

The function of the SH protein has not been heretofore defined. In a fusion assay in cells expressing plasmid-encoded proteins, efficient fusion of CV-1 cells by RSV proteins required the coexpression of the F, G and SH proteins (Heminway et al., *Virology* 200:801-805 (1994), incorporated herein by reference). Without wishing to be bound by theory, several functions of the RSV SH protein may exist: (i) it may enhance viral attachment or penetration (Heminway et al., supra.); (ii) it may be involved in virion morphogenesis; or (iii) it may have a "luxury" function distinct from a direct role in virus growth, such as interaction with components of the host immune system as recently described for the V protein of Sendai virus (Kato et al., *EMBO J.* 16:178-587 (1997), incorporated herein by reference). Function (i) or (ii) above may involve an activity that modifies membrane permeability, as has been suggested by others for some hydrophobic proteins of various viruses (Maramorosh et al. (eds.), *Advances in Virus Research* 45:61-112 (1995); Schubert et al., *FEBS Lett.* (1996); Lamb et al., *Virology* 229:1-11 (1997), each incorporated herein by reference). All of these potential activities of the SH protein may be incorporated within the invention according to the is methods and strategies described herein, to yield additional advantages in RSV recombinant vaccines.

Figure 7:
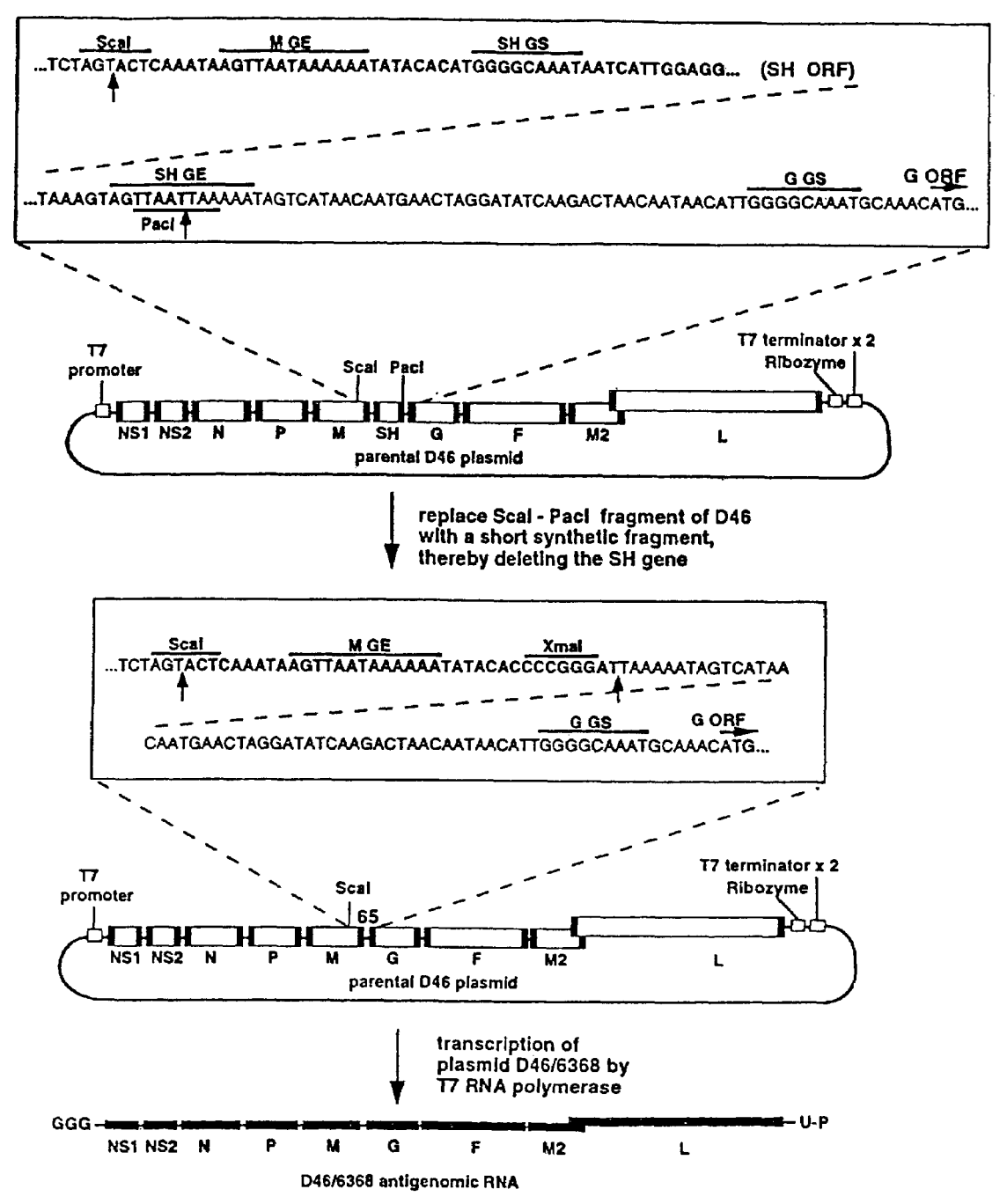

To produce a recombinant RSV having a selected disruption of SH gene function, the SH gene was deleted in its entirety from a parental RSV clone. The above described plasmid D46 plasmid is one such clone which encodes a complete antigenomic RNA of strain A2 of RSV, which was used successfully to recover recombinant RSV (See U.S. patent application Ser. No. 08/720/132; U.S. Provisional Patent Application No. 60/007,083, each incorporated herein by reference). This antigenome is one nt longer than the naturally-occurring genome and contains several optional restriction site markers. The D46 plasmid was modified so that the complete SH gene was deleted, yielding plasmid D46/6368 (FIG. 7).

The construction of plasmid D46/6368 involved two parental subclones, D50, which contains a T7 promoter attached to the left-hand end of the genome encompassing the leader region to the beginning of the L gene, and D39, which contains the end of M2 and the L gene attached at the downstream end to a hammerhead ribozyme and tandem T7 transcription terminators. The D50 plasmid was digested with ScaI (position 4189 in the complete 15,223-nucleotide antigenome sequence) and PacI (position 4623) and the resulting 435 bp fragment was replaced with a short DNA fragment constructed from two complementary oligonucleotides. In this exemplary deletion, the 435-bp fragment located between the ScaI and PacI sites corresponds to the very downstream end of the M gene, its GE signal, and the complete SH gene except for the last six nucleotides of its GE sequence (FIG. 7). This was replaced with the two synthetic partially complementary oligonucleotides, 5'-ACTCAAATA AGTTAATAAAAAATATCCCGGGAT-3' [SEQ ID NO: 3] (positive-sense strand, the M GE sequence is underlined, XmaI site is shown in italics, and the ScaI half-site and PacI sticky end at the left and right respectively are shown in bold italics) and 5'-CCCGGGATA TTTTTTATTAACTTATTTGAGT-3' [SEQ ID NO: 4] (negative-sense strand). This cDNA, called D50/6368, was used to accept the BamHI-MluI fragment of D39 containing the remainder of the antigenome. This resulted in the plasmid D46/6368 which encoded the complete antigenome except for the deleted sequence, an antigenome that is 14,825 nt long, 398 nt shorter than the antigenome encoding by the wild type plasmid D46. The sequence of the insert was confirmed by dideoxynucleotide sequence analysis. An XmaI site was optionally introduced so that inserts could easily be placed at this position in subsequent work.

Transfection, growth and passaging of virus, plaque purification, and antibody staining of viral plaques were generally performed according to the procedures described hereinabove, but with two modifications: (i) cytosine arabinoside, an inhibitor of vaccinia virus was not used; (ii) HEp-2 cells used for transfection were incubated at either 32° C. or 37° C., and all recovered viruses were propagated at 37° C.

To evaluate total RNA and poly(A)+ RNA, cells were scraped and resuspended in 100 µl of water, and total intracellular RNA was isolated using Trizol™ reagent (Life Technologies) according the manufacturer's recommendation (except that following isopropanol precipitation the RNA was extracted twice with phenol-chloroform followed by ethanol precipitation. Poly(A)+ RNA was isolated using the Oligotex mRNA kit (Qiagen, Chatsworth, Calif.).

To conduct reverse transcription and polymerase chain reaction (RT-PCR), the SH gene region was copied into cDNA and amplified. Total intracellular RNA was subjected to reverse transcription with Superscript II (Life Technologies) using as primer the positive sense synthetic oligonucleotide 5-GAAAGTATATATTATGTT-3' [SEQ ID NO: 5]. This primer is complementary to nucleotides 3958-3975, which are upstream of the SH gene. An aliquot of the cDNA product was used as template in PCR using as primer the abovementioned oligonucleotide together with the negative-sense oligonucleotide 5'-TATATAAGCACGATGATATG-3' [SEQ ID NO:6]. This latter primer corresponds to nucleotides 4763-4782 of the genome, which are downstream the SH gene. An initial 2 min. denaturation step was performed during which the Taq DNA polymerase was added, and then 33 cycles were performed (denaturation, 1 min. at 94° C.; annealing, 1 min. at 39° C.; elongation, 2 min. at 72° C.). The products were then analyzed on a 2.5% agarose gel.

For Northern blot hybridization, RNA was separated by electrophoresis on agarose gels in the presence of formaldehyde and blotted to nitrocellulose. The blots were hybridized with [$^{32}$P]-CTP-labeled DNA probes of the M, SH, G, F, M2 and L genes which were synthesized individually in vitro from cDNAs by Klenow polymerase with random priming using synthetic hexamers (Boehringer Mannheim, Indianapolis, Ind.). Hybridized radioactivity was quantitated using the Molecular Dynamics (Sunnyvale, Calif.) Phosphorlmager 445 SI.

$^{35}$S methionine labeling, immunoprecipitation, and polyacrylamide gel electrophoresis procedures were performed as described previously (Bukreyev et al., supra). Electrophoresis was conducted using pre-cast 4%-20% Tris-glycine gels (Novex).

For In vitro growth analysis, HEp-2, 293, CV-1, Vero, MRC-5, African green monkey kidney (AGMK), bovine turbinate (BT), and MDBK cell monolayers were used in a single-step growth cycle analysis. For each type of cells, three 25-cm$^2$ culture flasks were infected with 10$^7$ PFU of the D46/6368 (SH-minus) or D46 (wild type recombinant) virus. Opti-MEM (Life Technologies) with 2% fetal bovine serum (FBS) (Summit) was used for HEp-2, Vero, 293, BT, MRC-5, and AGMK cells; E-MEM (Life Technologies) with 1%, or 2% FBS was used for MDBK or BT cells, respectively. After 3 hours adsorption at 37° C., cells were washed with 4 ml medium three times each, 4 ml medium was added, and the cells were incubated at 37° C. with 5% $CO_2$. Then, at various times after inoculation (see below), 200 µl aliquots of medium supernatant were removed, adjusted to contain 100 mM magnesium sulfate and 50 mM HEPES buffer (pH 7.5), flash-frozen and stored at −70° C. until titration; each aliquot taken was replaced with an equal amount of fresh medium. For titration, HEp-2 cells (24-well plates) were infected with 10-fold dilutions of aliquots, and overlaid with Opti-MEM containing 2% FBS and 0.9% methylcellulose (MCB Reagents). After incubation for 7 days, the medium was removed and the cell monolayer was fixed with 80% methanol at 4° C. The plaques were incubated with a mixture of three monoclonal antibodies specific to RSV F protein, followed by goat anti-mouse IgG conjugated with horseradish peroxidase (Murphy et al., Vaccine 8:497-502 (1990), incorporated herein by reference).

Recovery of infectious, recombinant RSV lacking SH gene function followed the above described procedures, wherein the D46/6368 plasmid was cotransfected into HEp-2 cells together with plasmids encoding the N, P, L and M2 ORF1 proteins, and the cells were simultaneously infected with a recombinant of the MVA strain of vaccinia virus that expresses T7 RNA polymerase. Parallel cultures were transfected with the D46 wild type cDNA under the same conditions. Medium supernatants were harvested three days posttransfection and passaged once. After 6 days incubation at 37° C., an aliquot of medium supernatant representing each original transfection was plated onto fresh HEp-2 cells, incubated for six days under methylcellulose overlay, and stained by reaction with a mixture of three monoclonal antibodies specific to the RSV F protein followed by a second antibody conjugated with horseradish peroxidase. Morphology of plaques of wild type recombinant virus versus the SH-minus virus were very similar, except that the latter plaques were larger. Notably, plaques formed by each of the control and SH minus viruses contained syncytia.

Figure 8:
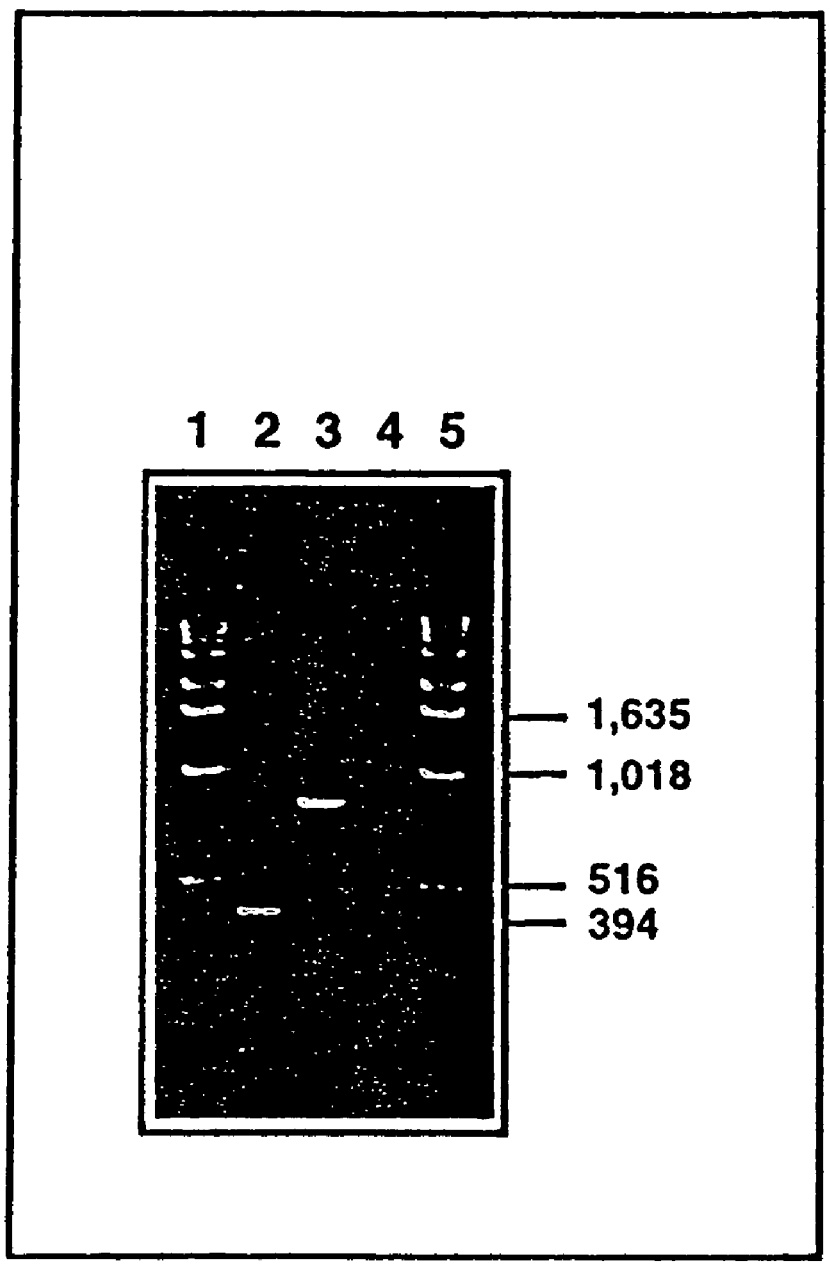
FIG. 8 provides results of RT-PCR analysis of total intracellular RNA from cells infected with the D46 wild type or D46/6368 SH-minus virus to confirm the deletion in the SH locus. RT was performed with a positive-sense primer that anneals upstream of the SH gene, and the PCR employed in addition a negative-sense primer that anneals downstream of the SH gene. Lanes: (1 and 5) markers consisting of the 1 Kb DNA ladder (Life Technologies, Gaithersburg, Md.); (2) D46/6368 RNA subjected to RT-PCR; (3) D46 RNA subjected to RT-PCR; (4) D46/6368 RNA subjected to PCR alone. PCR products were electrophoresed on a 2.5% agarose gel and stained with ethidium bromide. Nucleotides lengths of some marker DNA fragments are shown to the right.

To confirm the absence of the SH gene in the genome of recovered D46/6368 virus, cells were infected with the first passage of wild type or SH-minus recombinant virus, and total intracellular RNA was recovered and analyzed by RT-PCR. RT was performed with a positive-sense primer that annealed upstream of the SH gene, at genome positions 3958-3975. PCR was performed using the same primer together with a negative-sense primer representing nucleotides 4763-4782, downstream of the SH gene. As shown in FIG. 8, wild type D46 virus yielded a single PCR product corresponding to the predicted 824 bp fragment between positions 3958 and 4782 (lane 3), In the case of the D46/6368 virus, the PCR product was shorter and corresponded to the predicted 426 bp fragment containing the deletion (lane 2). The generation of The PCR products was dependent on the RT step, showing that they were derived from RNA rather than DNA, as expected. Thus, RT-PCR analysis demonstrates that the genome of D46/6368 virus contains the expected 398-nucleotide deletion at the SH locus.

Figure 9:
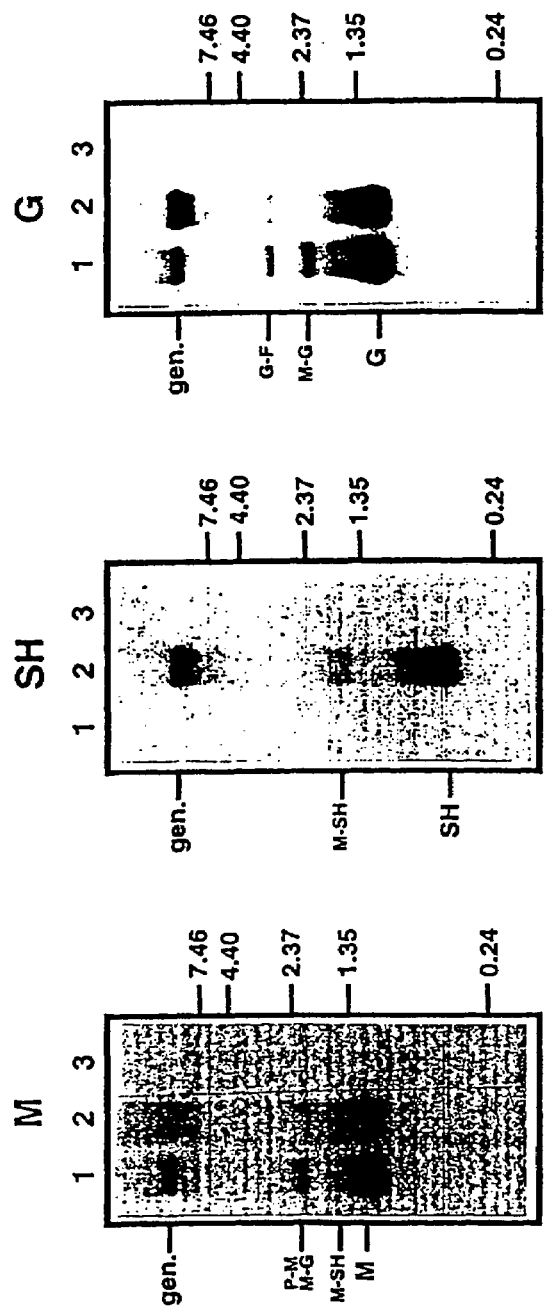
FIG. 9 shows Northern blot hybridization of RNAs encoded by the D46 wild type and D46/6368 SH-minus virus. Total intracellular RNA was isolated from infected cells and subjected to oligo(dT) chromatography without a prior denaturation step, conditions under which the selected. RNA also includes genomic RNA due to sandwich hybridization. RNAs were electrophoresed on formaldehyde-agarose gels and blotted onto nitrocellulose membrane. Replicate blots were hybridized individually with [$^{32}$P]-labeled DNA probes of the M, SH, G, F, M2, or L genes, as indicated. Lanes: (1) D46/6368 RNA; (2) D46 RNA; (3) uninfected HEp-2 cell RNA. Positions of the genomic RNA (gen.), mRNAs (large letters) and read-through transcripts (small letters) are shown on the left. The positions of the read-through transcripts P-M and M-G (M probe) coincide, as well as the positions of G-F and F-M2 transcripts (F probe). The positions of the 0.24-9.5 kb RNA ladder molecular weight markers (Life Technologies), which was run in parallel and visualized by hybridization with [$^{32}$P]-labeled DNA of phage lambda, are shown on the right.
Figure 9:
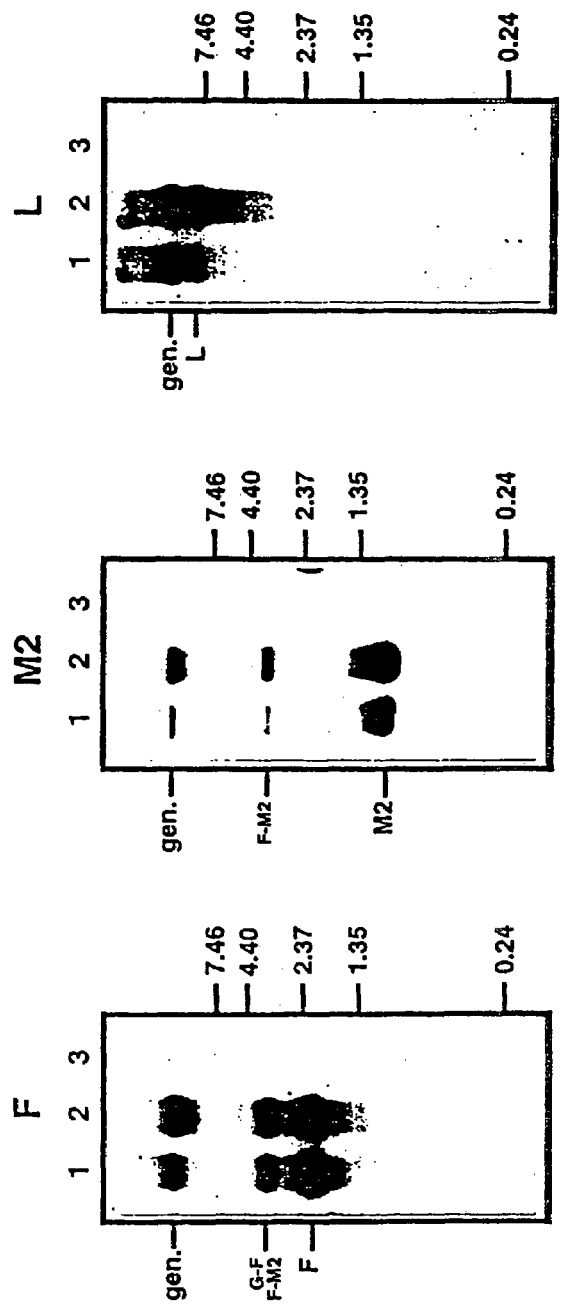

To examine the transcription of genes located upstream and downstream the SH gene, poly(A)+ mRNA was isolated from cells infected with the D46 or D46/6368 virus and analyzed by Northern blot hybridization (FIG. 9). The intracellular RNA purposefully was not denatured prior to poly(A)+ selection; thus, as shown below, the selected mRNA also contained genomic RNA due to sandwich hybridization to mRNA. This permitted simultaneous analysis of mRNA and genome, and the ability to relate the abundance of each mRNA to genomic RNA contained in the same gel lane made it possible to compare mRNA abundance between lanes. The blots were hybridized with [$^{32}$P]-labeled DNA probes which were synthesized from cDNA clones by random priming and thus contained probes of both polarities. Selected probes represented individually the M, SH, G, F, M2, and L genes (FIG. 9).

The SH probe hybridized to both subgenomic SH mRNA and genomic RNA in the case of the wild type D46 virus but not for the D46/6368 virus (FIG. 9). The probes specific for other RSV genes hybridized in each case to the genome and to the expected major monocistronic mRNA for both viruses. In addition, a number of previously described dicistronic readthrough mRNAs also were detected with both viruses, such as the F-M2, G-F and P-M mRNAs.

The G-specific probe hybridized to an novel species specific to the D46/6368 virus, which appeared to be a readthrough of the M and G genes. This combination was possible due to the deletion of the intervening SH gene. The same species, specific to D46/6468 but not D46, appeared to hybridize in addition only with the M-specific probe.

Relative levels of synthesis were subsequently quantified for each mRNA of D46 versus D46/6368. For each pairwise comparison, the amount of mRNA in a given gel lane was normalized relative to the amount of genome. This comparison showed D46/6368 versus D46 expressed the following mRNAs in the indicated ratio (D46/6368 to D46): M (1.1), G (1.3), F (0.61), M2 (0.32), and L (0.17).

To compare viral proteins synthesized by D46 versus D46/6368 RSV clones, HEp-2 cells were infected at an input multiplicity of infection of 2 PFU per cell and labeled by incubation with [$^{35}$S]methionine from 16 to 20 h post-infection. Cell lysates were prepared and analyzed directly or following immunoprecipitation using a rabbit antiserum raised against purified RSV virions. Total and immunoprecipitated proteins were subjected to PAGE on 4-20% gradient gels (FIG. 10).

Figure 10:
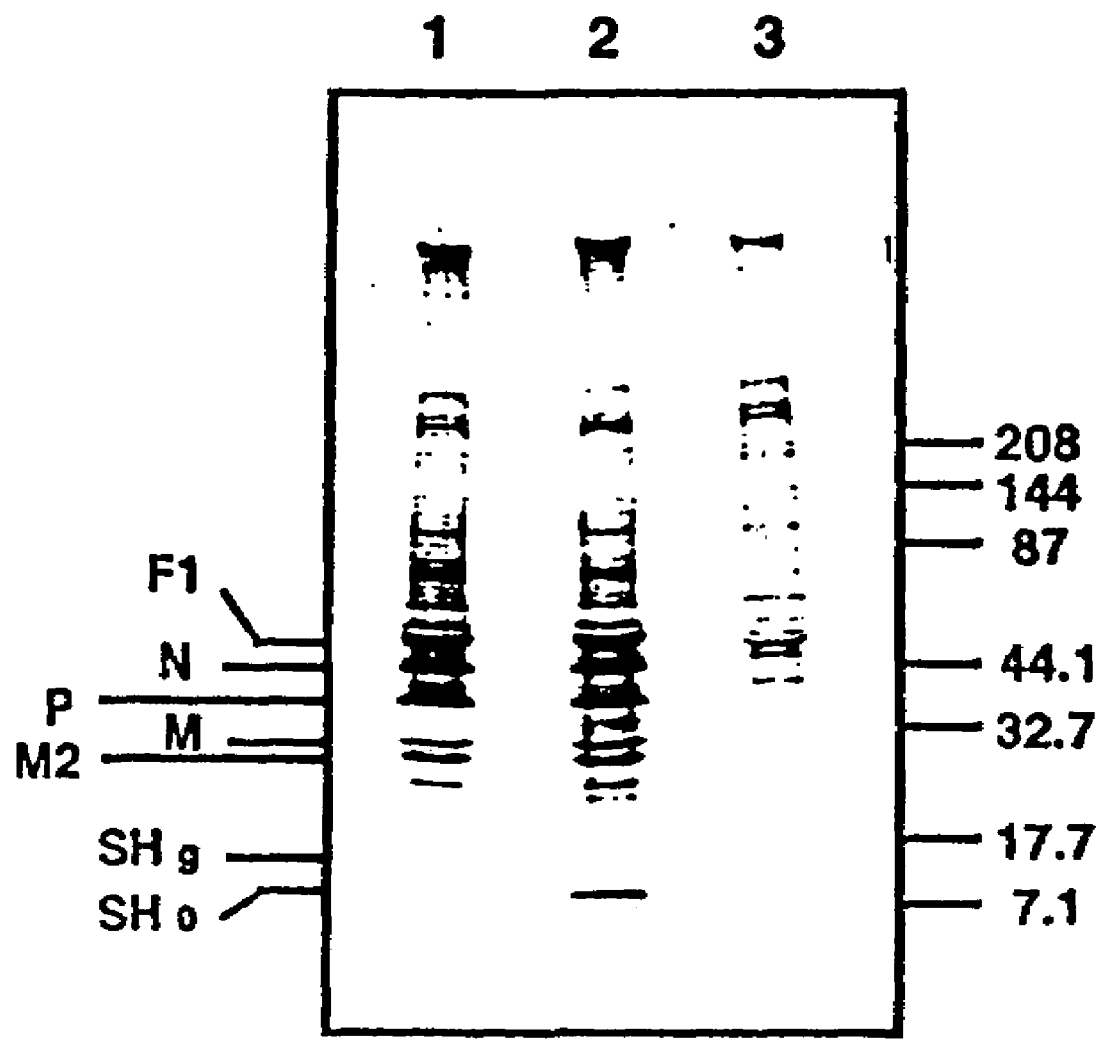
FIG. 10 shows SDS-PAGE of [$^{35}$S]-labeled RSV proteins synthesized in HEp-2 cells infected with the D46 wild type or D46/6368 SH-minus virus. Proteins were subjected to immunoprecipitation with antiserum raised against purified virions and analyzed by electrophoresis in pre-cast gradient 4%-20% Tris-glycine gels (Novex, San Diego, Calif.). Positions of viral proteins are indicated to the left; positions and molecular masses (in kilodaltons) of marker proteins (Kaleidoscope Prestained Standards, Bio-Rad, Richmond, Calif.), are shown to the right.

In the case of the D46 virus, the pattern of immunoprecipitated proteins included the unglycosylated form of SH protein, SH0, and the N-glycosylated form, SHg, whereas neither species was evident for the D46/6368 virus (FIG. 10). The SH0 protein also could be detected in the pattern of total infected-cell proteins in the case of D46, but not D46/6368. Otherwise, the patterns of proteins synthesized by D46 versus D46/6368 were essentially indistinguishable. Phosphorimager analysis of the N, P, M, F$_1$, and M2 proteins in the pattern of immunoprecipitated proteins showed that equivalent amounts were made by both viruses (FIG. 10).

As described above, preliminary comparison of the D46 and D46/6368 viruses by plaque assay indicated a difference in growth in vitro. Therefore, we further compared the two viruses with regard to plaque size in HEp-2 cells. Particular care was taken to ensure that the monolayers were young and not overgrown, since these variables can effect plaque size. After 7 days incubation at 37° C. under methylcellulose, the monolayers were fixed with methanol and photographed. This revealed a striking difference in plaque size. Measurement of 30 plaques of each virus viruses showed that the plaques of the D46/6368 virus were on average 70% larger than those of the D46 virus.

Figure 11:
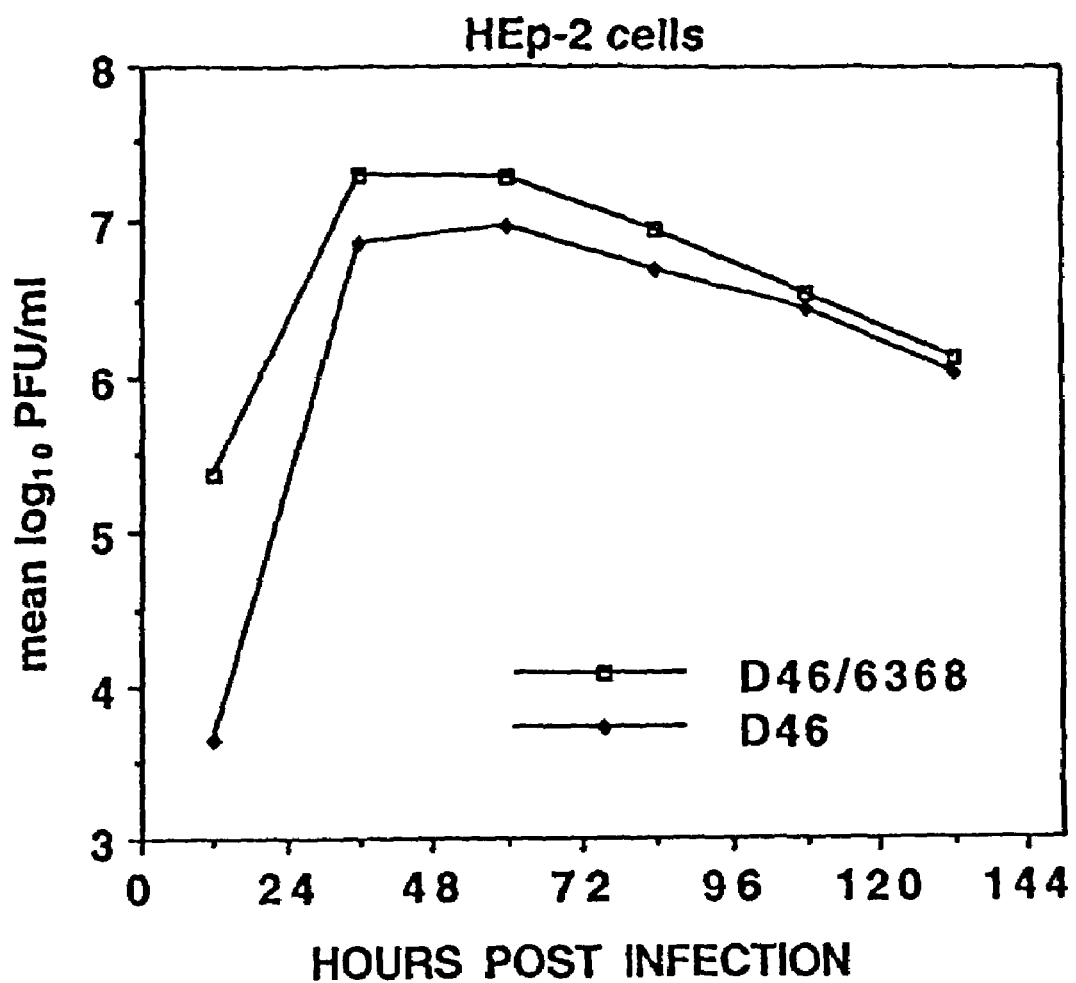
FIGS. 11-13 provide growth curves for D46 wild type and D46/6368 SH-minus viruses in HEp-2 cells (FIG. 11), 293 cells (FIG. 12), and AGMK-21 cells (FIG. 13). Triplicate cell monolayers in 25-cm$^2$ culture flasks were infected with 2 PFU per cell of either virus, and incubated at 37° C. Aliquots were taken at indicated time points, stored at −70° C., and titrated in parallel by plaque assay with antibody staining. Each point shown is the average titer of three infected cell monolayers.
Figure 12:
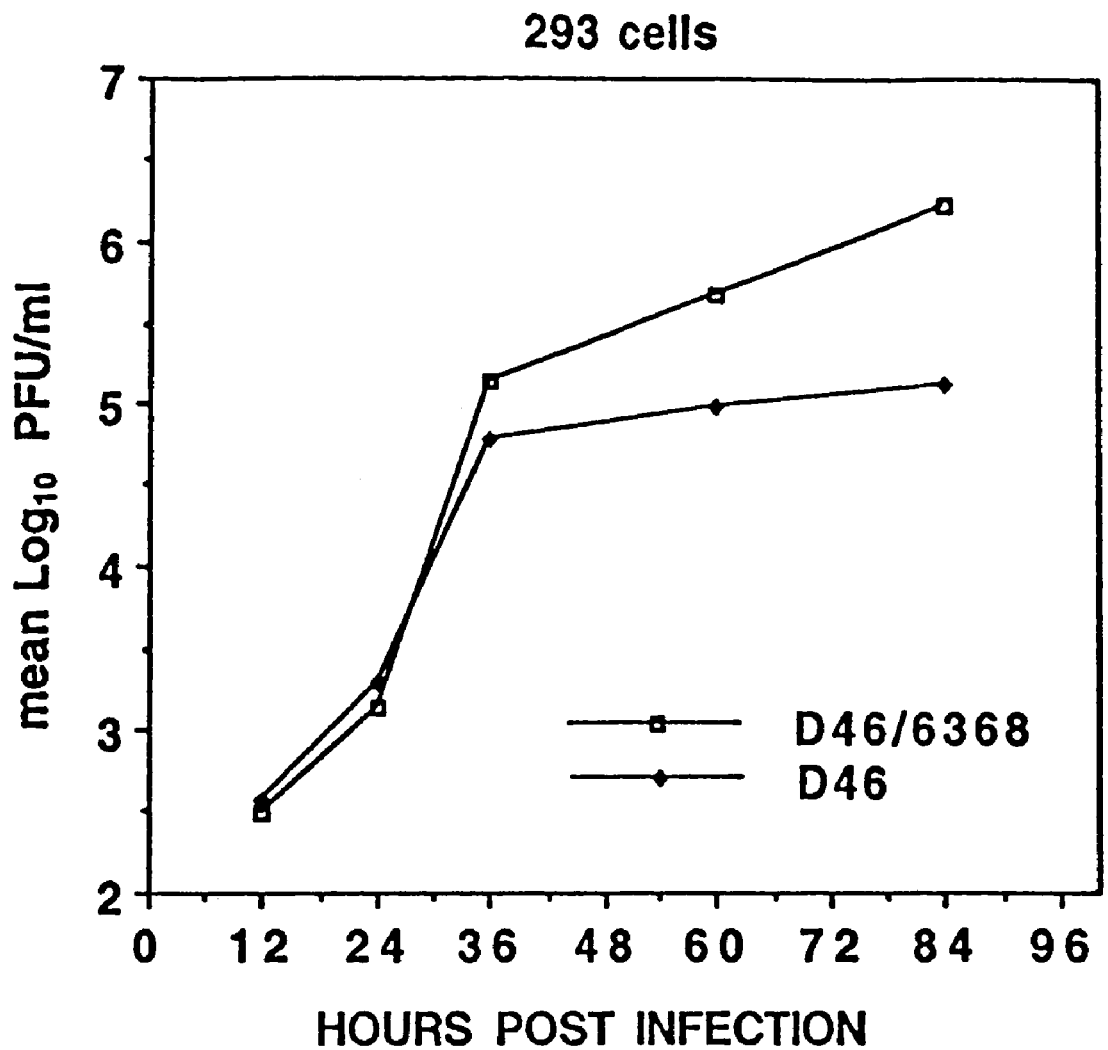
Figure 13:
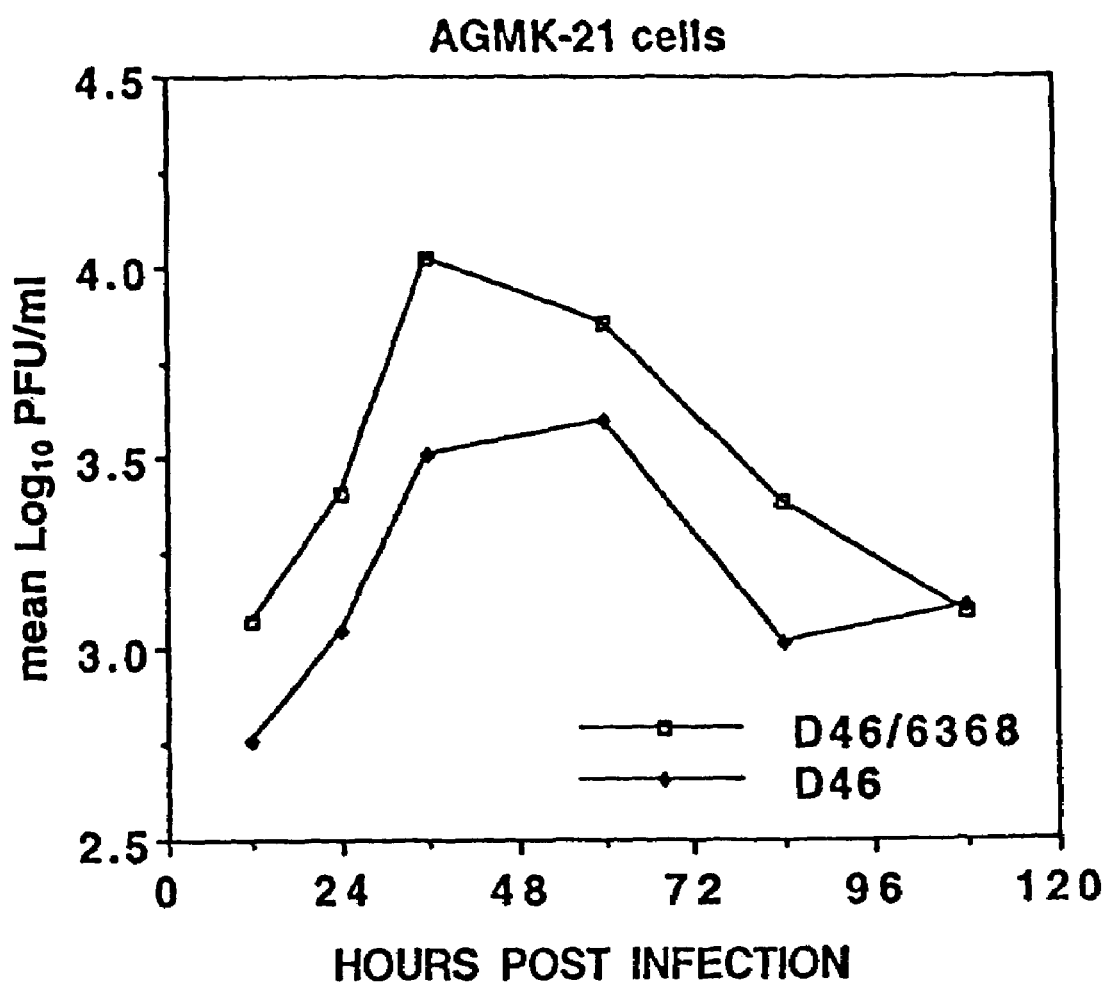

Further experiments were undertaken to render a growth curve analysis for eight different cell lines representing different species and different tissue origins, to compare efficiencies of replication of the D46 and D46/6368 viruses (Table 42). Triplicate monolayers of each type of cell were infected with either virus, and samples were taken at 12 or 24 hours intervals, and quantitated by plaque assay and antibody staining. Surprisingly, the D46/6368 virus grew to higher titers relative to the D46 wild type in three cell lines, namely HEp-2, 293 and AGMK-21 cells. In HEp-2 cells (FIG. 11), the titer of progeny D46/6368 virus at 36 hours post infection was 2.6 fold greater than for the D46 virus. In 293 cells (FIG. 12), the yield of D46/6368 virus was two fold greater than that of the D46 virus at 36 hours post infection, and this difference increased to 4.8 and 12.6-fold at 60 and 84 h post infection, respectively. In AGMK-21 cells (FIG. 13), the yield of D46/6368 virus was 3.2 times at 36 hours post infection. In MRC-5, Vero, CV-1, MDBK and BT cells, a significant difference in replication among mutant and wild-type virus was not observed, indicating that the growth of SH-minus RSV was not substantially affected by host range effects.

TABLE 42

Replication of D46/6368 Virus as Compared to D46 Virus in Various Cell Lines

| Cell Type | Host | Tissue Type | D46/6368 Virus Replication As Compared to D46 |
|---|---|---|---|
| HEp-2 | human | larynx | increased |
| 293 | human | kidney | increased |
| MRC-5 | human | lung | similar |
| Vero | monkey | kidney | similar |
| AGMK-21 | monkey | kidney | increased |
| CV-1 | monkey | kidney | similar |
| BT | bovine | turbinate | similar |
| MDBK | bovine | kidney | similar |

These and other findings herein demonstrate that deletion of the SH gene yields not only recoverable, infectious RSV, but a recombinant RSV which exhibits substantially improved growth in tissue culture, based on both yield of infectious virus and on plaque size. This improved growth in tissue culture specified by the SH deletion provides useful tools for developing RSV vaccines, for example by overcoming problems of poor RSV yields in culture. Moreover, these deletions are highly stable against genetic reversion, rendering RSV clones derived therefrom particularly useful as vaccine agents.

To evaluate replication, immunogenicity and protective efficacy of the exemplary SH-deletion clone in mice, respiratory-pathogen-free 13-week old BALB/c mice in groups of 24 were inoculated intranasally under light methoxyflurane anesthesia on day 0 with $10^6$ PFU per animal in a 0.1 ml inoculum of wild type recombinant D46 virus, SH-minus recombinant D46/6368 virus, or biologically-derived cold-passaged (cp) temperature-sensitive (ts) virus cpts248/404 (Firestone et al., supra, (1996), incorporated herein by reference). This latter virus has been extensively characterized in rodents, chimpanzees and humans, and is highly restricted in replication in the upper and lower respiratory tract of the mouse. At each of days 4, 5, 6 and 8 post-inoculation, six mice from each group were sacrificed by $CO_2$ asphyxiation, and nasal turbinates and lung tissue were obtained separately, homogenized, and used in plaque assay for quantitation of virus using the antibody staining procedure described above.

Figure 14:
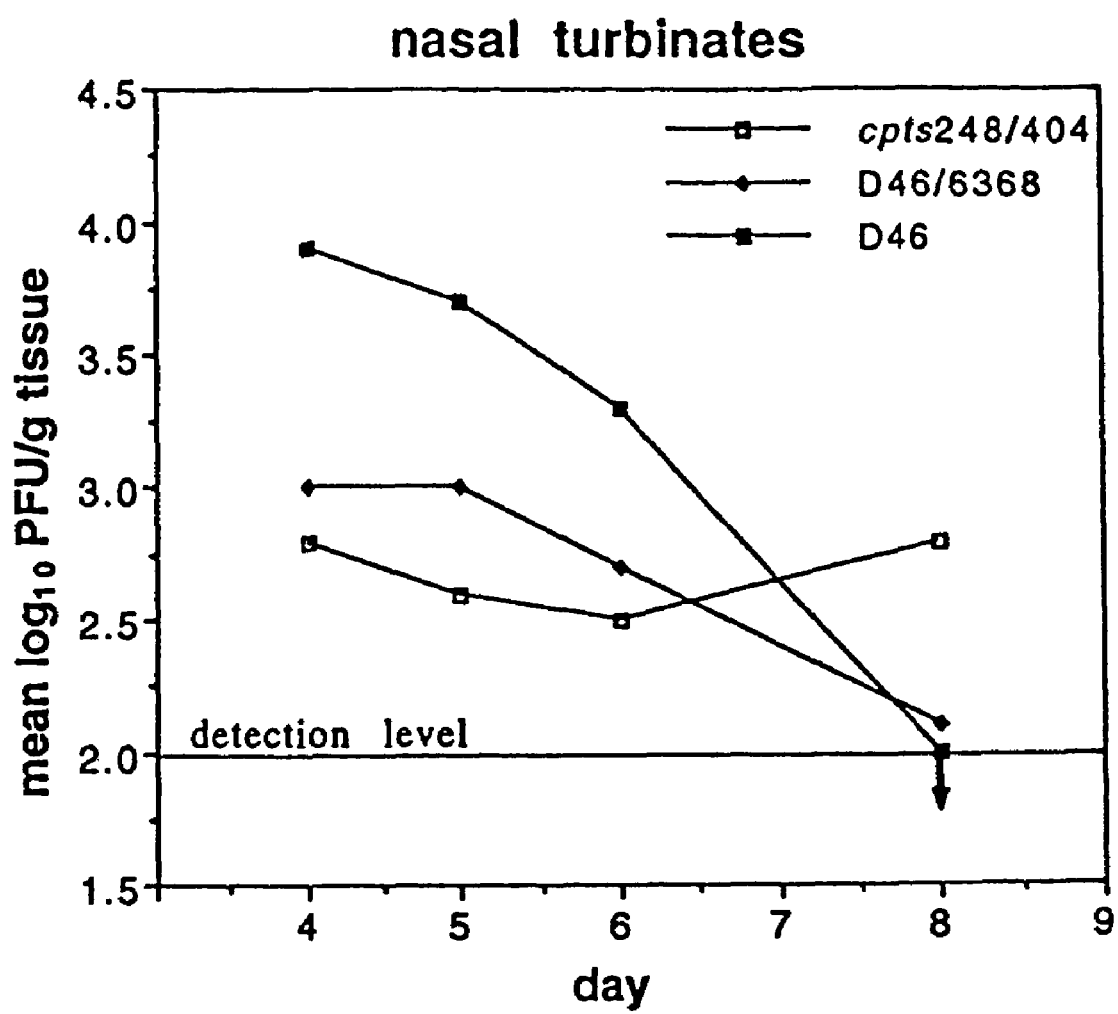
FIGS. 14 and 15 show kinetics of virus replication in the upper (FIG. 14) and lower (FIG. 15) respiratory tract of mice inoculated intranasally with the D46 wild type virus, D46/6368 SH-minus virus, or the biologically-derived cpts248/404 virus. Mice in groups of 24 were inoculated intranasally with 10$^6$ PFU of the indicated virus. Six mice from each group were sacrificed on the indicated day and the nasal turbinates and lung tissues were removed and homogenized, and levels of infectious virus were determined by plaque assay on individual specimens and mean log$_{10}$ titers were determined.
Figure 15:
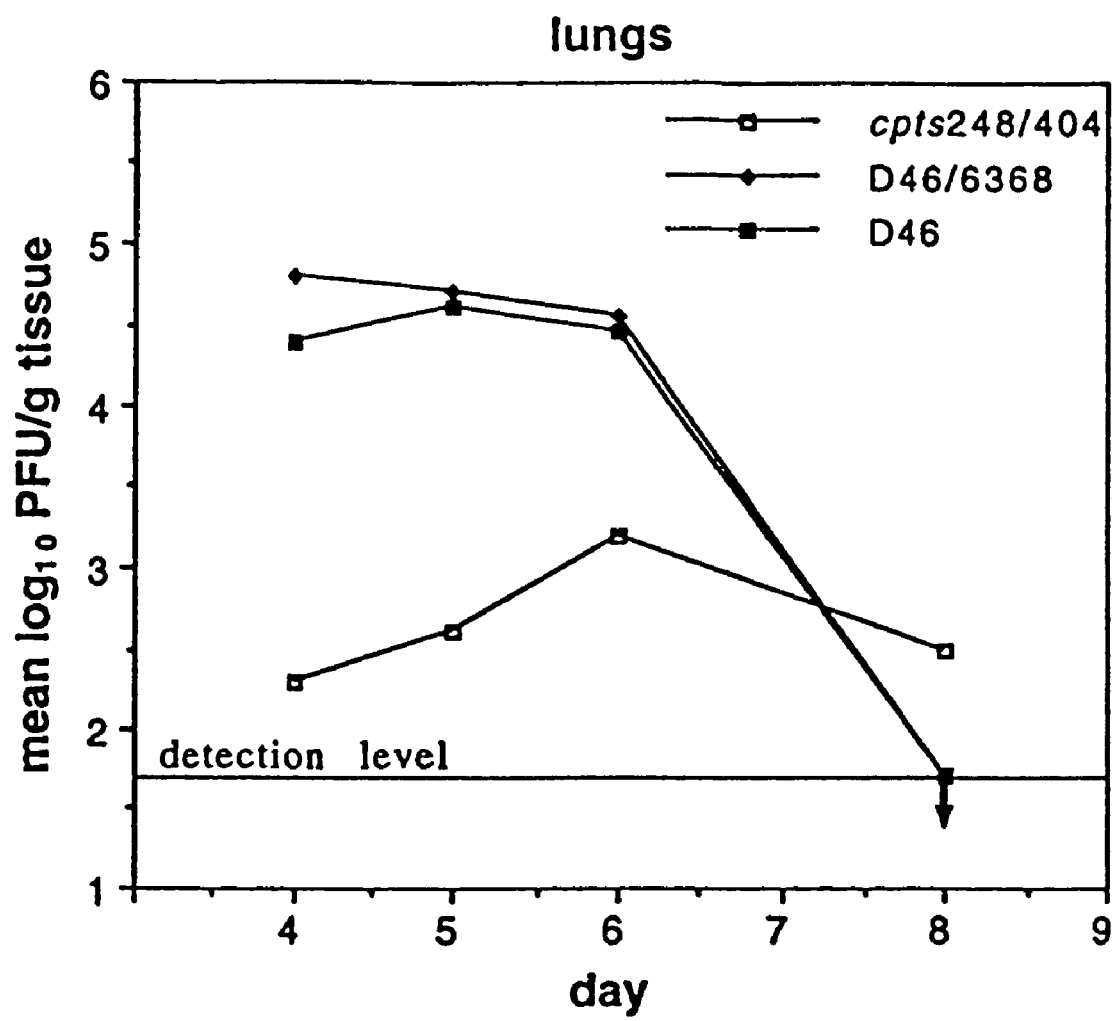

In the upper respiratory tract, the SH minus D46/6368 virus exhibited an attenuation phenotype (FIG. 14). In the present example, its level of replication was 10-fold lower than that of the wild type virus, and was comparable to that of the cpts248/404 virus. In contrast, in the lower respiratory tract (FIG. 15) the level of replication of the D46/6368 virus was very similar to that of the wild type, whereas the cpts248/404 virus was highly restricted. In additional studies, it was determined that the recombinant virus encoded by the parental D46 cDNA has a wild type phenotype with regard to replication and virulence in naive chimpanzees, a fully permissive experimental animal. This indicates that the parental recombinant virus, assembled as it was from a laboratory strain, contains a full complement of intact genes necessary for replication and virulence in a permissive host. These and other properties of exemplary gene deletion RSV strains render a host of methods and strains available for vaccine use.

To further evaluate immunogenicity and protective efficacy of recombinant RSV, four additional groups of mice were inoculated as described above with wild type recombinant, its SH-minus derivative, or the cpts248/404 virus, or were mock infected. Four weeks later the mice were anesthetized, serum samples were taken, and a challenge inoculation of $10^6$ PFU of biologically-derived RSV strain A2 per animal was administered intranasally. Four days later the animals were sacrificed and nasal turbinates and lung tissues were harvested and assayed for infectious RSV as described above. Serum IgG antibodies which bind to the RSV F protein were quantitated in an ELISA using F glycoprotein which had been immunoaffinity-purified from RSV Long strain infected cells (Murphy et al., supra, 1990).

The immunogenicity assays for the D46 wild type, D46/6368 SH-minus, and cpts248/404 viruses showed that mice which had been infected on day 0 with any of the three viruses developed high levels of F-specific serum antibodies (Table 43). All of these test hosts were highly resistant in both the upper and lower respiratory tracts to replication of RSV challenge virus. Thus, the SH-minus mutant could not be distinguished from its wild type parent on the basis of its ability to induce RSV-specific serum antibodies and protection in the mouse.

TABLE 43

The RSV D46/6368 SH-minus virus is immunogenic and protects the upper and lower respiratory tract of mice against wild-type challenge

| Immunizing Virus[1] | No. of Mice | Serum antibody titer[2] (reciprocal mean $log_2$) | | RSV A2 Replication after challenge[3] (mean $log_{10}$ pfu/g tissue) | |
|---|---|---|---|---|---|
| | | Day 0 | Day 28 | Nasal turbinates | Lungs |
| D46[4] | 6 | 7.3 | 15.0 | <2.0 | <1.7 |
| D46/6368[5] | 6 | 7.3 | 15.0 | 2.1 | <1.7 |
| cpts248/404 | 6 | 7.0 | 12.6 | 2.3 | <1.7 |
| none | 6 | 7.6 | 7.3 | 4.6 | 5.1 |

[1]Groups of BALB/c mice were immunized intranasally with $10^6$ pfu of the indicated virus on day 0.
[2]Serum IgG antibody response was quantitated in an ELISA using immunopurified F glycoprotein from RSV subgroup A.
[3]Mice were intranasally administered $10^6$ pfu of RSV A2 on day 28 and sacrificed 4 days later.
[4]Wild type recombinant virus.
[5]SH-minus recombinant virus.

Comparisons of the SH genes of different RSVs and different pneumoviruses provide additional tools and methods for generating useful RSV recombinant vaccines. For example, the two RSV antigenic subgroups, A and B, exhibit a relatively high degree of conservation in certain SH domains. In two such domains, the N-terminal region and putative membrane-spanning domains of RSV A and B display 84% identity at the amino acid level, while the C-terminal putative ectodomains are more divergent (approx. 50% identity) (Collins et al., supra, 1990). Comparison of the SH genes of two human RSV subgroup B strains, 8/60 and 18537, identified only a single amino acid difference (Anderson et al., supra). The SH proteins of human versus bovine RSV are approximately 40% identical, and share major structural features including (i) an asymmetric distribution of conserved residues similar to that described above; (ii) very similar hydrophobicity profiles; (iii) the presence of two N-linked glycosylation sites with one site being on each side of the hydrophobic region; and (iv) a single cysteine residue on the carboxyterininal side of the central hydrophobic region of each SH protein. (Anderson et al., supra). By evaluating these and other sequence similarities and differences, selections can be made of heterologous sequence(s) that can be substituted or inserted within infectious RSV clones, for example to yield vaccines having multi-specific immunogenic effects.

Transcriptional analyses for D46 and D46/6368 yielded other important findings within the present example. Overall transcription levels were substantially the same for both viruses, whereas, Northern blot analysis revealed certain differences in accumulation of individual mRNA species. Notably, transcription of the M gene, located upstream of the SH gene, was substantially the same for the two viruses. However, deletion of the SH gene resulted in increased transcription for its downstream neighbor, the G gene (FIG. 16). Based on these results, transcriptional levels of selected RSV genes can be modulated simply by changing the respective polarities or proximity of genes on the RSV map. For example, the D46 virus G gene is seventh in the gene order, whereas deletion of the SH gene places it in the sixth position, resulting in increased levels of transcription. The observed increase in transcription associated with this change in gene order was less than the 2.5 to 3-fold increase which has been reported in other recombinant viral systems (see, e.g., Kuo et al., supra, (1996)).

Another important finding revealed in the foregoing studies was that each of the genes downstream of the G gene (F, M2 and L) was expressed less efficiently in the SH-minus mutant, and there was a steeper gradient of polarity for D46/6368 versus the wild type D46 virus exhibited by these downstream genes (FIG. 16). Notably, the engineered M-G intergenic region of D46/6368 that was left following the SH deletion was 65 nt in length. In comparison, the longest naturally-occurring intergenic regions in strain A2 are the 44-nt M-SH, 46-nt F-M2, and 52-nt G-F intergenic regions, and strain 18537 has a F-M2 intergenic region of 56 nt (Johnson et al., *J. Gen. Virol.* 69:2901-2906 (1988), incorporated herein by reference). The naturally-occurring intergenic regions of strain A2, which range in size from one to 52 nt, did not substantially differ with regard to their effect on transcriptional readthrough and polarity in a dicistronic minigenome (Kuo et al, supra, (1996)). However, testing of regions longer than the 52-nt G-F region according to the methods of the invention may establish an upper limit after which the polymerase is affected more severely. Thus, the lower-than-expected increase in G gene transcription resulting from the change in gene order observed in the SH-minus deletion clones, as well as the reduced transcription of the downstream genes, may be attributable to the greater length of the intergenic region that was engineered between M and G. In this regard, adjustment in the selected length of intergenic regions of RSV clones within the invention is expected to provide yet additional tools and methods for generating useful RSV vaccines.

The above findings offer two additional methods for altering levels of RSV gene expression. First, the deletion of a nonessential gene can up-regulate the expression of downstream genes. Second, the insertion of longer than wild-type intergenic regions provide methods for decreasing the transcription of downstream genes. Decreased levels of expression of downstream genes are expected to specify attenuation phenotypes of the recombinant RSV in permissive hosts, e.g., chimpanzees and humans.

The finding that the SH-minus virus grows well in tissue culture and exhibits site-specific attenuation in the upper respiratory tract presents novel advantages for vaccine development. Current RSV strains under evaluation as live virus vaccines contain, e.g., cp mutations (acquired during extensive passage at progressively lower temperatures; to yield cpRSV strains). Exemplary cp mutations involve five amino acid substitutions in N, F and L, and do not confer temperature-sensitivity or cold-adaptation. These mutations further do not significantly affect growth in tissue culture. They are host range mutations, because they restrict replication in the respiratory tract of chimpanzees and humans approximately 100-fold in the lower respiratory tract. Another exemplary type of mutation, ts mutations, has been acquired by chemical mutagenesis of cpRSV. This type of mutation tends to preferentially restrict virus replication in the lower respiratory tract, due to the gradient of increasing body temperature from the upper to the lower respiratory tract. In contrast to these cp and ts mutants, the SH-minus mutants described herein have distinct phenotypes of greater restriction in the upper respiratory tract. This is particularly desirable for vaccine viruses for use in very young infants, because restriction of replication in the upper respiratory tract is required to ensure safe vaccine administration in this vulnerable age group whose members breath predominantly through the nose. Further, in any age group, reduced replication in the upper respiratory tract will reduce morbidity from otitis media. In addition to these advantages, the nature of SH deletion mutations, involving e.g., nearly 400 nt and ablation of an entire mRNA, represents a type of mutation which will be highly refractory to reversion.

EXAMPLE XIV

Figure 17:
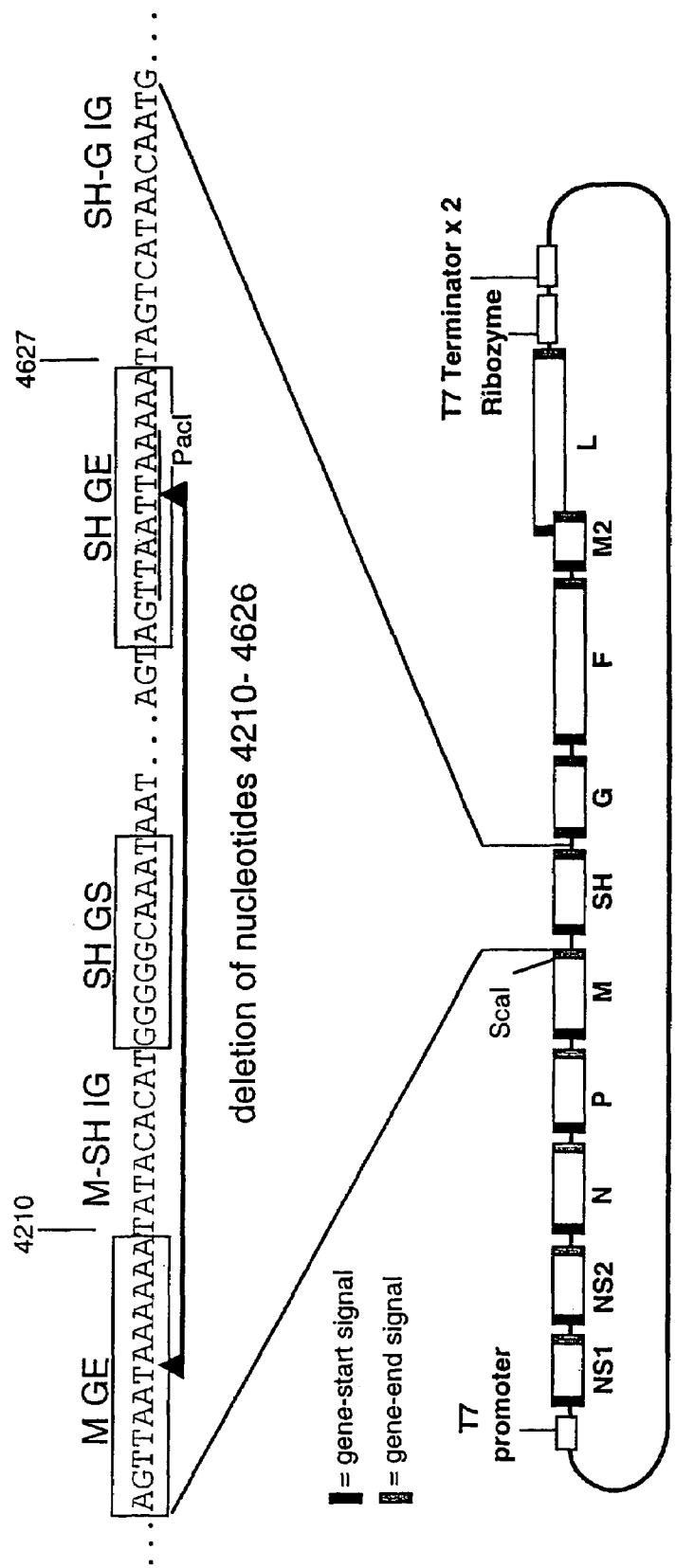
FIG. 17 depicts the D46 antigenome plasmid which was modified by deletion of the SH gene in such a way as to not insert any heterologous sequence into the recombinant virus. The sequence flanking the SH gene depicted at the top (SEQ ID NOS. 30 and 31. The MGE, M-SH intergenic (IG), SH GS, SH GE and SH-G IG sequences are shown. The area which was removed by the deletion is underlined, with the deletion points indicated with upward pointing triangles. The antigenome resulting from this deletion is D46/6340.

Recombinant RSV Having a Deletion of the SH Gene Without the Introduction of Heterologous Sequence This example describes the production of a recombinant RSV in which expression of the SH protein has been ablated by removing a polynucleotide sequence encoding the SH protein, without introducing heterologous sequence as was done in the preceding Example XIII. In that example, an RSV clone D46/6368 in which the SH coding sequence had been removed also featured an M-G intergenic region that was extended to 65 nucleotides in length compared to 52 nucleotides for the longest naturally occurring strain A2 intergenic region. Also, this engineered intergenic region contained heterologous sequence including a SmaI site. These changes yield, certain advantageous results, such as reducing the efficiency of transcription of downstream genes. However, for other applications it is desirable to make deletions or changes which are not accompanied by the introduction of heterologous sequence, as illustrated in the present Example (FIG. 17).

The D13 plasmid, described hereinabove (see Example VII), contains the T7 promoter attached to the left-hand end of the genome encompassing the leader region, and the NS1, NS2, N, P, M, and SH genes (sequence positions 1 to 4623 in the complete 15,223 antigenome sequence). The ScaI (position 4189) to PacI (position 4623) fragment was replaced with the two partially-complementary synthetic oligonucleotides: ACTCAAATA<u>AGTTAAT</u> [SEQ ID NO:7] (positive-sense strand, the ScaI half site is italicized to the left and the PacI sticky end is italicized to the right, and part of the GE signal is underlined), and <u>TAAC</u>TTATTTGAGT [SEQ ID NO:8] (negative sense, the ScaI half-site is italicized on the right, and part of the GE signal is underlined). This mutation resulted in the deletion of the M GE signal, the M-SH intergenic region and the complete SH gene, and had the effect of moving the SH GE signal up to replace that of the M gene. No heterologous nucleotides were introduced. The resulting cDNA, called D13/6340, was ligated with the G-F-M2 cDNA piece (see Example VII) to yield D50/6340, which spans from the leader region to the beginning of the L gene.

The StuI-BamHI fragment of D50/6340 (spanning positions 5613 to 8501, including the F and M2 genes) was excised and replaced with the equivalent fragment of D50-COR#1, which is isogenic except that it contains the two "HEK" changes to the F gene described hereinabove. The resulting D50/6340HEK was used to accept the BamHI-MluI fragment of D39sites#12, which contains the remainder of the antigenome cDNA and the flanking ribozyme and T7 transcription terminators (see Example IX). D39sites#12 is a version of D39 which contains the "sites" mutations (see Table 39). This resulted in plasmid D46/6340HEK, encoding an antigenome lacking the SH gene and containing the "HEK" and "sites" changes. The D46/6340 antigenome cDNA is 417 bp shorter than its parental D46 cDNA. The sequence of the ScaI PacI synthetic insert was confirmed by dideoxynucleotide sequencing. The cDNA was then used successfully to recover recombinant virus by the procedures described hereinabove. The recovered D46/6340 SH deletion virus resembled the D46/6368 SH deletion virus described in Example XIII on the basis of its plaque phenotype and growth characteristics.

EXAMPLE XV

Knock-Out of NS2 Protein Expression

This example illustrates ablation of synthesis of an RSV protein, NS2. The selected method for ablation in this instance was introduction of stop codons into a translational open reading frame (ORF).

D13 is a cDNA representing the left hand end of the complete antigenome cDNA, including the T7 promoter, leader region, and the NS1, NS2, N, P, M and SH genes (sequence: positions 1 to 4623) (FIG. 18). The AatII-AflIII fragment of this cDNA, containing the T7 promoter and NS1 and NS2 genes, was subcloned into a pGem vector and subjected to oligonucleotide-directed mutagenesis to introduce two translational stop codons into the NS2 ORF together with an XhoI site that was silent at the translational level and served as a marker (FIG. 18). The sequence of the mutation was confirmed, and the AatII-AflIII fragment was inserted into D13, which was then ligated with the PacI-BamHI fragment containing the G, F and M2 genes, to yield cDNA D50 containing the inserted mutations. This was then ligated with the insert of D39 to yield a complete antigenome cDNA which was used to recover recombinant virus. The presence of the mutation in the recombinant RSV was confirmed by sequencing of RT-PCR products and by XhoI digestion. In addition, the absence of synthesis of NS2 protein was confirmed by Western blot analysis using a rabbit antiserum raised against a synthetic peptide representing the C-terminus of NS2.

Figure 19:
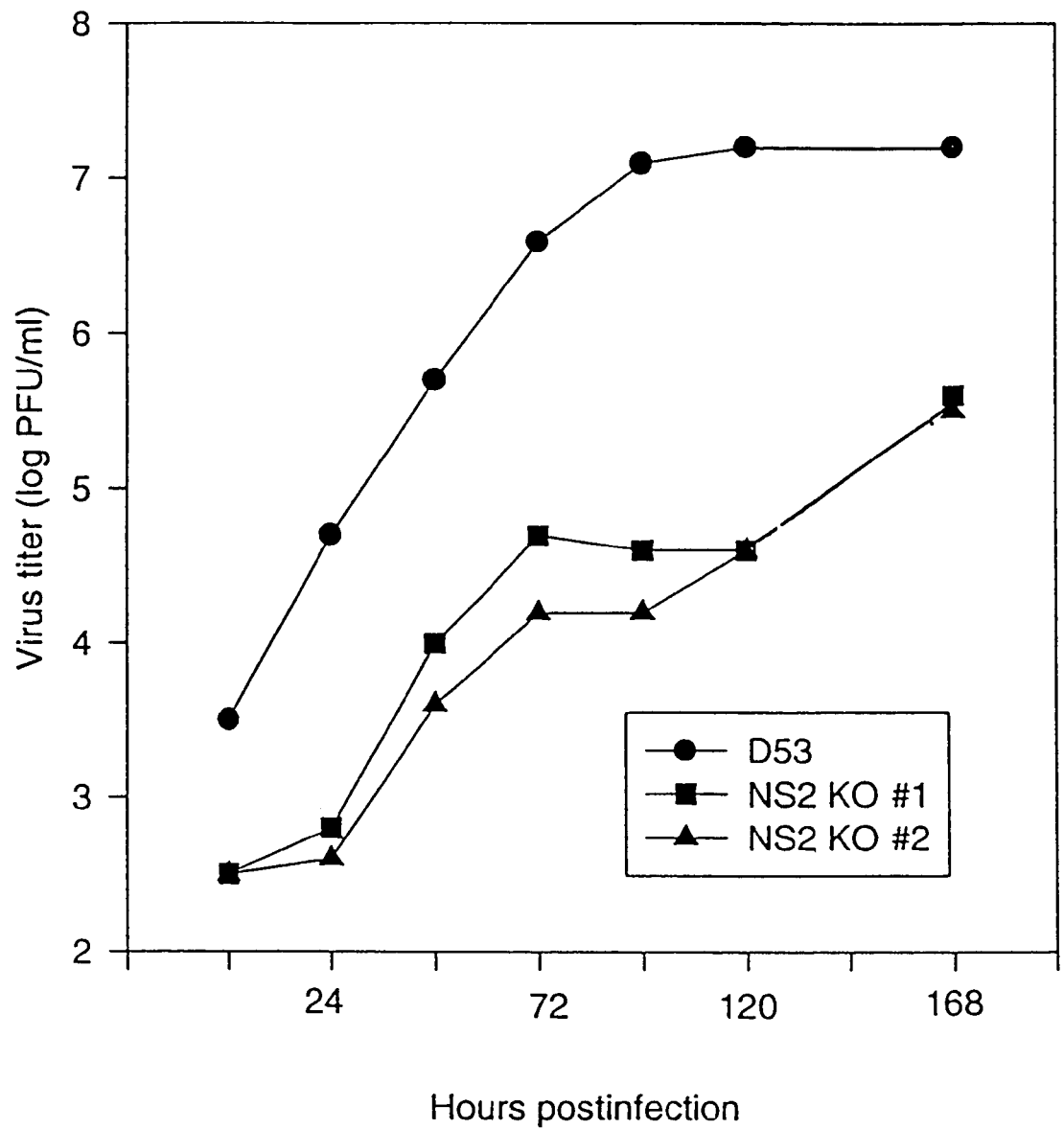
FIG. 19 compares production of infectious virus by wild type RSV (D53) versus NS2-knockout RSV in HEp-2 cells. Triplicate monolayers were infected with either virus at an input moi of three pfu/cell, and samples were taken at the indicated intervals and quantitated by plaque assay and immunostaining.

FIG. 19 shows growth curves comparing the NS2-knock-out virus with recombinant wild type, using the methods described above for the SH-minus virus. These results demonstrate that the rate of release of infectious virus was reduced for the NS2-knock-out virus compared to wild type. In addition, comparison of the plaques of the mutant and wild type viruses showed that those of the NS2-knock-out were greatly reduced in size. This type of mutation can thus be incorporated within viable recombinant RSV to yield altered phenotypes, in this case reduced rate of virus growth and reduced plaque size in vitro. These and other knock-out methods and mutants will therefore provide for yet additional recombinant RSV vaccine agents, based on the known correlation between reduced plaque size in vitro and attenuation in vivo.

EXAMPLE XVI

Modulation of RSV Phenotype by Alteration of Cis-Acting Regulatory Sequence Elements This example illustrates modulation of growth properties of a recombinant RSV virus by altering cis-acting transcription signals of exemplary genes, NS1 and NS2.

Figure 20:
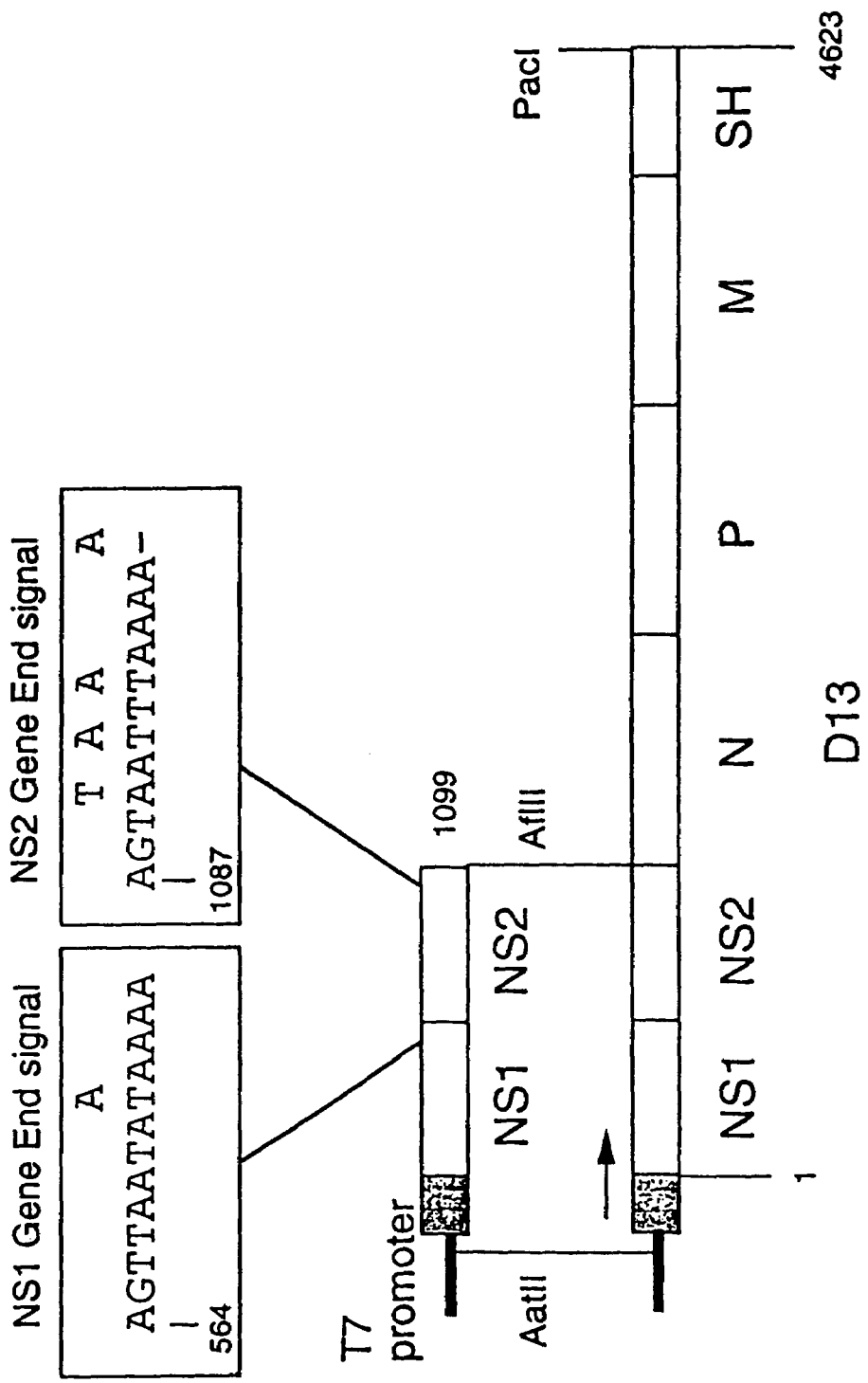
FIG. 20 depicts alteration of gene-end (GE) signals of the NS1 and NS2 genes. The cDNA insert of plasmid D13, representing the left hand end of the antigenome cDNA from the T7 promoter (shaded) to the PacI site at position 4623, is shown. The AatI-AflII fragment containing the T7 promoter and the NS1 and NS2 genes was subcloned into a pGem vector. It was modified by site-directed mutagenesis simultaneously at two sites, namely the NS1 and NS2 GE signals were each modified to be identical to that found in nature for the N gene. The sequences of the wild type NS1 SEQ ID NO: 34) and NS2 (SEQ ID NO: 35) GE signals are shown (and identified by sequence position relative to the complete antigenome sequence), and the nucleotide substitutions are shown above the line. The dash in the wild type sequence of the NS2 GE signal indicates that the mutation increased the length of the GE signal by one nucleotide.

The subcloned AatII-AflIII fragment of D13, representing the lefthand end of the genome, was subjected to oligonucleotide-directed mutagenesis to introduce changes at the GE signals of the NS1 and NS2 genes (FIG. 20). The NS1 GE signal sustained a single nucleotide substitution, whereas that of NS2 sustained three substitutions and one insertion. These changes had the effect of altering each signal to be identical to the naturally-occurring GE signal of the N gene.

These mutations were confirmed by dideoxynucleotide sequence analysis, and the AatII-flII fragment was replaced into D13, which in turn was taken through the above described steps to construct a complete D53 DNA containing the mutations. This clone was used to recover recombinant virus.

The GE-mutant virus was analyzed in HEp-2 cells and compared to wild type virus with respect to plaque size and growth curve. This showed that the plaques were larger (on average 30% greater) than those of wild type, and the rate of growth and yield of virus were increased. These results are consistent with modification of gene expression by altering cis-regulatory elements, for example to decrease levels of readthrough mRNAs and increase expression of proteins from downstream genes. The resulting recombinant viruses will preferably exhibit increased growth kinetics and increased plaque size, providing but one example of alteration of RSV phenotype by changing cis-acting regulatory elements in the genome or antigenome. These and other examples herein demonstrate a wide range of RSV mutations specific for phenotypic changes that are advantageous for providing effective vaccine agents.

EXAMPLE XVII

Recombinant RSV Having a Deletion of the NS1 Gene

This example describes the production of a recombinant RSV in which expression of the NS1 protein has been ablated by removal of the polynucleotide sequence encoding the protein. The NS1 protein is a small 139-amino acid species which is encoded by the first gene in the 3' to 5' RSV gene map (Collins and Wertz, Proc. Natl. Acad. Sci. USA 80:3208-3212 (1983), and Collins and Wertz, Virol. 243:442-451 (1985)). Its mRNA is the most abundant of the RSV mRNAs, consistent with the general finding that there is a gradient of transcription such that the efficiency of gene expression is reduced with increasing distance from the promoter at the 3' end. The NS1 protein is thought to be one of the most abundantly expressed RSV proteins, although a careful quantitative comparison remains to be done. Despite its abundance, the function of the NS1 protein has not yet been clearly identified. In the reconstituted RSV minigenome system (Grosfeld et al., J. Virol. 69:5677-5686 (1995), Collins et al., Proc. Natl. Acad. Sci. USA 93:81-85 (1996)), in which transcription and RNA replication of a minigenome is driven by viral proteins supplied by plasmids, the NS1 protein appeared to be a negative regulatory protein for both transcription and RNA replication. Thus, it might be a regulatory protein. It is very possible that other functions exist which remain to be identified. The NS1 protein does not have a known counterpart in other paramyxoviruses. Without wishing to be bound by theory, several functions of the NS1 protein may exist: (i) it may be a viral regulatory factor as suggested above, (ii) it may be involved in some other aspect of the viral growth cycle, (iii) it may interact with the host cell, such as to prevent apoptosis, and (iv) it may interact with the host immune system, such as to inhibit aspects of the host defense system such as interferon production, antigen processing or B or T cell functioning. All of these potential activities of the NS1 protein may yield additional advantages in RSV recombinant vaccines.

Figure 21:
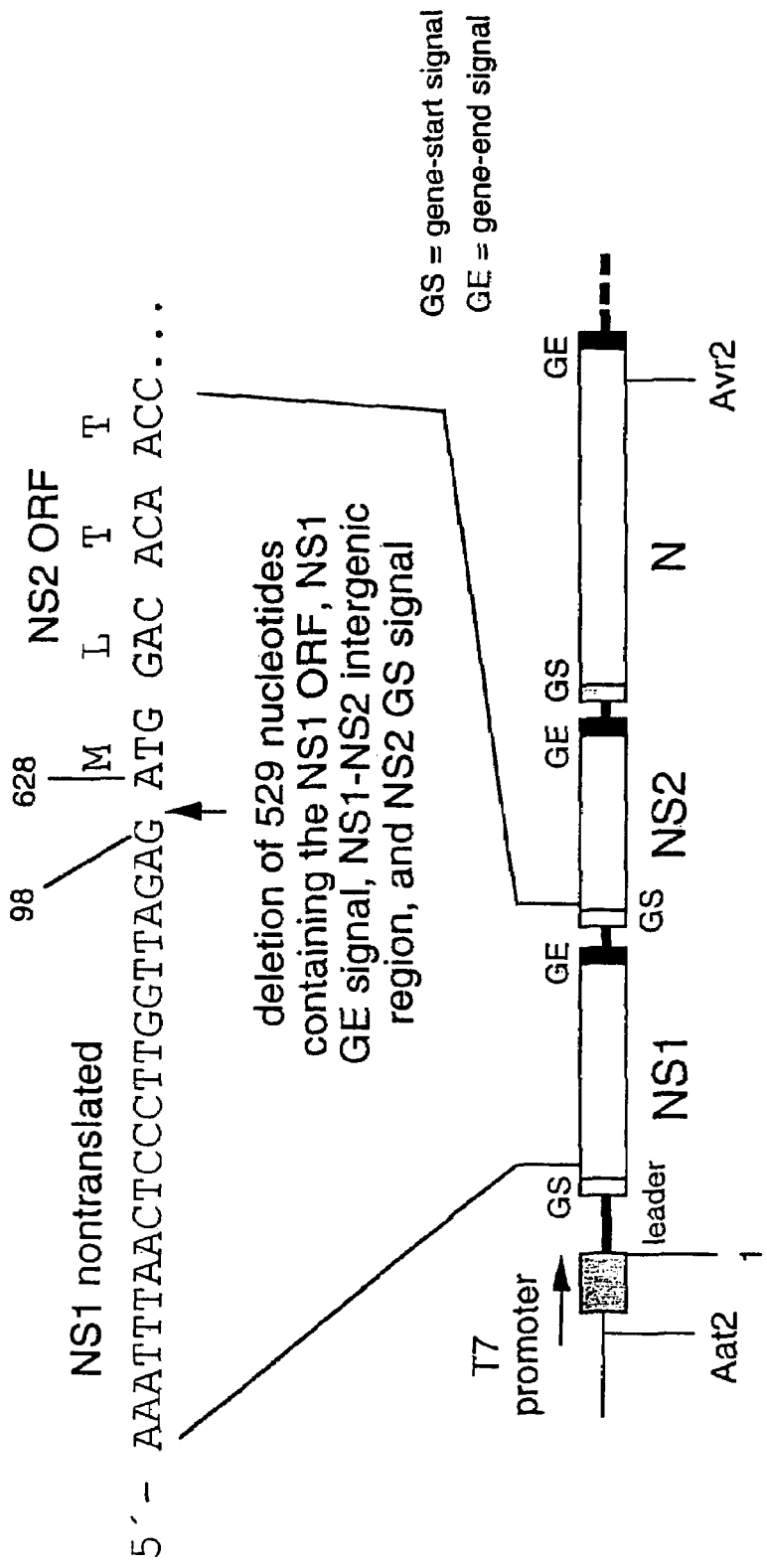
FIG. 21 depicts the deletion of the polynucleotide sequence encoding the NS1 protein. The left hand part of the D13 cDNA is shown at the bottom: D13 contains the left hand part of the antigenome cDNA, from the leader to the end of the SH gene, with the T7 promoter immediately upstream of the leader. The sequence on either side of the deletion point (upward arrow) is shown on top. The deletion spans from immediately before the translational start site of the NS1 ORF SEQ ID NO: 36) to immediately before that of the NS2 ORF (SEQ ID NO: 37 and 38). Thus, it has the effect of fusing the NS1 GS and upstream noncoding region to the NS2 ORF. This precludes the disruption of any cis-acting sequence elements which might extend into the NS1 gene due to its leader-proximal location.

To produce a recombinant RSV having a selected disruption of NS1 gene function, the sequence encoding the NS1 protein was deleted in its entirety from a parental RSV cDNA. In this exemplary deletion, the substrate for the mutagenesis reaction was plasmid D13, which was described hereinabove and contains the left hand end of the complete antigenome cDNA including the T7 RNA promoter, the leader region, and the NS1, NS2, N, P, M, and SH genes (sequence positions 1 to 4623). The mutagenesis was done by the method of Byrappa et al. (Byrappa et al., *Genome Res.* 5:404-407 (1995)), in which synthetic primers which incorporate the desired change are made to face in opposite directions on the plasmid, which is then amplified by PCR, ligated, and transformed into bacteria. The forward PCR primer was GACACAACCCA-CAATGATAATACACCAC [SEQ ID NO:9] (the second codon of the NS2 ORF is italicized), and the reverse PCR primer was CATCTCTAACCAAGGGAGTTAAATT-TAAGTGG [SEQ ID NO:10] (the complement to the initiation codon of the NS2 ORF is italicized). D13 was used as the template for PCR with a high-fidelity polymerase. The deletion was made to span from immediately upstream of the AUG start site of the NS1 ORF to immediately upstream of the AUG start site of the NS2 ORF (FIG. 21). This resulted in the deletion of 529 bp including the NS1 coding sequence, the NS1 GE signal, the NS1-NS2 intergenic region, and the NS2 GS signal. It had the effect of fusing the upstream end of the NS1 gene, namely its GS and non-protein-coding region, to the NS2 ORF. This part of the NS1 gene was retained expressly because it is immediately adjacent to the leader region and thus might contain sequences important in transcription or RNA replication. The region containing the mutation was confirmed by sequence analysis. Then, the ~2230 bp segment between the Aat2 and Avr2 sites (FIG. 21) was excised and inserted into a fresh copy of D13, a step that would thereby preclude the possibility of PCR error elsewhere in the RSV cDNA. The D13 plasmid containing the deletion of NS1 (D13ΔNS1) was used to construct a complete antigenome (D53ΔNS1) which contained the "HEK" and "sites" changes.

The D53ΔNS1 plasmid was then used to recover virus. Interestingly, the recovered RSVΔNS1 virus produced small plaques in tissue culture. The presence of the deletion was confirmed by RT-PCR. The fact that the RSVΔNS1 virus can grow, albeit with reduced efficiency, identifies the NS1 protein as an accessory protein, one that is dispensable to virus growth. The plaque size of the RSVΔNS1 virus was similar to that of the NS2-knock out virus described above in which expression of the NS2 protein was ablated by the introduction of translational stop codons into its coding sequence (Example XV). The small plaque phenotype is commonly associated with attenuating mutations. This type of mutation can thus be incorporated within viable recombinant RSV to yield altered phenotypes. These and other knock-out methods and mutants will therefore provide for yet additional recombinant RSV vaccine agents, based on the known correlation between plaque size in vitro and attenuation in vivo.

EXAMPLE XVIII

Recombinant RSV Having a Deletion of the NS2 Gene

This example describes the production of a recombinant RSV in which expression of the NS2 protein has been ablated by removal of a polynucleotide sequence encoding the protein. In Example XV, above, a recombinant virus (called NS2 knock-out or NS2-KO) was produced in which expression of the NS2 gene was ablated by the introduction of two translational stop codons into its coding sequence rather than by deletion of the coding sequence. Ablation of expression of the NS2 protein in the prototypic NS2-KO virus was associated with the small plaque phenotype and reduced kinetics of virus growth in vitro. Subsequent analysis showed that, upon passage of NS2 KO, it was possible to recover low levels of virus which had reverted to wild type growth characteristics. Sequence analysis showed that the two introduced translational stop codons had mutated into sense codons, albeit with coding assignments different than in the parental wild type virus. This was sufficient to restore synthesis of the NS2 protein as confirmed by Western blot analysis, which accounted for the wild type phenotype. The present strategy offers an improvement because the complete NS2 gene is removed and thus same-site reversion cannot occur.

The NS2 protein is a small 124-amino acid protein which is encoded by the second gene in the gene order (Collins and Wertz, *Proc. Natl. Acad. Sci. USA* 80:3208-3212 (1983), and Collins and Wertz, *Virol.* 243:442 451 (1985). Its mRNA is the second most abundant of the RSV mRNAs, and the NS2 protein is thought to be one of the most abundantly-expressed RSV proteins, although a careful quantitative comparison remains to be done. Despite its abundance, the function of the NS2 protein remains to be identified. In the reconstituted RSV minigenome system (Grosfeld et al., *J. Virol.* 69:5677-5686 (1995), Collins et al., *Proc. Natl. Acad. Sci. USA* 93:81-85 (1996)), in which transcription and RNA replication of a minigenome is driven by viral proteins supplied by plasmids, the NS2 protein had a modest negative regulatory effect against both transcription and RNA replication. Relatively high levels of NS2 protein expression were required to observe this effect, and so its significance is unclear. Thus, as suggested for the NS1 protein, NS2 might: (i) be a viral regulatory factor, (ii) be involved in some other aspect of the viral growth cycle, (iii) interact with the host cell, such as to prevent apoptosis, and (iv) interact with the host defense system, such as to inhibit aspects of the host immune system such as interferon production or aspects of antigen processing or B or T cell functioning. All of these potential activities of the NS2 protein may be incorporated within the invention according to the methods and strategies described herein, to yield additional advantages in RSV recombinant vaccines.

Figure 22:
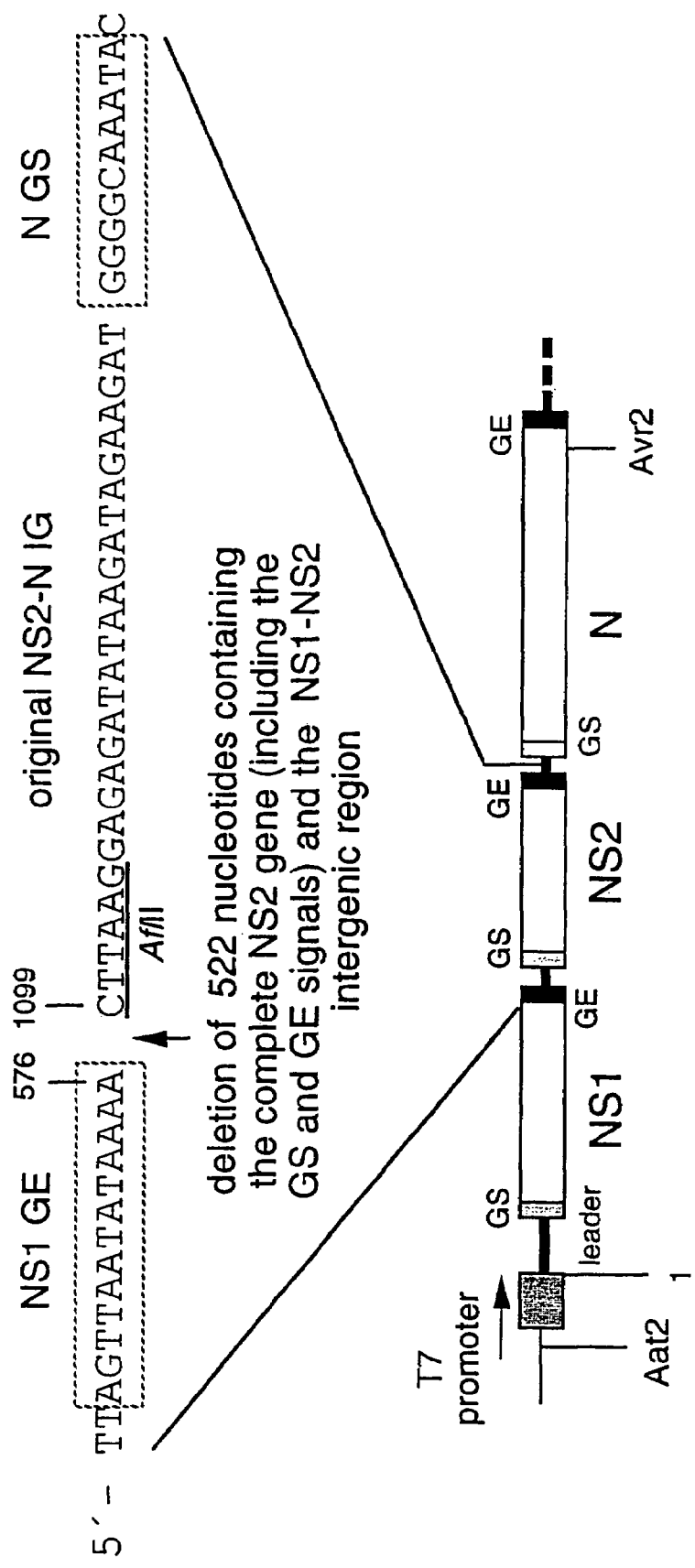
FIG. 22 depicts the deletion of the polynucleotide sequence encoding the NS2 mRNA. As described above, the left hand part of the D13 cDNA is shown along with the sequence on either side of the deletion point (upward arrow). The deletion spans from immediately downstream of the NS1 gene (SEQ ID NO: 39) to immediately downstream of the NS2 gene (SEQ ID NO: 40). Thus, the sequence encoding the NS2 mRNA has been deleted in its entirety, but no other sequence has been disrupted. The resulting cDNA and subsequent recovered recombinant virus are referred to as .DELTA.NS2.

To produce a recombinant RSV having a selected disruption of NS2 gene function, the sequence encoding its mRNA was deleted from a parental RSV cDNA. In this exemplary deletion, the substrate for the mutagenesis reaction was plasmid D13, which was mentioned previously and contains the left hand end of the complete antigenome cDNA including the T7 RNA promoter, the leader region, and the NS1, NS2, N, P, M, and SH genes (sequence positions 1 to 4623). The mutagenesis was done by the method of Byrappa et al. (Byrappa et al., *Genome Res.* 5:404-407 (1995)), in which synthetic primers which incorporate the desired change are made to face in opposite directions on the plasmid, which is then amplified by PCR, ligated, and transformed into bacteria. The forward PCR primer was TTAAGGAGAGATATAAGATAGAAGATG [SEQ ID NO:11] (sequence from the NS2 N intergenic region is underlined, and the first nucleotide of the N GS signal is italicized), and the reverse PCR primer was G TTTTATATTAACTAATGGTGTTAGTG [SEQ ID NO:12] (the complement to the NS1 GE signal is underlined). D13 was used as the template for PCR with a high-fidelity polymerase. The deletion was made to span from immediately downstream of the NS1 GE signal to immediately downstream of the NS2 GS signal (FIG. 22). Thus, the mutation deleted 522 nucleotides including the NS1-NS2 intergenic region and the complete NS2 gene (FIG. 22).

In the D13 plasmid containing the deletion, the region of the mutation was confirmed by sequence analysis. Then, the ~2230 bp segment between the Aat2 and Avr2 sites (FIG. 22) was excised and inserted into a fresh copy of D13, a step that would thereby preclude the possibility of PCR error elsewhere in the RSV cDNA. The D13 plasmid containing the deletion of NS2 (D13ΔNS2) was used to construct a complete antigenome (D53ΔNS2) which contained all of the "sites" and "HEK" changes.

The D53ΔNS2 plasmid was then used to recover virus. As is described above for the NS2-KO virus (see Example XV), the RSVΔNS2 produced small plaques. The presence of the deletion was confirmed by RT-PCR. The fact that the RSVΔNS2 virus can grow, albeit with reduced efficiency, identified the NS2 protein as an accessory protein, one that is dispensable to virus growth. The small plaque phenotype is commonly associated with attenuating mutations and can thus be incorporated within viable recombinant RSV to yield altered phenotypes. These and other knock-out methods and mutants will therefore provide for yet additional recombinant RSV vaccine agents, based on the known correlation between plaque size in vitro and attenuation in vivo.

EXAMPLE XIX

Ablation of the Translational Start Site for the Secreted Form of the G Glycoprotein This example describes the production of a recombinant RSV in which the translational start site for the secreted form of the G glycoprotein has been ablated. The RSV G protein is synthesized in two forms: as an anchored type II integral membrane protein and as a N terminally resected form which lacks essentially all of the membrane anchor and is secreted (Hendricks et al., *J. Virol.* 62:2228-2233 (1988)). The two forms have been shown to be derived by translational initiation at two different start sites: the longer form initiates at the first AUG of the G ORF, and the second initiates at the second AUG of the ORF at codon 48 and is further processed by proteolysis (Roberts et al., *J. Virol.* 68: 4538-4546 (1994)). The presence of this second start site is highly conserved, being present in all strains of human, bovine and ovine RSV sequenced to date. It has been suggested that the soluble form of the G protein-might mitigate host immunity by acting as a decoy to trap neutralizing antibodies. Also, soluble G has been implicated in preferential stimulation of a Th2-biased response, which in turn appears to be associated with enhanced immunopathology upon subsequent exposure to RSV. With regard to an RSV vaccine virus, it would be highly desirable to minimize antibody trapping or imbalanced stimulation of the immune system, and so it would be desirable to ablate expression of the secreted form of the G protein. This would represent a type of mutation whose action would be to qualitatively and/or quantitatively alter the host immune response, rather than to directly attenuate the virus.

Figure 23:
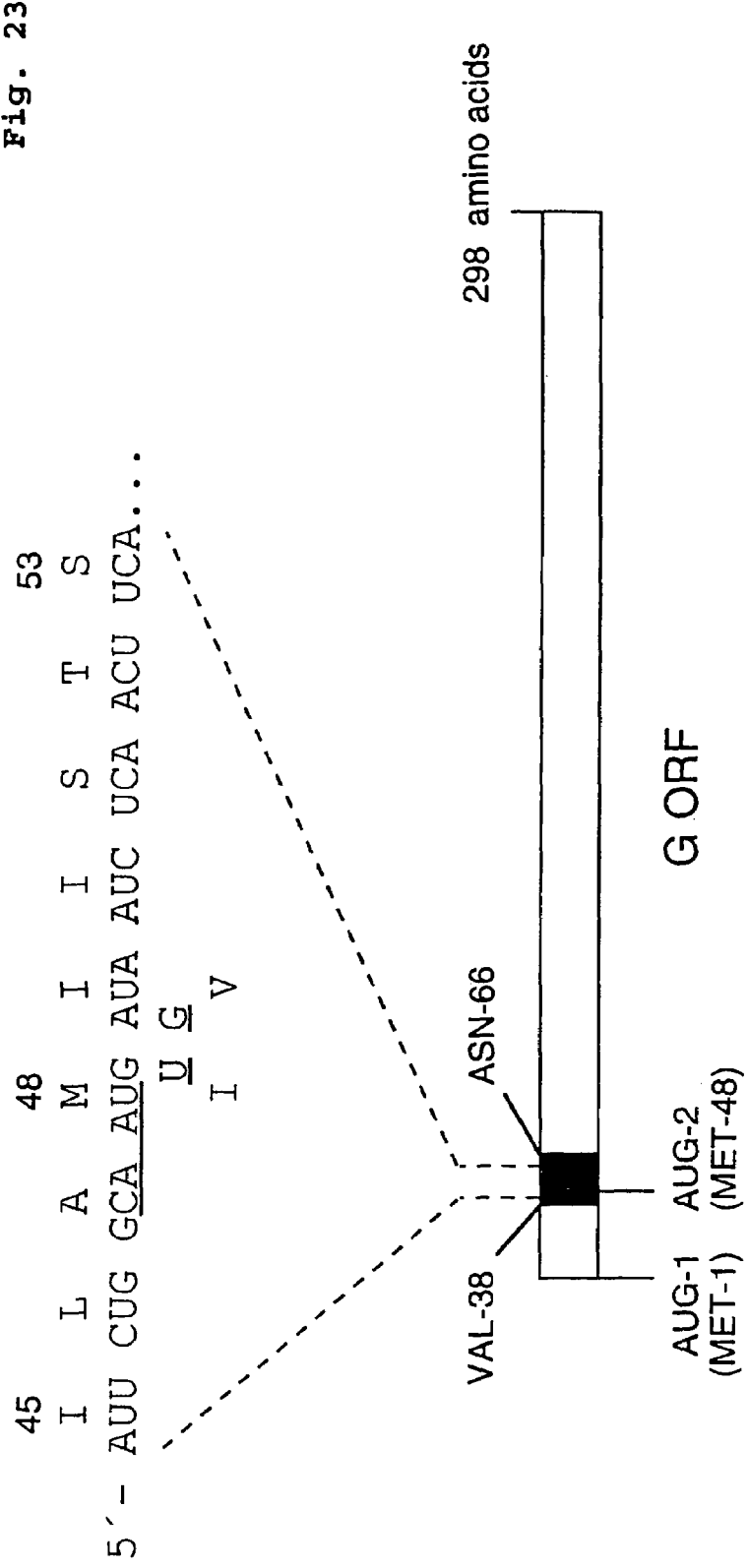
FIG. 23 depicts the ablation of the translational start site for the secreted form of the G protein. The 298-amino acid G protein is shown as an open rectangle with the signal-anchor sequence filled in. The amino acid sequence for positions 45 to 53 (SEQ ID NO: 41) is shown overhead to illustrate two nucleotide substitutions (SEQ ID NO: 42) which change amino acid 48 from methionine to isoleucine and amino acid 49 from isoleucine to valine. The former mutation eliminates the translational start site for the secreted form. The two mutations also create an MfeI site, which provides a convenient method for detecting the mutation. The resulting cDNA and subsequent recovered virus are referred to as M48I (methionine-48 to isoleucine-48).

Plasmid pUC19 bearing the G, F and M2 genes (see Example VII) was used as template in PCR mutagenesis by the procedure of Byrappa et al. (Byrappa et al., *Genome Res.* 5:404-407 (1995). The forward PCR primer was: TTATAAT-TGCAGCCATCATATTCATAGCCTCGG [SEQ ID NO:13], and the reverse primer was: GTGAAGTTGAGATTACAATTGCCAGAATGG [SEQ ID NO: 14] (the complement of the two nucleotide changes is underlined). This resulted in two amino acid coding changes (see FIG. 23), namely AUG-48 to AUU-48, which ablates the translational start site, and AUA-49 to GUA-49, which contributes to the insertion of an MfeI site for the purpose of monitoring the mutation.

The sequence surrounding the site of mutation was confirmed by dideoxynucleotide sequencing. Then, the PacI-StuI fragment, which contains the G gene, was substituted into plasmid D50, which is described hereinabove and contains the first nine genes from the leader to the beginning of the L gene. This was then used to construct a complete antigenome cDNA, D53/GM48I, which was used to recover virus. These mutations have previously been shown to ablate the expression of the secreted form of G under conditions where the G cDNA was expressed in isolation from the other RSV genes by a recombinant vaccinia virus (Roberts et al., *J. Virol.* 68:4538-4546 (1994)).

Figure 24:
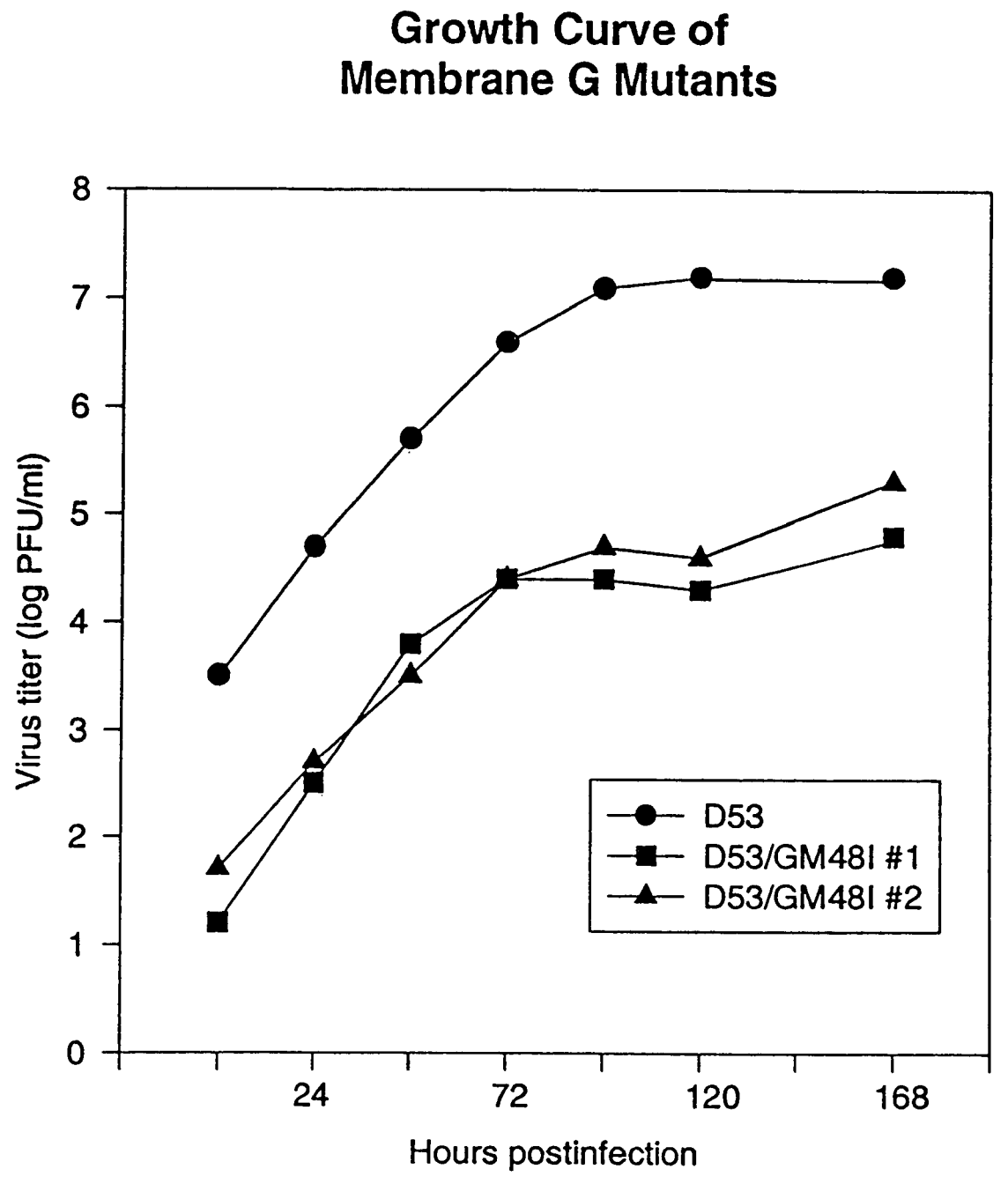

Two isolates of the recovered D53/M48I virus were evaluated for growth kinetics in vitro in parallel with wild type recombinant RSV (FIG. 24). This showed that both viruses grew somewhat more slowly, and to somewhat lower titers, than did the wild type. This difference in growth might be due to the reduced expression of the G protein, which would be expected to occur since the AUG-48 of the secreted form was eliminated whereas in this Example the AUG-1 of the membrane-bound form was not modified to increase its expression. In nature, the expression of AUG-1 of the G ORF is thought to be suboptimal because it is preceded in the G sequence by another AUG in another reading frame which opens a short ORF that overlaps AUG-1 of the G ORF and thus would reduce its expression. It might be anticipated that additional modification of the antigenome cDNA to eliminate this ORF might restore full growth properties. Alternatively, the mutations at position 48 and 49, acting alone or in concert, might be deleterious to the function of the G protein. The amino acid at position 49 could be restored to its natural coding assignment, and a different amino acid substitution could be chosen at position 48, which might restore full growth properties. These possibilities can be readily evaluated with the methods and materials described here. Nonetheless, the recover of the D53/GM48I virus shows that the translational start site for the secreted form can be ablated, and this virus is now available for evaluation in experimental animals and humans.

Although the foregoing invention has been described in some detail by way of illustration and example for purposes of clarity of understanding, it will be obvious that certain changes and modifications may be practiced within the scope of the appended claims.

What is claimed is:

1. An infectious recombinant respiratory syncytial virus (RSV) particle comprising a RSV genome or antigenome, a major nucleocapsid (N) protein, a nucleocapsid phosphoprotein (P), a large polymerase protein (L), and an M2ORF1 RNA polymerase elongation factor, wherein a modification is introduced within the genome or antigenome comprising a deletion, insertion, substitution, rearrangement, or point mutation of a gene or genome segment, or nucleotide modification of a cis-acting regulatory sequence or by introduction of a translation termination codon, wherein at least one of a SH, NS 1, NS2, or G gene is deleted in whole or in part, or the expression of at least one of a SH, NS1, NS2 or G gene is ablated, said recombinant RSV being attenuated by 10- to 1000-fold compared to wild type RSV in the respiratory tract of a primate host.

2. The recombinant RSV particle of claim 1, wherein expression of a selected RSV gene is reduced or ablated by introduction of one or more translation termination codons.

3. The recombinant RSV particle of claim 2, wherein expression of a selected RSV gene is reduced or ablated by introduction of multiple translation termination codons.

4. The recombinant RSV particle of claim 1, wherein expression of a selected RSV gene is reduced or ablated by introduction of a frame shift mutation in the gene.

5. The recombinant RSV particle of claim 1, wherein expression of a selected RSV gene is modulated by introduction, modification or ablation of a translational start site within the gene.

6. The recombinant RSV particle of claim 1, wherein the recombinant genome or antigenome is modified to incorporate at least one and up to a full complement of attenuating mutations present within a panel of biologically derived mutant human RSV strains, said panel comprising cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579).

7. The recombinant RSV particle of claim 6, wherein the recombinant genome or antigenome is modified to incorporate at least one and up to a full complement of attenuating mutations specifying an amino acid substitution at Val267 in the RSV N gene, Glu218 and/or Thr523 in the RSV F gene, Cys319, Phe 521, Gln831, Met1169, Tyr1321 and/or His 1690 in the RSV polymerase gene L, and a nucleotide substitution in the gene-start sequence of gene M2.

8. The recombinant RSV particle of claim 6, wherein the recombinant genome or antigenome incorporates at least two of said attenuating mutations.

9. The recombinant RSV particle of claim 1, wherein the recombinant genome or antigenome comprises a partial or complete human RSV genome or antigenome of one RSV subgroup or strain combined with a heterologous gene or gene segment from a different, human or non-human RSV subgroup or strain to form a chimeric genome or antigenome.

10. The recombinant RSV particle of claim 9, wherein the heterologous gene or gene segment is from a human RSV subgroup A, human RSV subgroup B, bovine RSV, or murine RSV.

11. The recombinant RSV particle of claim 9, wherein the chimeric genome or antigenome comprises a partial or complete human RSV A subgroup genome or antigenome combined with a heterologous gene or gene segment encoding a RSV F, G or SH glycoprotein or a cytoplasmic domain, transmembrane domain, ectodomain or immunogenic epitope thereof from a human RSV B subgroup virus.

12. The chimeric RSV particle of claim 11, wherein both human RSV B subgroup glycoprotein genes F and G are substituted to replace counterpart F and G glycoprotein genes in a partial RSV A genome or antigenome.

13. The recombinant RSV particle of claim 11, wherein the chimeric genome or antigenome comprises a partial or complete human RSV B subgroup genome or antigenome combined with a heterologous gene or gene segment from a human RSV A subgroup virus.

14. The recombinant RSV particle of claim 9, wherein the chimeric genome or antigenome comprises a partial or complete RSV background genome or antigenome of a human or bovine RSV combined with a heterologous gene or genome segment of a different RSV to form a human-bovine chimeric RSV genome or antigenome.

15. The recombinant RSV particle of claim 1, wherein the recombinant genome or antigenome incorporates a heterologous gene or genome segment from parainfluenza virus (PIV).

16. The recombinant RSV particle of claim 15, wherein the gene or genome segment encodes a PIV HN or F glycoprotein or immunogenic domain or epitope thereof.

17. The recombinant RSV particle of claim 15, wherein the genome segment encodes one or more immunogenic protein(s), protein domain(s) or epitope(s) HPIV1, HPIV2, and/or HPIV3.

18. The recombinant RSV particle of claim 1, wherein the recombinant genome or antigenome is further modified to encode a non-RSV molecule selected from a cytokine, a T-helper epitope, or a protein of a microbial pathogen capable of eliciting a protective immune response in a mammalian host.

19. The recombinant RSV of claim 1 which is a complete virus.

20. The recombinant RSV of claim 1 which is a subviral particle.

21. The recombinant RSV of claim 1, formulated in a dose of $10^3$ to $10^6$ PFU of attenuated virus.

22. A method for eliciting an immune response in a mammalian subject directed against respiratory syncytial virus, which comprises administering to the subject an immunologically sufficient amount of the isolated attenuated recombinant RSV of claim 1.

23. The method of claim 22, wherein the recombinant virus is administered in a dose of $10^3$ to $10^6$ PFU of the attenuated RSV.

24. The method of claim 22, wherein the recombinant virus is administered to the upper respiratory tract.

25. The method of claim 24, wherein the recombinant virus is administered by spray, droplet or aerosol.

26. The method of claim 22, wherein the recombinant virus is administered to an individual seronegative for antibodies to RSV or possessing transplacentally acquired maternal antibodies to RSV.

27. An immunogenic composition effective to elicit an immune response directed against RSV, which comprises an immunologically sufficient amount of the isolated attenuated recombinant RSV of claim 1 in a physiologically acceptable carrier.

28. The immunogenic composition of claim 27, formulated in a dose of $10^3$ to $10^6$ PFU of the attenuated RSV.

29. The immunogenic composition of claim 27, formulated for administration to the upper respiratory tract by spray, droplet or aerosol.

30. The immunogenic composition of claim 27, wherein the recombinant RSV elicits an immune response against human RSV A, human RSV B, or both.

31. An expression vector comprising an isolated polynucleotide molecule encoding a respiratory syncytial virus (RSV) genome or antigenome modified by a deletion, insertion, substitution, rearrangement, or mutation of a gene or genome segment or by nucleotide modification of a cis-acting regulatory sequence, wherein at least one of a SH, NS1, NS2, or G gene is deleted in whole or in part, or the expression of at least one of a SH, NS1, NS2 or G gene is ablated.

32. An isolated polynucleotide molecule comprising a respiratory syncytial virus (RSV) genome or antigenome which is modified by a deletion, insertion, substitution, rearrangement, or mutation of a gene or genome segment, or by nucleotide modification of a cis-acting regulatory sequence, or by introduction of a translation termination codon, wherein at least one of a SH, NS1, NS2, or G gene is deleted in whole or in part, or the expression of at least one of a SH, NS1, NS2 or G gene is ablated, said isolated polynucleotide encoding a recombinant RSV being attenuated by 10-fold to 1000-fold compared to wild type RSV in the respiratory tract of a primate host.

33. The isolated polynucleotide molecule of claim 32, wherein the cis-acting regulatory sequence is a gene-start (GS) signal or a (GE) signal.

34. The isolated polynucleotide molecule of claim 32, wherein at least one of a SH, NS1, NS2, or G gene is deleted in whole or in part.

35. The isolated polynucleotide molecule of claim 32, wherein expression of a selected RSV gene is reduced or ablated by introduction of one or more translation termination codons in the recombinant genome or antigenome.

36. The isolated polynucleotide molecule of claim 32, wherein expression of a selected RSV gene is reduced or ablated by introduction of a frame shift mutation in the gene.

37. The isolated polynucleotide molecule of claim 32, wherein expression of a selected RSV gene is modulated by introduction, modification or ablation of a translational start site within the gene.

38. The isolated polynucleotide molecule of claim 32, wherein the recombinant genome or antigenome is modified to incorporate one or more attenuating mutation(s) present in within a panel of biologically derived mutant human RSV strains, said panel comprising cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579).

39. The isolated polynucleotide molecule of claim 38, wherein the recombinant genome or antigenome is modified to incorporate at least one and up to a full complement of attenuating mutations specifying an amino acid substitution at Val 267 in the RSV N gene, Glu218 and/or Thr523 in the RSV F gene, Cys319, Phe 521, Gln831, Met1169, Tyr 1321 and/or His 1690 in the RSV polymerase gene L, and a nucleotide substitution in the gene-start sequence of gene M2.

40. The isolated polynucleotide molecule of claim 32, wherein the recombinant genome or antigenome comprises a partial or complete human RSV genome or antigenome of one RSV subgroup or strain combined with a heterologous gene or gene segment from a different, human or non-human RSV subgroup or strain to form a chimeric genome or antigenome.

41. The isolated polynucleotide molecule of claim 40, wherein the heterologous gene or gene segment is from a human RSV subgroup A, human RSV subgroup B, bovine RSV, or murine RSV.

42. The isolated polynucleotide molecule of claim 41, wherein the chimeric genome or antigenome comprises a partial or complete human RSV A subgroup genome or antigenome combined with a heterologous gene or gene segment encoding a RSV F, G or SH glycoprotein or a cytoplasmic domain, transmembrane domain, ectodomain or immunogenic epitope thereof from a human RSV B subgroup virus.

43. The isolated polynucleotide molecule of claim 42, wherein both human RSV B subgroup glycoprotein genes F and G are substituted to replace counterpart F and G glycoprotein genes in a partial RSV A genome or antigenome.

44. The recombinant RSV of claim 32, wherein the recombinant genome or antigenome comprises a partial or complete RSV background genome or antigenome of a human or bovine RSV combined with a heterologous gene or genome segment of a different RSV to form a human-bovine chimeric RSV genome or antigenome.

45. The isolated polynucleotide molecule of claim 32, wherein the recombinant genome or antigenome incorporates a heterologous gene or genome segment from parainfluenza virus (PIV).

46. The isolated polynucleotide molecule of claim 32, wherein the recombinant genome or antigenome is further modified to encode a non-RSV molecule selected from a cytokine, a T-helper epitope, or a protein of a microbial pathogen capable of eliciting a protective immune response in a mammalian host.

\* \* \* \* \*

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 15223 base pairs (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 1:

```
ACGCGAAAAA ATGCGTACAA CAAACTTGCA TAAACCAAAA AAATGGGGCA AATAAGAATT     60
TGATAAGTAC CACTTAAATT TAACTCCCTT GGTTAGAGAT GGGCAGCAAT TCATTGAGTA    120
TGATAAAAGT TAGATTACAA AATTTGTTTG ACAATGATGA AGTAGCATTG TTAAAAATAA    180
CATGCTATAC TGATAAATTA ATACATTTAA CTAATGCTTT GGCTAAGGCA GTGATACATA    240
CAATCAAATT GAATGGCATT GTGTTTGTGC ATGTTATTAC AAGTAGTGAT ATTTGCCCTA    300
ATAATAATAT TGTAGTAAAA TCCAATTTCA CAACAATGCC AGTACTACAA AATGGAGGTT    360
ATATATGGGA AATGATGGAA TTAACACATT GCTCTCAACC TAATGGTCTA CTAGATGACA    420
ATTGTGAAAT TAAATTCTCC AAAAAACTAA GTGATTCAAC AATGACCAAT TATATGAATC    480
AATTATCTGA ATTACTTGGA TTTGATCTTA ATCCATAAAT TATAATTAAT ATCAACTAGC    540
AAATCAATGT CACTAACACC ATTAGTTAAT ATAAAACTTA ACAGAAGACA AAAATGGGGC    600
AAATAAATCA ATTCAGCCAA CCCAACCATG GACACAACCC ACAATGATAA TACACCACAA    660
AGACTGATGA TCACAGACAT GAGACCGTTG TCACTTGAGA CCATAATAAC ATCACTAACC    720
AGAGACATCA TAACACACAA ATTTATATAC TTGATAAATC ATGAATGCAT AGTGAGAAAA    780
CTTGATGAAA AGCAGGCCAC ATTTACATTC CTGGTCAACT ATGAAATGAA ACTATTACAC    840
AAAGTAGGAA GCACTAAATA TAAAAAATAT ACTGAATACA ACACAAAATA TGGCACTTTC    900
CCTATGCCAA TATTCATCAA TCATGATGGG TTCTTAGAAT GCATTGGCAT TAAGCCTACA    960
AAGCATACTC CCATAATATA CAAGTATGAT CTCAATCCAT AAATTTCAAC ACAATATTCA   1020
CACAATCTAA AACAACAACT CTATGCATAA CTATACTCCA TAGTCCAGAT GGAGCCTGAA   1080
AATTATAGTA ATTTAAAACT TAAGGAGAGA TATAAGATAG AAGATGGGGC AAATACAACC   1140
ATGGCTCTTA GCAAAGTCAA GTTGAATGAT ACACTCAACA AAGATCAACT TCTGTCATCC   1200
AGCAAATACA CCATCCAACG GAGCACAGGA GATAGTATTG ATACTCCTAA TTATGATGTG   1260
CAGAAACACA TCAATAAGTT ATGTGGCATG TTATTAATCA CAGAAGATGC TAATCATAAA   1320
TTCACTGGGT TAATAGGTAT GTTATATGCG ATGTCTAGGT TAGGAAGAGA AGACACCATA   1380
AAAATACTCA GAGATGCGGG ATATCATGTA AAAGCAAATG GAGTAGATGT AACAACACAT   1440
CGTCAAGACA TTAATGGAAA AGAAATGAAA TTTGAAGTGT TAACATTGGC AAGCTTAACA   1500
ACTGAAATTC AAATCAACAT TGAGATAGAA TCTAGAAAAT CCTACAAAAA AATGCTAAAA   1560
GAAATGGGAG AGGTAGCTCC AGAATACAGG CATGACTCTC CTGATTGTGG GATGATAATA   1620
TTATGTATAG CAGCATTAGT AATAACTAAA TTAGCAGCAG GGGACAGATC TGGTCTTACA   1680
GCCGTGATTA GGAGAGCTAA TAATGTCCTA AAAAATGAAA TGAAACGTTA CAAAGGCTTA   1740
CTACCCAAGG ACATAGCCAA CAGCTTCTAT GAAGTGTTTG AAAAACATCC CCACTTTATA   1800
GATGTTTTTG TTCATTTTGG TATAGCACAA TCTTCTACCA GAGGTGGCAG TAGAGTTGAA   1860
GGGATTTTTG CAGGATTGTT TATGAATGCC TATGGTGCAG GGCAAGTGAT GTTACGGTGG   1920
GGAGTCTTAG CAAAATCAGT TAAAAATATT ATGTTAGGAC ATGCTAGTGT GCAAGCAGAA   1980
ATGGAACAAG TTGTTGAGGT TTATGAATAT GCCCAAAAAT TGGGTGGTGA AGCAGGATTC   2040
TACCATATAT TGAACAACCC AAAAGCATCA TTATTATCTT TGACTCAATT TCCTCACTTC   2100
TCCAGTGTAG TATTAGGCAA TGCTGCTGGC CTAGGCATAA TGGGAGAGTA CAGAGGTACA   2160
```

```
CCGAGGAATC AAGATCTATA TGATGCAGCA AAGGCATATG CTGAACAACT CAAAGAAAAT    2220

GGTGTGATTA ACTACAGTGT ACTAGACTTG ACAGCAGAAG AACTAGAGGC TATCAAACAT    2280

CAGCTTAATC CAAAAGATAA TGATGTAGAG CTTTGAGTTA ATAAAAAATG GGCAAATAA     2340

ATCATCATGG AAAAGTTTGC TCCTGAATTC CATGGAGAAG ATGCAAACAA CAGGGCTACT    2400

AAATTCCTAG AATCAATAAA GGGCAAATTC ACATCACCCA AAGATCCCAA GAAAAAAGAT    2460

AGTATCATAT CTGTCAACTC AATAGATATA GAAGTAACCA AGAAAGCCC TATAACATCA     2520

AATTCAACTA TTATCAACCC AACAAATGAG ACAGATGATA CTGCAGGGAA CAAGCCCAAT    2580

TATCAAAGAA AACCTCTAGT AAGTTTCAAA GAAGACCCTA CACCAAGTGA TAATCCCTTT    2640

TCTAAACTAT ACAAAGAAAC CATAGAAACA TTTGATAACA ATGAAGAAGA ATCCAGCTAT    2700

TCATACGAAG AAATAAATGA TCAGACAAAC GATAATATAA CAGCAAGATT AGATAGGATT    2760

GATGAAAAAT TAAGTGAAAT ACTAGGAATG CTTCACACAT TAGTAGTGGC AAGTGCAGGA    2820

CCTACATCTG CTCGGGATGG TATAAGAGAT GCCATGGTTG GTTTAAGAGA AGAAATGATA    2880

GAAAAAATCA GAACTGAAGC ATTAATGACC AATGACAGAT TAGAAGCTAT GGCAAGACTC    2940

AGGAATGAGG AAAGTGAAAA GATGGCAAAA GACACATCAG ATGAAGTGTC TCTCAATCCA    3000

ACATCAGAGA AATTGAACAA CCTATTGGAA GGGAATGATA GTGACAATGA TCTATCACTT    3060

GAAGATTTCT GATTAGTTAC CAATCTTCAC ATCAACACAC AATACCAACA GAAGACCAAC    3120

AAACTAACCA ACCCAATCAT CCAACCAAAC ATCCATCCGC CAATCAGCCA AACAGCCAAC    3180

AAAACAACCA GCCAATCCAA AACTAACCAC CCGGAAAAAA TCTATAATAT AGTTACAAAA    3240

AAAGGAAAGG GTGGGGCAAA TATGGAAACA TACGTGAACA AGCTTCACGA AGGCTCCACA    3300

TACACAGCTG CTGTTCAATA CAATGTCTTA GAAAAAGACG ATGACCCTGC ATCACTTACA    3360

ATATGGGTGC CCATGTTCCA ATCATCTATG CCAGCAGATT TACTTATAAA GAACTAGCT     3420

AATGTCAACA TACTAGTGAA ACAAATATCC ACACCCAAGG GACCTTCACT AAGAGTCATG    3480

ATAAACTCAA GAAGTGCAGT GCTAGCACAA ATGCCCAGCA AATTTACCAT ATGCGCTAAT    3540

GTGTCCTTGG ATGAAAGAAG CAAACTAGCA TATGATGTAA CCACACCCTG TGAAATCAAG    3600

GCATGTAGTC TAACATGCCT AAAATCAAAA AATATGTTGA CTACAGTTAA AGATCTCACT    3660

ATGAAGACAC TCAACCCTAC ACATGATATT ATTGCTTTAT GTGAATTTGA AAACATAGTA    3720

ACATCAAAAA AAGTCATAAT ACCAACATAC CTAAGATCCA TCAGTGTCAG AAATAAAGAT    3780

CTGAACACAC TTGAAAATAT AACAACCACT GAATTCAAAA ATGCTATCAC AAATGCAAAA    3840

ATCATCCCTT ACTCAGGATT ACTATTAGTC ATCACAGTGA CTGACAACAA AGGAGCATTC    3900

AAATACATAA AGCCACAAAG TCAATTCATA GTAGATCTTG GAGCTTACCT AGAAAAAGAA    3960

AGTATATATT ATGTTACCAC AAATTGGAAG CACACAGCTA CACGATTTGC AATCAAACCC    4020

ATGGAAGATT AACCTTTTTC CTCTACATCA GTGTGTTAAT TCATACAAAC TTTCTACCTA    4080

CATTCTTCAC TTCACCATCA CAATCACAAA CACTCTGTGG TTCAACCAAT CAAACAAAAC    4140

TTATCTGAAG TCCAGATCA TCCCAAGTCA TTGTTTATCA GATCTAGTAC TCAAATAAGT     4200

TAATAAAAAA TATACACATG GGGCAAATAA TCATTGGAGG AAATCCAACT AATCACAATA    4260

TCTGTTAACA TAGACAAGTC CACACACCAT ACAGAATCAA CCAATGGAAA ATACATCCAT    4320

AACAATAGAA TTCTCAAGCA AATTCTGGCC TTACTTTACA CTAATACACA TGATCACAAC    4380

AATAATCTCT TTGCTAATCA TAATCTCCAT CATGATTGCA ATACTAAACA AACTTTGTGA    4440

ATATAACGTA TTCCATAACA AAACCTTTGA GTTACCAAGA GCTCGAGTCA ACACATAGCA    4500
```

```
TTCATCAATC CAACAGCCCA AAACAGTAAC CTTGCATTTA AAAATGAACA ACCCCTACCT      4560

CTTTACAACA CCTCATTAAC ATCCCACCAT GCAAACCACT ATCCATACTA TAAAGTAGTT      4620

AATTAAAAAT AGTCATAACA ATGAACTAGG ATATCAAGAC TAACAATAAC ATTGGGGCAA      4680

ATGCAAACAT GTCCAAAAAC AAGGACCAAC GCACCGCTAA GACATTAGAA AGGACCTGGG      4740

ACACTCTCAA TCATTTATTA TTCATATCAT CGTGCTTATA TAAGTTAAAT CTTAAATCTG      4800

TAGCACAAAT CACATTATCC ATTCTGGCAA TGATAATCTC AACTTCACTT ATAATTGCAG      4860

CCATCATATT CATAGCCTCG GCAAACCACA AAGTCACACC AACAACTGCA ATCATACAAG      4920

ATGCAACAAG CCAGATCAAG AACACAACCC CAACATACCT CACCCAGAAT CCTCAGCTTG      4980

GAATCAGTCC CTCTAATCCG TCTGAAATTA CATCACAAAT CACCACCATA CTAGCTTCAA      5040

CAACACCAGG AGTCAAGTCA ACCCTGCAAT CCACAACAGT CAAGACCAAA ACACAACAA      5100

CAACTCAAAC ACAACCCAGC AAGCCCACCA CAAAACAACG CCAAACAAA CCACCAAGCA      5160

AACCCAATAA TGATTTTCAC TTTGAAGTGT TCAACTTTGT ACCCTGCAGC ATATGCAGCA      5220

ACAATCCAAC CTGCTGGGCT ATCTGCAAAA GAATACCAAA CAAAAACCA GGAAAGAAAA      5280

CCACTACCAA GCCCACAAAA AAACCAACCC TCAAGACAAC CAAAAAAGAT CCCAAACCTC      5340

AAACCACTAA ATCAAAGGAA GTACCCACCA CCAAGCCCAC AGAAGAGCCA ACCATCAACA      5400

CCACCAAAAC AAACATCATA ACTACACTAC TCACCTCCAA CACCACAGGA ATCCAGAAC      5460

TCACAAGTCA AATGGAAACC TTCCACTCAA CTTCCTCCGA AGGCAATCCA AGCCCTTCTC      5520

AAGTCTCTAC AACATCCGAG TACCCATCAC AACCTTCATC TCCACCCAAC ACACCACGCC      5580

AGTAGTTACT TAAAAACATA TTATCACAAA AGGCCTTGAC CAACTTAAAC AGAATCAAAA      5640

TAAACTCTGG GGCAAATAAC AATGGAGTTG CTAATCCTCA AAGCAAATGC AATTACCACA      5700

ATCCTCACTG CAGTCACATT TTGTTTTGCT TCTGGTCAAA ACATCACTGA AGAATTTTAT      5760

CAATCAACAT GCAGTGCAGT TAGCAAAGGC TATCTTAGTG CTCTGAGAAC TGGTTGGTAT      5820

ACCAGTGTTA TAACTATAGA ATTAAGTAAT ATCAAGAAAA ATAAGTGTAA TGGAACAGAT      5880

GCTAAGGTAA AATTGATAAA ACAAGAATTA GATAAATATA AAAATGCTGT AACAGAATTG      5940

CAGTTGCTCA TGCAAAGCAC ACAAGCAACA AACAATCGAG CCAGAAGAGA ACTACCAAGG      6000

TTTATGAATT ATACACTCAA CAATGCCAAA AAACCAATG TAACATTAAG CAAGAAAAGG      6060

AAAAGAAGAT TCTTGGTTT TTTGTTAGGT GTTGGATCTG CAATCGCCAG TGGCGTTGCT      6120

GTATCTAAGG TCCTGCACCT AGAAGGGGAA GTGAACAAGA TCAAAAGTGC TCTACTATCC      6180

ACAAACAAGG CTGTAGTCAG CTTATCAAAT GGAGTTAGTG TTTTAACCAG CAAAGTGTTA      6240

GACCTCAAAA ACTATATAGA TAAACAATTG TTACCTATTG TGAACAAGCA AAGCTGCAGC      6300

ATATCAAATA TAGAAACTGT GATAGAGTTC CAACAAAAGA ACAACAGACT ACTAGAGATT      6360

ACCAGGGAAT TTAGTGTTAA TGCAGGCGTA ACTACACCTG TAAGCACTTA CATGTTAACT      6420

AATAGTGAAT TATTGTCATT AATCAATGAT ATGCCTATAA CAAATGATCA GAAAAAGTTA      6480

ATGTCCAACA ATGTTCAAAT AGTTAGACAG CAAAGTTACT CTATCATGTC CATAATAAAA      6540

GAGGAAGTCT TAGCATATGT AGTACAATTA CCACTATATG GTGTTATAGA TACACCCTGT      6600

TGGAAACTAC ACACATCCCC TCTATGTACA ACCAACACAA AAGAAGGGTC CAACATCTGT      6660

TTAACAAGAA CTGACAGAGG ATGGTACTGT GACAATGCAG GATCAGTATC TTTCTTCCCA      6720

CAAGCTGAAA CATGTAAAGT TCAATCAAAT CGAGTATTTT GTGACACAAT GAACAGTTTA      6780

ACATTACCAA GTGAAGTAAA TCTCTGCAAT GTTGACATAT TCAACCCCAA ATATGATTGT      6840

AAAATTATGA CTTCAAAAAC AGATGTAAGC AGCTCCGTTA TCACATCTCT AGGAGCCATT      6900
```

```
GTGTCATGCT ATGGCAAAAC TAAATGTACA GCATCCAATA AAAATCGTGG AATCATAAAG    6960

ACATTTTCTA ACGGGTGCGA TTATGTATCA AATAAAGGGG TGGACACTGT GTCTGTAGGT    7020

AACACATTAT ATTATGTAAA TAAGCAAGAA GGTAAAAGTC TCTATGTAAA AGGTGAACCA    7080

ATAATAAATT TCTATGACCC ATTAGTATTC CCCTCTGATG AATTTGATGC ATCAATATCT    7140

CAAGTCAACG AGAAGATTAA CCAGAGCCTA GCATTTATTC GTAAATCCGA TGAATTATTA    7200

CATAATGTAA ATGCTGGTAA ATCCACCACA AATATCATGA TAACTACTAT AATTATAGTG    7260

ATTATAGTAA TATTGTTATC ATTAATTGCT GTTGGACTGC TCTTATACTG TAAGGCCAGA    7320

AGCACACCAG TCACACTAAG CAAAGATCAA CTGAGTGGTA TAAATAATAT TGCATTTAGT    7380

AACTAAATAA AAATAGCACC TAATCATGTT CTTACAATGG TTTACTATCT GCTCATAGAC    7440

AACCCATCTG TCATTGGATT TTCTTAAAAT CTGAACTTCA TCGAAACTCT CATCTATAAA    7500

CCATCTCACT TACACTATTT AAGTAGATTC CTAGTTTATA GTTATATAAA ACACAATTGC    7560

ATGCCAGATT AACTTACCAT CTGTAAAAAT GAAAACTGGG GCAAATATGT CACGAAGGAA    7620

TCCTTGCAAA TTTGAAATTC GAGGTCATTG CTTAAATGGT AAGAGGTGTC ATTTTAGTCA    7680

TAATTATTTT GAATGGCCAC CCCATGCACT GCTTGTAAGA CAAAACTTTA TGTTAAACAG    7740

AATACTTAAG TCTATGGATA AAGTATAGA TACCTTATCA GAAATAAGTG GAGCTGCAGA    7800

GTTGGACAGA ACAGAAGAGT ATGCTCTTGG TGTAGTTGGA GTGCTAGAGA GTTATATAGG    7860

ATCAATAAAC AATATAACTA AACAATCAGC ATGTGTTGCC ATGAGCAAAC TCCTCACTGA    7920

ACTCAATAGT GATGATATCA AAAAGCTGAG GGACAATGAA GAGCTAAATT CACCCAAGAT    7980

AAGAGTGTAC AATACTGTCA TATCATATAT TGAAAGCAAC AGGAAAAACA ATAAACAAAC    8040

TATCCATCTG TTAAAAAGAT TGCCAGCAGA CGTATTGAAG AAAACCATCA AAAACACATT    8100

GGATATCCAT AAGAGCATAA CCATCAACAA CCCAAAAGAA TCAACTGTTA GTGATACAAA    8160

TGACCATGCC AAAAATAATG ATACTACCTG ACAAATATCC TTGTAGTATA ACTTCCATAC    8220

TAATAACAAG TAGATGTAGA GTTACTATGT ATAATCAAAA GAACACACTA TATTTCAATC    8280

AAAACAACCC AATAACCAT ATGTACTCAC CGAATCAAAC ATTCAATGAA ATCCATTGGA    8340

CCTCTCAAGA ATTGATTGAC ACAATTCAAA ATTTTCTACA ACATCTAGGT ATTATTGAGG    8400

ATATATATAC AATATATATA TTAGTGTCAT AACACTCAAT TCTAACACTC ACCACATCGT    8460

TACATTATTA ATTCAAACAA TTCAAGTTGT GGGACAAAAT GGATCCCATT ATTAATGGAA    8520

ATTCTGCTAA TGTTTATCTA ACCGATAGTT ATTTAAAAGG TGTTATCTCT TTCTCAGAGT    8580

GTAATGCTTT AGGAAGTTAC ATATTCAATG GTCCTTATCT CAAAAATGAT TATACCAACT    8640

TAATTAGTAG ACAAAATCCA TTAATAGAAC ACATGAATCT AAAGAAACTA AATATAACAC    8700

AGTCCTTAAT ATCTAAGTAT CATAAAGGTG AAATAAAATT AGAAGAACCT ACTTATTTTC    8760

AGTCATTACT TATGACATAC AAGAGTATGA CCTCGTCAGA ACAGATTGCT ACCACTAATT    8820

TACTTAAAAA GATAATAAGA AGAGCTATAG AAATAAGTGA TGTCAAAGTC TATGCTATAT    8880

TGAATAAACT AGGGCTTAAA GAAAAGGACA AGATTAAATC CAACAATGGA CAAGATGAAG    8940

ACAACTCAGT TATTACGACC ATAATCAAAG ATGATATACT TTCAGCTGTT AAAGATAATC    9000

AATCTCATCT TAAAGCAGAC AAAAATCACT CTACAAAACA AAAAGACACA ATCAAAACAA    9060

CACTCTTGAA GAAATTGATG TGTTCAATGC AACATCCTCC ATCATGGTTA ATACATTGGT    9120

TTAACTTATA CACAAAATTA AACAACATAT TAACACAGTA TCGATCAAAT GAGGTAAAAA    9180

ACCATGGGTT TACATTGATA GATAATCAAA CTCTTAGTGG ATTTCAATTT ATTTTGAACC    9240
```

```
AATATGGTTG TATAGTTTAT CATAAGGAAC TCAAAAGAAT TACTGTGACA ACCTATAATC   9300

AATTCTTGAC ATGGAAAGAT ATTAGCCTTA GTAGATTAAA TGTTTGTTTA ATTACATGGA   9360

TTAGTAACTG CTTGAACACA TTAAATAAAA GCTTAGGCTT AAGATGCGGA TTCAATAATG   9420

TTATCTTGAC ACAACTATTC CTTTATGGAG ATTGTATACT AAAGCTATTT CACAATGAGG   9480

GGTTCTACAT AATAAAAGAG GTAGAGGGAT TTATTATGTC TCTAATTTTA AATATAACAG   9540

AAGAAGATCA ATTCAGAAAA CGATTTTATA ATAGTATGCT CAACAACATC ACAGATGCTG   9600

CTAATAAAGC TCAGAAAAAT CTGCTATCAA GAGTATGTCA TACATTATTA GATAAGACAG   9660

TGTCCGATAA TATAATAAAT GGCAGATGGA TAATTCTATT AAGTAAGTTC CTTAAATTAA   9720

TTAAGCTTGC AGGTGACAAT AACCTTAACA ATCTGAGTGA ACTATATTTT TTGTTCAGAA   9780

TATTTGGACA CCCAATGGTA GATGAAAGAC AAGCCATGGA TGCTGTTAAA ATTAATTGCA   9840

ATGAGACCAA ATTTTACTTG TTAAGCAGTC TGAGTATGTT AAGAGGTGCC TTTATATATA   9900

GAATTATAAA AGGGTTTGTA ATAATTACA  ACAGATGGCC TACTTTAAGA AATGCTATTG   9960

TTTTACCCTT AAGATGGTTA ACTTACTATA AACTAAACAC TTATCCTTCT TGTTGGAAC   10020

TTACAGAAAG AGATTTGATT GTGTTATCAG GACTACGTTT CTATCGTGAG TTTCGGTTGC   10080

CTAAAAAGT  GGATCTTGAA ATGATTATAA ATGATAAAGC TATATCACCT CCTAAAAATT   10140

TGATATGGAC TAGTTTCCCT AGAAATTACA TGCCATCACA CATACAAAAC TATATAGAAC   10200

ATGAAAAATT AAAATTTTCC GAGAGTGATA AATCAAGAAG AGTATTAGAG TATTATTTAA   10260

GAGATAACAA ATTCAATGAA TGTGATTTAT ACAACTGTGT AGTTAATCAA AGTTATCTCA   10320

ACAACCCTAA TCATGTGGTA TCATTGACAG GCAAAGAAAG AGAACTCAGT GTAGGTAGAA   10380

TGTTTGCAAT GCAACCGGGA ATGTTCGAC  AGGTTCAAAT ATTGGCAGAG AAAATGATAG   10440

CTGAAAACAT TTTACAATTC TTTCCTGAAA GTCTTACAAG ATATGGTGAT CTAGAACTAC   10500

AAAAAATATT AGAACTGAAA GCAGGAATAA GTAACAAATC AAATCGCTAC AATGATAATT   10560

ACAACAATTA CATTAGTAAG TGCTCTATCA TCACAGATCT CAGCAAATTC AATCAAGCAT   10620

TTCGATATGA AACGTCATGT ATTTGTAGTG ATGTGCTGGA TGAACTGCAT GGTGTACAAT   10680

CTCTATTTTC CTGGTTACAT TTAACTATTC CTCATGTCAC AATAATATGC ACATATAGGC   10740

ATGCACCCCC CTATATAGGA GATCATATTG TAGATCTTAA CAATGTAGAT GAACAAAGTG   10800

GATTATATAG ATATCACATG GGTGGCATCG AAGGGTGGTG TCAAAAACTA TGGACCATAG   10860

AAGCTATATC ACTATTGGAT CTAATATCTC TCAAAGGGAA ATTCTCAATT ACTGCTTTAA   10920

TTAATGGTGA CAATCAATCA ATAGATATAA GCAAACCAAT CAGACTCATG GAAGGTCAAA   10980

CTCATGCTCA AGCAGATTAT TTGCTAGCAT TAAATAGCCT TAAATTACTG TATAAAGAGT   11040

ATGCAGGCAT AGGCCACAAA TTAAAGGAA CTGAGACTTA TATATCACGA GATATGCAAT    11100

TTATGAGTAA AACAATTCAA CATAACGGTG TATATTACCC AGCTAGTATA AAGAAAGTCC   11160

TAAGAGTGGG ACCGTGGATA AACACTATAC TTGATGATTT CAAAGTGAGT CTAGAATCTA   11220

TAGGTAGTTT GACACAAGAA TTAGAATATA GAGGTGAAAG TCTATTATGC AGTTTAATAT   11280

TTAGAAATGT ATGGTTATAT AATCAGATTG CTCTACAATT AAAAAATCAT GCATTATGTA   11340

ACAATAAACT ATATTTGGAC ATATTAAAGG TTCTGAAACA CTTAAAAACC TTTTTTAATC   11400

TTGATAATAT TGATACAGCA TTAACATTGT ATATGAATTT ACCCATGTTA TTTGGTGGTG   11460

GTGATCCCAA CTTGTTATAT CGAAGTTTCT ATAGAAGAAC TCCTGACTTC CTCACAGAGG   11520

CTATAGTTCA CTCTGTGTTC ATACTTAGTT ATTATACAAA CCATGACTTA AAAGATAAAC   11580

TTCAAGATCT GTCAGATGAT AGATTGAATA AGTTCTTAAC ATGCATAATC ACGTTTGACA   11640
```

```
AAAACCCTAA TGCTGAATTC GTAACATTGA TGAGAGATCC TCAAGCTTTA GGGTCTGAGA    11700

GACAAGCTAA AATTACTAGC GAAATCAATA GACTGGCAGT TACAGAGGTT TTGAGTACAG    11760

CTCCAAACAA AATATTCTCC AAAAGTGCAC AACATTATAC TACTACAGAG ATAGATCTAA    11820

ATGATATTAT GCAAAATATA GAACCTACAT ATCCTCATGG GCTAAGAGTT GTTTATGAAA    11880

GTTTACCCTT TTATAAAGCA GAGAAAATAG TAAATCTTAT ATCAGGTACA AAATCTAAA    11940

CTAACATACT GGAAAAAACT TCTGCCATAG ACTTAACAGA TATTGATAGA GCCACTGAGA    12000

TGATGAGGAA AAACATAACT TTGCTTATAA GGATACTTCC ATTGGATTGT AACAGAGATA    12060

AAAGAGAGAT ATTGAGTATG GAAAACCTAA GTATTACTGA ATTAAGCAAA TATGTTAGGG    12120

AAAGATCTTG GTCTTTATCC AATATAGTTG GTGTTACATC ACCCAGTATC ATGTATACAA    12180

TGGACATCAA ATATACTACA AGCACTATAT CTAGTGGCAT AATTATAGAG AAATATAATG    12240

TTAACAGTTT AACACGTGGT GAGAGAGGAC CCACTAAACC ATGGGTTGGT TCATCTACAC    12300

AAGAGAAAAA AACAATGCCA GTTTATAATA GACAAGTCTT AACCAAAAAA CAGAGAGATC    12360

AAATAGATCT ATTAGCAAAA TTGGATTGGG TGTATGCATC TATAGATAAC AAGGATGAAT    12420

TCATGGAAGA ACTCAGCATA GGAACCCTTG GGTTAACATA TGAAAAGGCC AAGAAATTAT    12480

TTCCACAATA TTTAAGTGTC AATTATTTGC ATCGCCTTAC AGTCAGTAGT AGACCATGTG    12540

AATTCCCTGC ATCAATACCA GCTTATAGAA CAACAAATTA TCACTTTGAC ACTAGCCCTA    12600

TTAATCGCAT ATTAACAGAA AAGTATGGTG ATGAAGATAT TGACATAGTA TTCCAAAACT    12660

GTATAAGCTT TGGCCTTAGT TTAATGTCAG TAGTAGAACA ATTTACTAAT GTATGTCCTA    12720

ACAGAATTAT TCTCATACCT AAGCTTAATG AGATACATTT GATGAAACCT CCCATATTCA    12780

CAGGTGATGT TGATATTCAC AAGTTAAAAC AAGTGATACA AAAACAGCAT ATGTTTTTAC    12840

CAGACAAAAT AAGTTTGACT CAATATGTGG AATTATTCTT AAGTAATAAA ACACTCAAAT    12900

CTGGATCTCA TGTTAATTCT AATTTAATAT TGGCACATAA AATATCTGAC TATTTTCATA    12960

ATACTTACAT TTTAAGTACT AATTTAGCTG ACATTGGAT TCTGATTATA CAACTTATGA    13020

AAGATTCTAA AGGTATTTTT GAAAAAGATT GGGGAGAGGG ATATATAACT GATCATATGT    13080

TTATTAATTT GAAAGTTTTC TTCAATGCTT ATAAGACCTA TCTCTTGTGT TTTCATAAAG    13140

GTTATGGCAA AGCAAAGCTG GAGTGTGATA TGAACACTTC AGATCTTCTA TGTGTATTGG    13200

AATTAATAGA CAGTAGTTAT TGGAAGTCTA TGTCTAAGGT ATTTTTAGAA CAAAAAGTTA    13260

TCAAATACAT TCTTAGCCAA GATGCAAGTT TACATAGAGT AAAAGGATGT CATAGCTTCA    13320

AATTATGGTT TCTTAAACGT CTTAATGTAG CAGAATTCAC AGTTTGCCCT TGGGTTGTTA    13380

ACATAGATTA TCATCCAACA CATATGAAAG CAATATTAAC TTATATAGAT CTTGTTAGAA    13440

TGGGATTGAT AAATATAGAT AGAATACACA TTAAAAATAA ACACAAATTC AATGATGAAT    13500

TTTATACTTC TAATCTCTTC TACATTAATT ATAACTTCTC AGATAATACT CATCTATTAA    13560

CTAAACATAT AAGGATTGCT AATTCTGAAT TAGAAAATAA TTACAACAAA TTATATCATC    13620

CTACACCAGA AACCCTAGAG AATATACTAG CCAATCCGAT TAAAAGTAAT GACAAAAAGA    13680

CACTGAATGA CTATTGTATA GGTAAAAATG TTGACTCAAT AATGTTACCA TTGTTATCTA    13740

ATAAGAAGCT TATTAAATCG TCTGCAATGA TTAGAACCAA TTACAGCAAA CAAGATTGT    13800

ATAATTTATT CCCTATGGTT GTGATTGATA GAATTATAGA TCATTCAGGC AATACAGCCA    13860

AATCCAACCA ACTTTACACT ACTACTTCCC ACCAAATATC CTTAGTGCAC AATAGCACAT    13920

CACTTTACTG CATGCTTCCT TGGCATCATA TTAATAGATT CAATTTTGTA TTTAGTTCTA    13980
```

```
CAGGTTGTAA AATTAGTATA GAGTATATTT TAAAAGATCT TAAAATTAAA GATCCCAATT    14040

GTATAGCATT CATAGGTGAA GGAGCAGGGA ATTTATTATT GCGTACAGTA GTGGAACTTC    14100

ATCCTGACAT AAGATATATT TACAGAAGTC TGAAAGATTG CAATGATCAT AGTTTACCTA    14160

TTGAGTTTTT AAGGCTGTAC AATGGACATA TCAACATTGA TTATGGTGAA AATTTGACCA    14220

TTCCTGCTAC AGATGCAACC AACAACATTC ATTGGTCTTA TTTACATATA AAGTTTGCTG    14280

AACCTATCAG TCTTTTTGTC TGTGATGCCG AATTGTCTGT AACAGTCAAC TGGAGTAAAA    14340

TTATAATAGA ATGGAGCAAG CATGTAAGAA AGTGCAAGTA CTGTTCCTCA GTTAATAAAT    14400

GTATGTTAAT AGTAAAATAT CATGCTCAAG ATGATATTGA TTTCAAATTA GACAATATAA    14460

CTATATTAAA AACTTATGTA TGCTTAGGCA GTAAGTTAAA GGGATCGGAG GTTTACTTAG    14520

TCCTTACAAT AGGTCCTGCG AATATATTCC CAGTATTTAA TGTAGTACAA AATGCTAAAT    14580

TGATACTATC AAGAACCAAA AATTTCATCA TGCCTAAGAA AGCTGATAAA GAGTCTATTG    14640

ATGCAAATAT TAAAAGTTTG ATACCCTTTC TTTGTTACCC TATAACAAAA AAAGGAATTA    14700

ATACTGCATT GTCAAAACTA AGAGTGTTG TTAGTGGAGA TATACTATCA TATTCTATAG     14760

CTGGACGTAA TGAAGTTTTC AGCAATAAAC TTATAAATCA TAAGCATATG AACATCTTAA    14820

AATGGTTCAA TCATGTTTTA AATTTCAGAT CAACAGAACT AAACTATAAC CATTTATATA    14880

TGGTAGAATC TACATATCCT TACCTAAGTG AATTGTTAAA CAGCTTGACA ACCAATGAAC    14940

TTAAAAAACT GATTAAAATC ACAGGTAGTC TGTTATACAA CTTTCATAAT GAATAATGAA    15000

TAAAGATCTT ATAATAAAAA TTCCCATAGC TATACACTAA CACTGTATTC AATTATAGTT    15060

ATTAAAAATT AAAAATCATA TAATTTTTTA AATAACTTTT AGTGAACTAA TCCTAAAGTT    15120

ATCATTTTAA TCTTGGAGGA ATAAATTTAA ACCCTAATCT AATTGGTTTA TATGTGTATT    15180

AACTAAATTA CGAGATATTA GTTTTGACA CTTTTTTTCT CGT                      15223

(2) INFORMATION FOR SEQ ID NO: 2:

(i) SEQUENCE CHARACTERISTICS:
        (A) LENGTH: 15225 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

ACGCGAAAAA ATGCGTACTA CAAACTTGCA CATTCGGAAA AATGGGGCA ATAAGAATT        60

TGATAAGTGC TATTTAAGTC TAACCTTTTC AATCAGAAAT GGGGTGCAAT TCACTGAGCA     120

TGATAAAGGT TAGATTACAA AATTTATTTG ACAATGACGA AGTAGCATTG TTAAAAATAA     180

CATGTTATAC TGACAAATTA ATTCTTCTGA CCAATGCATT AGCCAAAGCA GCAATACATA     240

CAATTAAATT AAACGGTATA GTTTTTATAC ATGTTATAAC AAGCAGTGAA GTGTGCCCTG     300

ATAACAACAT TGTAGTAAAA TCTAACTTTA CAACAATGCC AATATTACAA AACGGAGGAT     360

ACATATGGGA ATTGATTGAG TTGACACACT GCTCTCAATT AAACGGTCTA ATGGATGATA     420

ATTGTGAAAT CAAATTTTCT AAAAGACTAA GTGACTCAGT AATGACTAAT TATATGAATC     480

AAATATCTGA TTTACTTGGG CTTGATCTCA ATTCATGAAT TATGTTTAGT CTAACTCAAT    540

AGACATGTGT TTATTACCAT TTTAGTTAAT ATAAAAACTC ATCAAGGGA AATGGGGCAA     600

ATAAACTCAC CTAATCAATC AAACTATGAG CACTACAAAT GACAACACTA CTATGCAAAG    660

ATTAATGATC ACGGACATGA GACCCCTGTC GATGGATTCA ATAATAACAT CTCTCACCAA    720
```

-continued

```
AGAAATCATC ACACACAAAT TCATATACTT GATAAACAAT GAATGTATTG TAAGAAAACT    780
TGATGAAAGA CAAGCTACAT TTACATTCTT AGTCAATTAT GAGATGAAGC TACTGCACAA    840
AGTAGGGAGT ACCAAATACA AGAAATACAC TGAATATAAT ACAAAATATG GCACTTTCCC    900
CATGCCTATA TTTATCAATC ATGGCGGGTT TCTAGAATGT ATTGGCATTA AGCCTACAAA    960
ACACACTCCT ATAATATACA AATATGACCT CAACCCGTAA ATTCCAACAA AAAAAACCAA   1020
CCCAACCAAA CCAAGCTATT CCTCAAACAA CAATGCTCAA TAGTTAAGAA GGAGCTAATC   1080
CGTTTTAGTA ATTAAAAATA AAAGTAAAGC CAATAACATA AATTGGGGCA ATACAAAGA    1140
TGGCTCTTAG CAAAGTCAAG TTAAATGATA CATTAAATAA GGATCAGCTG CTGTCATCCA   1200
GCAAATACAC TATTCAACGT AGTACAGGAG ATAATATTGA CACTCCCAAT TATGATGTGC   1260
AAAAACACCT AAACAAACTA TGTGGTATGC TATTAATCAC TGAAGATGCA AATCATAAAT   1320
TCACAGGATT AATAGGTATG TTATATGCTA TGTCCAGGTT AGGAAGGGAA GACACTATAA   1380
AGATACTTAA AGATGCTGGA TATCATGTTA AAGCTAATGG AGTAGATATA ACAACATATC   1440
GTCAAGATAT AAATGGAAAG GAAATGAAAT TCGAAGTATT AACATTATCA AGCTTGACAT   1500
CAGAAATACA AGTCAATATT GAGATAGAAT CTAGAAAATC CTACAAAAAA ATGCTAAAAG   1560
AGATGGGAGA AGTGGCTCCA GAATATAGGC ATGATTCTCC AGACTGTGGG ATGATAATAC   1620
TGTGTATAGC AGCACTTGTA ATAACCAAAT TAGCAGCAGG AGACAGATCA GGTCTTACAG   1680
CAGTAATTAG GAGGGCAAAC AATGTCTTAA AAAATGAAAT AAAACGCTAC AAGGGTCTCA   1740
TACCAAAGGA TATAGCTAAC AGTTTTTATG AAGTGTTTGA AAAACACCCT CATCTTATAG   1800
ATGTTTTTGT GCACTTTGGC ATTGCACAAT CATCAACAAG AGGGGGTAGT AGAGTTGAAG   1860
GAATCTTTGC AGGATTGTTT ATGAATGCCT ATGGTTCAGG GCAAGTAATG CTAAGATGGG   1920
GAGTTTTAGC CAAATCTGTA AAAAATATCA TGCTAGGTCA TGCTAGTGTC CAGGCAGAAA   1980
TGGAGCAAGT TGTGGAAGTC TATGAGTATG CACAGAAGTT GGGAGGAGAA GCTGGATTCT   2040
ACCATATATT GAACAATCCA AAAGCATCAT TGCTGTCATT AACTCAATTT CCTAACTTCT   2100
CAAGTGTGGT CCTAGGCAAT GCAGCAGGTC TAGGCATAAT GGGAGAGTAT AGAGGTACGC   2160
CAAGAAACCA GGATCTTTAT GATGCAGCCA AAGCATATGC AGAGCAACTC AAAGAAAATG   2220
GAGTAATAAA CTACAGTGTA TTAGACTTAA CAGCAGAAGA ATTGGAAGCC ATAAAGAATC   2280
AACTCAACCC TAAAGAAGAT GATGTAGAGC TTTAAGTTAA CAAAAAATAC GGGGCAAATA   2340
AGTCAACATG GAGAAGTTTG CACCTGAATT TCATGGAGAA GATGCAAATA ACAAAGCTAC   2400
CAAATTCCTA GAATCAATAA AGGGCAAGTT CGCATCATCC AAAGATCCTA AGAAGAAAGA   2460
TAGCATAATA TCTGTTAACT CAATAGATAT AGAAGTAACC AAAGAGAGCC CGATAACATC   2520
TGGCACCAAC ATCATCAATC AACAAGTGA AGCCGACAGT ACCCCAGAAA CCAAAGCCAA    2580
CTACCCAAGA AAACCCCTAG TAAGCTTCAA AGAAGATCTC ACCCCAAGTG ACAACCCTTT   2640
TTCTAAGTTG TACAAAGAAA CAATAGAAAC ATTTGATAAC AATGAAGAAG AATCTAGCTA   2700
CTCATATGAA GAGATAAATG ATCAAACAAA TGACAACATT ACAGCAAGAC TAGATAGAAT   2760
TGATGAAAAA TTAAGTGAAA TATTAGGAAT GCTCCATACA TTAGTAGTTG CAAGTGCAGG   2820
ACCCACTTCA GCTCGCGATG GAATAAGAGA TGCTATGGTT GGTCTGAGAG AAGAAATGAT   2880
AGAAAAAATA AGAGCGGAAG CATTAATGAC CAATGATAGG TTAGAGGCTA TGGCAAGACT   2940
TAGGAATGAG GAAAGCGAAA AAATGGCAAA AGACACCTCA GATGAAGTGC CTCTTAATCC   3000
AACTTCCAAA AAATTGAGTG ACTTGTTGGA AGACAACGAT AGTGACAATG ATCTGTCACT   3060
TGATGATTTT TGATCAGTGA TCAACTCACT CAGCAATCAA CAACATCAAT AAAACAGACA   3120
```

```
TCAATCCATT GAATCAACTG CCAGACCGAA CAAACAAATG TCCGTCAGCG GAACCACCAA    3180

CCAATCAATC AACCAACTGA TCCATCAGCA ACCTGACGAA ATTAACAATA TAGTAACAAA    3240

AAAGAACAA GATGGGGCAA ATATGGAAAC ATACGTGAAC AAGCTTCACG AAGGCTCCAC     3300

ATACACAGCA GCTGTTCAGT ACAATGTTCT AGAAAAGAT GATGATCCTG CATCACTAAC     3360

AATATGGGTG CCTATGTTCC AGTCATCTGT ACCAGCAGAC TTGCTCATAA AGAACTTGC     3420

AAGCATCAAC ATACTAGTGA AGCAGATCTC TACGCCCAAA GGACCTTCAC TACGAGTCAC    3480

GATTAACTCA AGAAGTGCTG TGCTGGCTCA AATGCCTAGT AATTTCATCA TAAGCGCAAA    3540

TGTATCATTA GATGAAAGAA GCAAATTAGC ATATGATGTA ACTACACCTT GTGAAATCAA    3600

AGCATGCAGT CTAACATGCT TAAAAGTGAA AAGTATGTTA ACTACAGTCA AGATCTTAC    3660

CATGAAGACA TTCAACCCCA CTCATGAGAT CATTGCTCTA TGTGAATTTG AAAATATTAT    3720

GACATCAAAA AGAGTAATAA TACCAACCTA TCTAAGACCA ATTAGTGTCA AAACAAGGA    3780

TCTGAACTCA CTAGAAAACA TAGCAACCAC CGAATTCAAA AATGCTATCA CCAATGCGAA    3840

AATTATTCCC TATGCTGGAT TAGTATTAGT TATCACAGTT ACTGACAATA AAGGAGCATT    3900

CAAATATATC AAGCCACAGA GTCAATTTAT AGTAGATCTT GGTGCCTACC TAGAAAAAGA    3960

GAGCATATAT TATGTGACTA CTAATTGGAA GCATACAGCT ACACGTTTTT CAATCAAACC    4020

ACTAGAGGAT TAAATTTAAT TATCAACACT GAATGACAGG TCCACATATA TCCTCAAACT    4080

ACACACTATA TCCAAACATC ATGAACATCT ACACTACACA CTTCATCACA CAAACCAATC    4140

CCACTCAAAA TCCAAAATCA CTACCAGCCA CTATCTGCTA GACCTAGAGT GCGAATAGGT    4200

AAATAAAACC AAAATATGGG GTAAATAGAC ATTAGTTAGA GTTCAATCAA TCTCAACAAC    4260

CATTTATACC GCCAATTCAA TACATATACT ATAAATCTTA AAATGGGAAA TACATCCATC    4320

ACAATAGAAT TCACAAGCAA ATTTTGGCCC TATTTTACAC TAATACATAT GATCTTAACT    4380

CTAATCTCTT TACTAATTAT AATCACTATT ATGATTGCAA TACTAAATAA GCTAAGTGAA    4440

CATAAAACAT TCTGTAACAA TACTCTTGAA CTAGGACAGA TGCATCAAAT CAACACATAG    4500

TGCTCTACCA TCATGCTGTG TCAAATTATA ATCCTGTATA TATAAACAAA CAAATCCAAT    4560

CTTCTCACAG AGTCATGGTG TCGCAAAACC ACGCCAACTA TCATGGTAGC ATAGAGTAGT    4620

TATTTAAAAA TTAACATAAT GATGAATTAT TAGTATGGGA TCAAAACAA CATTGGGGCA     4680

AATGCAACCA TGTCCAAACA CAAGAATCAA CGCACTGCCA GGACTCTAGA AAAGACCTGG    4740

GATACTCTCA ATCATCTAAT TGTAATATCC TCTTGTTTAT ACAGATTAAA TTTAAAATCT    4800

ATAGCACAAA TAGCACTATC AGTTCTGGCA ATGATAATCT CAACCTCTCT CATAATTGCA    4860

GCCATATAT TCATCATCTC TGCCAATCAC AAAGTTACAC TAACAACGGT CACAGTTCAA     4920

ACAATAAAAA ACCACACTGA AAAAACATC ACCACCTACC TTACTCAAGT CCCACCAGAA     4980

AGGGTTAGCT CATCCAAACA ACCTACAACC ACATCACCAA TCCACACAAA TTCAGCCACA    5040

ACATCACCCA ACACAAAGTC AGAAACACAC CACACAACAG CACAAACCAA AGGCAGAACC    5100

ACCACCTCAA CACAGACCAA CAAGCCGAGC ACAAAACCAC GCCTAAAAAA TCCACCAAAA    5160

AAACCAAAAG ATGATTACCA TTTTGAAGTG TTCAACTTCG TTCCCTGTAG TATATGTGGC    5220

AACAATCAAC TTTGCAAATC CATCTGTAAA ACAATACCAA GCAACAAACC AAAGAAGAAA    5280

CCAACCATCA AACCCACAAA CAAACCAACC ACCAAAACCA CAAACAAAAG AGACCCAAAA    5340

ACACCAGCCA AAACGACGAA AAAAGAAACT ACCACCAACC CAACAAAAAA ACCAACCCTC    5400

ACGACCACAG AAAGAGACAC CAGCACCTCA CAATCCACTG TGCTCGACAC AACCACATTA    5460
```

```
GAACACACAA TCCAACAGCA ATCCCTCCAC TCAACCACCC CCGAAAACAC ACCCAACTCC    5520

ACACAAACAC CCACAGCATC CGAGCCCTCT ACATCAAATT CCACCCAAAA TACCCAATCA    5580

CATGCTTAGT TATTCAAAAA CTACATCTTA GCAGAAAACC GTGACCTATC AAGCAAGAAC    5640

GAAATTAAAC CTGGGGCAAA TAACCATGGA GCTGCTGATC CACAGGTTAA GTGCAATCTT    5700

CCTAACTCTT GCTATTAATG CATTGTACCT CACCTCAAGT CAGAACATAA CTGAGGAGTT    5760

TTACCAATCG ACATGTAGTG CAGTTAGCAG AGGTTATTTT AGTGCTTTAA GAACAGGTTG    5820

GTATACCAGT GTCATAACAA TAGAATTAAG TAATATAAAA GAAACCAAAT GCAATGGAAC    5880

TGACACTAAA GTAAAACTTA TAAAACAAGA ATTAGATAAG TATAAGAATG CAGTGACAGA    5940

ATTACAGCTA CTTATGCAAA ACACACCAGC TGCCAACAAC CGGGCCAGAA GAGAAGCACC    6000

ACAGTATATG AACTATACAA TCAATACCAC TAAAAACCTA AATGTATCAA TAAGCAAGAA    6060

GAGGAAACGA AGATTTCTGG GCTTCTTGTT AGGTGTAGGA TCTGCAATAG CAAGTGGTAT    6120

AGCTGTATCC AAAGTTCTAC ACCTTGAAGG AGAAGTGAAC AAGATCAAAA ATGCTTTGTT    6180

ATCTACAAAC AAAGCTGTAG TCAGTCTATC AAATGGGGTC AGTGTTTTAA CCAGCAAAGT    6240

GTTAGATCTC AAGAATTACA TAAATAACCA ATTATTACCC ATAGTAAATC AACAGAGCTG    6300

TCGCATCTCC AACATTGAAA CAGTTATAGA ATTCCAGCAG AAGAACAGCA GATTGTTGGA    6360

AATCAACAGA GAATTCAGTG TCAATGCAGG TGTAACAACA CCTTTAAGCA CTTACATGTT    6420

AACAAACAGT GAGTTACTAT CATTGATCAA TGATATGCCT ATAACAAATG ATCAGAAAAA    6480

ATTAATGTCA AGCAATGTTC AGATAGTAAG GCAACAAAGT TATTCTATCA TGTCTATAAT    6540

AAAGGAAGAA GTCCTTGCAT ATGTTGTACA GCTACCTATC TATGGTGTAA TAGATACACC    6600

TTGCTGGAAA TTACACACAT CACCTCTATG CACCACCAAC ATCAAAGAAG GATCAAATAT    6660

TTGTTTAACA AGGACTGATA GAGGATGGTA TTGTGATAAT GCAGGATCAG TATCCTTCTT    6720

TCCACAGGCT GACACTTGTA AAGTACAGTC CAATCGAGTA TTTTGTGACA CTATGAACAG    6780

TTTGACATTA CCAAGTGAAG TCAGCCTTTG TAACACTGAC ATATTCAATT CCAAGTATGA    6840

CTGCAAAATT ATGACATCAA AAACAGACAT AAGCAGCTCA GTAATTACTT CTCTTGGAGC    6900

TATAGTGTCA TGCTATGGTA AAACTAAATG CACTGCATCC AACAAAAATC GTGGGATTAT    6960

AAAGACATTT TCTAATGGTT GTGACTATGT GTCAAACAAA GGAGTAGATA CTGTGTCAGT    7020

GGGCAACACT TTATACTATG TAAACAAGCT GGAAGGCAAG AACCTTTATG TAAAAGGGGA    7080

ACCTATAATA AATTACTATG ACCCTCTAGT GTTTCCTTCT GATGAGTTTG ATGCATCAAT    7140

ATCTCAAGTC AATGAAAAAA TCAATCAAAG TTTAGCTTTT ATTCGTAGAT CTGATGAATT    7200

ACTACATAAT GTAAATACTG GCAAATCTAC TACAAATATT ATGATAACTA CAATTATTAT    7260

AGTAATCATT GTAGTATTGT TATCATTAAT AGCTATTGGT TTGCTGTTGT ATTGCAAAGC    7320

CAAAAACACA CCAGTTACAC TAAGCAAAGA CCAACTAAGT GGAATCAATA ATATTGCATT    7380

CAGCAAATAG ACAAAAAACC ACCTGATCAT GTTTCAACAA CAGTCTGCTG ATCACCAATC    7440

CCAAATCAAC CCATAACAAA CACTTCAACA TCACAGTACA GGCTGAATCA TTTCTTCACA    7500

TCATGCTACC CACACAACTA AGCTAGATCC TTAACTCATA GTTACATAAA AACCTCAAGT    7560

ATCACAATCA AACACTAAAT CAACACATCA TTCACAAAAT TAACAGCTGG GGCAAATATG    7620

TCGCGAAGAA ATCCTTGTAA ATTTGAGATT AGAGGTCATT GCTTGAATGG TAGAAGATGT    7680

CACTACAGTC ATAATTACTT TGAATGGCCT CCTCATGCCT TACTAGTGAG GCAAACTTC    7740

ATGTTAAACA AGATACTCAA GTCAATGGAC AAAAGCATAG ACACTTTGTC TGAAATAAGT    7800

GGAGCTGCTG AACTGGACAG AACAGAAGAA TATGCTCTTG GTATAGTTGG AGTGCTAGAG    7860
```

```
AGTTACATAG GATCTATAAA CAACATAACA AAACAATCAG CATGTGTTGC TATGAGTAAA    7920

CTTCTTATTG AGATCAATAG TGATGACATT AAAAAGCTGA GAGATAATGA AGAACCCAAT    7980

TCACCTAAGA TAAGAGTGTA CAATACTGTT ATATCATACA TTGAGAGCAA TAGAAAAAAC    8040

AACAAGCAAA CAATCCATCT GCTCAAAAGA CTACCAGCAG ACGTGCTGAA GAAGACAATA    8100

AAAAACACAT TAGATATCCA CAAAAGCATA ATCATAAGCA ACCCAAAAGA GTCAACCGTG    8160

AATGATCAAA ATGACCAAAC CAAAAATAAT GATATTACCG GATAAATATC CTTGTAGTAT    8220

ATCATCCATA TTGATTTCAA GTGAAAGCAT GATTGCTACA TTCAATCATA AAACATATT    8280

ACAATTTAAC CATAACCATT TGGATAACCA CCAGCGTTTA TTAAATAATA TATTTGATGA    8340

AATTCATTGG ACACCTAAAA ACTTATTAGA TGCCACTCAA CAATTTCTCC AACATCTTAA    8400

CATCCCTGAA GATATATATA CAATATATAT ATTAGTGTCA TAATGCTTGG CCATAACGAT    8460

TCTATATCAT CCAACCATAA AACTATCTTA ATAAGGTTAT GGGACAAAAT GGATCCCATT    8520

ATTAATGGAA ACTCTGCTAA TGTGTATCTA ACTGATAGTT ATTTAAAAGG TGTTATCTCT    8580

TTTTCAGAAT GTAATGCTTT AGGGAGTTAC CTTTTTAACG GCCCTTATCT CAAAATGAT    8640

TACACCAACT TAATTAGTAG ACAAAGTCCA CTACTAGAGC ATATGAATCT TAAAAAACTA    8700

ACTATAACAC AGTCATTAAT ATCTAGATAT CATAAAGGTG AACTGAAATT AGAAGAACCA    8760

ACTTATTTCC AGTCATTACT TATGACATAT AAAAGCATGT CCTCGTCTGA ACAAATTGCT    8820

ACAACTAACT TACTTAAAAA AATAATACGA AGAGCTATAG AAATAAGTGA TGTAAAGGTG    8880

TACGCCATCT TGAATAAACT AGGACTAAAG GAAAAGGACA GAGTTAAGCC CAACAATAAT    8940

TCAGGTGATG AAAACTCAGT ACTTACAACT ATAATTAAAG ATGATATACT TTCGGCTGTG    9000

GAAAGCAATC AATCATATAC AAATTCAGAC AAAAATCACT CAGTAAATCA AAATATCACT    9060

ATCAAAACAA CACTCTTGAA AAAATTGATG TGTTCAATGC AACATCCTCC ATCATGGTTA    9120

ATACACTGGT TCAATTTATA TACAAATTA AATAACATAT TAACACAATA TCGATCAAAT    9180

GAGGTAAAAA GTCATGGGTT TATATTAATA GATAATCAAA CTTTAAGTGG TTTTCAGTTT    9240

ATTTTAAATC AATATGGTTG TATCGTTTAT CATAAAGGAC TCAAAAAAAT CACAACTACT    9300

ACTTACAATC AATTTTTAAC ATGGAAAGAC ATCAGCCTTA GCAGATTAAA TGTTTGCTTA    9360

ATTACTTGGA TAAGTAATTG TTTGAATACA TTAAATAAAA GCTTAGGGCT GAGATGTGGA    9420

TTCAATAATG TTGTGTTATC ACAATTATTT CTTTATGGAG ATTGTATACT GAAATTATTT    9480

CATAATGAAG GCTTCTACAT AATAAAAGAA GTAGAGGGAT TTATTATGTC TTTAATTCTA    9540

AACATAACAG AAGAAGATCA ATTTAGGAAA CGATTTTATA ATAGCATGCT AAATAACATC    9600

ACAGATGCAG CTATTAAGGC TCAAAAGAAC CTACTATCAA GGGTATGTCA CACTTTATTA    9660

GACAAGACAG TGTCTGATAA TATCATAAAT GGTAAATGGA TAATCCTATT AAGTAAATTT    9720

CTTAAATTGA TTAAGCTTGC AGGTGATAAT AATCTCAATA ATTTGAGTGA GCTATATTTT    9780

CTCTTCAGAA TCTTTGGACA TCCAATGGTT GATGAAAGAC AAGCAATGGA TGCTGTAAGA    9840

ATTAACTGTA ATGAAACTAA GTTCTACTTA TTAAGTAGTC TAAGTACGTT AAGAGGTGCT    9900

TTCATTTATA GAATCATAAA AGGGTTTGTA ATACCTACA ACAGATGGCC CACTTTAAGG    9960

AATGCTATTG TCCTACCTCT AAGATGGTTA AACTATTATA AACTTAATAC TTATCCATCT    10020

CTACTTGAAA TCACAGAAAA TGATTTGATT ATTTTATCAG GATTGCGGTT CTATCGTGAA    10080

TTTCATCTGC CTAAAAAAGT GGATCTTGAA ATGATAATAA ATGACAAAGC CATTTCACCT    10140

CCAAAAGATC TAATATGGAC TAGTTTTCCT AGAAATTACA TGCCATCACA TATACAAAAT    10200
```

```
TATATAGAAC ATGAAAAGTT GAAGTTCTCT GAAAGCGACA GATCAAGAAG AGTACTAGAG    10260

TATTACTTGA GAGATAATAA ATTCAATGAA TGCGATCTAT ACAATTGTGT AGTCAATCAA    10320

AGCTATCTCA ACAACTCTAA TCACGTGGTA TCACTAACTG GTAAAGAAAG AGAGCTCAGT    10380

GTAGGTAGAA TGTTTGCTAT GCAACCAGGT ATGTTTAGGC AAATCCAAAT CTTAGCAGAG    10440

AAAATGATAG CCGAAAATAT TTTACAATTC TTCCCTGAGA GTTTGACAAG ATATGGTGAT    10500

CTAGAGCTTC AAAAGATATT AGAATTAAAA GCAGGAATAA GCAACAAGTC AAATCGTTAT    10560

AATGATAACT ACAACAATTA TATCAGTAAA TGTTCTATCA TTACAGATCT TAGCAAATTC    10620

AATCAAGCAT TTAGATATGA AACATCATGT ATCTGCAGTG ATGTATTAGA TGAACTGCAT    10680

GGAGTACAAT CTCTGTTCTC TTGGTTGCAT TTAACAATAC CTCTTGTCAC AATAATATGT    10740

ACATATAGAC ATGCACCTCC TTTCATAAAG GATCATGTTG TTAATCTTAA TGAAGTTGAT    10800

GAACAAAGTG GATTATACAG ATATCATATG GGTGGTATTG AGGGCTGGTG TCAAAAACTG    10860

TGGACCATTG AAGCTATATC ATTATTAGAT CTAATATCTC TCAAAGGGAA ATTCTCTATC    10920

ACAGCTCTGA TAAATGGTGA TAATCAGTCA ATTGATATAA GTAAACCAGT TAGACTTATA    10980

GAGGGTCAGA CCCATGCTCA AGCAGATTAT TTGTTAGCAT TAAATAGCCT TAAATTGCTA    11040

TATAAAGAGT ATGCAGGTAT AGGCCATAAG CTTAAGGGAA CAGAGACCTA TATATCCCGA    11100

GATATGCAGT TCATGAGCAA AACAATCCAG CACAATGGGA TGTACTATCC AGCCAGTATC    11160

AAAAAAGTCC TGAGAGTAGG TCCATGGATA AATACAATAC TTGATGATTT TAAAGTTAGT    11220

TTAGAATCTA TAGGTAGCTT AACACAGGAG TTAGAATACA GAGGGGAAAG CTTATTATGC    11280

AGTTTAATAT TTAGGAACAT TTGGTTATAC AATCAAATTG CTTTGCAACT CCGAAATCAT    11340

GCATTATGTA ACAATAAGCT ATATTTAGAT ATATTGAAAG TATTAAAACA CTTAAAAACT    11400

TTTTTTAATC TTGATAGTAT CGATATGGCG TTATCATTGT ATATGAATTT GCCTATGCTG    11460

TTTGGTGGTG GTGATCCTAA TTTGTTTATAT CGAAGCTTTT ATAGGAGAAC TCCAGACTTC    11520

CTTACAGAAG CTATAGTACA TTCAGTGTTT GTGTTGAGCT ATTATACTGG TCACGATTTA    11580

CAAGATAAGC TCCAGGATCT TCCAGATGAT AGACTGAACA AATTCTTGAC ATGTGTCATC    11640

ACATTCGATA AAAATCCCAA TGCCGAGTTT GTAACATTGA TGAGGGATCC ACAGGCGTTA    11700

GGGTCTGAAA GGCAAGCTAA AATTACTAGT GAGATTAATA GATTAGCAGT AACAGAAGTC    11760

TTAAGTATAG CTCCAAACAA AATATTTTCT AAAAGTGCAC AACATTATAC TACCACTGAG    11820

ATTGATCTAA ATGACATTAT GCAAAATATA GAACCAACTT ACCCTCATGG ATTAAGAGTT    11880

GTTTATGAAA GTCTACCTTT TTATAAAGCA GAAAAATAG TTAATCTTAT ATCAGGAACA    11940

AAATCCATAA CTAATATACT TGAAAAAACA TCAGCAATAG ATACAACTGA TATTAATAGG    12000

GCTACTGATA TGATGAGGAA AAATATAACT TTACTTATAA GGATACTTCC ACTAGATTGT    12060

AACAAAGACA AAAGAGAGTT ATTAAGTTTA GAAAATCTTA GTATAACTGA ATTAAGCAAG    12120

TATGTAAGAG AAAGATCTTG GTCATTATCC AATATAGTAG GAGTAACATC GCCAAGTATT    12180

ATGTTCACAA TGGACATTAA ATATACAACT AGCACTATAG CCAGTGGTAT AATTATAGAA    12240

AAATATAATG TTAATAGTTT AACTCGTGGT GAAAGAGGAC CTACTAAGCC ATGGGTAGGT    12300

TCATCTACGC AGGAGAAAAA AACAATGCCA GTGTACAATA GACAAGTTTT AACCAAAAAG    12360

CAAAGAGACC AAATAGATTT ATTAGCAAAA TTAGACTGGG TATATGCATC CATAGACAAC    12420

AAAGATGAAT TCATGGAAGA ACTGAGTACT GGAACACTTG GACTGTCATA TGAAAAAGCC    12480

AAAAAGTTGT TTCCACAATA TCTAAGTGTC AATTATTTAC ACCGTTTAAC AGTCAGTAGT    12540

AGACCATGTG AATTCCCTGC ATCAATACCA GCTTATAGAA CAACAAATTA TCATTTCGAT    12600
```

```
ACTAGTCCTA TCAATCATGT ATTAACAGAA AAGTATGGAG ATGAAGATAT CGACATTGTG    12660

TTTCAAAATT GCATAAGTTT TGGTCTTAGC CTGATGTCGG TTGTGGAACA ATTCACAAAC    12720

ATATGTCCTA ATAGAATTAT TCTCATACCG AAGCTGAATG AGATACATTT GATGAAACCT    12780

CCTATATTTA CAGGAGATGT TGATATCATC AAGTTGAAGC AAGTGATACA AAAACAGCAT    12840

ATGTTCCTAC CAGATAAAAT AAGTTTAACC CAATATGTAG AATTATTCCT AAGTAACAAA    12900

GCACTTAAAT CTGGATCTAA CATCAATTCT AATTTAATAT TAGTACATAA AATGTCTGAT    12960

TATTTTCATA ATGCTTATAT TTTAAGTACT AATTTAGCTG ACATTGGAT TCTAATTATT     13020

CAACTTATGA AAGATTCAAA AGGTATTTTT GAAAAAGATT GGGGAGAGGG GTACATAACT    13080

GATCATATGT TCATTAATTT GAATGTTTTC TTTAATGCTT ATAAGACTTA TTTGCTATGT    13140

TTTCATAAAG GTTATGGTAA AGCAAAATTA GAATGTGATA TGAACACTTC AGATCTTCTT    13200

TGTGTTTTGG AGTTAATAGA CAGTAGCTAC TGGAAATCTA TGTCTAAAGT TTTCCTAGAA    13260

CAAAAAGTCA TAAAATACAT AGTCAATCAA GACACAAGTT TGCATAGAAT AAAAGGCTGT    13320

CACAGTTTTA AGTTGTGGTT TTTAAAACGC CTTAATAATG CTAAATTTAC CGTATGCCCT    13380

TGGGTTGTTA ACATAGATTA TCACCCAACA CATATGAAAG CTATATTATC TTACATAGAT    13440

TTAGTTAGAA TGGGGTTAAT AAATGTAGAT AAATTAACCA TTAAAAATAA AAACAAATTC    13500

AATGATGAAT TTTACACATC AAATCTCTTT ACATTAGTT ATAACTTTTC AGACAACACT     13560

CATTTGCTAA CAAAACAAAT AAGAATTGCT AATTCAGAAT TAGAAGATAA TTATAACAAA    13620

CTATATCACC CAACCCCAGA AACTTTAGAA AATATATCAT TAATTCCTGT TAAAAGTAAT    13680

AATAGTAACA AACCTAAATT TTGTATAAGT GGAAATACCG AATCTATAAT GATGTCAACA    13740

TTCTCTAATA AAATGCATAT TAAATCTTCC ACTGTTACCA CAAGATTCAA TTATAGCAAA    13800

CAAGACTTGT ACAATTTATT TCCAAATGTT GTGATAGACA GGATTATAGA TCATTCAGGT    13860

AATACAGCAA AATCTAACCA ACTTTACATC ACCACTTCAC ATCAGACATC TTTAGTAAGG    13920

AATAGTGCAT CACTTTATTG CATGCTTCCT TGGCATCATG TCAATAGATT AACTTTGTA    13980

TTTAGTTCCA CAGGATGCAA GATCAGTATA GAGTATATTT AAAAGATCT TAAGATTAAG     14040

GACCCCAGTT GTATAGCATT CATAGGTGAA GGAGCTGGTA ACTTATTATT ACGTACGGTA    14100

GTAGAACTTC ATCCAGACAT AAGATACATT TACAGAAGTT TAAAAGATTG CAATGATCAT    14160

AGTTTACCTA TTGAATTTCT AAGATTATAC AACGGGCATA TAAACATAGA TTATGGTGAG    14220

AATTTAACCA TTCCTGCTAC AGATGCAACT AATAACATTC ATTGGTCTTA TTTACATATA    14280

AAATTTGCAG AACCTATTAG CATCTTTGTC TGCGATGCTG AATTACCTGT TACAGCCAAT    14340

TGGAGTAAAA TTATAATTGA ATGGAGTAAG CATGTAAGAA AGTGCAAGTA CTGTTCTTCT    14400

GTAAATAGAT GCATTTTAAT CGCAAAATAT CATGCTCAAG ATGATATTGA TTTCAAATTA    14460

GATAACATTA CTATATTAAA AACTTACGTG TGCCTAGGTA GCAAGTTAAA AGGATCTGAA    14520

GTTTACTTAG TCCTTACAAT AGGCCCTGCA AATATACTTC CTGTTTTTGA TGTTGTGCAA    14580

AATGCTAAAT TGATTTTTTC AAGAACTAAA AATTTCATTA TGCCTAAAAA AACTGACAAG    14640

GAATCTATCG ATGCAAATAT TAAAAGCTTA ATACCTTTCC TTTGTTACCC TATAACAAAA    14700

AAAGGAATTA AGACTTCATT GTCAAAATTG AAGAGTGTAG TTAATGGGGA TATATTATCA    14760

TATTCTATAG CTGGACGTAA TGAAGTATTC AGCAACAAGC TTATAAACCA CAAGCATATG    14820

AATATCCTAA AATGGCTAGA TCATGTTTTA AATTTTAGAT CAGCTGAACT TAATTACAAT    14880

CATTTATACA TGATAGAGTC CACATATCCT TACTTAAGTG AATTGTTAAA TAGTTTAACA    14940
```

```
ACCAATGAGC TCAAGAAACT GATTAAAATA ACAGGTAGTG TACTATACAA CCTTCCCAAC    15000

GAACAGTAAC TTAAAATATC ATTAACAAGT TTGGTCAAAT TTAGATGCTA ACACATCATT    15060

ATATTATAGT TATTAAAAAA TATGCAAACT TTTCAATAAT TTAGCTTACT GATTCCAAAA    15120

TTATCATTTT ATTTTTAAGG GGTTGAATAA AAGTCTAAAA CTAACAATGA TACATGTGCA    15180

TTTACAACAC AACGAGACAT TAGTTTTTGA CACTTTTTTT CTCGT                    15225
```

(2) INFORMATION FOR SEQ ID NO: 3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
ACTCAAATAA GTTAATAAAA AATATCCCGG GAT                                 33
```

(2) INFORMATION FOR SEQ ID NO: 4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

```
CCCGGGATAT TTTTTATTAA CTTATTTGAG T                                   31
```

(2) INFORMATION FOR SEQ ID NO: 5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
GAAAGTATAT ATTATGTT                                                  18
```

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
TATATAAGCA CGATGATATG                                                20
```

(2) INFORMATION FOR SEQ ID NO: 7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

ACTCAAATAA GTTAAT                                                           16

(2) INFORMATION FOR SEQ ID NO: 8:

(i) SEQUENCE CHARACTERISTICS:
           (A) LENGTH: 14 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 8:

TAACTTATTT GAGT                                                             14

(2) INFORMATION FOR SEQ ID NO: 9:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 9:

GACACAACCC ACAATGATAA TACACCAC                                              28

(2) INFORMATION FOR SEQ ID NO: 10:

(i) SEQUENCE CHARACTERISTICS:
           (A) LENGTH: 32 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 10:

CATCTCTAAC CAAGGGAGTT AAATTTAAGT GG                                         32

(2) INFORMATION FOR SEQ ID NO: 11:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 11:

TTAAGGAGAG ATATAAGATA GAAGATG                                               27

(2) INFORMATION FOR SEQ ID NO: 12:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 12:

-continued

```
GTTTTATATT AACTAATGGT GTTAGTG                                27
```

(2) INFORMATION FOR SEQ ID NO: 13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

```
TTATAATTGC AGCCATCATA TTCATAGCCT CGG                         33
```

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

```
GTGAAGTTGA GATTACAATT GCCAGAATGG                             30
```